(12) United States Patent
Braido et al.

(10) Patent No.: US 12,193,888 B2
(45) Date of Patent: Jan. 14, 2025

(54) EXTENDED REALITY (XR) APPLICATIONS FOR CARDIAC ARRHYTHMIA PROCEDURES

(71) Applicant: Medtronic, Inc., Boulder, CO (US)

(72) Inventors: Peter N. Braido, Linwood, MN (US); Mina S. Fahim, New Brighton, MN (US); Ross D. Hinrichsen, Minneapolis, MN (US); William Harding, Chandler, AZ (US); Julia Schraut, Shoreview, MN (US); Monica M. Bolin, Hugo, MN (US); Nicolas Coulombe, Anjou (CA); Dan Wittenberger, Blainville (CA); Jean-Pierre Lalonde, Candiac (CA); Megan Harris, Andover, MN (US); Angela Burgess, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 542 days.

(21) Appl. No.: 17/334,473

(22) Filed: May 28, 2021

(65) Prior Publication Data

US 2021/0369393 A1    Dec. 2, 2021

Related U.S. Application Data

(60) Provisional application No. 63/058,632, filed on Jul. 30, 2020, provisional application No. 63/032,289, (Continued)

(51) Int. Cl.
*A61B 90/00* (2016.01)
*A61B 5/00* (2006.01)
(Continued)

(52) U.S. Cl.
CPC .......... *A61B 90/361* (2016.02); *A61B 5/0035* (2013.01); *A61B 5/0044* (2013.01); (Continued)

(58) Field of Classification Search
USPC ............. 382/100–159, 173–305; 704/1–275; 706/1–62, 900–903; 600/500–595, (Continued)

(56) References Cited

U.S. PATENT DOCUMENTS

| 7,187,964 B2 | 3/2007 | Khoury |
| 7,892,165 B2 | 2/2011 | Nakamura |

(Continued)

FOREIGN PATENT DOCUMENTS

| WO | WO-2001020552 A1 | 3/2001 |
| WO | WO-2009148317 A1 | 12/2009 |

(Continued)

OTHER PUBLICATIONS

Care, Bruce; Method, Apparatus, and Operating System for Real-time Monitoring and Management of Patients' Health Status and Medical Treatment Regimens; 2000 (Year: 2000).*

(Continued)

*Primary Examiner* — Marcellus J Augustin
(74) *Attorney, Agent, or Firm* — Michael Best & Friedrich LLP

(57) ABSTRACT

Novel tools and techniques are provided for implementing intelligent assistance ("IA") ecosystem, and, in some cases, for implementing extended reality ("XR") for cardiac arrhythmia procedures. In various embodiments, a computing system might receive device data associated with a device(s) configured to perform a cardiac arrhythmia procedure to provide effective heart rhythm, might receive imaging data associated with an imaging device(s) configured to generate images of a portion(s) of a patient. The (Continued)

computing system might analyze the received device data and imaging data (collectively "received data"), might map the received data to a 3D or 4D representation of the portion(s) of the patient based on the analysis, and might generate and present (using a user experience ("UX") device) one or more XR images or experiences based on the mapping.

18 Claims, 77 Drawing Sheets

Related U.S. Application Data filed on May 29, 2020, provisional application No. 63/032,283, filed on May 29, 2020, provisional application No. 63/032,278, filed on May 29, 2020.

(51) Int. Cl.
| | |
|---|---|
| A61B 5/06 | (2006.01) |
| A61B 18/14 | (2006.01) |
| A61B 34/10 | (2016.01) |
| A61B 34/20 | (2016.01) |
| A61B 34/30 | (2016.01) |
| G06T 19/00 | (2011.01) |
| G16H 30/20 | (2018.01) |

(52) U.S. Cl.
CPC .......... *A61B 5/068* (2013.01); *A61B 18/1492* (2013.01); *A61B 34/10* (2016.02); *A61B 34/20* (2016.02); *A61B 34/30* (2016.02); *G06T 19/006* (2013.01); *G16H 30/20* (2018.01); *A61B 5/0036* (2018.08); *A61B 2034/102* (2016.02); *A61B 2034/105* (2016.02); *A61B 2034/2046* (2016.02); *A61B 2090/365* (2016.02)

(58) Field of Classification Search
USPC ........... 600/1–183; 604/890.1–892.1, 1–316; 901/1–50
See application file for complete search history.

(56) References Cited

U.S. PATENT DOCUMENTS

| | | | |
|---|---|---|---|
| 7,998,095 | B2 | 8/2011 | McAuley |
| 8,460,282 | B2 | 6/2013 | McAuley |
| 8,482,859 | B2 | 7/2013 | Border et al. |
| 8,768,022 | B2 | 7/2014 | Miga et al. |
| 8,792,693 | B2 | 7/2014 | Satish et al. |
| 8,902,254 | B1 | 12/2014 | Laughlin et al. |
| 9,128,281 | B2 | 9/2015 | Osterhout et al. |
| 9,134,534 | B2 | 9/2015 | Border et al. |
| 9,223,134 | B2 | 12/2015 | Miller et al. |
| 9,232,982 | B2 | 1/2016 | Soler et al. |
| 9,298,884 | B1 | 3/2016 | Ahmad |
| 9,317,743 | B2 | 4/2016 | Datta et al. |
| 9,452,294 | B2 | 9/2016 | Kaula et al. |
| 9,492,241 | B2 | 11/2016 | Joskowicz et al. |
| 9,526,443 | B1 | 12/2016 | Berme et al. |
| 9,615,788 | B2 | 4/2017 | Kaula et al. |
| 9,639,953 | B2 | 5/2017 | Moraviec |
| 9,642,606 | B2 | 5/2017 | Charles et al. |
| 9,659,104 | B2 | 5/2017 | Soon-Shiong et al. |
| 9,687,301 | B2 | 6/2017 | Lee et al. |
| 9,720,505 | B2 | 8/2017 | Gribetz et al. |
| 9,740,296 | B2 | 8/2017 | Cohen et al. |
| 9,767,608 | B2 | 9/2017 | Lee et al. |
| 9,773,312 | B2 | 9/2017 | Lee |
| 9,855,103 | B2 | 1/2018 | Tsekos et al. |
| 9,866,767 | B2 | 1/2018 | Jones |
| 9,870,060 | B2 | 1/2018 | Marggraff et al. |
| 9,875,540 | B2 | 1/2018 | Blumhofer et al. |
| 9,888,973 | B2 | 2/2018 | Olson et al. |
| 9,911,225 | B2 | 3/2018 | Engel et al. |
| 9,928,588 | B2 | 3/2018 | Vilsmeier |
| 9,947,104 | B2 | 4/2018 | Seiler et al. |
| 9,986,983 | B2 | 6/2018 | Weingarten et al. |
| 10,026,227 | B2 | 7/2018 | Laughlin et al. |
| 10,152,796 | B2 | 12/2018 | Guo et al. |
| 10,180,572 | B2 | 1/2019 | Osterhout et al. |
| 2002/0198891 | A1 | 12/2002 | Li et al. |
| 2007/0173861 | A1 | 7/2007 | Strommer et al. |
| 2008/0033527 | A1 | 2/2008 | Nunez et al. |
| 2010/0198346 | A1 | 8/2010 | Keogh et al. |
| 2012/0188352 | A1 | 7/2012 | Wittenberg et al. |
| 2013/0035757 | A1 | 2/2013 | Zentgraf et al. |
| 2014/0128726 | A1 | 5/2014 | Quill et al. |
| 2014/0176661 | A1 | 6/2014 | Smurro et al. |
| 2014/0296704 | A1 | 10/2014 | Alves De Inda et al. |
| 2016/0019716 | A1 | 1/2016 | Huang et al. |
| 2016/0085774 | A1 | 3/2016 | Bhamidipati et al. |
| 2016/0350303 | A1 | 12/2016 | Fischer et al. |
| 2017/0021132 | A1 | 1/2017 | Laby et al. |
| 2017/0098333 | A1 | 4/2017 | Varga |
| 2017/0103581 | A1 | 4/2017 | Mullins et al. |
| 2017/0109484 | A1 | 4/2017 | Herger et al. |
| 2017/0206419 | A1 | 7/2017 | Mullins |
| 2017/0258586 | A1 | 7/2017 | Marquez et al. |
| 2017/0221387 | A1 | 8/2017 | Lampotang et al. |
| 2017/0293805 | A1 | 10/2017 | Kontschieder et al. |
| 2017/0323148 | A1 | 11/2017 | Sarkar et al. |
| 2017/0323473 | A1* | 11/2017 | Wright ................ A61B 8/0858 |
| 2017/0340396 | A1 | 11/2017 | Romo et al. |
| 2018/0012416 | A1 | 1/2018 | Jones et al. |
| 2018/0286129 | A1* | 10/2018 | Harviainen .......... G02B 27/017 |
| 2019/0180513 | A1* | 6/2019 | Kohler ............... G02B 27/0093 |
| 2019/0183576 | A1* | 6/2019 | Fahim ................. A61B 90/36 |
| 2019/0183577 | A1* | 6/2019 | Fahim ................. G02B 27/01 |
| 2019/0298450 | A1 | 10/2019 | Dasi et al. |
| 2019/0350671 | A1 | 11/2019 | Varshney et al. |
| 2019/0362556 | A1 | 11/2019 | Ben-Dor et al. |
| 2019/0384764 | A1 | 12/2019 | Taylor |
| 2020/0060765 | A1 | 2/2020 | Fahim et al. |
| 2020/0129136 | A1 | 4/2020 | Harding et al. |
| 2020/0251213 | A1* | 8/2020 | Tran ...................... G06N 20/00 |
| 2021/0169581 | A1* | 6/2021 | Calloway ............. A61B 34/30 |
| 2021/0369394 | A1 | 12/2021 | Braido et al. |

FOREIGN PATENT DOCUMENTS

| | | | |
|---|---|---|---|
| WO | WO-2021-243310 A1 | 12/2021 | |
| WO | WO-2021-243311 A1 | 12/2021 | |
| WO | WO-2021-243314 A1 | 12/2021 | |
| WO | WO-2021243313 A1 | 12/2021 | |

OTHER PUBLICATIONS

Yajima Masami; Biological Information Processing Device, Biological Information Processing Method, Program, and Storage Medium; 2019 (Year: 2019).*
International Search Report & Written Opinion, International Application No. PCT/US2021/035033 mailed on Sep. 14, 2021, 16 pages.
International Search Report & Written Opinion, International Application No. PCT/US2021/035034 mailed on Sep. 16, 2021, 16 pages.
Zhang Q et al: "Dynamic real-time 4D cardiac MDCT image display using GPU-accelerated volume rendering", Computerized Medical Imaging and Graphics, Pergamon Press, New York, NY, US, vol. 33, No. 6, Sep. 1, 2009, 16 pages.
Azizian Mahdi et al: "Intraoperative 3D stereo visualization for image-guided cardiac ablation", Medical Imaging 2011: Visualization, Image-Guided Procedures, and Modeling, SPIE, vol. 7964, No. 1, Mar. 2, 2011, 8 pages.
Linte C A et al: "Virtual and Augmented Medical Imaging Environments: Enabling Technology for Minimally Invasive Cardiac Interventional Guidance", IEEE Reviews in Biomedical Engineering, IEEE, USA, vol. 3, Jan. 1, 2010, 23 pages.

(56) References Cited

OTHER PUBLICATIONS

Robb A. Using patient specific anatomic models, IEEE Engineering in Medicine and Biology Magazine, IEEE Service Center, Pisacataway, NJ, US, vol. 15, No. 2, Mar. 1, 1996, 10 pages.
International Search Report & Written Opinion, International Application No. PCT/US2021/035036 mailed on Sep. 16, 2021, 16 pages.
International Search Report & Written Opinion, International Application No. PCT/US2021/035037 mailed on Sep. 16, 2021, 16 pages.
Suematsu et al., "Robotic-assisted closure of atrial septal defect under real-time three-dimensional echo guide in vitro study", CP Journal of cardio-Thoracic Surgery, vol. 32, No. 4, dated Sep. 6, 2007, 4 pages.
International Search Report & Written Opinion, International Application No. PCT/US2021/037655 mailed on Oct. 4, 2021, 19 pages.
Silva et al. "Medical Imaging archiving: a comparison between several NoSQL solutions." IEEE EMBS International Conference on Information Technology Applications in Biomedicine (ITAB) [online], 2014 [Retrieved on Aug. 12, 2021], Retrieved from the Internet: <URL: https://doi.org/10.1109/BHI.2014.6864305>, see entire document, especially p. 65, Abstract; p. 66, col. 1, para 2-4, 5 pages.

* cited by examiner

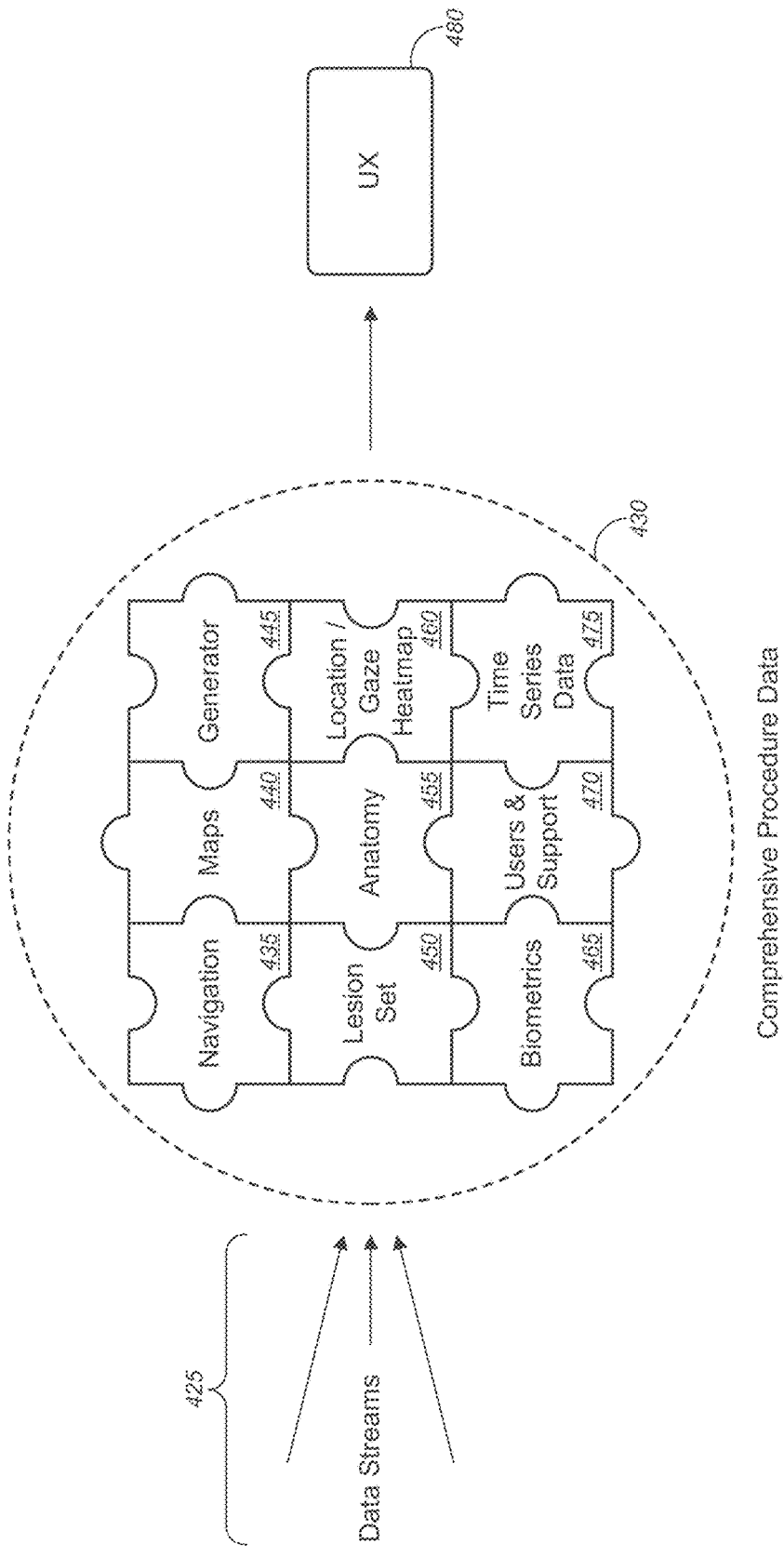

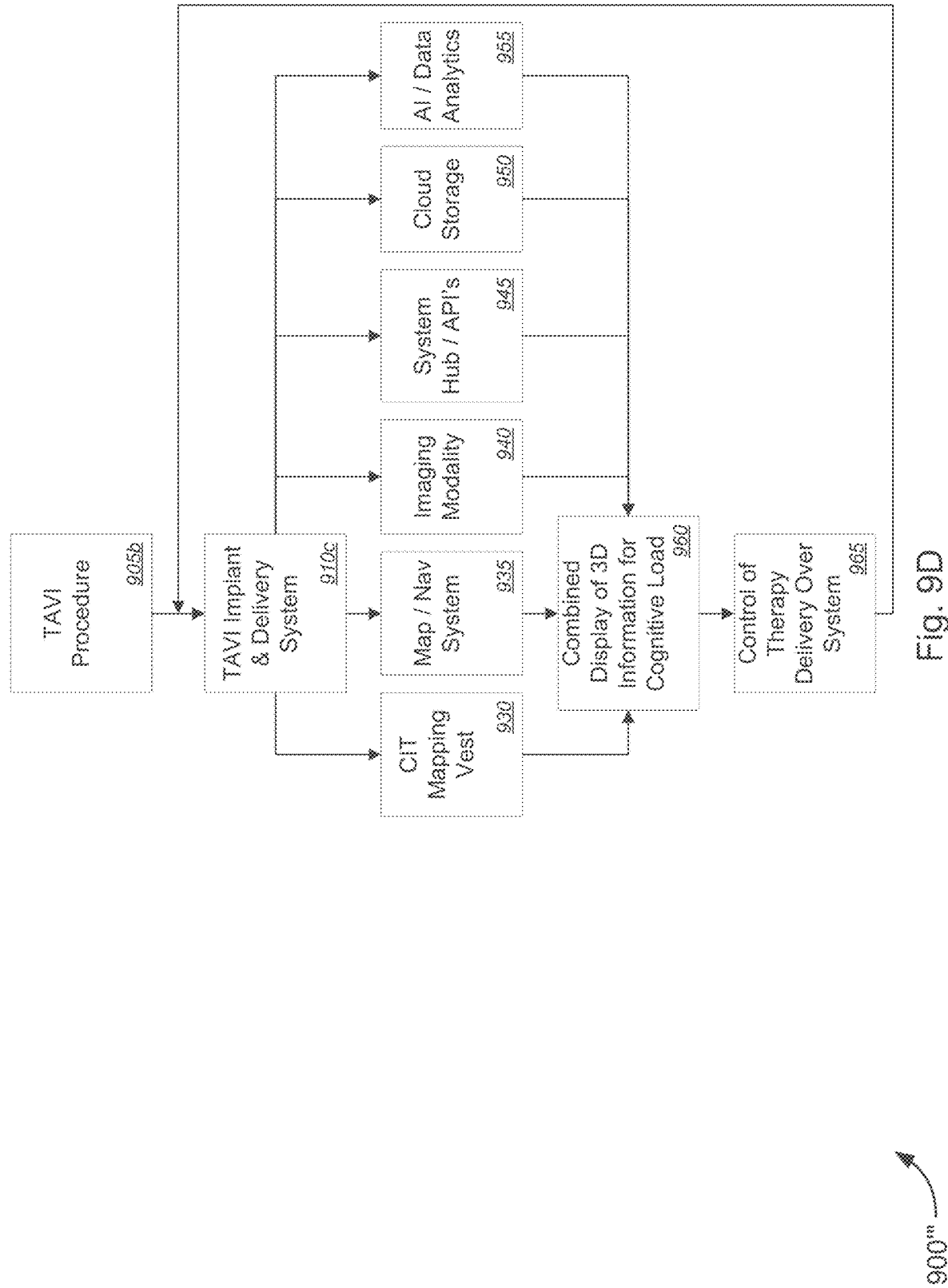

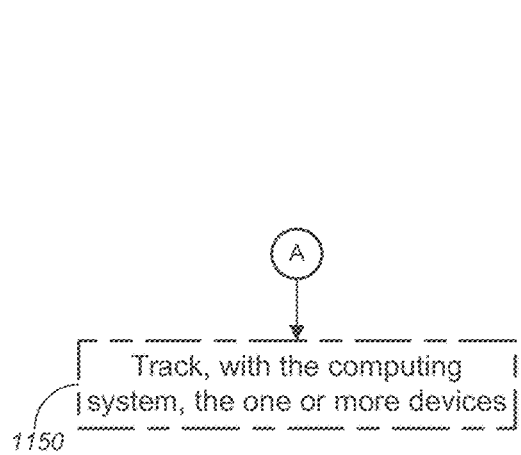
1100 → Fig. 11B
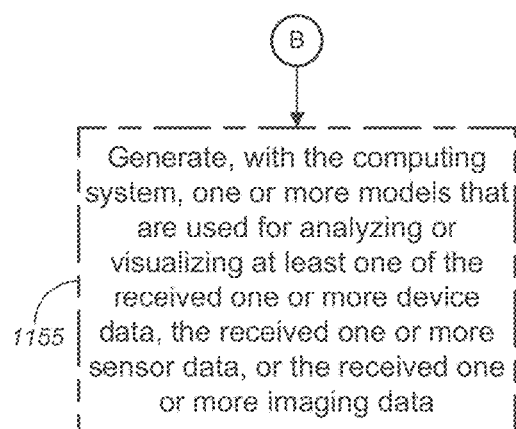
1100 → Fig. 11C
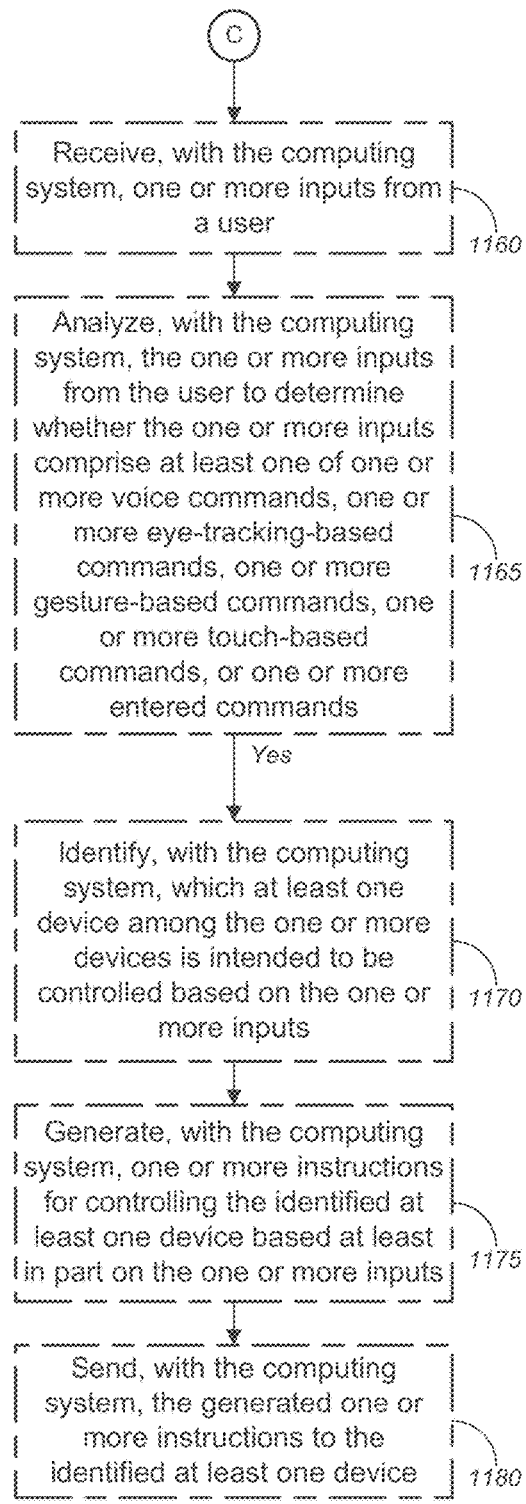
1100 → Fig. 11D

1200

1200

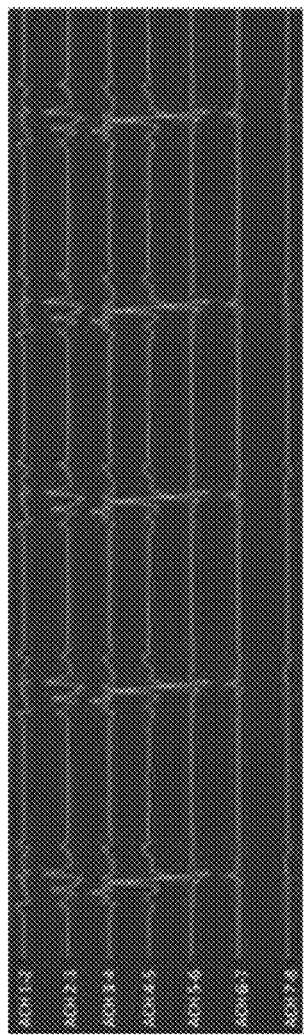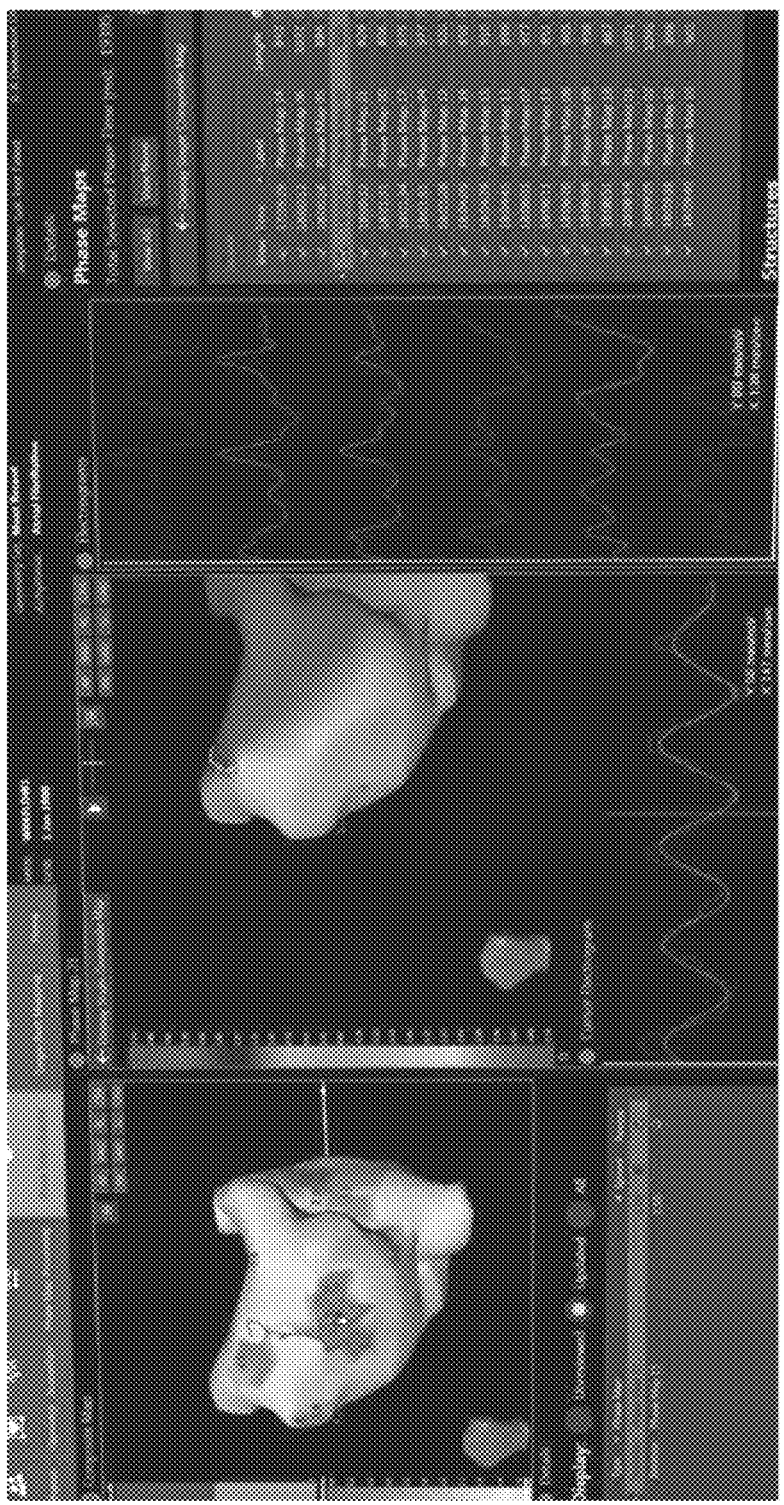
Fig. 12E

1200

1200

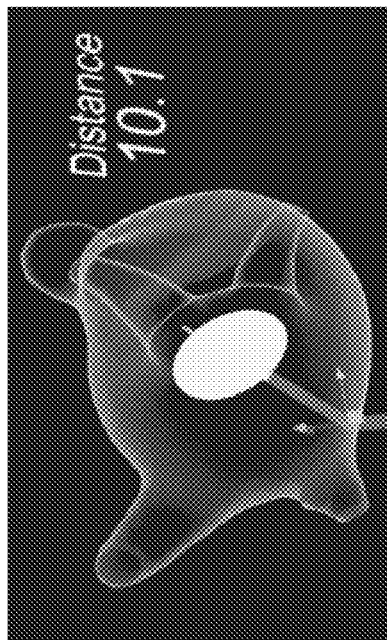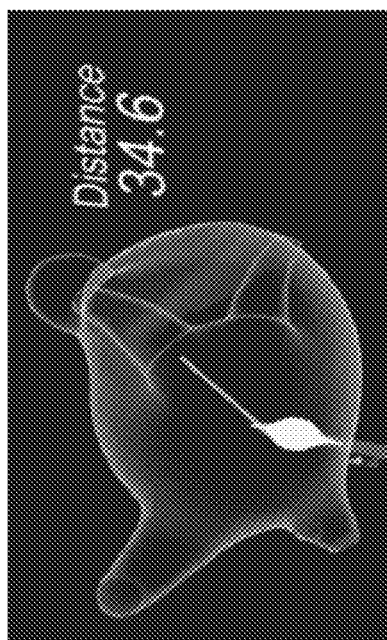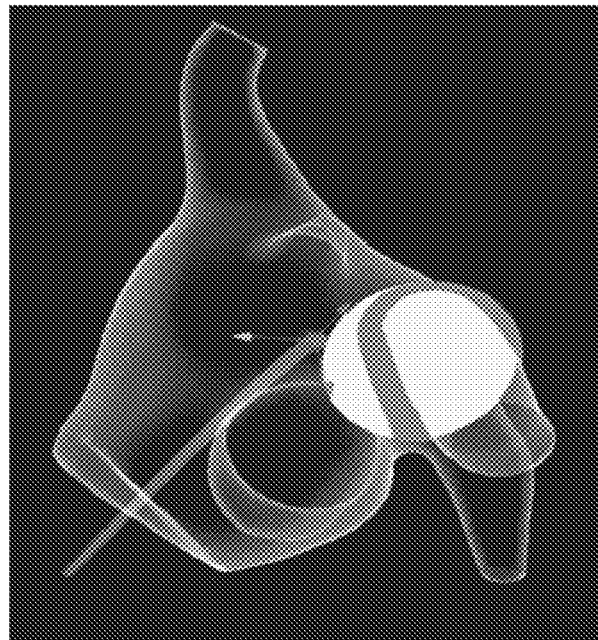
Fig. 12J

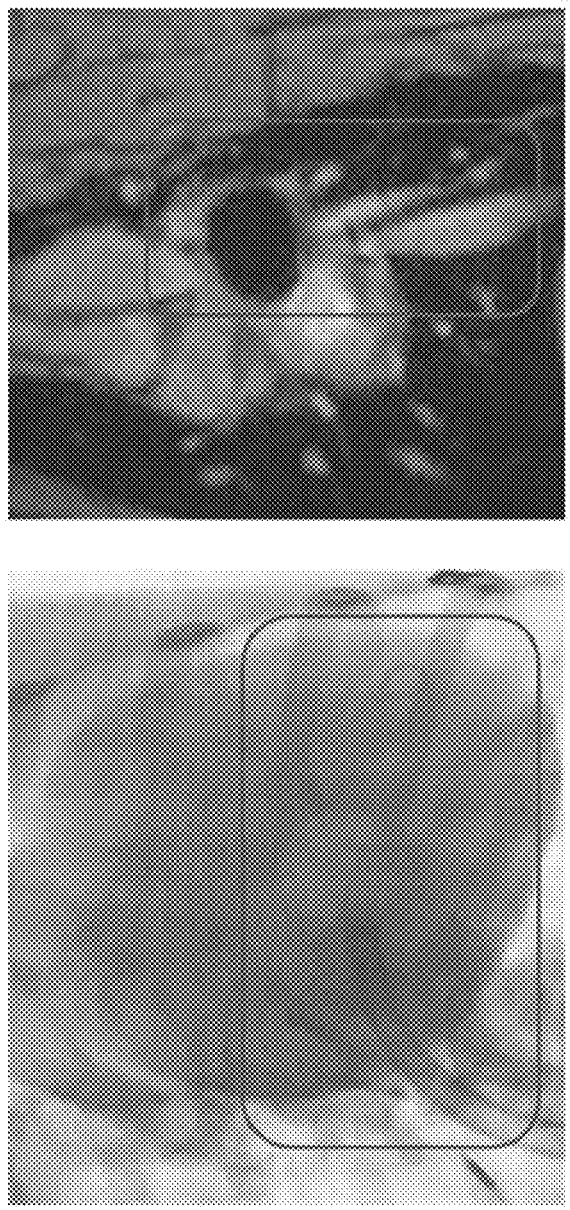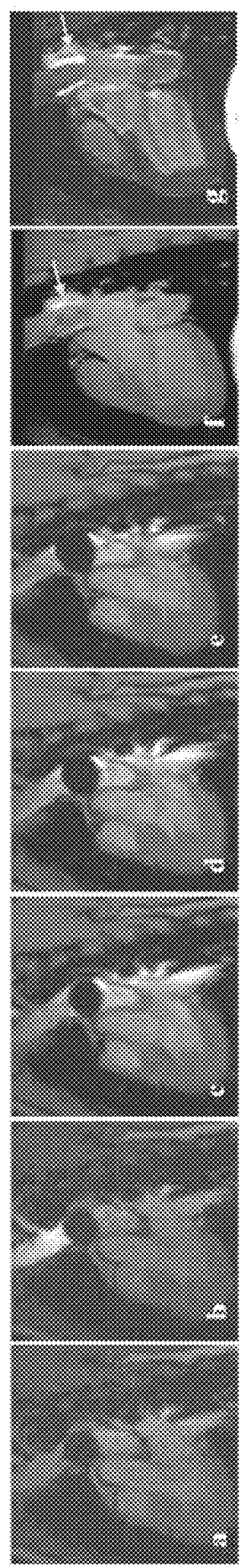
Fig. 12U
1200

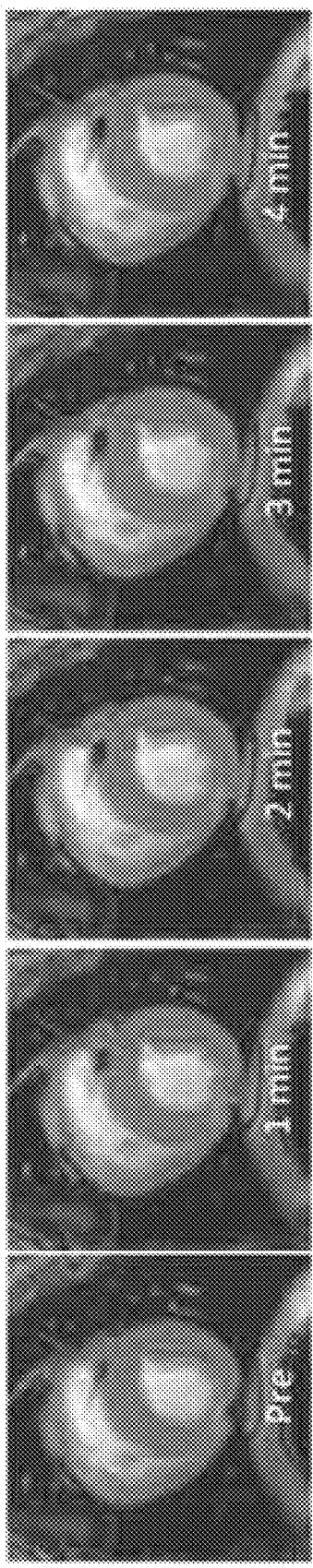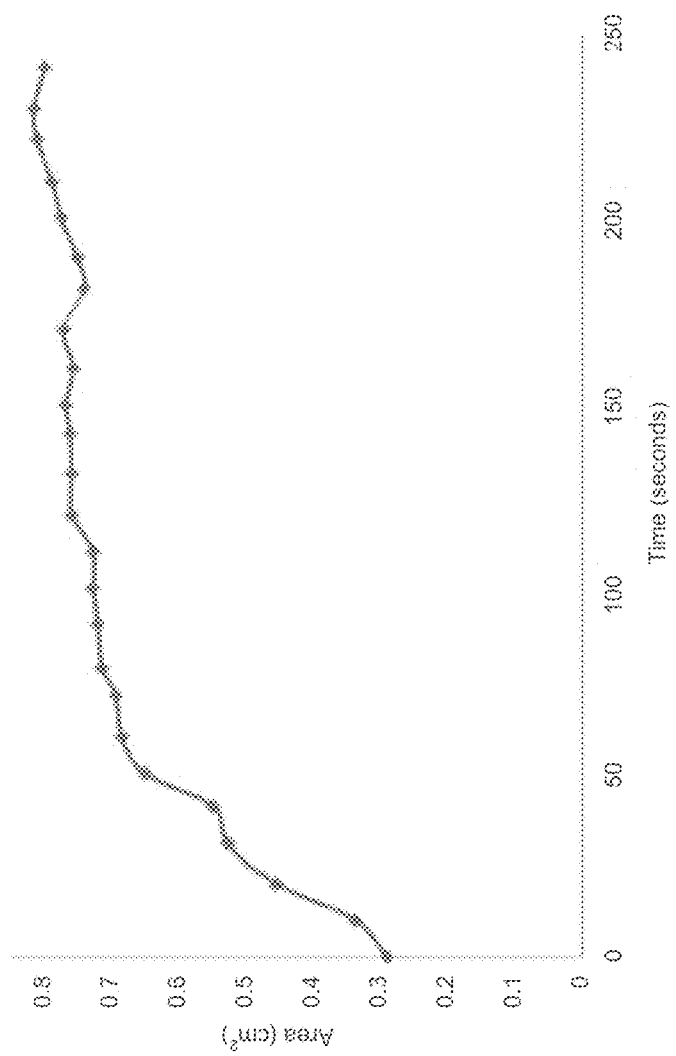
Fig. 12W
1200

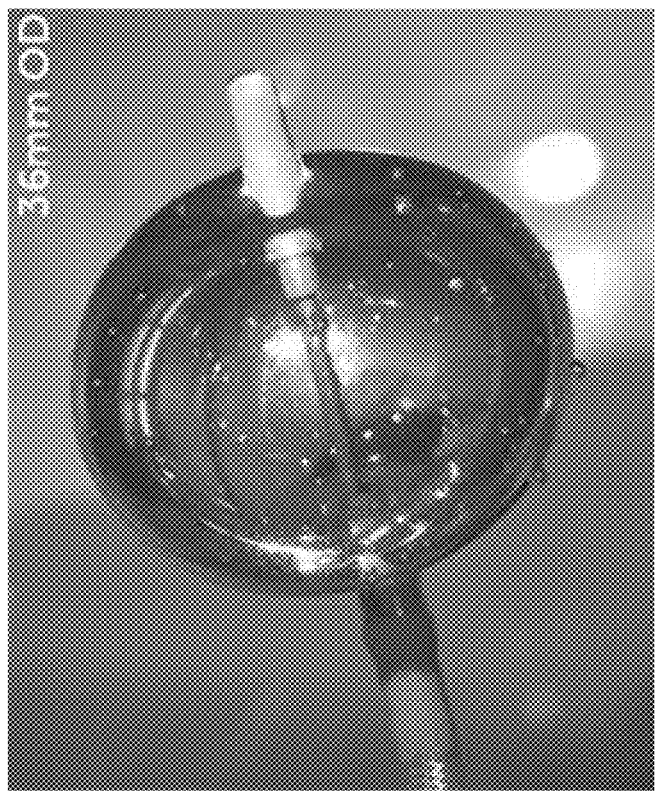
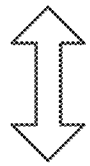
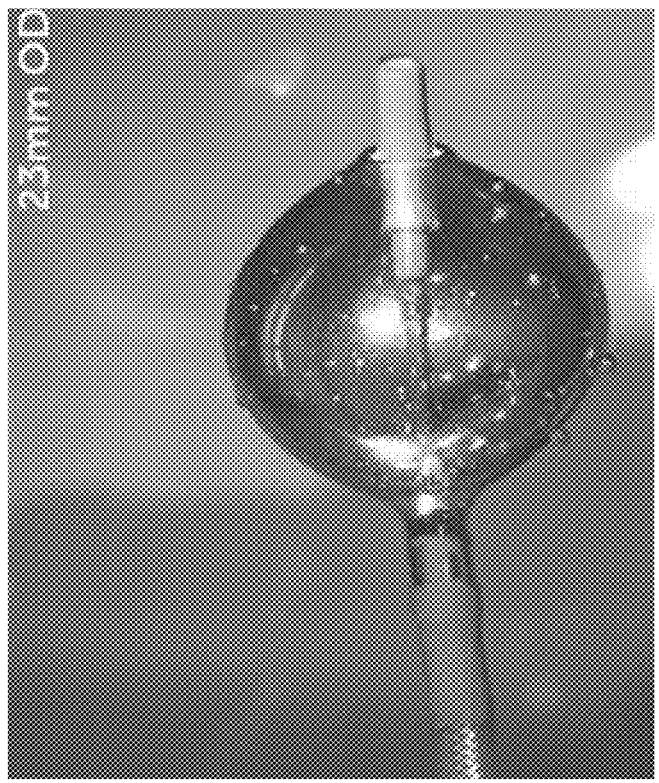
Fig. 12X
1200

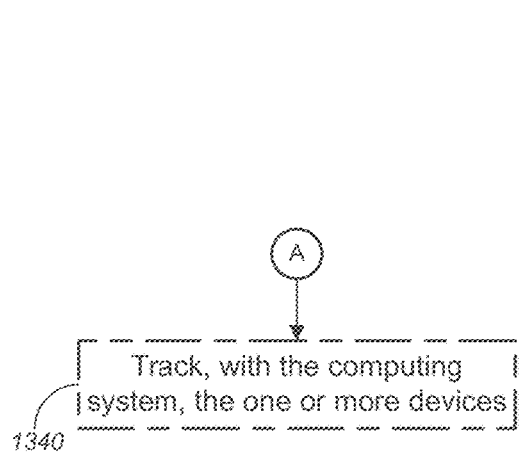
1300 — Fig. 13B
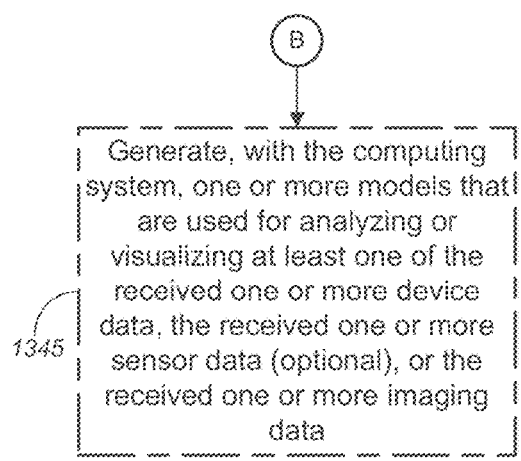
1300 — Fig. 13C
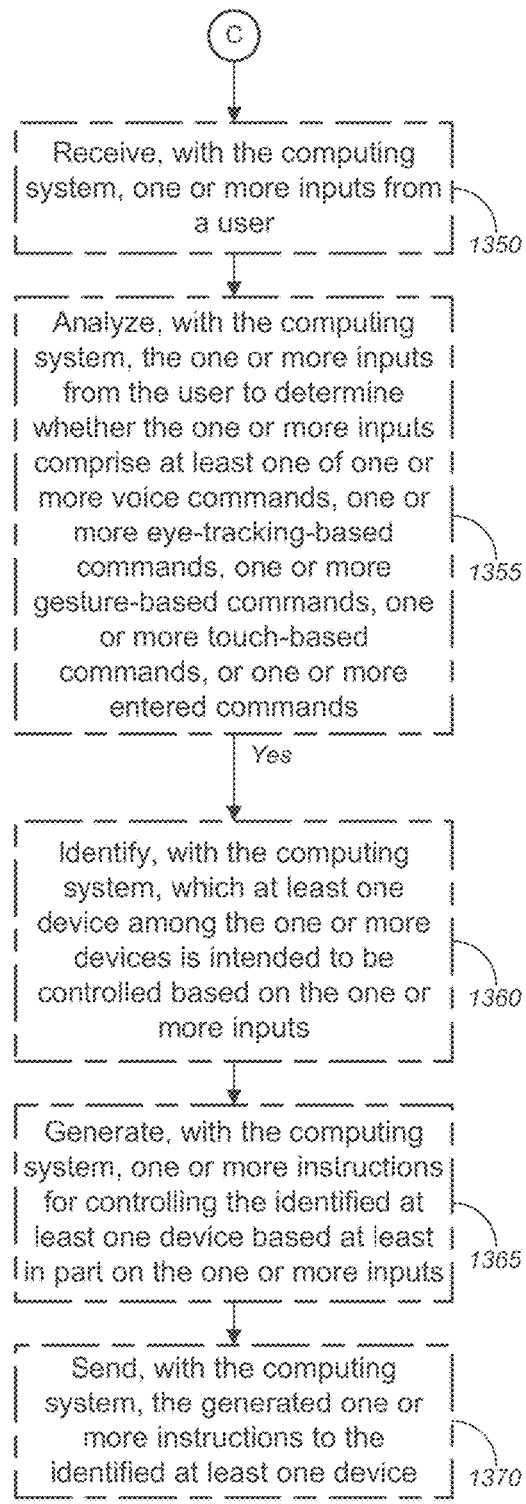
1300 — Fig. 13D

Before TMVI
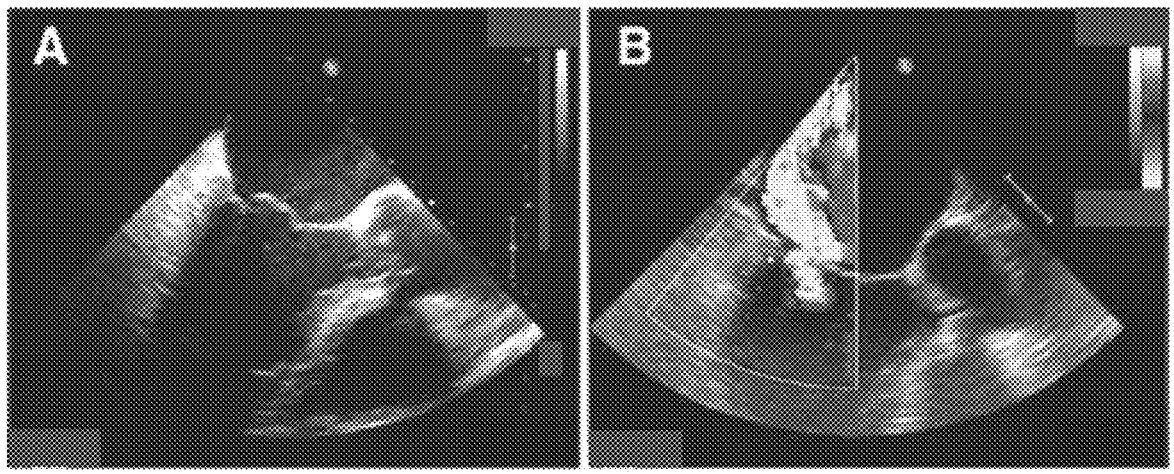
After TMVI
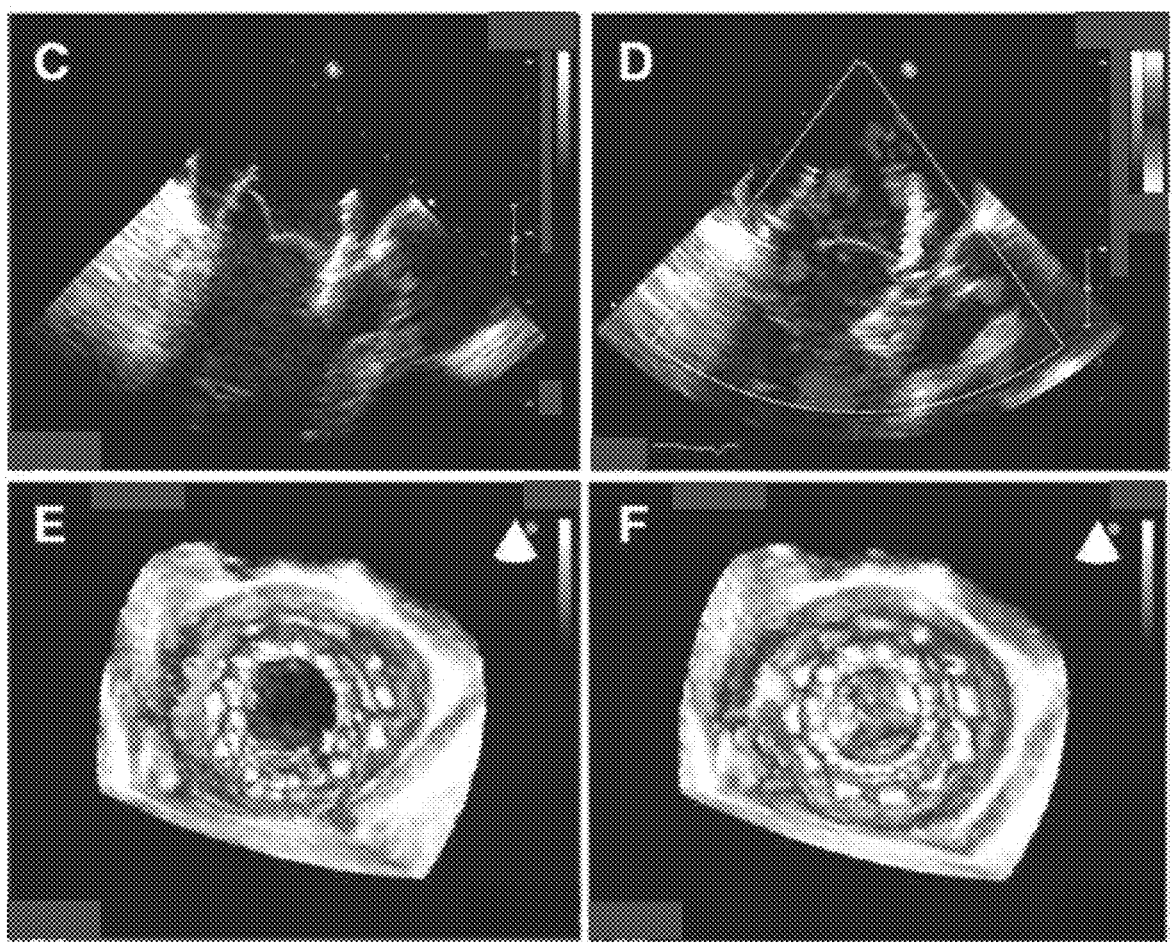
1400
Fig. 14F

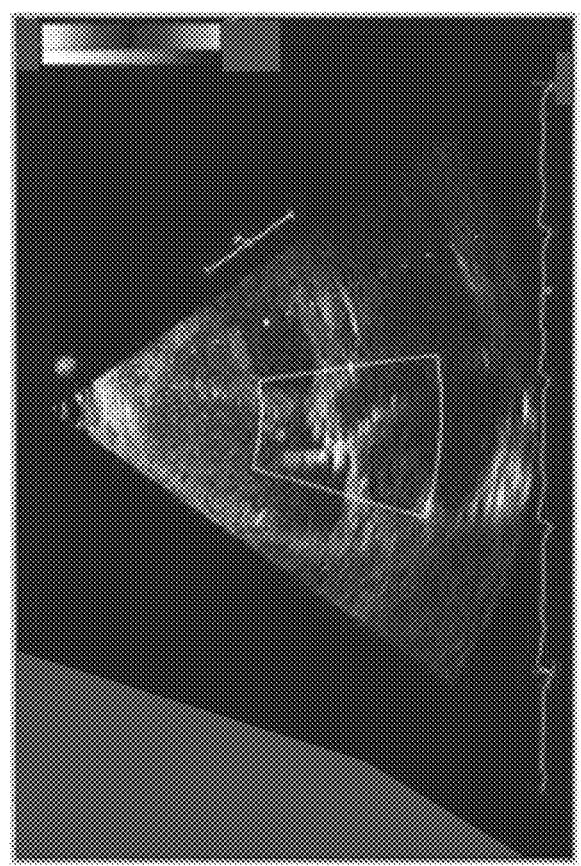
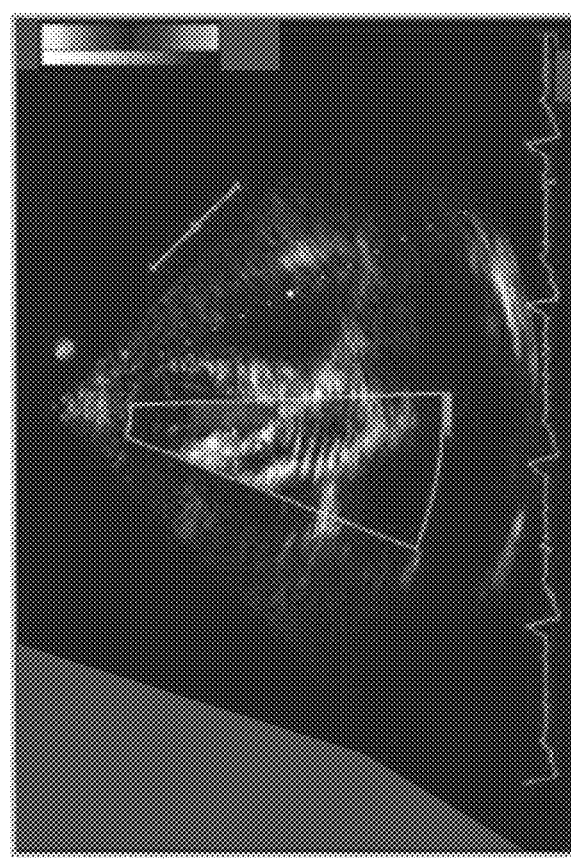
Fig. 14G

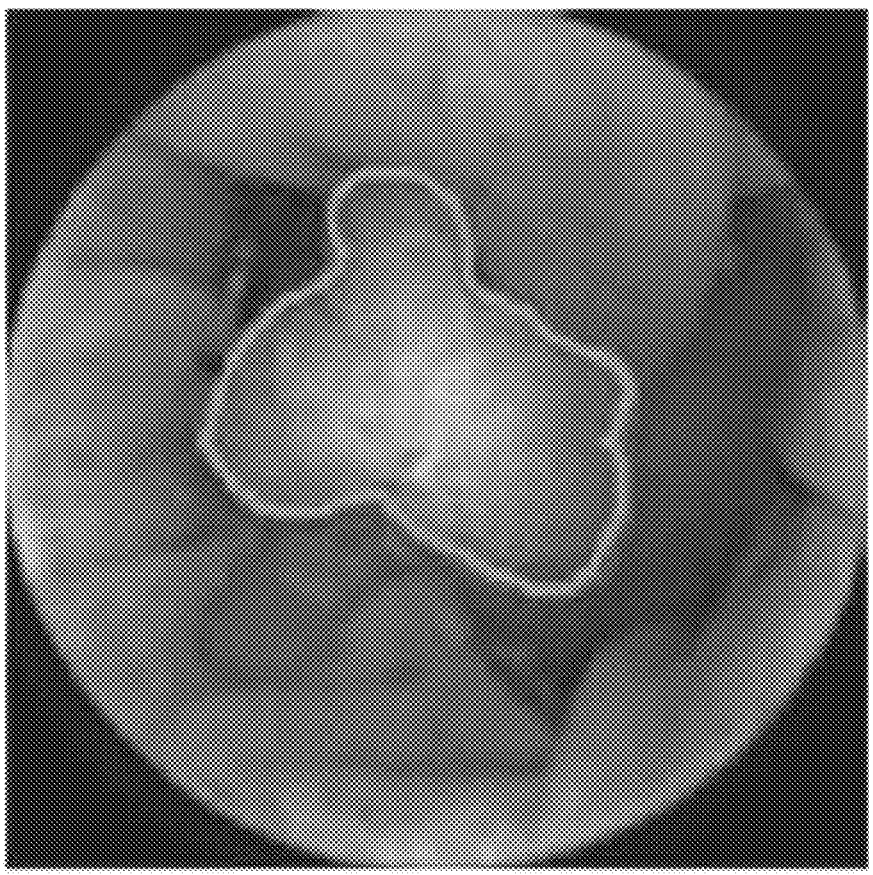
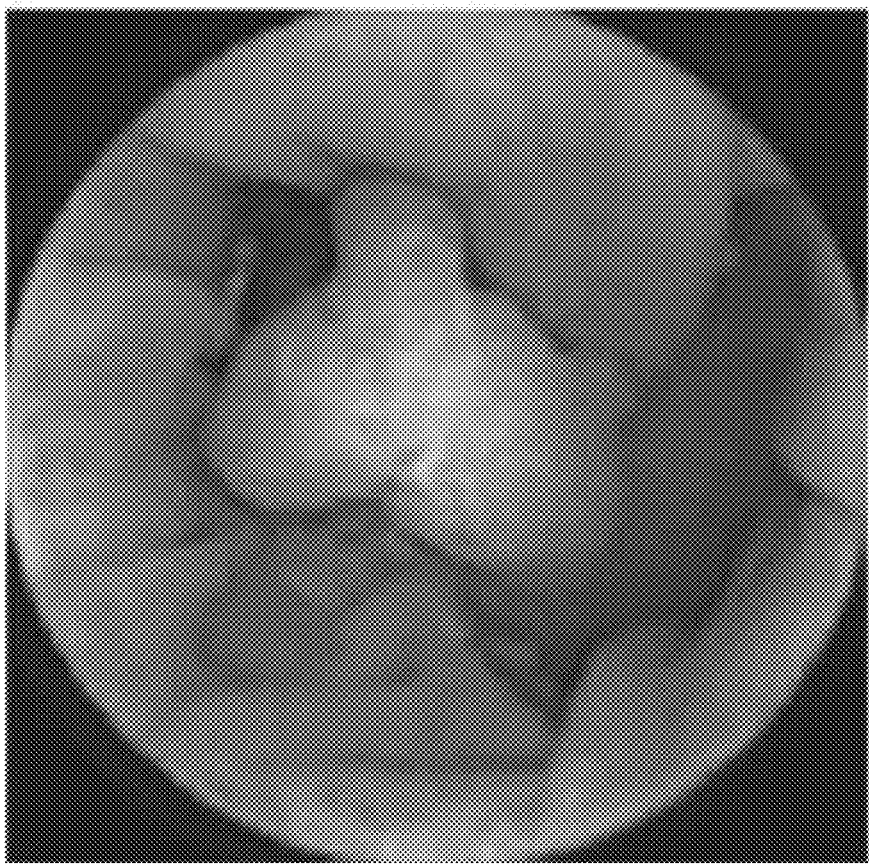
Fig. 14K
1400

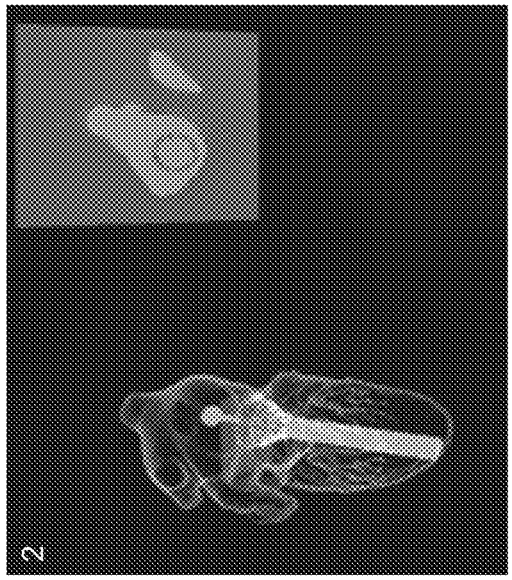
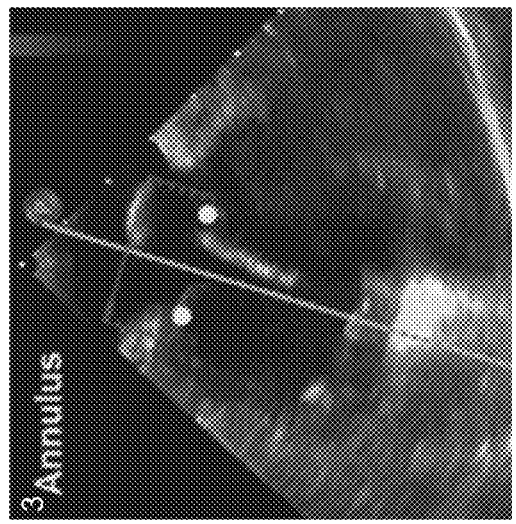
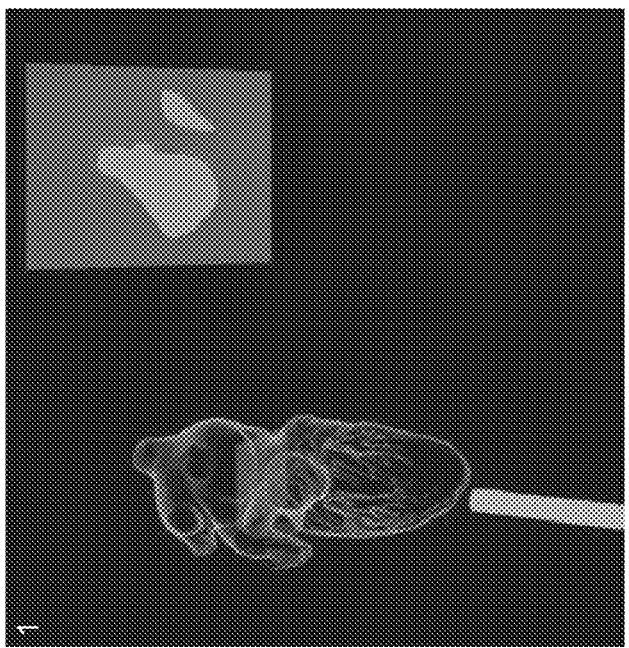
Fig. 14L

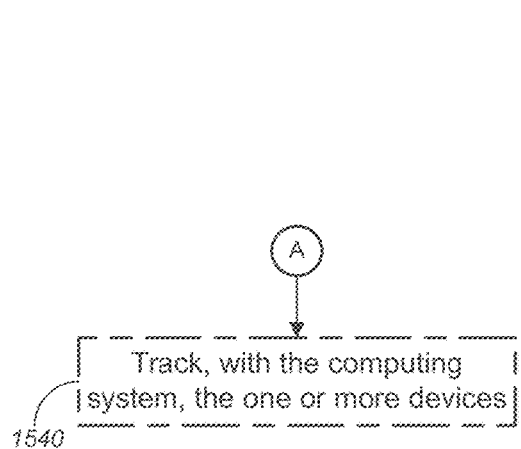
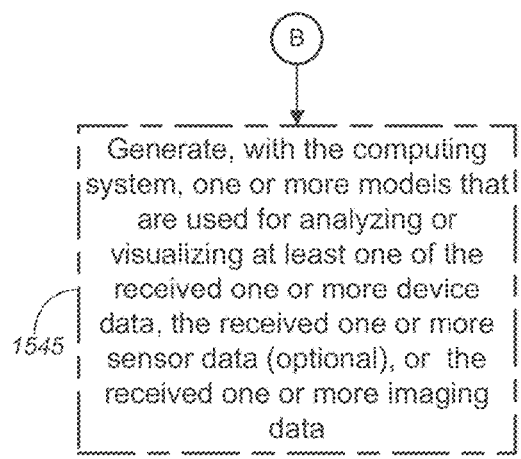
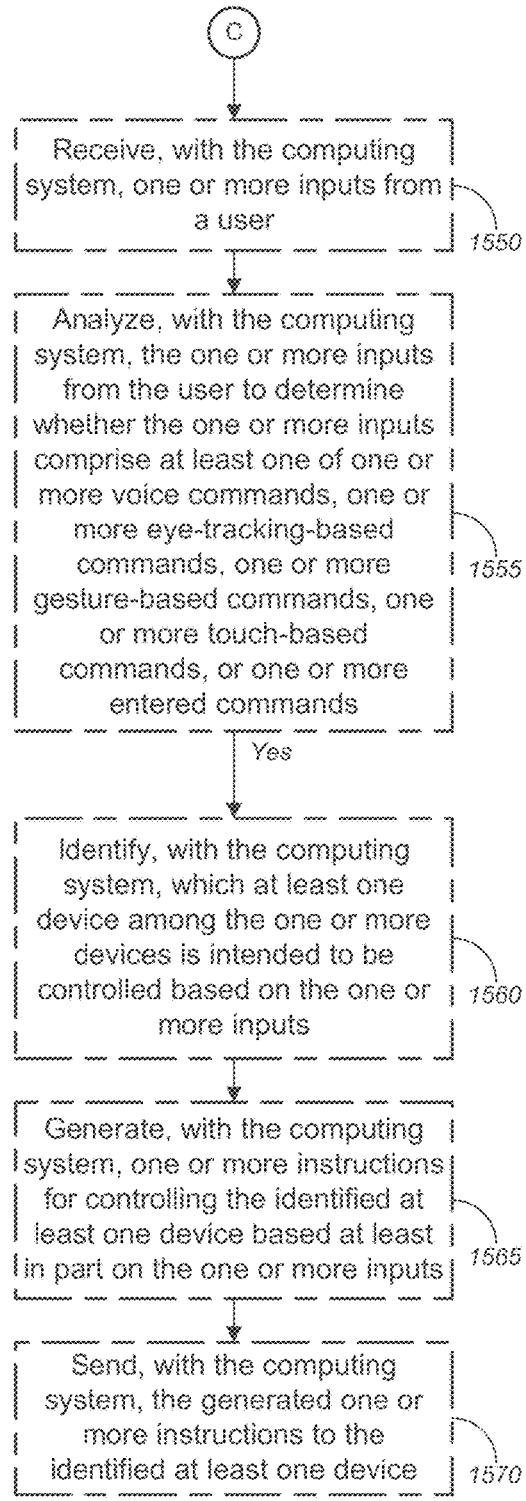

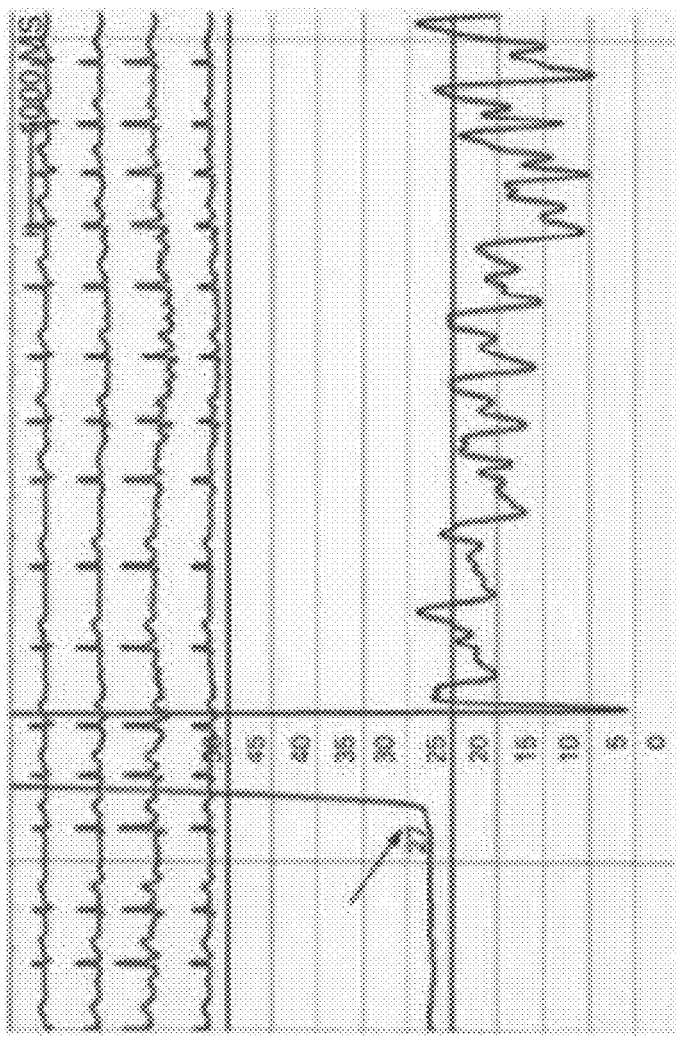
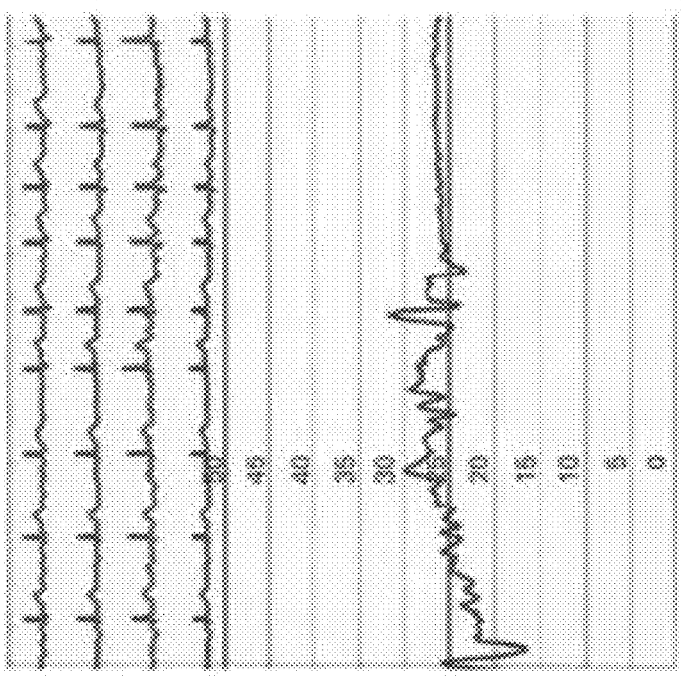
Fig. 16F

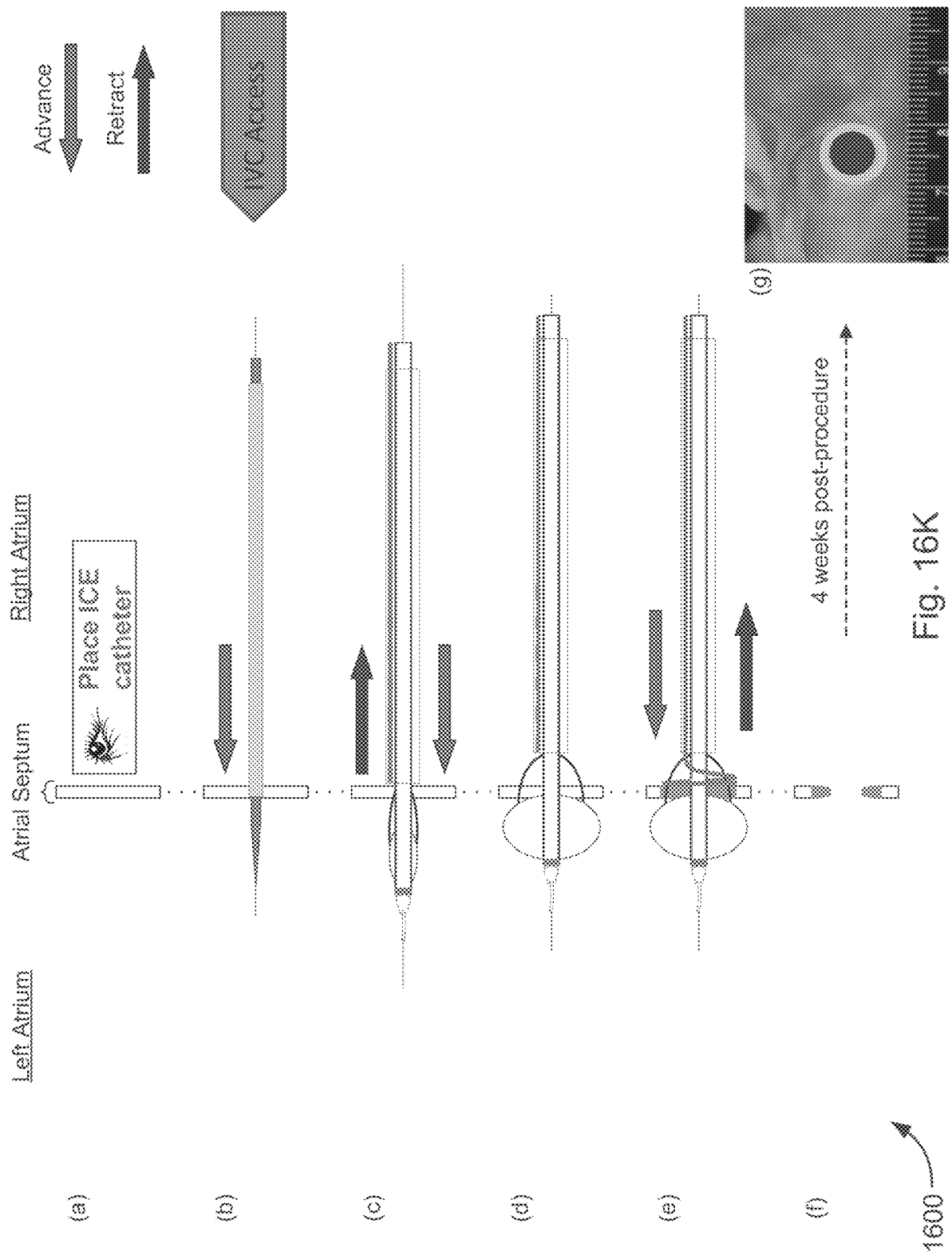

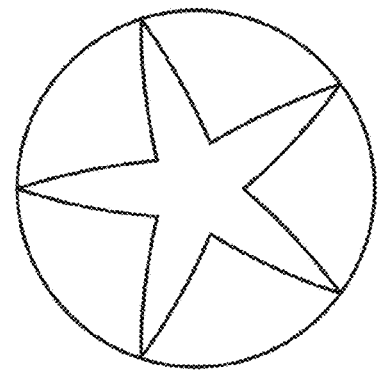
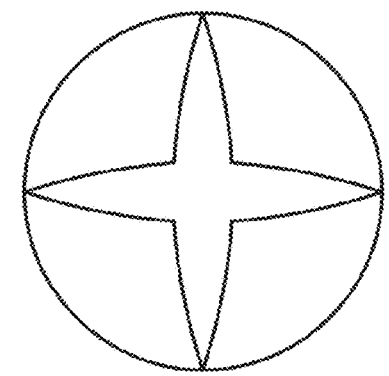
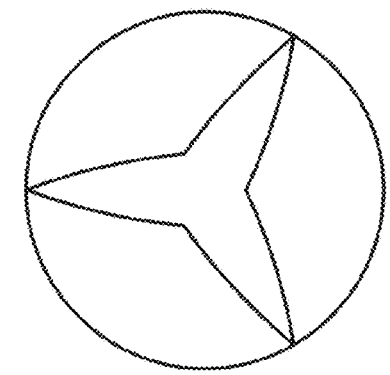
Fig. 16L
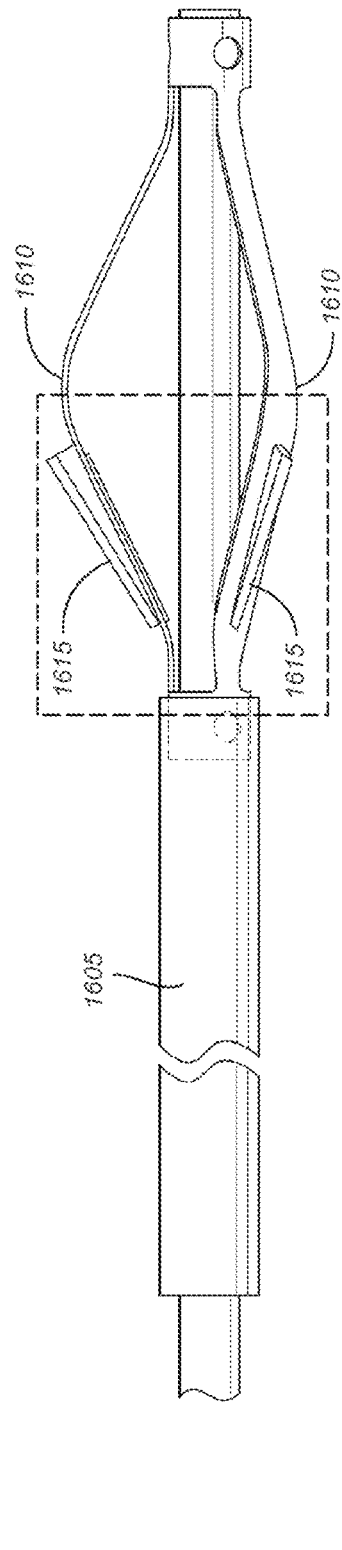
Fig. 16M

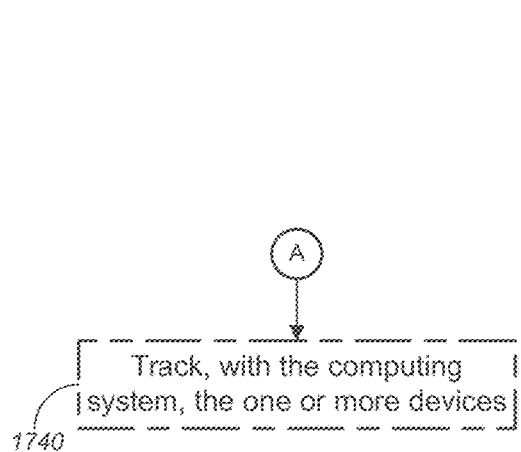
1700 → Fig. 17B
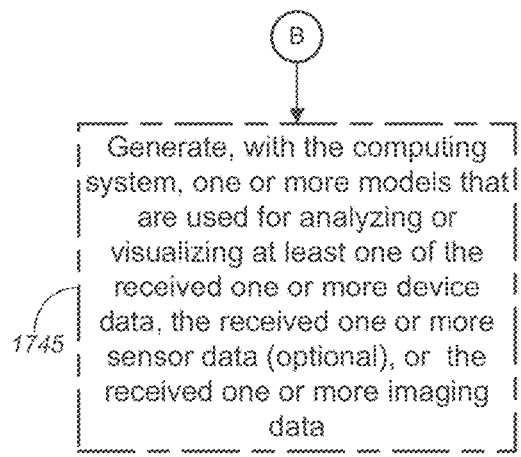
1700 → Fig. 17C
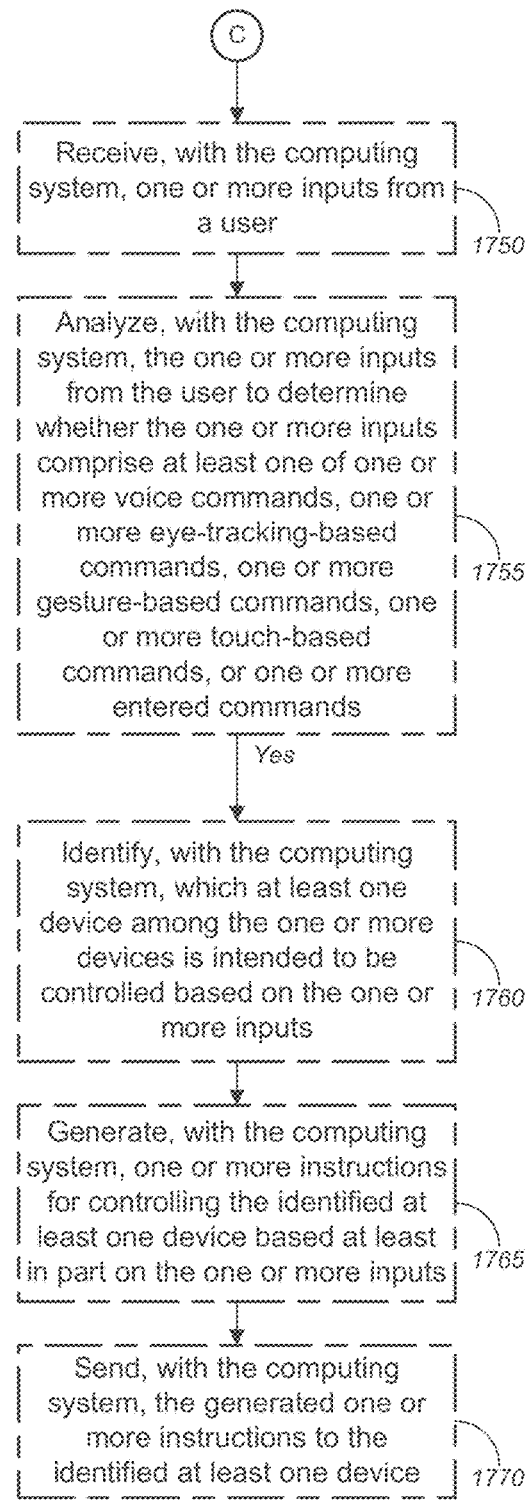
1700 → Fig. 17D

EXTENDED REALITY (XR) APPLICATIONS FOR CARDIAC ARRHYTHMIA PROCEDURES

CROSS-REFERENCES TO RELATED APPLICATIONS

This application claims priority to each of U.S. Patent Application Ser. No. 63/032,278 (the "'278 Application"), filed May 29, 2020 by Peter N. Braido et al., entitled, "Intelligent Assistance (IA) Ecosystem," U.S. Patent Application Ser. No. 63/032,283 (the "'283 Application"), filed May 29, 2020 by Peter N. Braido et al., entitled, "Extended Reality (XR) Applications for Cardiac Arrhythmia Procedures," U.S. Patent Application Ser. No. 63/032,289 (the "'289 Application"), filed May 29, 2020 by Peter N. Braido et al., entitled, "Extended Reality (XR) Applications for Cardiac Blood Flow Procedures," and U.S. Patent Application Ser. No. 63/058,632 (the "'632 Application"), filed Jul. 30, 2020 by Peter Braido et al., entitled, "Extended Reality (XR) Applications for Cardiac Shunting Procedures," the disclosure of each of which is incorporated herein by reference in its entirety for all purposes. The application may also be related to U.S. Patent Application Ser. No. 63/075,413 (the "'413 Application"), filed Sep. 8, 2020 by Mark Palmer et al., entitled, "Imaging Discovery Utility for Augmenting Clinical Image Management," the disclosure of which is incorporated herein by reference in its entirety for all purposes.

The respective disclosures of these applications/patents (which this document refers to collectively as the "Related Applications") are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, and apparatuses for implementing medical assistance technologies, and, more particularly, to methods, systems, and apparatuses for implementing intelligent assistance ("IA") ecosystem, and, in some cases, to methods, systems, and apparatuses for implementing extended reality ("XR") for cardiac arrhythmia procedures.

BACKGROUND

Traditionally, during medical operations or procedures, a surgeon or other medical professional would perform the operation or procedure by hand or using (then up-to-date) surgical tools and instruments, with any imaging and mapping of the progress of the operation or procedure being divorced from or otherwise separate from use of the surgical tools and instruments. This leads to significant effort on the medical professional to fully grasp the situation while juggling the difficulties of the operation or procedure itself, which may lead to complications or issues during the operation or procedure, particularly for complex ones. In some cases, this may also lead to cognitive overload for the medical professional, as well as the medical professional literally not having enough hands to operate all the tools.

More recently, the use of augmented reality or mixed reality to aid in the medical professional during operations or procedures has led to improvements in the system, allowing for more successful outcomes to the operations or procedures. Such recent developments, however, do not fully implement compilation of surgical tool or instrument data, imaging data, and patient data, or integrate the compilation of such data with data analytics and artificial intelligence ("AI") or machine learning or deep learning, and with an intuitive extended reality ("XR") implementation, and, in some cases, also with interfacing robotics to achieve an intelligent assistance ("IA") ecosystem as described in detail below.

Hence, there is a need for more robust and scalable solutions for implementing medical assistance technologies, and, more particularly, to methods, systems, and apparatuses for implementing intelligent assistance ("IA") ecosystem.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 4A-4C are schematic diagrams illustrating various non-limiting examples of platform networks and data management of an IA ecosystem, in accordance with various embodiments.

FIGS. 9A-9H are schematic diagrams illustrating various non-limiting examples of process stacks for implementing an IA ecosystem, in accordance with various embodiments.

FIGS. 11A-11E are flow diagrams illustrating another method for implementing an IA ecosystem, in accordance with various embodiments.

FIGS. 13A-13D are flow diagrams illustrating a method for implementing a cardiac arrhythmia procedure using an IA ecosystem, in accordance with various embodiments.

FIGS. 14A-14M are schematic diagrams or images illustrating various non-limiting examples related to implementing a cardiac blood flow procedure using an IA ecosystem, in accordance with various embodiments.

FIGS. 15A-15D are flow diagrams illustrating a method for implementing a cardiac blood flow procedure using an IA ecosystem, in accordance with various embodiments.

FIGS. 16A-16M are schematic diagrams or images illustrating various non-limiting examples related to implementing a cardiac shunting procedure using an IA ecosystem, in accordance with various embodiments.

FIGS. 17A-17D are flow diagrams illustrating a method for implementing a cardiac shunting procedure using an IA ecosystem, in accordance with various embodiments.

DETAILED DESCRIPTION OF CERTAIN EMBODIMENTS

Overview

Figure 1:
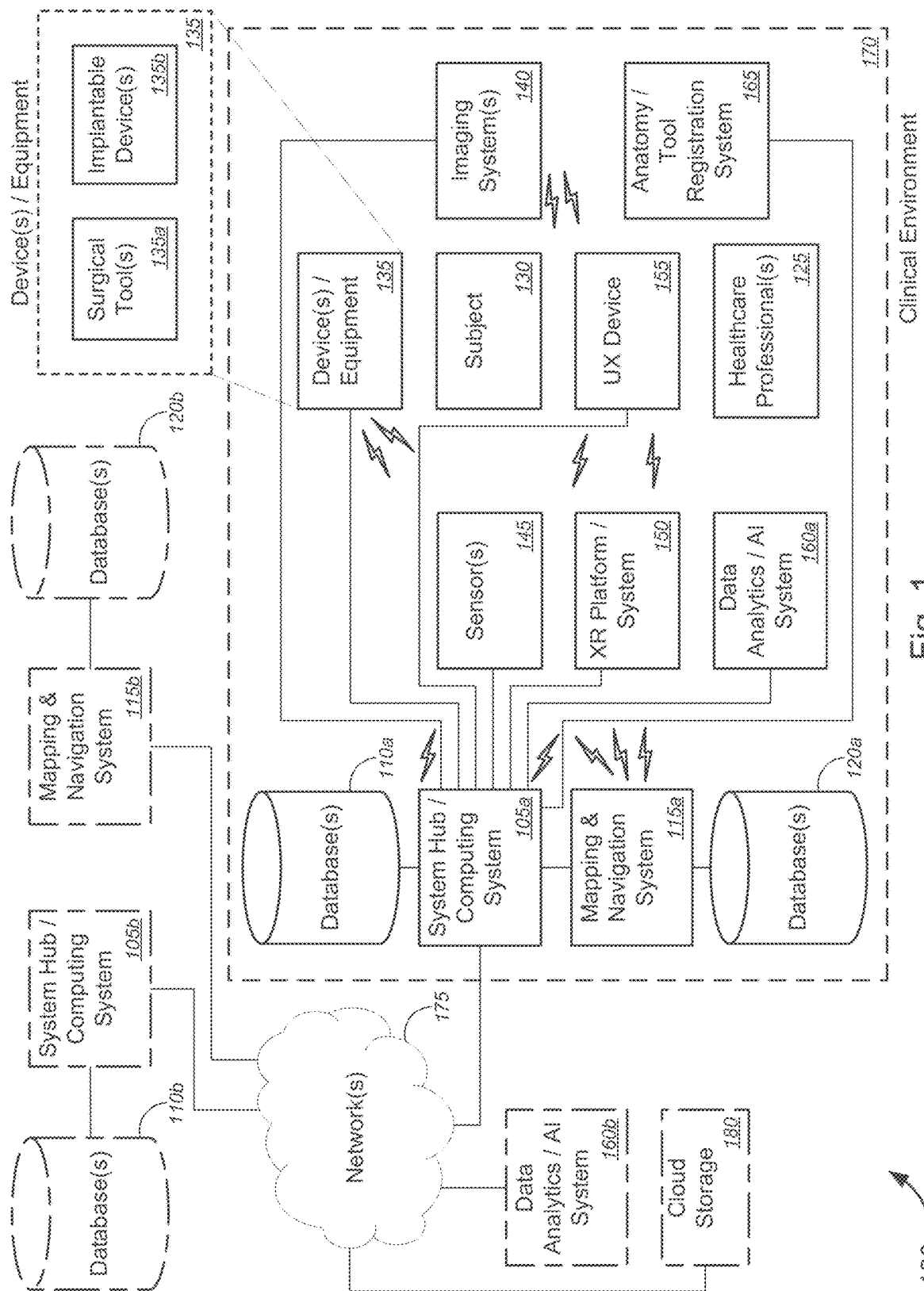
FIG. 1 is a schematic diagram illustrating a system for implementing intelligent assistance ("IA") ecosystem, in accordance with various embodiments.

Various embodiments provide tools and techniques for implementing medical assistance technologies, and, more particularly, to methods, systems, and apparatuses for implementing intelligent assistance ("IA") ecosystem.

In various embodiments, a computing system might receive one or more device data associated with each of one or more devices configured to perform one or more first tasks (in some cases, to perform one or more medical tasks, surgical operations, or procedures (which are less intrusive than surgical operations), or the like (collectively, "medical procedures" or the like)). The computing system might receive one or more sensor data associated with one or more sensors configured to monitor at least one of biometric data, biological data, genetic data, cellular data, or procedure-related data of a subject (or patient), and might receive one or more imaging data associated with each of one or more imaging devices configured to generate images of at least one or more portions of the subject (or patient). The computing system might analyze the received one or more device data, the received one or more sensor data, and the received one or more imaging data, and might map two or more of the received one or more device data, the received one or more sensor data, or the received one or more imaging data to a three-dimensional ("3D") or four-dimensional ("4D") representation (i.e., a 3D representation plus at least one of real-time updates, dynamic modeling, or data streaming, and/or the like) of the at least one or more portions of the subject (or patient), based at least in part on the analysis. The computing system might then generate one or more XR images (or one or more XR experiences), based at least in part on the mapping, and might present the generated one or more XR images (or one or more XR experiences) using a UX device.

In some embodiments, the one or more XR images might include, without limitation, at least one of one or more AR images, one or more AR videos, one or more VR images, one or more VR videos, one or more MR images, one or more MR videos, one or more XR images, or one or more XR videos, and/or the like. In some instances, at least one of the received one or more device data, the received one or more sensor data, and the received one or more imaging data might be real-time or near-real-time data that is received by the computing system in real-time or near-real-time.

According to some embodiments, the generated one or more XR images might be presented to provide one or more of: a guide for a medical professional (e.g., a doctor, a surgeon, a cardiologist, an electrophysiologist, a cardiac surgeon, a neurosurgeon, a radiologist, a scenographer, a nurse practitioner, a nurse, a medical specialist, a medical imaging specialist, and/or the like, or the like), a navigation tool during a medical procedure, a proximity detection tool during a medical procedure, a 3D or 4D visualization view of the at least one or more portions of the subject, a heads-up display of the one or more device data, a heads-up display of biological data of the subject, a heads-up display of chemical data of the subject, a heads-up display of physiological data of the subject, or a heads-up display of procedure-related data of the subject, and/or the like. In some instances, generating the one or more XR images might comprise combining, with the computing system, the received one or more device data, the received one or more sensor data, and the received one or more imaging data into a combined 3D or 4D representation, based at least in part on the analysis and mapping; and generating, with the computing system, the one or more XR images based on the combined 3D or 4D representation.

In some embodiments, the computing system might track the one or more devices or equipment, in some cases, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In accordance with the various embodiments described herein, the intelligent assistance ("IA") ecosystem, unlike conventional medical assistance technologies, fully implements compilation of surgical tool or instrument data, imaging data, and patient data, while integrating the compilation of such data with data analytics and artificial intelligence ("AI") or machine learning or deep learning, with an intuitive extended reality ("XR") implementation, and, in some cases, with pre-operative planning and/or interfacing robotics. Such IA ecosystem provides for better safety and efficacy, while reducing costs of operation of the system, increasing throughput of procedures, providing predictable procedure durations, increasing longevity of physician careers (e.g., by wearing lead during fluoroscopy), and/or the like.

These and other aspects of the intelligent assistance ("IA") ecosystem are described in greater detail with respect to the figures.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Various embodiments described herein, while embodying (in some cases) software products or computer programs, computer-performed methods, and/or computer systems, represent tangible, concrete improvements to existing technological areas, including, without limitation, medical operation technology, medical procedure technology, medical imaging technology, medical visualization and mapping technology, medical assistance technology, and/or the like. In other aspects, certain embodiments, can improve the functioning of user equipment or systems themselves (e.g., medical operation system, medical procedure system, medical imaging system, medical visualization and mapping system, medical assistance system, etc.), for example, by receiving, with a computing system, one or more device data associated with each of one or more devices configured to perform one or more first tasks; receiving, with the computing system, one or more sensor data associated with one or more sensors configured to monitor at least one of biometric data, biological data, genetic data, cellular data, or procedure-related data of a subject; receiving, with the computing system, one or more imaging data associated with each of one or more imaging devices configured to generate images of at least one or more portions of the subject; analyzing, with the computing system, the received one or more device data, the received one or more sensor data, and the received one or more imaging data; mapping, with the computing system, two or more of the received one or more device data, the received one or more sensor data, or the received one or more imaging data to a three-dimensional ("3D") or a four-dimensional ("4D") representation of the at least one or more portions of the subject, based at least in part on the analysis; generating, with the computing system, one or more extended reality ("XR") images, based at least in part on the mapping; and presenting, with the computing system and using a user experience ("UX") device, the generated one or more XR images; and/or the like.

In particular, to the extent any abstract concepts are present in the various embodiments, those concepts can be implemented as described herein by devices, software, systems, and methods that involve specific novel functionality (e.g., steps or operations), such as, implementing an intelligent assistance ("IA") ecosystem that receives and combines the one or more device data associated with each of the one or more devices configured to perform the one or more first tasks, the one or more sensor data associated with the one or more sensors configured to monitor at least one of biometric data, biological data, genetic data, cellular data, or procedure-related data of the subject, and the one or more imaging data associated with each of the one or more imaging devices configured to generate images of at least one or more portions of the subject; that analyzes and maps two or more of the received one or more device data, the received one or more sensor data, or the received one or more imaging data to a 3D or a 4D representation of the at least one or more portions of the subject, based at least in part on the analysis; that generates the one or more XR images; and that presents (using the UX device) the generated one or more XR images; and/or the like, to name a few examples, that extend beyond mere conventional computer processing operations. These functionalities can produce tangible results outside of the implementing computer system, including, merely by way of example, optimized and comprehensive IA ecosystem that achieves better safety and efficacy, while reducing costs of operation of the system, increasing throughput of procedures, providing predictable procedure durations, increasing longevity of physician careers (e.g., by wearing lead during fluoroscopy), and/or the like, at least some of which may be observed or measured by users, patients, and/or service providers.

In an aspect, a method is provided for presenting extended reality ("XR") experiences. The method might comprise receiving, with a computing system, one or more device data associated with each of one or more devices configured to perform one or more medical procedures; receiving, with the computing system, one or more sensor data associated with one or more sensors configured to monitor at least one of biometric data, biological data, genetic data, cellular data, or procedure-related data of a patient; receiving, with the computing system, one or more imaging data associated with each of one or more imaging devices configured to generate images of at least one or more portions of the patient; analyzing, with the computing system, the received one or more device data, the received one or more sensor data, and the received one or more imaging data; mapping, with the computing system, two or more of the received one or more device data, the received one or more sensor data, or the received one or more imaging data to a four-dimensional ("4D") representation of the at least one or more portions of the patient, based at least in part on the analysis; generating, with the computing system, one or more extended reality ("XR") experiences, based at least in part on the mapping, wherein the one or more XR experiences comprise at least three or more of the one or more XR images, one or more XR sounds, one or more XR haptic or tactile responses, one or more XR simulated smells, or one or more XR simulated tastes; and presenting, with the computing system and using a user experience ("UX") device, the generated one or more XR experiences.

In another aspect, a method is provided for presenting extended reality ("XR") experiences. The method might comprise receiving, with a computing system, one or more device data associated with each of one or more devices configured to perform one or more first tasks; receiving, with the computing system, one or more sensor data associated with one or more sensors configured to monitor at least one of biometric data, biological data, genetic data, cellular data, or procedure-related data of a subject; receiving, with the computing system, one or more imaging data associated with each of one or more imaging devices configured to generate images of at least one or more portions of the subject; analyzing, with the computing system, the received one or more device data, the received one or more sensor data, and the received one or more imaging data; mapping, with the computing system, two or more of the received one or more device data, the received one or more sensor data, or the received one or more imaging data to a three-dimensional ("3D") or a four-dimensional ("4D") representation of the at least one or more portions of the subject, based at least in part on the analysis; generating, with the computing system, one or more extended reality ("XR") images, based at least in part on the mapping; and presenting, with the computing system and using a user experience ("UX") device, the generated one or more XR images.

In some embodiments, the computing system might comprise at least one of an XR computing system, a medical procedure computing system, a hub computing system, a 3D graphical processing unit, a cluster computing system, a 4D graphics computing system, a server computer, a cloud computing system, or a distributed computing system, and/or the like. In some cases, the one or more devices might comprise at least one of one or more catheters, one or more catheter interconnect or interface cables, one or more valves, one or more balloons, one or more leads, one or more pacemakers, one or more defibrillators, one or more neuromodulation devices, one or more neurostimulation devices, one or more rigid robotic devices, one or more soft robotic devices, one or more stents, one or more needles, one or more grafts, one or more occluders, one or more shunts, one or more orthopedic screws, one or more orthopedic plates, one or more orthopedic rods, one or more vertebral sponges, one or more therapeutic delivery devices, one or more implant delivery devices, one or more diagnostic devices, one or more diagnostic catheters, one or more implant devices, one or more surgical tools, one or more biologics, one or more drug pumps, one or more genes, one or more cells, one or more organs, one or more organelles, one or more delivery pharmaceuticals, one or more biopsy tools, one or more excision tools, one or more ablation tools, one or more monitoring devices, one or more cameras, one or more imaging tools, one or more fiducials, one or more staples, one or more anchors, one or more meshes, one or more vascular cannulae, one or more circulatory pumps, one or more valve repair devices, one or more embolic protection devices, one or more cardiomyoplasty tools, one or more vascular closure tools, one or more septal closure tools, one or more ventricular closure tools, one or more lasers, one or more plaque removal tools, one or more guide wires, one or more introducers, one or more sheaths, one or more pillcams, one or more clips, one or more capsules, one or more microbiomes, one or more microbes of bacterial vectors, one or more microbes of viral vectors, one or more microbes of prion vectors, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment, and/or the like.

According to some embodiments, the one or more sensors might comprise at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography (EOG) sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some embodiments, the one or more imaging devices might comprise at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

According to some embodiments, the one or more first tasks might comprise at least one of a surgical procedure, a left atrial appendage ("LAA") procedure, a tissue ablation procedure, a transcatheter aortic valve repair ("TAVr") procedure, a transcatheter aortic valve replacement ("TAVR") procedure, a transcatheter mitral valve repair ("TMVr") procedure, a transcatheter mitral valve replacement ("TMVR") procedure, a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, an implant procedure, a home care ventilation procedure, a lung cancer procedure, an aneurysm flow diversion procedure, a deep brain stimulation procedure, a shunt procedure, a bone grafting procedure, an insulin pump installation procedure, a continuous glucose monitoring system installation procedure, a colon disease procedure, a gastroparesis therapy, a hernia surgery, a bowel control therapy, a microwave ablation procedure, a reflux testing and treatment, a weight-loss surgery, a bone conduction hearing therapy, a sinus surgery, a thyroid surgery, a treatment for ear infections, a balloon angioplasty, a stenting procedure, an atrial septal defect ("ASD") treatment procedure, a cardiac shunt treatment procedure, a heart bypass surgery, a cardiac mapping procedure, a cardiac resynchronization therapy ("CRT") device installation procedure, a catheter ablation procedure, an endovascular repair procedure, a heart monitor installation procedure, an implantable cardioverter defibrillator ("ICD") device installation procedure, an extravascular ICD ("EV-ICD") device installation procedure, a minimally invasive endovascular repair procedure, a pacemaker installation procedure, a miniature leadless implant installation procedure, an implantable sensor installation procedure, a remote monitoring device installation procedure, a surgical heart valve repair and replacement procedure, a transcatheter pulmonary valve ("TPV") therapy, a varicose vein therapy, a ventricular assist device ("VAD") installation procedure, an intra-aortic balloon pump ("IABP") implantation procedure, a heart transplant operation, a back surgery, a bone tumor treatment, a drug pump installation procedure, a spinal cord stimulation procedure, a targeted drug delivery procedure, a balloon kyphoplasty procedure, a cervical disc replacement procedure, a cervical fusion procedure, a sacroiliac joint fusion procedure, a sacral neuromodulation procedure, or a percutaneous tibial neuromodulation procedure, and/or the like.

In some embodiments, the subject might comprise one of a human patient, a large animal, a small animal, an organ, an organelle, one or more organs on a chip, one or more tissue constructs, one or more cells, one or more microbes of bacterial vectors, one or more microbes of viral vectors, one or more microbes of prion vectors, one or more genes, deoxyribonucleic acid ("DNA"), ribonucleic acid ("RNA"), one or more hormones, one or more biochemicals, one or more molecules, one or more tissues, one or more blood vessels, or one or more bones, and/or the like. In some instances, the one or more XR images might comprise at least one of one or more augmented reality ("AR") images, one or more AR videos, one or more virtual reality ("VR") images, one or more VR videos, one or more mixed reality ("MR") images, one or more MR videos, one or more XR images, or one or more XR videos, and/or the like.

According to some embodiments, the UX device might comprise at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

In some embodiments, at least one of the received one or more device data, the received one or more sensor data, and the received one or more imaging data might be real-time or near-real-time data that is received by the computing system in real-time or near-real-time. In some cases, the generated one or more XR images might be presented to provide one or more of: a guide for a medical professional, a navigation tool during a medical procedure, a proximity detection tool during a medical procedure, a 3D or 4D visualization view of the at least one or more portions of the subject, a heads-up display of the one or more device data, a heads-up display of biological data of the subject, a heads-up display of chemical data of the subject, a heads-up display of physiological data of the subject, or a heads-up display of procedure-related data of the subject, and/or the like.

According to some embodiments, generating the one or more XR images might comprise: combining, with the computing system, the received one or more device data, the received one or more sensor data, and the received one or more imaging data into a combined 3D or 4D representation, based at least in part on the analysis and mapping; and generating, with the computing system, the one or more XR images based on the combined 3D or 4D representation.

In some embodiments, the method might further comprise tracking, with the computing system, the one or more devices, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

According to some embodiments, the method might further comprise generating, with the computing system, one or more models that are used for analyzing or visualizing at least one of the received one or more device data, the received one or more sensor data, and the received one or more imaging data.

In some embodiments, the method might further comprise receiving, with the computing system, one or more inputs from a user; analyzing, with the computing system, the one or more inputs from the user to determine whether the one or more inputs comprise at least one of one or more voice commands, one or more eye-tracking-based commands, one or more gesture-based commands, one or more touch-based commands, or one or more entered commands; and based on a determination that the one or more inputs comprise at least one of one or more voice commands, one or more eye-tracking-based commands, one or more gesture-based commands, or one or more entered commands, identifying, with the computing system, which at least one device among the one or more devices is intended to be controlled based on the one or more inputs, generating, with the computing system, one or more instructions for controlling the identified at least one device based at least in part on the one or more inputs, and sending, with the computing system, the generated one or more instructions to the identified at least one device.

According to some embodiments, the method might further comprise generating, with the computing system, one or more XR experiences comprising at least three or more of the one or more XR images, one or more XR sounds, one or more XR haptic or tactile responses, one or more XR simulated smells, or one or more XR simulated tastes, based at least in part on the mapping; and presenting, with the computing system and using the UX device, the generated one or more XR experiences.

In yet another aspect, an apparatus is provided for presenting extended reality ("XR") experiences. The apparatus might comprise at least one processor and a non-transitory computer readable medium communicatively coupled to the at least one processor. The non-transitory computer readable medium might have stored thereon computer software comprising a set of instructions that, when executed by the at least one processor, causes the apparatus to: receive one or more device data associated with each of one or more devices configured to perform one or more first tasks; receive one or more sensor data associated with one or more sensors configured to monitor at least one of biometric data, biological data, genetic data, cellular data, or procedure-related data of a subject; receive one or more imaging data associated with each of one or more imaging devices configured to generate images of at least one or more portions of the subject; analyze the received one or more device data, the received one or more sensor data, and the received one or more imaging data; map two or more of the received one or more device data, the received one or more sensor data, or the received one or more imaging data to a three-dimensional ("3D") or a four-dimensional ("4D") representation of the at least one or more portions of the subject, based at least in part on the analysis; generate one or more extended reality ("XR") images, based at least in part on the mapping; and present, using a user experience ("UX") device, the generated one or more XR images.

According to some embodiments, the apparatus might comprise at least one of an XR computing system, a medical procedure computing system, a hub computing system, a 3D graphical processing unit, a cluster computing system, a 4D graphics computing system, a server computer, a cloud computing system, or a distributed computing system, and/or the like.

In still another aspect, a system is provided for presenting extended reality ("XR") experiences. The system might comprise one or more devices configured to perform one or more first tasks; one or more sensors configured to monitor at least one of biometric data, biological data, genetic data, cellular data, or procedure-related data of a subject; one or more imaging devices configured to generate images of at least one or more portions of the subject; a computing system; and a user experience ("UX") device.

The computing system might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the computing system to: receive one or more device data associated with each of the one or more devices; receive one or more sensor data associated with the one or more sensors; receive one or more imaging data associated with each of the one or more imaging devices; analyze the received one or more device data, the received one or more sensor data, and the received one or more imaging data; map two or more of the received one or more device data, the received one or more sensor data, or the received one or more imaging data to a three-dimensional ("3D") or a four-dimensional ("4D") representation of the at least one or more portions of the subject, based at least in part on the analysis; generate one or more extended reality ("XR") images, based at least in part on the mapping; and send the generated one or more XR images to the UX device.

The UX device might comprise at least one second processor and a second non-transitory computer readable medium communicatively coupled to the at least one second processor. The second non-transitory computer readable medium might have stored thereon computer software comprising a second set of instructions that, when executed by the at least one second processor, causes the UX device to: receive the generated one or more XR images; and present the received one or more XR images to a user.

In some embodiments, the computing system might comprise at least one of an XR computing system, a medical procedure computing system, a hub computing system, a 3D graphical processing unit, a cluster computing system, a 4D graphics computing system, a server computer, a cloud computing system, or a distributed computing system, and/or the like. In some cases, the one or more devices might comprise at least one of one or more catheters, one or more catheter interconnect or interface cables, one or more valves, one or more balloons, one or more leads, one or more pacemakers, one or more defibrillators, one or more neuromodulation devices, one or more neurostimulation devices, one or more rigid robotic devices, one or more soft robotic devices, one or more stents, one or more needles, one or more grafts, one or more occluders, one or more shunts, one or more orthopedic screws, one or more orthopedic plates, one or more orthopedic rods, one or more vertebral sponges, one or more therapeutic delivery devices, one or more implant delivery devices, one or more diagnostic devices, one or more diagnostic catheters, one or more implant devices, one or more surgical tools, one or more biologics, one or more drug pumps, one or more genes, one or more cells, one or more organs, one or more organelles, one or more delivery pharmaceuticals, one or more biopsy tools, one or more excision tools, one or more ablation tools, one or more monitoring devices, one or more cameras, one or more imaging tools, one or more fiducials, one or more staples, one or more anchors, one or more meshes, one or more vascular cannulae, one or more circulatory pumps, one or more valve repair devices, one or more embolic protection devices, one or more cardiomyoplasty tools, one or more vascular closure tools, one or more septal closure tools, one or more ventricular closure tools, one or more lasers, one or more plaque removal tools, one or more guide wires, one or more introducers, one or more sheaths, one or more pillcams, one or more clips, one or more capsules, one or more microbiomes, one or more microbes of bacterial vectors, one or more microbes of viral vectors, one or more microbes of prion vectors, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment, and/or the like.

According to some embodiments, the one or more sensors might comprise at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography (EOG) sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some embodiments, the one or more imaging devices might comprise at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

According to some embodiments, the one or more first tasks might comprise at least one of a surgical procedure, a left atrial appendage ("LAA") procedure, a tissue ablation procedure, a transcatheter aortic valve repair ("TAVr") procedure, a transcatheter aortic valve replacement ("TAVR") procedure, a transcatheter mitral valve repair ("TMVr") procedure, a transcatheter mitral valve replacement ("TMVR") procedure, a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, an implant procedure, a home care ventilation procedure, a lung cancer procedure, an aneurysm flow diversion procedure, a deep brain stimulation procedure, a shunt procedure, a bone grafting procedure, an insulin pump installation procedure, a continuous glucose monitoring system installation procedure, a colon disease procedure, a gastroparesis therapy, a hernia surgery, a bowel control therapy, a microwave ablation procedure, a reflux testing and treatment, a weight-loss surgery, a bone conduction hearing therapy, a sinus surgery, a thyroid surgery, a treatment for ear infections, a balloon angioplasty, a stenting procedure, an atrial septal defect ("ASD") treatment procedure, a cardiac shunt treatment procedure, a heart bypass surgery, a cardiac mapping procedure, a cardiac resynchronization therapy ("CRT") device installation procedure, a catheter ablation procedure, an endovascular repair procedure, a heart monitor installation procedure, an implantable cardioverter defibrillator ("ICD") device installation procedure, an extravascular ICD ("EV-ICD") device installation procedure, a minimally invasive endovascular repair procedure, a pacemaker installation procedure, a miniature leadless implant installation procedure, an implantable sensor installation procedure, a remote monitoring device installation procedure, a surgical heart valve repair and replacement procedure, a transcatheter pulmonary valve ("TPV") therapy, a varicose vein therapy, a ventricular assist device ("VAD") installation procedure, an intra-aortic balloon pump ("IABP") implantation procedure, a heart transplant operation, a back surgery, a bone tumor treatment, a drug pump installation procedure, a spinal cord stimulation procedure, a targeted drug delivery procedure, a balloon kyphoplasty procedure, a cervical disc replacement procedure, a cervical fusion procedure, a sacroiliac joint fusion procedure, a sacral neuromodulation procedure, or a percutaneous tibial neuromodulation procedure, and/or the like.

In some embodiments, the subject might comprise one of a human patient, a large animal, a small animal, an organ, an organelle, one or more organs on a chip, one or more tissue constructs, one or more cells, one or more microbes of bacterial vectors, one or more microbes of viral vectors, one or more microbes of prion vectors, one or more genes, deoxyribonucleic acid ("DNA"), ribonucleic acid ("RNA"), one or more hormones, one or more biochemicals, one or more molecules, one or more tissues, one or more blood vessels, or one or more bones, and/or the like.

According to some embodiments, the UX device might comprise at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

In some embodiments, at least one of the received one or more device data, the received one or more sensor data, and the received one or more imaging data might be real-time or near-real-time data that is received by the computing system in real-time or near-real-time.

In an aspect, a method is provided for presenting extended reality ("XR") experiences. The method might comprise receiving, with a computing system, one or more device data associated with each of one or more devices configured to perform a cardiac arrhythmia procedure to provide effective heart rhythm; receiving, with the computing system, one or more imaging data associated with each of one or more imaging devices configured to generate images of at least one or more portions of a patient; analyzing, with the computing system, the received one or more device data and the received one or more imaging data; and mapping, with the computing system, the received one or more device data and the received one or more imaging data to a three-dimensional ("3D") or a four-dimensional ("4D") representation of the at least one or more portions of the patient, based at least in part on the analysis. The method might further comprise generating, with the computing system, one or more extended reality ("XR") experiences, based at least in part on the mapping; and presenting, with the computing system and using a user experience ("UX") device, the generated one or more XR experiences.

In some embodiments, the computing system might comprise at least one of an XR computing system, a medical procedure computing system, a hub computing system, a 3D graphical processing unit, a cluster computing system, a 4D graphics computing system, a server computer, a cloud computing system, or a distributed computing system, and/or the like.

According to some embodiments, the one or more devices might comprise at least one of one or more catheters, one or more catheter interconnect or interface cables, one or more balloons, one or more leads, one or more pacemakers, one or more defibrillators, one or more neuromodulation devices, one or more neurostimulation devices, one or more rigid robotic devices, one or more soft robotic devices, one or more needles, one or more occluders, one or more diagnostic catheters, one or more surgical tools, one or more biologics, one or more drug pumps, one or more genes, one or more cells, one or more organs, one or more organelles, one or more delivery pharmaceuticals, one or more ablation tools, one or more monitoring devices, one or more cameras, one or more imaging tools, one or more fiducials, one or more vascular cannulae, one or more cardiomyoplasty tools, one or more vascular closure tools, one or more septal closure tools, one or more ventricular closure tools, one or more lasers, one or more guide wires, one or more introducers, one or more sheaths, one or more microbes of bacterial vectors, one or more microbes of viral vectors, one or more microbes of prion vectors, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment, and/or the like.

In some embodiments, the one or more imaging devices might comprise at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

Merely by way of example, in some cases, the cardiac arrhythmia procedure might comprise at least one of a surgical procedure, a left atrial appendage ("LAA") procedure, a tissue ablation procedure, an atrial fibrillation ("AF") procedure, a balloon angioplasty, a cardiac mapping procedure, a catheter ablation procedure, a heart monitor installation procedure, an implantable cardioverter defibrillator ("ICD") device installation procedure, an extravascular ICD ("EV-ICD") device installation procedure, a pacemaker installation procedure, a miniature leadless implant installation procedure, an implantable sensor installation procedure, a remote monitoring device installation procedure, a cryoballoon or cryoablation catheter procedure, a pulsed field ablation ("PFA") procedure, an electroporation procedure, a radio frequency ("RF") ablation procedure, a microwave ("MW") ablation procedure, a laser ablation procedure, a radiation ablation procedure, a microwave ablation procedure, or a high intensity focused ultrasound ("HIFU") procedure, and/or the like.

According to some embodiments, the patient might comprise one of a human patient, a large animal, or a small animal, and/or the like. In some cases, the one or more XR experiences might comprise at least one of one or more augmented reality ("AR") images, one or more AR videos, one or more virtual reality ("VR") images, one or more VR videos, one or more mixed reality ("MR") images, one or more MR videos, one or more XR images, or one or more XR videos, and/or the like. In some instances, generating the one or more XR experiences might comprise generating, with the computing system, one or more XR experiences comprising at least three or more of the one or more XR images, one or more XR sounds, one or more XR haptic or tactile responses, one or more XR simulated smells, or one or more XR simulated tastes, based at least in part on the mapping.

In some embodiments, the UX device might comprise at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

According to some embodiments, the method might further comprise receiving, with the computing system, one or more sensor data associated with one or more sensors configured to monitor at least one of biometric data, biological data, genetic data, cellular data, or procedure-related data of the patient; and analyzing, with the computing system, the received one or more sensor data. In such cases, mapping, with the computing system, the received one or more device data and the received one or more imaging data to a three-dimensional ("3D") or a four-dimensional ("4D") representation of the at least one or more portions of the patient might comprise mapping, with the computing system, two or more of the received one or more device data, the received one or more sensor data, or the received one or more imaging data to a three-dimensional ("3D") or a four-dimensional ("4D") representation of the at least one or more portions of the patient, based at least in part on the analysis.

In some cases, generating the one or more XR experiences comprise combining, with the computing system, the received one or more device data, the received one or more sensor data, and the received one or more imaging data into a combined 3D or 4D representation, based at least in part on the analysis and mapping; and generating, with the computing system, the one or more XR experiences based on the combined 3D or 4D representation. In some instances, the method might further comprise generating, with the computing system, one or more models that are used for analyzing or visualizing at least one of the received one or more device data, the received one or more sensor data, or the received one or more imaging data.

In some embodiments, the one or more sensors might comprise at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography (EOG) sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some instances, at least one of the received one or more device data, the received one or more sensor data, and the received one or more imaging data might be real-time or near-real-time data that is received by the computing system in real-time or near-real-time. In some cases, the generated one or more XR experiences might be presented to provide one or more of: a guide for a medical professional, a navigation tool during the cardiac arrhythmia procedure, a proximity detection tool during the cardiac arrhythmia procedure, a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient, and/or the like.

According to some embodiments, the method might further comprise tracking, with the computing system, the one or more devices, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In some embodiments, the method might further comprise receiving, with the computing system, one or more inputs from a user; analyzing, with the computing system, the one or more inputs from the user to determine whether the one or more inputs comprise at least one of one or more voice commands, one or more eye-tracking-based commands, one or more gesture-based commands, one or more touch-based commands, or one or more entered commands; and based on a determination that the one or more inputs comprise at least one of one or more voice commands, one or more eye-tracking-based commands, one or more gesture-based commands, or one or more entered commands, identifying, with the computing system, which at least one device among the one or more devices is intended to be controlled based on the one or more inputs, generating, with the computing system, one or more instructions for controlling the identified at least one device based at least in part on the one or more inputs, and sending, with the computing system, the generated one or more instructions to the identified at least one device.

In another aspect, an apparatus is provided for presenting extended reality ("XR") experiences. The apparatus might comprise at least one processor and a non-transitory computer readable medium communicatively coupled to the at least one processor. The non-transitory computer readable medium might have stored thereon computer software comprising a set of instructions that, when executed by the at least one processor, causes the apparatus to: receive one or more device data associated with each of one or more devices configured to perform a cardiac arrhythmia procedure to provide effective heart rhythm; receive one or more imaging data associated with each of one or more imaging devices configured to generate images of at least one or more portions of a patient; analyze the received one or more device data, the received one or more sensor data, and the received one or more imaging data; map the received one or more device data and the received one or more imaging data to a three-dimensional ("3D") or a four-dimensional ("4D") representation of the at least one or more portions of the patient, based at least in part on the analysis; generate one or more extended reality ("XR") experiences, based at least in part on the mapping; and present, using a user experience ("UX") device, the generated one or more XR experiences.

In yet another aspect, a system is provided for presenting extended reality ("XR") experiences. The system might comprise one or more devices configured to perform a cardiac arrhythmia procedure to provide effective heart rhythm, one or more imaging devices configured to generate images of at least one or more portions of a patient, a computing system, and a user experience ("UX") device. The computing system might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the computing system to: receive one or more device data associated with each of the one or more devices; receive one or more imaging data associated with each of the one or more imaging devices; analyze the received one or more device data and the received one or more imaging data; map the received one or more device data and the received one or more imaging data to a three-dimensional ("3D") or a four-dimensional ("4D") representation of the at least one or more portions of the patient, based at least in part on the analysis; generate one or more extended reality ("XR") experiences, based at least in part on the mapping; and send the generated one or more XR experiences to the UX device.

The UX device might comprise at least one second processor and a second non-transitory computer readable medium communicatively coupled to the at least one second processor. The second non-transitory computer readable medium might have stored thereon computer software comprising a second set of instructions that, when executed by the at least one second processor, causes the UX device to: receive the generated one or more XR experiences; and present the received one or more XR experiences to a user.

In some embodiments, the computing system might comprise at least one of an XR computing system, a medical procedure computing system, a hub computing system, a 3D graphical processing unit, a cluster computing system, a 4D graphics computing system, a server computer, a cloud computing system, or a distributed computing system, and/or the like.

In an aspect, a method is provided for presenting extended reality ("XR") experiences. The method might comprise receiving, with a computing system, one or more device data associated with each of one or more devices configured to perform a cardiac blood flow procedure to provide effective blood flow through a heart and to or from blood vessels of a patient; receiving, with the computing system, one or more imaging data associated with each of one or more imaging devices configured to generate images of at least one or more portions of the patient; analyzing, with the computing system, the received one or more device data and the received one or more imaging data; and mapping, with the computing system, the received one or more device data and the received one or more imaging data to a three-dimensional ("3D") or a four-dimensional ("4D") representation of the at least one or more portions of the patient, based at least in part on the analysis. The method might further comprise generating, with the computing system, one or more extended reality ("XR") experiences, based at least in part on the mapping; and presenting, with the computing system and using a user experience ("UX") device, the generated one or more XR experiences.

In some embodiments, the computing system might comprise at least one of an XR computing system, a medical procedure computing system, a hub computing system, a 3D graphical processing unit, a cluster computing system, a 4D graphics computing system, a server computer, a cloud computing system, or a distributed computing system, and/or the like.

According to some embodiments, the one or more devices might comprise at least one of one or more catheters, one or more catheter interconnect or interface cables, one or more valves, one or more balloons, one or more rigid robotic devices, one or more soft robotic devices, one or more stents, one or more needles, one or more occluders, one or more diagnostic catheters, one or more surgical tools, one or more monitoring devices, one or more cameras, one or more imaging tools, one or more fiducials, one or more staples, one or more anchors, one or more meshes, one or more vascular cannulae, one or more circulatory pumps, one or more valve repair devices, one or more embolic protection devices, one or more vascular closure tools, one or more septal closure tools, one or more ventricular closure tools, one or more lasers, one or more plaque removal tools, one or more guide wires, one or more introducers, one or more sheaths, one or more pillcams, one or more clips, one or more capsules, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment, and/or the like.

In some embodiments, the one or more imaging devices might comprise at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

Merely by way of example, in some cases, the cardiac blood flow procedure might comprise at least one of a surgical procedure, a left atrial appendage ("LAA") procedure, a transcatheter aortic valve repair ("TAVr") procedure, a transcatheter aortic valve replacement ("TAVR") procedure, a transcatheter mitral valve repair ("TMVr") procedure, a transcatheter mitral valve replacement ("TMVR") procedure, a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, a coronary angioplasty procedure, a stenting procedure, a heart bypass procedure, a cardiac mapping procedure, an endovascular repair procedure a minimally invasive endovascular repair procedure, a surgical heart valve repair and replacement procedure, a transcatheter pulmonary valve ("TPV") therapy, a ventricular assist device ("VAD") installation procedure, an intra-aortic balloon pump ("IABP") implantation procedure, or a heart transplant operation, and/or the like.

According to some embodiments, the patient might comprise one of a human patient, a large animal, or a small animal, and/or the like. In some cases, the one or more XR experiences might comprise at least one of one or more augmented reality ("AR") images, one or more AR videos, one or more virtual reality ("VR") images, one or more VR videos, one or more mixed reality ("MR") images, one or more MR videos, one or more XR images, or one or more XR videos, and/or the like. In some instances, generating the one or more XR experiences might comprise generating, with the computing system, one or more XR experiences comprising at least three or more of the one or more XR images, one or more XR sounds, one or more XR haptic or tactile responses, one or more XR simulated smells, or one or more XR simulated tastes, based at least in part on the mapping.

In some embodiments, the UX device might comprise at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

According to some embodiments, the method might further comprise receiving, with the computing system, one or more sensor data associated with one or more sensors configured to monitor at least one of biometric data, biological data, genetic data, cellular data, or procedure-related data of the patient; and analyzing, with the computing system, the received one or more sensor data. In such cases, mapping, with the computing system, the received one or more device data and the received one or more imaging data to a three-dimensional ("3D") or a four-dimensional ("4D") representation of the at least one or more portions of the patient might comprise mapping, with the computing system, two or more of the received one or more device data, the received one or more sensor data, or the received one or more imaging data to a three-dimensional ("3D") or a four-dimensional ("4D") representation of the at least one or more portions of the patient, based at least in part on the analysis.

In some cases, generating the one or more XR experiences comprise combining, with the computing system, the received one or more device data, the received one or more sensor data, and the received one or more imaging data into a combined 3D or 4D representation, based at least in part on the analysis and mapping; and generating, with the computing system, the one or more XR experiences based on the combined 3D or 4D representation. In some instances, the method might further comprise generating, with the computing system, one or more models that are used for analyzing or visualizing at least one of the received one or more device data, the received one or more sensor data, or the received one or more imaging data.

In some embodiments, the one or more sensors might comprise at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography (EOG) sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some instances, at least one of the received one or more device data, the received one or more sensor data, and the received one or more imaging data might be real-time or near-real-time data that is received by the computing system in real-time or near-real-time. In some cases, the generated one or more XR experiences might be presented to provide one or more of: a guide for a medical professional, a navigation tool during the cardiac blood flow procedure, a proximity detection tool during the cardiac blood flow procedure, a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient, and/or the like.

According to some embodiments, the method might further comprise tracking, with the computing system, the one or more devices, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In some embodiments, the method might further comprise receiving, with the computing system, one or more inputs from a user; analyzing, with the computing system, the one or more inputs from the user to determine whether the one or more inputs comprise at least one of one or more voice commands, one or more eye-tracking-based commands, one or more gesture-based commands, one or more touch-based commands, or one or more entered commands; and based on a determination that the one or more inputs comprise at least one of one or more voice commands, one or more eye-tracking-based commands, one or more gesture-based commands, or one or more entered commands, identifying, with the computing system, which at least one device among the one or more devices is intended to be controlled based on the one or more inputs, generating, with the computing system, one or more instructions for controlling the identified at least one device based at least in part on the one or more inputs, and sending, with the computing system, the generated one or more instructions to the identified at least one device.

In another aspect, an apparatus is provided for presenting extended reality ("XR") experiences. The apparatus might comprise at least one processor and a non-transitory computer readable medium communicatively coupled to the at least one processor. The non-transitory computer readable medium might have stored thereon computer software comprising a set of instructions that, when executed by the at least one processor, causes the apparatus to: receive one or more device data associated with each of one or more devices configured to perform a cardiac blood flow procedure to provide effective blood flow through a heart and to or from blood vessels of a patient; receive one or more imaging data associated with each of one or more imaging devices configured to generate images of at least one or more portions of the patient; analyze the received one or more device data, the received one or more sensor data, and the received one or more imaging data; map the received one or more device data and the received one or more imaging data to a three-dimensional ("3D") or a four-dimensional ("4D") representation of the at least one or more portions of the patient, based at least in part on the analysis; generate one or more extended reality ("XR") experiences, based at least in part on the mapping; and present, using a user experience ("UX") device, the generated one or more XR experiences.

In yet another aspect, a system is provided for presenting extended reality ("XR") experiences. The system might comprise one or more devices configured to perform a cardiac blood flow procedure to provide effective blood flow through a heart and to or from blood vessels of a patient, one or more imaging devices configured to generate images of at least one or more portions of the patient, a computing system, and a user experience ("UX") device. The computing system might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the computing system to: receive one or more device data associated with each of the one or more devices; receive one or more imaging data associated with each of the one or more imaging devices; analyze the received one or more device data and the received one or more imaging data; map the received one or more device data and the received one or more imaging data to a three-dimensional ("3D") or a four-dimensional ("4D") representation of the at least one or more portions of the patient, based at least in part on the analysis; generate one or more extended reality ("XR") experiences, based at least in part on the mapping; and send the generated one or more XR experiences to the UX device.

The UX device might comprise at least one second processor and a second non-transitory computer readable medium communicatively coupled to the at least one second processor. The second non-transitory computer readable medium might have stored thereon computer software comprising a second set of instructions that, when executed by the at least one second processor, causes the UX device to: receive the generated one or more XR experiences; and present the received one or more XR experiences to a user.

In some embodiments, the computing system might comprise at least one of an XR computing system, a medical procedure computing system, a hub computing system, a 3D graphical processing unit, a cluster computing system, a 4D graphics computing system, a server computer, a cloud computing system, or a distributed computing system, and/or the like.

In an aspect, a method is provided for presenting extended reality ("XR") experiences. The method might comprise receiving, with a computing system, one or more device data associated with each of one or more devices configured to perform a cardiac shunting procedure to change a cardiac blood flow pattern to improve cardiac blood flow efficiency or cardiac pumping efficiency; receiving, with the computing system, one or more imaging data associated with each of one or more imaging devices configured to generate images of at least one or more portions of a patient; analyzing, with the computing system, the received one or more device data and the received one or more imaging data; and mapping, with the computing system, the received one or more device data and the received one or more imaging data to a three-dimensional ("3D") or a four-dimensional ("4D") representation of the at least one or more portions of the patient, based at least in part on the analysis. The method might further comprise generating, with the computing system, one or more extended reality ("XR") experiences, based at least in part on the mapping; and presenting, with the computing system and using a user experience ("UX") device, the generated one or more XR experiences.

In some embodiments, the computing system might comprise at least one of an XR computing system, a medical procedure computing system, a hub computing system, a 3D graphical processing unit, a cluster computing system, a 4D graphics computing system, a server computer, a cloud computing system, or a distributed computing system, and/or the like.

According to some embodiments, the one or more devices might comprise at least one of one or more catheters, one or more catheter interconnect or interface cables, one or more valves, one or more balloons, one or more leads, one or more pacemakers, one or more defibrillators, one or more neuromodulation devices, one or more neurostimulation devices, one or more rigid robotic devices, one or more soft robotic devices, one or more stents, one or more needles, one or more occluders, one or more shunts, one or more diagnostic catheters, one or more surgical tools, one or more ablation tools, one or more monitoring devices, one or more cameras, one or more imaging tools, one or more fiducials, one or more staples, one or more anchors, one or more meshes, one or more vascular cannulae, one or more circulatory pumps, one or more valve repair devices, one or more embolic protection devices, one or more cardiomyoplasty tools, one or more vascular closure tools, one or more septal closure tools, one or more ventricular closure tools, one or more lasers, one or more plaque removal tools, one or more guide wires, one or more introducers, one or more sheaths, one or more clips, one or more capsules, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment.

In some embodiments, the one or more imaging devices might comprise at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

Merely by way of example, in some cases, the cardiac shunting procedure might comprise at least one of a surgical procedure, a left atrial appendage ("LAA") procedure, a tissue ablation procedure, a transcatheter aortic valve repair ("TAVr") procedure, a transcatheter aortic valve replacement ("TAVR") procedure, a transcatheter mitral valve repair ("TMVr") procedure, a transcatheter mitral valve replacement ("TMVR") procedure, a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, a shunt procedure, a coronary angioplasty procedure, a balloon angioplasty, a stenting procedure, an atrial septal defect ("ASD") treatment procedure, a cardiac shunt treatment procedure, a heart bypass procedure, a cardiac mapping procedure, a cardiac resynchronization therapy ("CRT") device installation procedure, a catheter ablation procedure, an endovascular repair procedure, a heart monitor installation procedure, an implantable cardioverter defibrillator ("ICD") device installation procedure, an extravascular ICD ("EV-ICD") device installation procedure, a minimally invasive endovascular repair procedure, a miniature leadless implant installation procedure, an implantable sensor installation procedure, a surgical heart valve repair and replacement procedure, a transcatheter pulmonary valve ("TPV") therapy, a ventricular assist device ("VAD") installation procedure, an intra-aortic balloon pump ("IABP") implantation procedure, a heart transplant operation, a cryoballoon or cryoablation catheter procedure, a pulsed field ablation ("PFA") procedure, an electroporation procedure, a radio frequency ("RF") ablation procedure, a microwave ("MW") ablation procedure, a laser ablation procedure, a radiation ablation procedure, a microwave ablation procedure, or a high intensity focused ultrasound ("HIFU") procedure, and/or the like.

According to some embodiments, the patient might comprise one of a human patient, a large animal, or a small animal, and/or the like. In some cases, the one or more XR experiences might comprise at least one of one or more augmented reality ("AR") images, one or more AR videos, one or more virtual reality ("VR") images, one or more VR videos, one or more mixed reality ("MR") images, one or more MR videos, one or more XR images, or one or more XR videos, and/or the like. In some instances, generating the one or more XR experiences might comprise generating, with the computing system, one or more XR experiences comprising at least three or more of the one or more XR images, one or more XR sounds, one or more XR haptic or tactile responses, one or more XR simulated smells, or one or more XR simulated tastes, based at least in part on the mapping.

In some embodiments, the UX device might comprise at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

According to some embodiments, the method might further comprise receiving, with the computing system, one or more sensor data associated with one or more sensors configured to monitor at least one of biometric data, biological data, genetic data, cellular data, or procedure-related data of the patient; and analyzing, with the computing system, the received one or more sensor data. In such cases, mapping, with the computing system, the received one or more device data and the received one or more imaging data to a three-dimensional ("3D") or a four-dimensional ("4D") representation of the at least one or more portions of the patient might comprise mapping, with the computing system, two or more of the received one or more device data, the received one or more sensor data, or the received one or more imaging data to a three-dimensional ("3D") or a four-dimensional ("4D") representation of the at least one or more portions of the patient, based at least in part on the analysis.

In some cases, generating the one or more XR experiences comprise combining, with the computing system, the received one or more device data, the received one or more sensor data, and the received one or more imaging data into a combined 3D or 4D representation, based at least in part on the analysis and mapping; and generating, with the computing system, the one or more XR experiences based on the combined 3D or 4D representation. In some instances, the method might further comprise generating, with the computing system, one or more models that are used for analyzing or visualizing at least one of the received one or more device data, the received one or more sensor data, or the received one or more imaging data.

In some embodiments, the one or more sensors might comprise at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography (EOG) sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some instances, at least one of the received one or more device data, the received one or more sensor data, and the received one or more imaging data might be real-time or near-real-time data that is received by the computing system in real-time or near-real-time. In some cases, the generated one or more XR experiences might be presented to provide one or more of: a guide for a medical professional, a navigation tool during the cardiac shunting procedure, a proximity detection tool during the cardiac shunting procedure, a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient, and/or the like.

According to some embodiments, the method might further comprise tracking, with the computing system, the one or more devices, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In some embodiments, the method might further comprise receiving, with the computing system, one or more inputs from a user; analyzing, with the computing system, the one or more inputs from the user to determine whether the one or more inputs comprise at least one of one or more voice commands, one or more eye-tracking-based commands, one or more gesture-based commands, one or more touch-based commands, or one or more entered commands; and based on a determination that the one or more inputs comprise at least one of one or more voice commands, one or more eye-tracking-based commands, one or more gesture-based commands, or one or more entered commands, identifying, with the computing system, which at least one device among the one or more devices is intended to be controlled based on the one or more inputs, generating, with the computing system, one or more instructions for controlling the identified at least one device based at least in part on the one or more inputs, and sending, with the computing system, the generated one or more instructions to the identified at least one device.

In another aspect, an apparatus is provided for presenting extended reality ("XR") experiences. The apparatus might comprise at least one processor and a non-transitory computer readable medium communicatively coupled to the at least one processor. The non-transitory computer readable medium might have stored thereon computer software comprising a set of instructions that, when executed by the at least one processor, causes the apparatus to: receive one or more device data associated with each of one or more devices configured to perform a cardiac shunting procedure to change a cardiac blood flow pattern to improve cardiac blood flow efficiency or cardiac pumping efficiency; receive one or more imaging data associated with each of one or more imaging devices configured to generate images of at least one or more portions of a patient; analyze the received one or more device data, the received one or more sensor data, and the received one or more imaging data; map the received one or more device data and the received one or more imaging data to a three-dimensional ("3D") or a four-dimensional ("4D") representation of the at least one or more portions of the patient, based at least in part on the analysis; generate one or more extended reality ("XR") experiences, based at least in part on the mapping; and present, using a user experience ("UX") device, the generated one or more XR experiences.

In yet another aspect, a system is provided for presenting extended reality ("XR") experiences. The system might comprise one or more devices configured to perform a cardiac shunting procedure to change a cardiac blood flow pattern to improve cardiac blood flow efficiency or cardiac pumping efficiency, one or more imaging devices configured to generate images of at least one or more portions of a patient, a computing system, and a user experience ("UX") device. The computing system might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the computing system to:

receive one or more device data associated with each of the one or more devices; receive one or more imaging data associated with each of the one or more imaging devices; analyze the received one or more device data and the received one or more imaging data; map the received one or more device data and the received one or more imaging data to a three-dimensional ("3D") or a four-dimensional ("4D") representation of the at least one or more portions of the patient, based at least in part on the analysis; generate one or more extended reality ("XR") experiences, based at least in part on the mapping; and send the generated one or more XR experiences to the UX device.

The UX device might comprise at least one second processor and a second non-transitory computer readable medium communicatively coupled to the at least one second processor. The second non-transitory computer readable medium might have stored thereon computer software comprising a second set of instructions that, when executed by the at least one second processor, causes the UX device to: receive the generated one or more XR experiences; and present the received one or more XR experiences to a user.

In some embodiments, the computing system might comprise at least one of an XR computing system, a medical procedure computing system, a hub computing system, a 3D graphical processing unit, a cluster computing system, a 4D graphics computing system, a server computer, a cloud computing system, or a distributed computing system, and/or the like.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Specific Exemplary Embodiments

We now turn to the embodiments as illustrated by the drawings. FIGS. 1-19 illustrate some of the features of the method, system, and apparatus for implementing medical assistance technologies, and, more particularly, to methods, systems, and apparatuses for implementing intelligent assistance ("IA") ecosystem, as referred to above. The methods, systems, and apparatuses illustrated by FIGS. 1-19 refer to examples of different embodiments that include various components and steps, which can be considered alternatives or which can be used in conjunction with one another in the various embodiments. The description of the illustrated methods, systems, and apparatuses shown in FIGS. 1-19 is provided for purposes of illustration and should not be considered to limit the scope of the different embodiments.

With reference to the figures, FIG. 1 is a schematic diagram illustrating a system 100 for implementing intelligent assistance ("IA") ecosystem, in accordance with various embodiments.

In the non-limiting embodiment of FIG. 1, system 100 might comprise a system hub or computing system 105a and corresponding database(s) 110a. In some cases, the database(s) 110a may be local to the system hub or computing system 105a. In some cases, the database(s) 110a may be external, yet communicatively coupled to the system hub or computing system 105a. In other cases, the database(s) 110a may be local integrated within the system hub or computing system 105a. System 100, according to some embodiments, might further comprise mapping and navigation system 115a and corresponding database(s) 120a. Like database(s) 110a, the database(s) 120a may be local to the mapping and navigation system 115a. In some cases, the database(s) 120a may be external, yet communicatively coupled to the mapping and navigation system 115a. In other cases, the database(s) 120a may be local integrated within the mapping and navigation system 115a. System 100, according to some embodiments, might further comprise mapping and navigation system 115a and corresponding database(s) 120a.

System 100 might include, without limitation, at least one of one or more healthcare professionals 125, a subject 130, one or more devices or equipment 135, one or more imaging systems 140, one or more sensors 145, an extended reality ("XR") platform or system 150, a user experience ("UX") device 155, a data analytics or artificial intelligence ("AI") system 160a, or an anatomy or tool registration system 165, and/or the like. In some instances, the system hub or computing system 105a and corresponding database(s) 110a, the mapping and navigation system 115a and corresponding database(s) 120a, and the at least one of the one or more healthcare professionals 125, the subject 130, the one or more devices or equipment 135, the one or more imaging systems 140, the one or more sensors 145, the XR platform or system 150, the UX device 155, the data analytics or AI system 160a, or the anatomy or tool registration system 165, and/or the like, may be located or disposed within clinical environment 170. In some cases, the clinical environment 170 might include, but is not limited to, a clinic, a hospital, an operating room, an emergency room, a physician's office, or a laboratory, or the like.

In some embodiments, the system hub or computing system 105a might include, without limitation, at least one of an XR computing system, a medical procedure computing system, a hub computing system, a three-dimensional ("3D") graphical processing unit, a cluster computing system, a four-dimensional ("4D") graphics computing system, a server computer, a cloud computing system, or a distributed computing system, and/or the like. In some instances, the one or more healthcare professionals 125 might include, without limitation, at least one of one or more doctors, one or more surgeons, one or more cardiologists, one or more electrophysiologists, one or more cardiac surgeons, one or more neurosurgeons, one or more radiologists, one or more scenographers, one or more nurse practitioners, one or more nurses, one or more medical specialists, one or more medical imaging specialists, and/or the like. In some cases, the subject 130 might include, but is not limited to, one of a human patient; a large animal (e.g., pig, sheep, dog, etc.); a small animal (e.g., rabbit, rat, mouse, etc.); an organ (e.g., explant, transplant, decellularized, deceased, generated, synthetic, etc.); an organelle; one or more organs on a chip; one or more tissue constructs; one or more cells; one or more microbes of bacterial vectors; one or more microbes of viral vectors; one or more microbes of prion vectors; one or more genes, deoxyribonucleic acid ("DNA"), ribonucleic acid ("RNA"); one or more hormones, one or more biochemicals, one or more molecules; one or more tissues, one or more blood vessels, or one or more bones; and/or the like.

According to some embodiments, the one or more devices or equipment 135—which might include surgical tool(s) 135a, implantable device(s) 135, or the like—might include, but is not limited, at least one of one or more catheters, one or more catheter interconnect or interface cables, one or more valves, one or more balloons, one or more leads, one or more pacemakers, one or more defibrillators, one or more neuromodulation devices, one or more neurostimulation devices, one or more rigid robotic devices, one or more soft robotic devices, one or more stents, one or more needles, one or more grafts, one or more occluders, one or more shunts, one or more orthopedic screws, one or more orthopedic plates, one or more orthopedic rods, one or more vertebral sponges, one or more therapeutic delivery devices, one or more implant delivery devices, one or more diagnostic devices, one or more diagnostic catheters, one or more implant devices, one or more surgical tools, one or more biologics, one or more drug pumps, one or more genes, one or more cells, one or more organs, one or more organelles, one or more delivery pharmaceuticals, one or more biopsy tools, one or more excision tools, one or more ablation tools, one or more monitoring devices, one or more cameras, one or more imaging tools, one or more fiducials, one or more staples, one or more anchors, one or more meshes, one or more vascular cannulae, one or more circulatory pumps, one or more valve repair devices, one or more embolic protection devices, one or more cardiomyoplasty tools, one or more vascular closure tools, one or more septal closure tools, one or more ventricular closure tools, one or more lasers, one or more plaque removal tools, one or more guide wires, one or more introducers, one or more sheaths, one or more pillcams, one or more clips, one or more capsules, one or more microbiomes, one or more microbes of bacterial vectors, one or more microbes of viral vectors, one or more microbes of prion vectors, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors (e.g., implantable pulmonary artery sensor(s), or the like), or one or more capital equipment, and/or the like. The one or more devices or equipment 135 might be configured to perform one or more tasks.

In some embodiments, the one or more tasks might include, without limitation, at least one of a surgical procedure, a left atrial appendage ("LAA") procedure, a tissue ablation procedure, a transcatheter aortic valve repair ("TAVr") procedure, a transcatheter aortic valve replacement ("TAVR") procedure (e.g., with the Evolut™ PRO+TAVR system, or the like), a transcatheter mitral valve repair ("TMVr") procedure, a transcatheter mitral valve replacement ("TMVR") procedure (e.g., with the Intrepid™ TMVR system, or the like), a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, an implant procedure, a home care ventilation procedure, a lung cancer procedure, an aneurysm flow diversion procedure, a deep brain stimulation procedure, a shunt procedure, a bone grafting procedure, an insulin pump installation procedure, a continuous glucose monitoring system installation procedure, a colon disease procedure, a gastroparesis therapy, a hernia surgery, a bowel control therapy, a microwave ablation procedure, a reflux testing and treatment, a weight-loss surgery, a bone conduction hearing therapy, a sinus surgery, a thyroid surgery, a treatment for ear infections, a balloon angioplasty, a stenting procedure, an atrial septal defect ("ASD") treatment procedure, a cardiac shunt treatment procedure, a heart bypass surgery, a cardiac mapping procedure, a cardiac resynchronization therapy ("CRT") device installation procedure, a catheter ablation procedure, an endovascular repair procedure, a heart monitor installation procedure, an implantable cardioverter defibrillator ("ICD") device installation procedure, an extravascular ICD ("EV-ICD") device installation procedure, a minimally invasive endovascular repair procedure, a pacemaker installation procedure, a miniature leadless implant installation procedure, an implantable sensor installation procedure, a remote monitoring device installation procedure, a surgical heart valve repair and replacement procedure, a transcatheter pulmonary valve ("TPV") therapy (e.g., Melody™ TPV therapy, Harmony™ TPV therapy, or the like), a varicose vein therapy, a ventricular assist device ("VAD") installation procedure, an intra-aortic balloon pump ("IABP") implantation procedure, a heart transplant operation, a back surgery, a bone tumor treatment, a drug pump installation procedure, a spinal cord stimulation procedure, a targeted drug delivery procedure, a balloon kyphoplasty procedure, a cervical disc replacement procedure, a cervical fusion procedure, a sacroiliac joint fusion procedure, a sacral neuromodulation procedure, or a percutaneous tibial neuromodulation procedure, and/or the like.

According to some embodiments, the one or more imaging devices or systems 140 might include, but are not limited to, at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

In some embodiments, the one or more sensors 145 might include, without limitation, at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography (EOG) sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

According to some embodiments, the XR platform or system 150 might include, without limitation, at least one of an XR headset, a set of XR goggles, a pair of XR-enabled eyewear, an XR-enabled smartphone mounted in a headset, an XR helmet, a mixed reality ("MR") headset, a set of MR goggles, a pair of MR-enabled eyewear, an MR-enabled smartphone mounted in a headset, an MR helmet, a virtual reality ("VR") headset, a set of VR goggles, a pair of VR-enabled eyewear, a VR-enabled smartphone mounted in a headset, a VR helmet, an augmented reality ("AR") headset, a set of AR goggles, a pair of AR-enabled eyewear, an AR-enabled smartphone mounted in a headset, or an AR helmet, and/or the like. Herein, VR might refer to a simulated experience that uses fully virtual constructs generated by a computing system or the like, while AR might refer to an interactive experience of a real-world environment where objects in the real-world are enhanced or augmented by computer-generated perceptual information (in some cases, including visual, auditory, haptic, somatosensory, and/or olfactory information). MR might refer to a merging of the real and virtual worlds to produce new environments and visualizations in which physical and virtual objects co-exist and interact in real-time (in some cases, MR might include AR plus physical interaction and information from the environment that goes beyond just visual aspects, or the like). XR might refer to real and virtual combined environments and human-machine interactions generated by a computing system or the like, and includes AR, MR, and/or VR.

In some instances, the XR platform or system 150 might generate one or more XR experiences including, but not limited to, at least three or more of the one or more XR images, one or more XR sounds, one or more XR haptic or tactile responses, one or more XR simulated smells, or one or more XR simulated tastes, and/or the like, in some cases, based at least in part on the mapping performed by the mapping and navigation system 115a. In some instances, the mapping and navigation system 115a might include, but is not limited to, at least one of an electroanatomic mapping ("EAM") system, an electromagnetic ("EM") mapping and/or navigation system, a radiofrequency identification ("RFID") mapping and/or navigation system, an impedance-based mapping and/or navigation system, an ultrasound ("US") mapping and/or navigation system, an optical mapping and/or navigation system, a high-density mapping catheter (e.g., Achieve™ mapping catheter, Achieve Advance™ mapping catheter, Marinr™ CS mapping catheter, Marinr™ MC mapping catheter, Marinr™ MCXL mapping catheter, Marinr™ SC mapping catheter, StableMapr™ mapping catheter, or the like), one or more patient patches, or navigation hardware and software, and/or the like.

In some embodiments, the UX device 155 might include, without limitation, at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

Merely by way of example, in some cases, alternative or additional to the system hub or computing system 105a and corresponding database 110a, the mapping and navigation system 115a and corresponding database 120a, and/or data analytics or AI system 160a being disposed within clinical environment 170, system 100 might comprise remote system hub or computing system 105b and corresponding database(s) 110b, remote mapping and navigation system 115*b* and corresponding database(s) 120*b*, and/or data analytics or AI system 160*b* that communicatively couple with the system hub or computing system 105*a* (or communications system (not shown)) disposed within the clinical environment 170 via one or more networks 175. According to some embodiments, system 100 might further comprise (optional) cloud storage 180, which communicatively couples with the system hub or computing system 105*a* via the one or more networks 175. Merely by way of example, network(s) 175 might each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, network(s) 175 might each include an access network of an Internet service provider ("ISP"). In another embodiment, network(s) 175 might each include a core network of the ISP, and/or the Internet.

According to some embodiments, one or more catheter interconnect or interface cables may be used. In some instances, the one or more catheter interconnect or interface cables might include a chip or memory device that is used to store, collect, and transfer data for the XR database. The chip or memory device may also be used to authenticate the device (e.g., as being compatible with the system or as being procedure-qualified, or the like), and may include security features that, when enabled, prevents information from being read or written. For single use devices, this chip or memory device can limit the number of uses to 1. In this manner, the catheter interconnect or interface cables may be used to meet certain business and/or healthcare conditions: (1) to restrict to single use of a device; (2) to authenticate the device as a real, approved device; (3) to secure the data stored on the device for access by only authorized users; and/or the like. In addition, the catheter interconnect or interface cables may also be used to achieve future additional business and/or healthcare conditions, including, but not limited to: (4) storing, collecting, and/or transferring data for XR applications; and/or the like. To incorporate a chip or memory device into a catheter, the chip or memory device might be mounted on a printed circuit board ("PCB"), which could include other hardware to enable features including, but not limited to: device or procedure sensing (e.g., temperature, orientation, acceleration, position, pressure, humidity, audio record, etc.); wireless communication (e.g., Bluetooth™, network, RFID, etc.); manufacturing and/or device history data storage and transfer to XR information database; and/or the like.

In operation, system hub or computing system 105*a* or 105*b* (collectively, "computing system" or the like) might receive one or more device data associated with each of one or more devices configured to perform one or more first tasks (in some cases, to perform one or more medical procedures, or the like). Herein, the one or more medical procedures might include, without limitation, at least one of one or more medical tasks, one or more surgical operations, or one or more procedures (which are less intrusive than surgical operations), and/or the like, performed by a medical professional. The computing system might receive one or more sensor data associated with one or more sensors configured to monitor at least one of biometric data, biological data, genetic data, cellular data, or procedure-related data of a subject (or patient), and might receive one or more imaging data associated with each of one or more imaging devices configured to generate images of at least one or more portions of the subject (or patient). The computing system might analyze the received one or more device data, the received one or more sensor data, and the received one or more imaging data, and might map two or more of the received one or more device data, the received one or more sensor data, or the received one or more imaging data to a 3D or a 4D representation (i.e., a 3D representation plus at least one of real-time updates, dynamic modeling, or data streaming, and/or the like) of the at least one or more portions of the subject (or patient), based at least in part on the analysis. The computing system might then generate one or more XR images (or one or more XR experiences), based at least in part on the mapping, and might present the generated one or more XR images (or one or more XR experiences) using a UX device 155. According to some embodiments, the one or more XR images might be dynamic images, which might include an overlay of data models depicting at least one of electrical pulses, blood flow, tissue movement, damage, stress, and/or the like, and thus may not be a still frame in 3D.

In some embodiments, the one or more XR images might include, without limitation, at least one of one or more AR images, one or more AR videos, one or more VR images, one or more VR videos, one or more MR images, one or more MR videos, one or more XR images, or one or more XR videos, and/or the like. In some instances, at least one of the received one or more device data, the received one or more sensor data, and the received one or more imaging data might be real-time or near-real-time data that is received by the computing system in real-time or near-real-time.

According to some embodiments, the generated one or more XR images might be presented to provide one or more of: a guide for a medical professional (e.g., healthcare professional(s) 125, or the like), a navigation tool during a medical procedure, a proximity detection tool during a medical procedure, a 3D or 4D visualization view of the at least one or more portions of the subject, a heads-up display of the one or more device data, a heads-up display of biological data of the subject, a heads-up display of chemical data of the subject, a heads-up display of physiological data of the subject, or a heads-up display of procedure-related data of the subject, and/or the like. In some instances, generating the one or more XR images might comprise combining, with the computing system, the received one or more device data, the received one or more sensor data, and the received one or more imaging data into a combined 3D or 4D representation, based at least in part on the analysis and mapping; and generating, with the computing system, the one or more XR images based on the combined 3D or 4D representation.

In some embodiments, the computing system might track the one or more devices (e.g., devices or equipment 135, or the like), in some cases, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

According to some embodiments, the computing system might generate one or more models that are used for analyzing or visualizing at least one of the received one or more device data, the received one or more sensor data, and the received one or more imaging data, and/or the like.

Alternatively, or additionally, the computing system might receive one or more inputs from a user; and might analyze the one or more inputs from the user to determine whether the one or more inputs comprise at least one of one or more voice commands, one or more eye-tracking-based commands, one or more gesture-based commands, one or more touch-based commands, or one or more entered commands, and/or the like. Based on a determination that the one or more inputs comprise at least one of one or more voice commands, one or more eye-tracking-based commands, one or more gesture-based commands, or one or more entered commands, the computing system might identify which at least one device among the one or more devices is intended to be controlled based on the one or more inputs, might generate one or more instructions for controlling the identified at least one device based at least in part on the one or more inputs, and might send the generated one or more instructions to the identified at least one device.

In some embodiments, the computing system might generate one or more XR experiences including, but not limited to, at least three or more of the one or more XR images, one or more XR sounds, one or more XR haptic or tactile responses, one or more XR simulated smells, or one or more XR simulated tastes, and/or the like, based at least in part on the mapping. According to some embodiments, the one or more XR images might be dynamic images, which might include an overlay of data models depicting at least one of electrical pulses, blood flow, tissue movement, damage, stress, and/or the like, and thus may not be a still frame in 3D. The computing system might then present the generated one or more XR experiences using the UX device.

In some aspects, the IA ecosystem, which is a combination of components (as represented, e.g., by components in system 100 of FIG. 1 for example) and the interactions of these components to analyze various different types of data associated with the patient (e.g., physical human or animal patient, simulated human or animal patient, etc.) or subject (e.g., organs, tissue, cells, microbes, etc.) and data associated with devices used for implementing therapy to map such combination of data to a 3D or 4D representation of the portions of the patient or the subject and to present such mapped data to the healthcare professional as generated XR experiences to aid in delivery of therapy to the patient or the subject, might achieve one or more of the following features or functionalities: (1) fast visualization to shorten procedure time; (2) less recurrence for optimal patient outcomes; (3) lower healthcare utilization costs and lower capital equipment costs; (4) flexibility; and/or (5) fluoroless implementation; or the like. To achieve fast visualization, the IA ecosystem might implement one or more of the following: identify targets in seconds or minutes, maintain occlusion and contact, and/or titrate dosage to reduce number of ablations (thus shortening procedure time), or the like. To achieve less recurrence, the IA ecosystem might implement one or more of the following: utilize powerful predictive analytics in comparison with existing visualization systems, visualize and personalize to patient-specific anatomy, implement multiple checkpoints during each procedure to ensure best patient outcomes, and/or collect occlusion assessment and lesion tagging data, or the like. To achieve lower costs, the IA ecosystem might implement one or more of the following: avoid using expensive capital equipment (e.g., using handheld and/or portable devices instead of million-dollar mapping/navigation systems, etc.) and/or utilizing MR or XR, which is more than 70% less costly than existing mapping and visualization systems used in arrhythmia treatment or the like. In this manner, throughput for the healthcare facility may be achieved, while incurring fewer adverse events and re-admittances, with better efficacy thus lowering number of recurrences (if any) and halting progression into other disease states, or the like. To achieve flexibility, the IA ecosystem might implement one or more of the following: utilize an open system that uses MR or XR with any energy source and/or implement remote sales operation (to achieve geographic flexibility in hard-to-reach locations), or the like. To achieve fluoroless implementation, the IA ecosystem might implement one or more of the following: avoid radiation exposure and/or achieve high resolution imaging of internal cardiac structures without exposing patients to radiation, or the like. According to some embodiments, to reduce use of fluoro, the IA ecosystem might be used in a smarter and faster implementation, thus reducing fluoro use. Although fluoro may be (and has been) used to map and register or merge imaging modalities, with the protective lead being removed to perform the rest of the procedure in XR, the IA ecosystem may also use other imaging modalities (including, without limitation, ultrasound, or the like, as described herein), by democratizing the skills to run these other imaging modalities, and to tag the anatomy and devices for tracking through the image(s).

Alternatively, or additionally, the IA ecosystem, as represented by FIG. 1 for example, may achieve one or more of the following features or functionalities: (6) improved therapy delivery accuracy for intended targets for better efficacy; (7) reduction in adjacent structure damage; (8) reduced cognitive load for the healthcare professional; (9) reduced exposure to radiation for the patient and/or healthcare professional; (10) simulated patient dye for target organs or tissue; (11) reduction in the number of people needed due to increased control by the user or operator; (12) improved telementoring; (13) improved telemedicine; and/or (14) enables social distancing or total separation (to address pandemic-related issues, such as COVID-19 issues, or the like). In some embodiments, the IA ecosystem, as represented by FIG. 1 for example, may be intended to put the right data in the right place at the right time, thus simplifying the procedure for a person/robot delivering the therapy. For example, the IA ecosystem may reduce the cognitive overload on the user (i.e., healthcare professional, etc.) by focusing on conveying enhanced pertinent information to make optimal decisions at the point of delivery. In this manner, the IA ecosystem is fast, accurate, predictive, and provides rich visualization imbedded with decision-making data including, but not limited to, distances, trajectories, boundaries of adjacent sensitive anatomy, etc.

To implement the IA ecosystem, once the anatomy can be visualized and the location of therapy delivery can be navigated to, the choice of device(s) and how to control the device(s) is the next building block. It may be a robotic system like the Hugo/Einstein for soft tissues (Mazor for bone), catheters, delivery systems, surgical tools, etc., such as described above with respect to the one or more devices or equipment 135, or the like. In order for a physician or healthcare professional (such as healthcare professionals 125, or the like) to have real time actionable data, sensors (such as sensors 145, or the like) need to be employed in the system on the patient (e.g., subject 130, or the like), provider, tools, and equipment (e.g., devices or equipment 135, or the like). For example, the visualization tool such as XR hardware (including, but not limited to, Microsoft HoloLens®, or the like) might have several cameras and sensors (not only for visualization) to measure key biometrics in a non-contact manner. In some instances, the visualization tool such as XR hardware may utilize photogrammetry for calibration and/or fiducials (i.e., markers or objects placed in a field of view or imaging system for use as a point of reference or measure, or the like). Depending on the procedure and the need, there may be several sensors that can be employed, for example, eye gazing on the Hugo robot might shut down the system to avoid inadvertent movement or injury, which could be employed via the HoloLens headset on any therapy delivery (including, without limitation, TAVR, TMVR, tumor ablation, cardiac ablation, etc.).

Now that the sensors have gathered the data, the data must be processed for use by the physician or healthcare professional. For instance, a general workflow for processing the data might include the following: (i) problem definition (including, but not limited to, objectives, hypotheses, measurement, cohorts, and/or end points, or the like); (ii) data collection (including, but not limited to, access, transfer, governance, and/or storage of data including, without limitation, internal/external data, historical data, batch data, streaming data, and/or log data, or the like); (iii) data curation (including, but not limited to, quality, cleaning, merging, segmenting, and/or transforming, or the like); (iv) model building (including, but not limited to, features, test models, test analytics, and/or validation, or the like); (v) analysis (including, but not limited to, exploring, analyzing, adjusting, and/or repeating one or more of data mining, AI machine learning or deep learning, statistical analysis, and/or natural language processing, or the like); (vi) visualization (including, but not limited to, graphical, tabular, and/or dashboard visualization of real-time, near-real-time, and/or aggregate data, or the like); (vii) insight and action (including, but not limited to, trends, what, why, and/or how, or the like); and (viii) follow-up (including, but not limited to, prescribing follow-up and long-term monitoring, or the like). Such general workflow may be used to process the three V's of big data—namely, volume (including, without limitation, health records, insurance, transactions, and/or mobile sensors, or the like), velocity (including, without limitation, batch, near-real-time, real-time, and/or streaming, or the like), and variety (including, without limitation, structured, unstructured, semi-structured, and/or the like).

The types of data, sources, and processing methods or analytics might include, but are not limited to, auto-segmentation; geometric analyses; device stabilization and filtering; algorithms; anomalies; outliers; trends over time; image identification or recognition; mobile sensors; measures and prediction for custom, group, etc. (e.g., procedural times, cost, fluoroscopy use, contrast use, team performances, or the like); device acute or chronic performance prediction (e.g. rhythm prediction before and during ablation, or the like); reimbursement or insurance analytics or treatment; health records; transactions; prescriptive modeling; predictive modeling; forecasting or extrapolation; diagnostic or statistical analyses; dashboards or alerts; query or drilldown; Ad hoc reports; standard reports; IoT; data mining; and/or the like. Alternatively, or additionally, the types of data, sources, and processing methods or analytics might include, without limitation, structured; unstructured; semi-structured; multi-device factors; multi-comorbidity factors; data analytics; data privacy; data science; data visualization; simulations; predictions; recommendations; probability of success and adverse events; precise and personalized care; optimizing therapy delivery; evidence based medicine; value-based healthcare ("VBHC"); predictive analytics; prescriptive analytics; care management and real-time patient monitoring; computer aided detection ("CADe"); computer aided diagnosis ("CADx"); medical image processing; device feedback; subject feedback; demographics, global, regional, local, racial, social, familial, diet, mental, emotional, spiritual, attitudinal, genetic, lifestyle, insurance, economic factors, or the like; pre-procedural; intraprocedural; post-procedural; chronic; and/or the like.

In a specific, non-limiting example data use case (i.e., utilizing the HoloLens or the like), goals of a solution architecture for analytics and machine learning might include, but are not limited to: telemetry capture (including, without limitation, 3D positioning of a catheter in real-time, procedure duration and ablation accuracy, heart rhythm, electrical signal reduction, scarred or destroyed tissue, and other vitals, or the like); providing for retrospective analytics (including, without limitation, analyzing individual and arbitrary aggregations of procedures on an ad hoc basis, answering common questions to drive data-driven improvements to procedure (e.g., "how much times is spent in various areas of the heart?" and "what was the accuracy and outcome of the procedure?" or the like)); machine learning integration (including, without limitation, real-time and offline or batch, support proposed use cases (e.g., providing real-time prediction of impact that the procedure has had on electrical signal and prognosis; providing real-time estimate of tissue scarred or destroyed, including percentage considered "in excess"; providing information regarding depth, width, and/or permanency of tissue damage or destruction (e.g., some ablation types like reversible (compared with irreversible) electroporation actually open up cell walls to all for drugs to enter then heal and close up, or the like)); providing real-time anomaly detection of vitals, including dips, peaks, and long-term trend variance; recommending patient-specific ablation locations to reduce probability of repeat surgery; recommending path optimization for procedure based on patient-specific anatomy; or the like)).

With so many data sources, the packaging of display of these into a user interface (such as a UX device, or the like) to only have the right information, at the right time, and in the right place needs to be done to minimize cognitive overload. Although we have shown 3D screen and 3D headset examples, several UX types and feedback loops that can be employed are as described above with respect to UX device 155. All of the parts of the system need to communicate in a seamless manner in order to be useful in real time. The parts of a non-limiting XR or IA ecosystem, according to some embodiments, might include, without limitation, headset; tethered unit; cloud; data warehouse; data lake; computer processor; and/or the like. Lastly, the application of the ecosystem can be deployed on various subjects (as described above with respect to subject 130).

These and other functions of the system 100 (and its components) are described in greater detail below with respect to FIGS. 2-17.

Figure 2A:
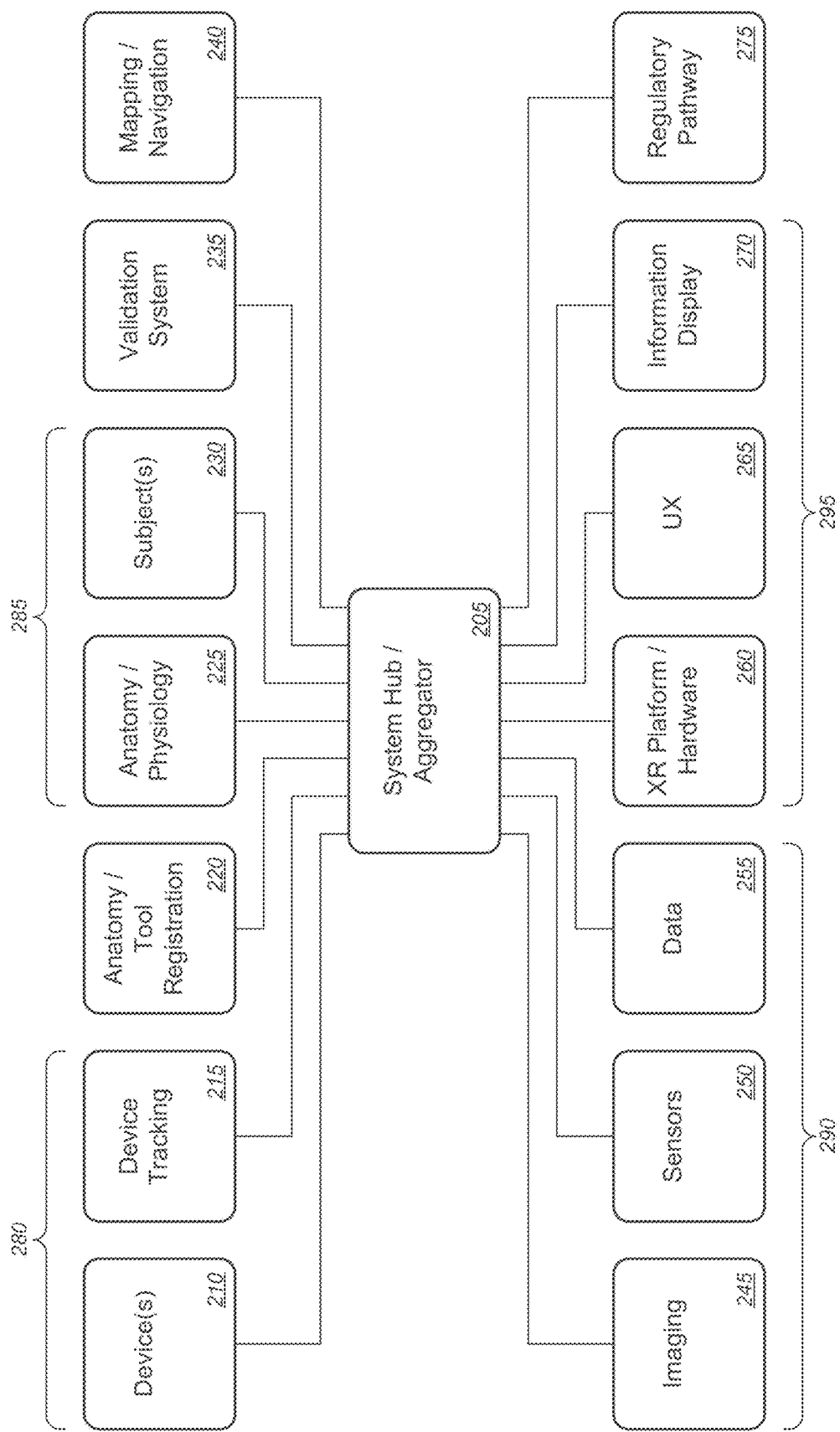
FIGS. 2A-2C are schematic diagrams illustrating various non-limiting examples of building blocks for an IA ecosystem, in accordance with various embodiments.
Figure 2B:
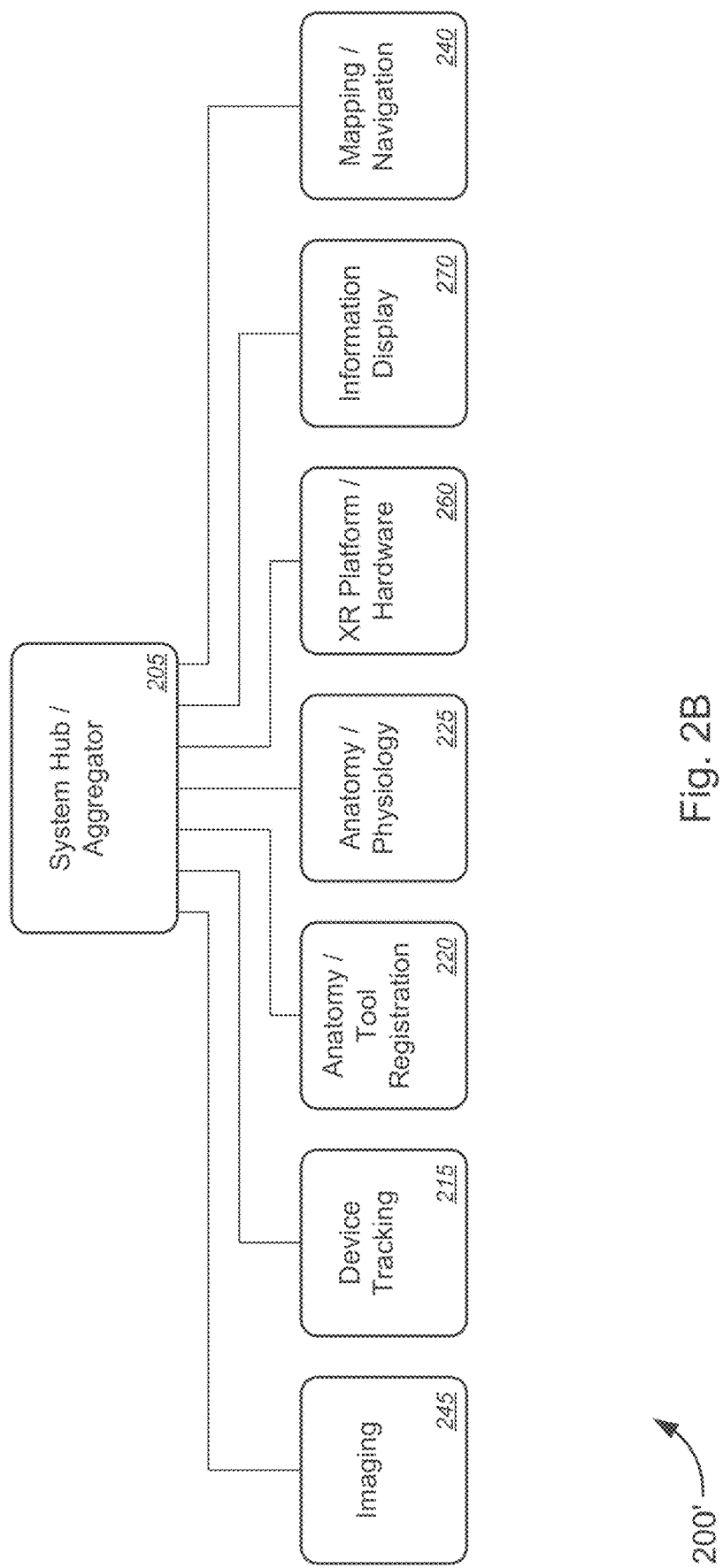
Figure 2C:
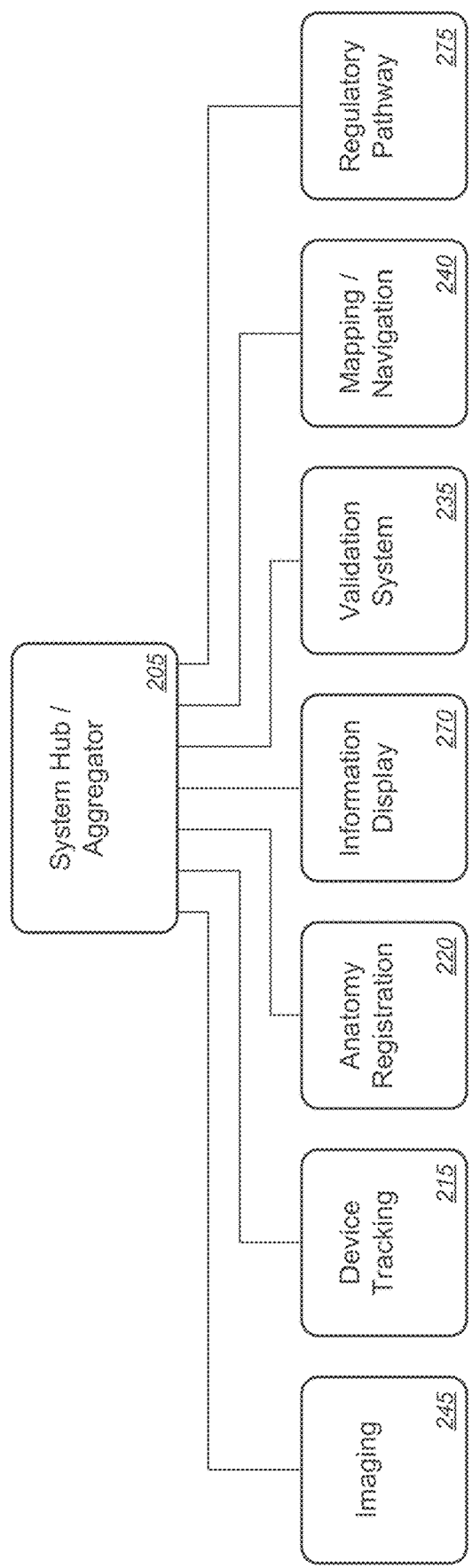

FIGS. 2A-2C (collectively, "FIG. 2") are schematic diagrams illustrating various non-limiting examples 200, 200', and 200" of building blocks for an IA ecosystem, in accordance with various embodiments.

With reference to the non-limiting example 200 of FIG. 2A, the IA ecosystem 200 might comprise a system hub or aggregator (block 205) and a plurality of components or building blocks of the IA ecosystem (blocks 210-275) that are communicatively coupled with the system hub or aggregator (at block 205). In some embodiments, the plurality of components might include, without limitation, at least one of one or more devices (block 210) configured to perform one or more tasks, a device tracking system (block 215) configured to track each device, an anatomy and/or tool registration system (block 220) configured to register anatomy of a subject and/or tools used, anatomy or physiology (block 225) (i.e., anatomy or physiology of subjects, or the like), one or more subjects (block 230), a validation system (block 235) configured to validate information, a mapping or navigation system (block 240), one or more imaging systems (block 245), one or more sensors (block 250), data (particularly, regarding the one or more devices and/or the device tracking, or the like) (block 255), extended reality ("XR") platform or hardware (block 260), user experience ("UX") device or system (block 265), information display (block 270), or regulatory pathway system (block 275), and/or the like. The blocks 210 and 215 corresponding to the one or more devices and the device tracking system, respectively, are directed to or focused on the device or instrument aspects 280 of the system, while the blocks 225 and 230 corresponding to the anatomy or physiology and the one or more subjects, respectively, are directed to or focused on the subject aspects 285. Likewise, the blocks 245-255 corresponding to the one or more imaging systems, the one or more sensors, and the data, respectively, are directed to or focused on the data collection aspects 290 of the system, while the blocks 260-270 corresponding to the XR hardware, the UX device or system, and the information display, respectively, are directed to or focused on the user interface aspects 295.

According to some embodiments, the one or more devices (at block 210) might include, but are not limited, at least one of one or more catheters, one or more catheter interconnect or interface cables, one or more valves, one or more balloons, one or more leads, one or more pacemakers, one or more defibrillators, one or more neuromodulation devices, one or more neurostimulation devices, one or more rigid robotic devices, one or more soft robotic devices, one or more stents, one or more needles, one or more grafts, one or more occluders, one or more shunts, one or more orthopedic screws, one or more orthopedic plates, one or more orthopedic rods, one or more vertebral sponges, one or more therapeutic delivery devices, one or more implant delivery devices, one or more diagnostic devices, one or more diagnostic catheters, one or more implant devices, one or more surgical tools, one or more biologics, one or more drug pumps, one or more genes, one or more cells, one or more organs, one or more organelles, one or more delivery pharmaceuticals, one or more biopsy tools, one or more excision tools, one or more ablation tools, one or more monitoring devices, one or more cameras, one or more imaging tools, one or more fiducials, one or more staples, one or more anchors, one or more meshes, one or more vascular cannulae, one or more circulatory pumps, one or more valve repair devices, one or more embolic protection devices, one or more cardiomyoplasty tools, one or more vascular closure tools, one or more septal closure tools, one or more ventricular closure tools, one or more lasers, one or more plaque removal tools, one or more guide wires, one or more introducers, one or more sheaths, one or more pillcams, one or more clips, one or more capsules, one or more microbiomes, one or more microbes of bacterial vectors, one or more microbes of viral vectors, one or more microbes of prion vectors, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment, and/or the like.

In some cases, the one or more devices (at block 210) might include one or more first devices including, but not limited to, at least one of one or more catheters, one or more valves, one or more balloons, one or more leads, one or more stents, one or more needles, one or more grafts, one or more occluders, one or more shunts, one or more orthopedic screws, one or more orthopedic plates, one or more orthopedic rods, one or more vertebral sponges, one or more diagnostic catheters, one or more surgical tools, one or more drug pumps, one or more biopsy tools, one or more excision tools, one or more staples, one or more anchors, one or more meshes, one or more vascular cannulae, one or more circulatory pumps, one or more valve repair devices, one or more embolic protection devices, one or more cardiomyoplasty tools, one or more vascular closure tools, one or more septal closure tools, one or more ventricular closure tools, one or more plaque removal tools, one or more guide wires, one or more introducers, one or more sheaths, one or more clips, or one or more capsules, and/or the like.

In some instances, the one or more devices (at block 210) might include one or more second devices including, but not limited to, at least one of one or more catheter interconnect or interface cables, one or more rigid robotic devices, one or more soft robotic devices, one or more diagnostic devices, one or more monitoring devices, one or more cameras, one or more imaging tools, one or more fiducials, one or more lasers, one or more pillcams, or one or more ablation tools, and/or the like. In some cases, the one or more devices (at block 210) might include one or more third devices including, but not limited to, at least one of one or more pacemakers, one or more defibrillators, one or more neuromodulation devices, one or more neurostimulation devices, one or more therapeutic delivery devices, one or more implant delivery devices, one or more implant devices, an ICD device, an EV-ICD, a miniature leadless implant, or one or more implantable sensors, and/or the like.

In some instances, the one or more devices (at block 210) might include one or more fourth devices including, but not limited to, at least one of one or more biologics, one or more genes, one or more cells, one or more organs, one or more organelles, one or more delivery pharmaceuticals, one or more microbiomes, one or more microbes of bacterial vectors, one or more microbes of viral vectors, or one or more microbes of prion vectors, and/or the like. In some cases, the one or more devices (at block 210) might include one or more fifth devices including, but not limited to, at least one of a PVAC, one or more energy delivery tools, a CEDS, a PFA system, a PFA console, an electroporation system, an electroporation control console, a cryoballoon or a cryoablation catheter, a cryoablation console, a RF ablation-based system, an RF ablation control console, a MW ablation-based system, a MW ablation control console, a laser ablation-based system, a laser ablation control console, a radiation ablation-based system, a radiation ablation control console, a microwave ablation-based system, a HIFU system, a HIFU control console, or one or more capital equipment, and/or the like.

In some embodiments, the one or more tasks performed by the one or more devices might include, without limitation, at least one of a surgical procedure, a left atrial appendage ("LAA") procedure, a tissue ablation procedure, a transcatheter aortic valve repair ("TAVr") procedure, a transcatheter aortic valve replacement ("TAVR") procedure (e.g., with the Evolut™ PRO+TAVR system, or the like), a transcatheter mitral valve repair ("TMVr") procedure, a transcatheter mitral valve replacement ("TMVR") procedure (e.g., with the Intrepid™ TMVR system, or the like), a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, an implant procedure, a home care ventilation procedure, a lung cancer procedure, an aneurysm flow diversion procedure, a deep brain stimulation procedure, a shunt procedure, a bone grafting procedure, an insulin pump installation procedure, a continuous glucose monitoring system installation procedure, a colon disease procedure, a gastroparesis therapy, a hernia surgery, a bowel control therapy, a microwave ablation procedure, a reflux testing and treatment, a weight-loss surgery, a bone conduction hearing therapy, a sinus surgery, a thyroid surgery, a treatment for ear infections, a balloon angioplasty, a stenting procedure, an atrial septal defect ("ASD") treatment procedure, a cardiac shunt treatment procedure, a heart bypass surgery, a cardiac mapping procedure, a cardiac resynchronization therapy ("CRT") device installation procedure, a catheter ablation procedure, an endovascular repair procedure, a heart monitor installation procedure, an implantable cardioverter defibrillator ("ICD") device installation procedure, an extravascular ICD ("EV-ICD") device installation procedure, a minimally invasive endovascular repair procedure, a pacemaker installation procedure, a miniature leadless implant installation procedure, an implantable sensor installation procedure, a remote monitoring device installation procedure, a surgical heart valve repair and replacement procedure, a transcatheter pulmonary valve ("TPV") therapy (e.g., Melody™ TPV therapy, Harmony™ TPV therapy, or the like), a varicose vein therapy, a ventricular assist device ("VAD") installation procedure, an intra-aortic balloon pump ("IABP") implantation procedure, a heart transplant operation, a back surgery, a bone tumor treatment, a drug pump installation procedure, a spinal cord stimulation procedure, a targeted drug delivery procedure, a balloon kyphoplasty procedure, a cervical disc replacement procedure, a cervical fusion procedure, a sacroiliac joint fusion procedure, a sacral neuromodulation procedure, or a percutaneous tibial neuromodulation procedure, and/or the like.

In some cases, the one or more tasks might include one or more first tasks including, without limitation, at least one of a surgical procedure, a TAVr procedure, a TAVR procedure (e.g., with the Evolut™ PRO+TAVR system, or the like), a TMVr procedure, a TMVR procedure (e.g., with the Intrepid™ TMVR system, or the like), a TPVr procedure, a TPVR procedure, a TTVr procedure, a TTVR procedure, a mitral clip repair procedure, a minimally invasive endovascular repair procedure, a surgical heart valve repair and replacement procedure, a TPV therapy (e.g., Melody™ TPV therapy, Harmony™ TPV therapy, or the like), or an endovascular repair procedure, and/or the like.

In some instances, the one or more tasks might include one or more second tasks including, without limitation, at least one of a LAA procedure, a lung cancer procedure, an aneurysm flow diversion procedure, a deep brain stimulation procedure, a bone grafting procedure, a colon disease procedure, a gastroparesis therapy, a hernia surgery, a bowel control therapy, a reflux testing and treatment, a weight-loss surgery, a bone conduction hearing therapy, a sinus surgery, a thyroid surgery, a treatment for ear infections, a balloon angioplasty, an ASD treatment procedure, a cardiac shunt treatment procedure, a heart bypass surgery, a varicose vein therapy, a heart transplant operation, a back surgery, a bone tumor treatment, a spinal cord stimulation procedure, a targeted drug delivery procedure, a balloon kyphoplasty procedure, a cervical disc replacement procedure, a cervical fusion procedure, a sacroiliac joint fusion procedure, a sacral neuromodulation procedure, or a percutaneous tibial neuromodulation procedure, and/or the like.

In some cases, the one or more tasks might include one or more third tasks including, without limitation, at least one of an implant procedure, an insulin pump installation procedure, a continuous glucose monitoring system installation procedure, a CRT device installation procedure, a heart monitor installation procedure, an ICD device installation procedure, an EV-ICD device installation procedure, a pacemaker installation procedure, a miniature leadless implant installation procedure, an implantable sensor installation procedure, a remote monitoring device installation procedure, a VAD installation procedure, an IABP implantation procedure, or a drug pump installation procedure, and/or the like. In some instances, the one or more tasks might include one or more fourth tasks including, without limitation, at least one of a tissue ablation procedure, a shunt procedure, a microwave ablation procedure, a stenting procedure, a cardiac mapping procedure, a catheter ablation procedure, or a home care ventilation procedure, and/or the like.

Any one of (or a combination of two or more of) these tasks may be performed by corresponding first through fourth devices.

According to some embodiments, each of the one or more subjects (at block 230) might include, but is not limited to, one of a human patient, a large animal, a small animal, an organ, an organelle, one or more organs on a chip, one or more tissue constructs, one or more cells, one or more microbes of bacterial vectors, one or more microbes of viral vectors, one or more microbes of prion vectors, one or more genes, deoxyribonucleic acid ("DNA"), ribonucleic acid ("RNA"), one or more hormones, one or more biochemicals, one or more molecules, one or more tissues, one or more blood vessels, or one or more bones, and/or the like.

In some cases, the one or more subjects might include one or more first subjects including, without limitation, at least one of a human patient, a large animal, or a small animal, and/or the like. In some instances, the one or more subjects might include one or more second subjects including, without limitation, at least one of an organ, an organelle, one or more organs on a chip, one or more tissue constructs, one or more cells, one or more molecules, one or more tissues, one or more blood vessels, or one or more bones, and/or the like. In some cases, the one or more subjects might include one or more third subjects including, without limitation, at least one of one or more microbes of bacterial vectors, one or more microbes of viral vectors, one or more microbes of prion vectors, and/or the like. In some instances, the one or more subjects might include one or more fourth subjects including, without limitation, at least one of one or more genes, DNA, RNA, one or more hormones, one or more biochemicals, and/or the like.

In some embodiments, the mapping or navigation system (at block 240) might include, without limitation, at least one of an XR computing system, a medical procedure computing system, a hub computing system, a three-dimensional ("3D") graphical processing unit, a cluster computing system, a four-dimensional ("4D") graphics computing system, a server computer, a cloud computing system, or a distributed computing system, and/or the like. In some cases, the one or more mapping or navigation systems might include one or more first mapping or navigation systems including, without limitation, at least one of an XR computing system, a medical procedure computing system, a 3D graphical processing unit, or a 4D graphics computing system, and/or the like.

In some instances, the one or more mapping or navigation systems might include one or more second mapping or navigation systems including, without limitation, at least one of a hub computing system, a cluster computing system, or a server computer, and/or the like.

In some cases, the one or more mapping or navigation systems might include one or more third mapping or navigation systems including, without limitation, at least one of a cloud computing system or a distributed computing system, and/or the like.

Any one of (or combination of two or more of) these mapping or navigation systems may be used for any of the first through fourth tasks performed by corresponding first through fifth devices on corresponding first through fourth subjects. Specific non-limiting example combinations of these systems and devices are described below with respect to FIG. 9, in terms of specific example procedures in the context of pre-operative planning, intra-operative adjustments, and post-operative monitoring (as described below with respect to FIG. 3C, or the like).

According to some embodiments, the one or more imaging systems (at block 245) might include, but are not limited to, at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

In some cases, the one or more imaging systems might include one or more first imaging systems including, without limitation, at least one of a MRI system, a DTI system, a MRA system, an ASL system, a MEG system, a MRS system, a DSC MRI system, a BOLD system, or a FLAIR system, and/or the like.

In some instances, the one or more imaging systems might include one or more second imaging systems including, without limitation, at least one of a CT system, a SPECT system, a CTA system, a PET system, or an OCT system, and/or the like.

In some cases, the one or more imaging systems might include one or more third imaging systems including, without limitation, at least one of a US system, a TEE system, an ICE system, a TTE system, an IVUS system, or an EWI system, and/or the like.

In some instances, the one or more imaging systems might include one or more fourth imaging systems including, without limitation, at least one of a neuro-endoscopy system, an OIS system, an endoscopy system, a bioluminescent system, a triboluminescence system, an image fusion system, or a microscope, and/or the like.

In some cases, the one or more imaging systems might include one or more fifth imaging systems including, without limitation, an EEG system, and/or the like.

In some instances, the one or more imaging systems might include one or more sixth imaging systems including, without limitation, at least one of a fluoroscopy system, an X-ray system, a 3D scanning system, an IR system, or a UV system, and/or the like.

Any one of (or combination of two or more of) these imaging systems may be used, in conjunction with any one of (or combination of two or more of) the above mapping or navigation systems for any of the first through fourth tasks performed by corresponding first through fifth devices on corresponding first through fourth subjects. Specific non-limiting example combinations of these systems and devices are described below with respect to FIG. 9, in terms of specific example procedures in the context of pre-operative planning, intra-operative adjustments, and post-operative monitoring (as described below with respect to FIG. 3C, or the like).

In some embodiments, the one or more sensors (at block 250) might include, without limitation, at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography ("EOG") sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some cases, the one or more sensors might include one or more first sensors including, without limitation, at least one of one or more blood velocity sensors, one or more blood volume sensors, one or more blood pressure sensors, one or more heart rate sensors, one or more pulse sensors, one or more oxygen sensors, one or more $CO_2$ sensors, one or more hormonal sensors, one or more fluid levels, one or more biomarker sensors, one or more genetic sensors, one or more blood chemistry sensors, one or more tissue matrix sensors, one or more bacteria sensors, one or more respiration sensors, one or more emotional stress sensors, one or more sleep sensors, one or more ischemia sensors, one or more HCT level sensors, one or more brainwave sensors, or one or more pain sensors, and/or the like.

In some instances, the one or more sensors might include one or more second sensors including, without limitation, at least one of one or more gas sensors, one or more optical sensors, one or more impedance sensors, one or more ultrasound sensors, one or more flow sensors, one or more electrical sensors, one or more voltage sensors, one or more amperage sensors, one or more wattage sensors, one or more chemical sensors, one or more pH sensors, one or more motion sensors, one or more proximity sensors, one or more light sensors, one or more sound sensors, one or more laser sensors, one or more doppler sensors, one or more mechanical sensors, one or more IR sensors, one or more UV sensors, one or more moisture sensors, one or more humidity sensors, one or more temperature sensors, one or more pressure sensors, one or more force sensors, one or more strain sensors, one or more stress sensors, one or more olfactory sensors, one or more viscosity sensors, one or more EMI sensors, one or more vibration sensors, one or more sound wave sensors, one or more magnetic sensors, one or more visible light sensors, or one or more radiation sensors, and/or the like.

In some cases, the one or more sensors might include one or more third sensors including, without limitation, at least one of one or more diagnostic sensors, one or more surgical sensors, one or more wearable sensors, one or more DIC sensors, one or more cameras, one or more perfusion sensors, one or more EMG sensors, one or more EOG sensors, one or more cardiac hemodynamics sensors, one or more photographic plate sensors, one or more polymer-metal sensors, one or more electrochemical sensors, one or more biometric sensors, or one or more EEG sensors, and/or the like. In some instances, the one or more sensors might include one or more fourth sensors including, without limitation, at least one of one or more surgeon fatigue sensors or one or more compliance sensors, and/or the like. In some cases, the one or more sensors might include one or more fifth sensors including, without limitation, at least one of one or more CCDs or one or more photo diode arrays, and/or the like.

In some instances, the one or more sensors might include one or more sixth sensors including, without limitation, at least one of one or more tissue contractility sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, or one or more metabolic process sensors, and/or the like. In some cases, the one or more sensors might include one or more seventh sensors including, without limitation, at least one of one or more chronically implanted sensors, and/or the like. In some instances, the one or more sensors might include one or more eighth sensors including, without limitation, at least one of one or more contactless optical sensors, one or more IR-based temperature sensors, one or more blood pressure sensors, one or more heart rate sensors, one or more motion sensors, one or more respiratory rate sensors, one or more fiducial alignment sensors, one or more tool recognition sensors, one or more collision detection sensors, one or more room traffic flow sensors, one or more surgeon fatigue sensors, one or more cognitive overload sensors, and/or the like.

According to some embodiments, the user interface ("UI") aspects 295 (at blocks 260-270) might include, but not limited to, at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

In some cases, the one or more UI aspects might include one or more first UI aspects including, without limitation, at least one of a headset, UX glasses, a supplement to existing glasses, UX contact lenses, or a HUD device, and/or the like. In some instances, the one or more UI aspects might include one or more second UI aspects including, without limitation, at least one of a viewing window or a microscope, and/or the like. In some cases, the one or more UI aspects might include one or more third UI aspects including, without limitation, at least one of headphones or a 3D spatial sound system, and/or the like. In some instances, the one or more UI aspects might include one or more fourth UI aspects including, without limitation, at least one of an olfactory simulation system, a taste simulation system, a sensory neuro-perception system, a sensory conversion system, or a haptic feedback system, and/or the like.

In some cases, the one or more UI aspects might include one or more fifth UI aspects including, without limitation, at least one of a telemonitoring system, a rigid robotic device control and sensory feedback system, a soft robotic device control and sensory feedback system, a control system for nanostructures, a control system for cells, a control system for genes, or a nanoparticle reconstruction system, and/or the like. In some instances, the one or more UI aspects might include one or more sixth UI aspects including, without limitation, at least one of an eye control system, a voice control system, a remote control system, a gesture-based control system, a sign language-based control system, a body-part-based control system, a joystick, a mouse, a blow-based control system, a neuro-interface system, or a peripheral nerve-computer interface system, and/or the like.

In some cases, the one or more UI aspects might include one or more seventh UI aspects including, without limitation, at least one of a 2D screen display, a 3D refractive display, a parallel reality system, a projection system, a fan-based display, a water-based display, an ionized air-based display, an ionized laser-based display, a smoke-based display, a sand-based display, a particulate-based display, a 3D printed reconstruction system, or a customized view generation system, and/or the like. In some instances, the one or more UI aspects might include one or more eighth UI aspects including, without limitation, at least one of a ghosting and prediction system, a master-slave control system, or an annotation system, and/or the like.

Turning to the non-limiting examples 200' and 200" of FIGS. 2B and 2C, respectively, subsets of the IA ecosystem may be employed for particular implementations, procedures, operations, or tasks. For example, referring to the non-limiting example 200' of FIG. 2B, for applications involving ablation of cardiac arrhythmias (e.g., atrial fibrillation, flutter, etc.) or cardiac structure applications (e.g., heart valve applications, left atrial appendage closure device applications, annuloplasty ring applications, etc.), IA ecosystem 200' might comprise system hub or aggregator 205 and a plurality of building blocks, including, but not limited to, one or more imaging systems (block 245), device tracking system (block 215), anatomy and/or tool registration system (block 220), anatomy or physiology (block 225), XR platform or hardware (block 260), information display (block 270), and/or mapping or navigation system (block 240), or the like.

With reference to the non-limiting example 200" of FIG. 2C, for cardiac or heart applications (e.g., aortic stent applications, peripheral vascular clearing device applications (e.g., applications involving use of a rotablator, which is a special catheter having a tip that spins at high speed to grind away plaque on artery walls, or the like), etc.), IA ecosystem 200" might comprise system hub or aggregator 205 and a plurality of building blocks, including, without limitation, one or more imaging systems (block 245), device tracking system (block 215), anatomy registration system (block 220), information display (block 270), validation system (block 235), mapping or navigation system (block 240), and regulatory pathway system (block 275), or the like.

Although particular example applications are provided above (such as with respect to FIGS. 2B and 2C), the various embodiments are not so limited, and the IA ecosystem may utilize any combination of building blocks 205-270 as appropriate or as desired to perform any suitable medical procedure or application.

Figure 3A:
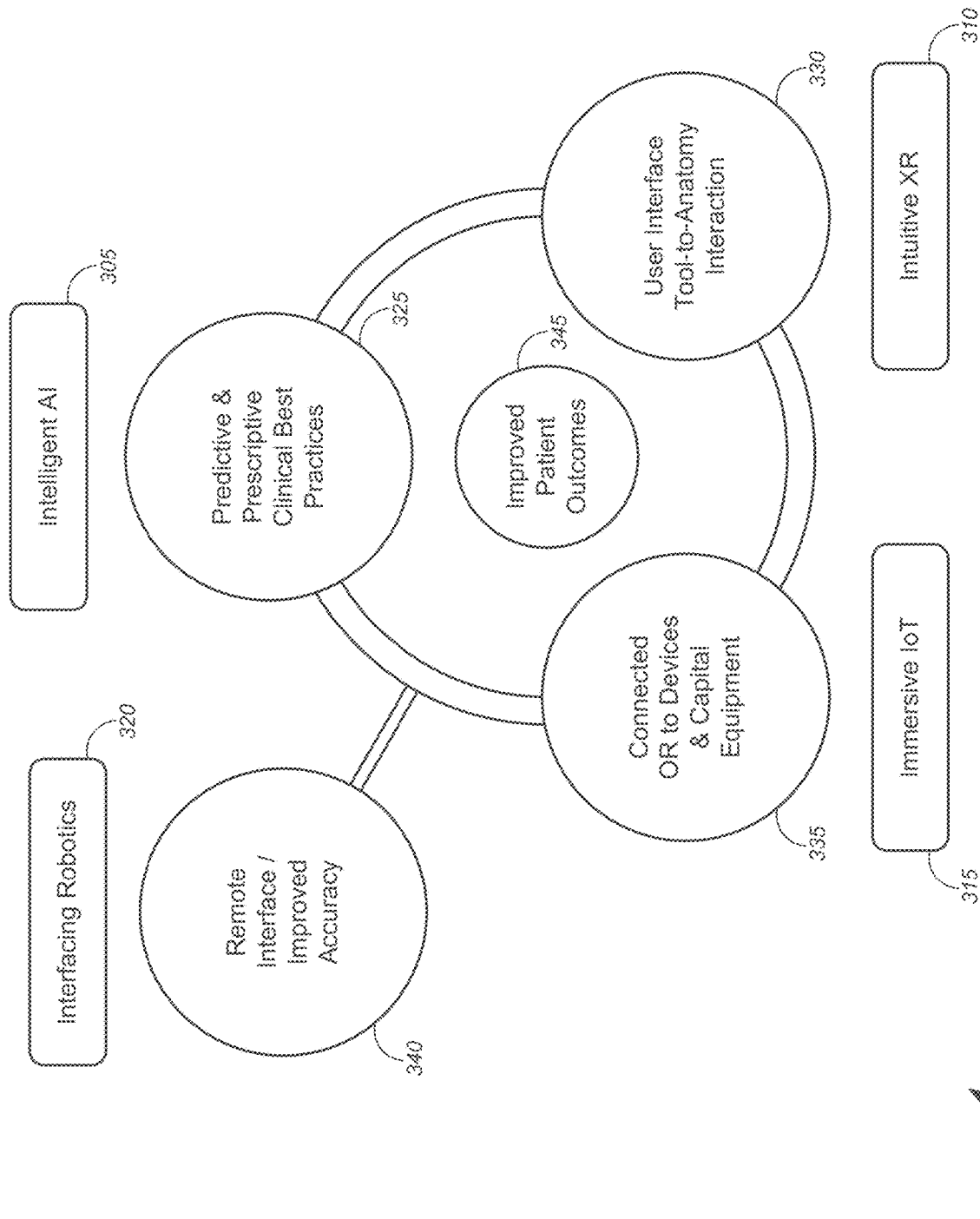
FIGS. 3A and 3B are schematic diagrams illustrating various non-limiting examples of components for implementing an IA ecosystem, in accordance with various embodiments.
Figure 3B:
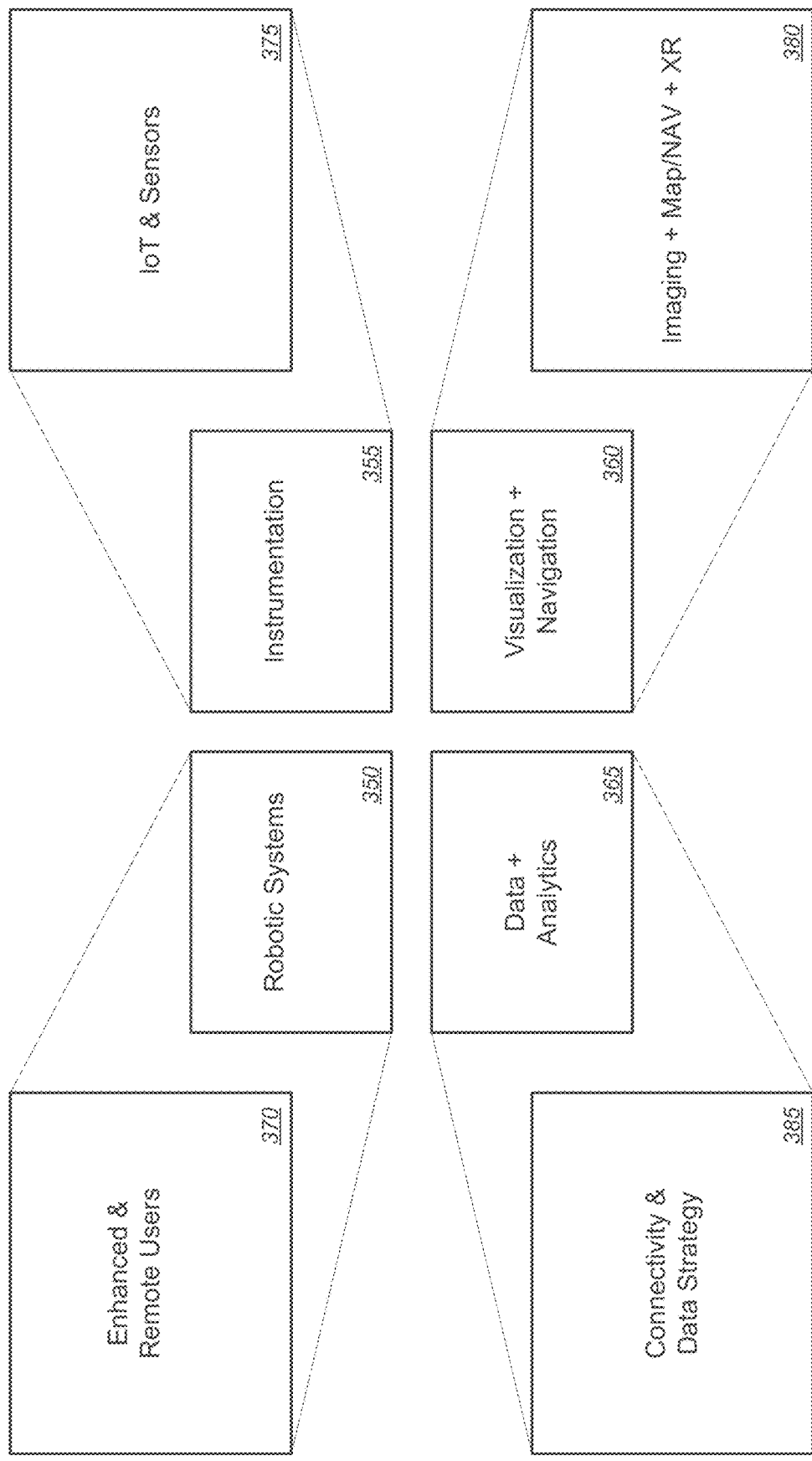
Figure 3C:
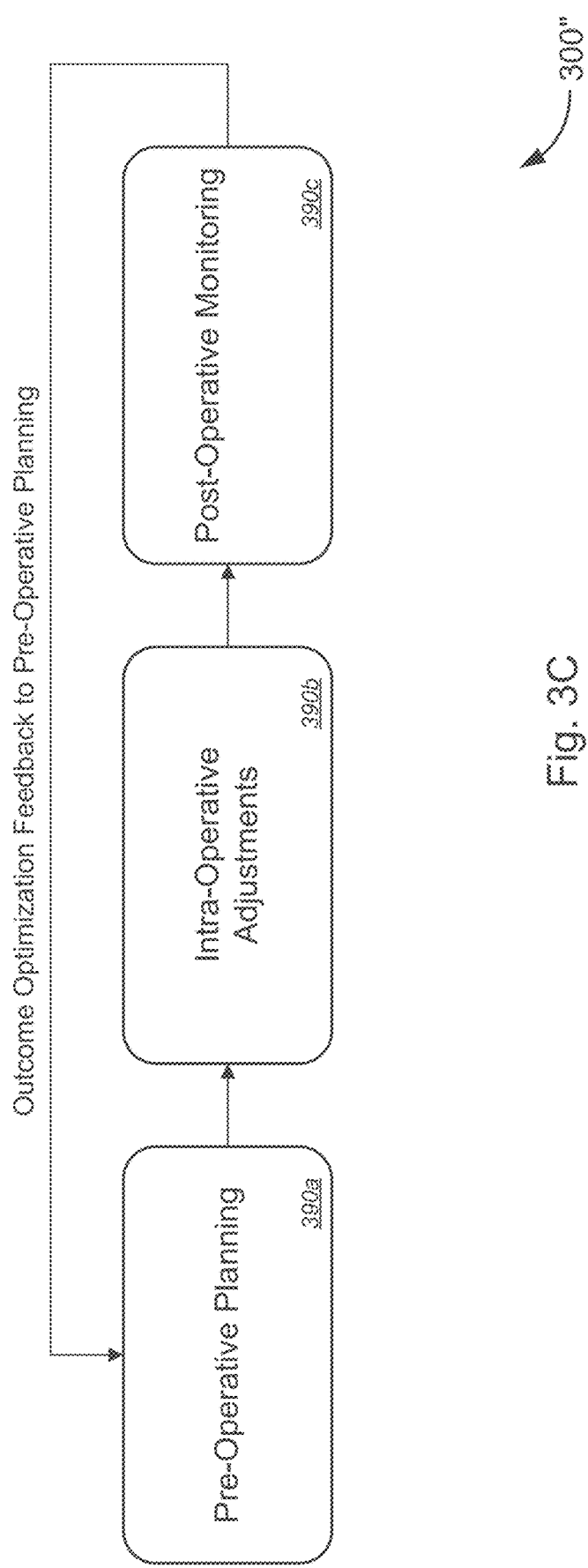
FIG. 3C is a schematic block flow diagram illustrating a non-limiting example of workflow optimization of an IA ecosystem, in accordance with various embodiments.

FIGS. 3A-3C (collectively, "FIG. 3") depict aspects of an IA ecosystem, in accordance with various embodiments. FIGS. 3A and 3B are schematic diagrams illustrating various non-limiting examples 300 and 300' of components for implementing an IA ecosystem, in accordance with various embodiments. FIG. 3C is a schematic block flow diagram illustrating a non-limiting example 300" of workflow optimization of an IA ecosystem, in accordance with various embodiments.

Referring to the non-limiting example 300 of FIG. 3A, an IA ecosystem 300 might comprise an intelligent artificial intelligence ("AI") 305, an intuitive extended reality ("XR") system 210, an immersive Internet of things ("IoT") system 315, and/or interfacing robotics 320, or the like, that can provide at least one of the following features or functionalities: (a) predictive and prescriptive clinical best practices; (b) user interface tool-to-anatomy interaction; (c) connected operating room ("OR") to devices and capital equipment; and (d) remote interface and/or improved accuracy; respectively. Together, these features and functionalities of the combined components of the IA ecosystem 300 lead to improved patient outcomes 345.

With reference to the non-limiting example 300' of FIG. 3B, an IA ecosystem 300' might comprise robotics systems 350, instrumentation 355, visualization and navigation 360, and/or data and analytics 365, or the like, that can provide at least one of the following features or functionalities: (i) enhanced and remote users; (ii) IoT and sensors; (iii) imaging (e.g., electromechanical wave imaging ("EWI") ultrasound, or the like), mapping or navigation, and XR; and (iv) connectivity and data strategy; respectively. Together, these features and functionalities of the combined components of the IA ecosystem 300' lead to reduced variability in diagnostic and therapeutic surgical procedures.

Although particular examples of the IA ecosystem are described above, the various embodiments are not so limited, and the IA ecosystem may comprise some (although not all) of these components (e.g., with or without the robotics systems, or the like), while still achieving improved operational functionalities and features over conventional systems.

Turning to FIG. 3C, the non-limiting example 300" of an IA ecosystem workflow for implementing a procedure (or task), in some embodiments, may employ the following three stages: (1) a Pre-Operative Planning Stage 390a; (2) an Intra-Operative Adjustments Stage 390b; and (3) a Post-Operative Monitoring Stage 390c. The process may start at the Pre-Operative Planning Stage 390a, then proceed to the Intra-Operative Adjustments Stage 390b, subsequently proceed to the Post-Operative Monitoring Stage 390c, and loop back (as necessary) to the Pre-Operative Planning Stage 390a, with the cycle looping as many times as required or as desired to ensure continued optimization of the procedure (or task). According to some embodiments, during these three stages, the non-limiting example 300" of an IA ecosystem workflow for implementing a procedure (or task) can be performed virtually, e.g., based on sensor data from one or more sensors, one or more imaging systems, and/or tracking (or mapping and navigation) systems as described herein. In some cases, the IA ecosystem may be used as a simulator for training physicians/users in which the sensor data from one or more sensors, one or more imaging systems, and/or one or more tracking (or mapping and navigation) systems may be generated based on historical data of previous procedures or based on simulated data generated by a computing system (e.g., artificial intelligence ("AI") and/or machine learning system, or the like) that are based at least in part on historical data of previous procedures or the like.

At the Pre-Operative Planning Stage 390a, the IA ecosystem may collect sensor data from one or more sensors, one or more imaging systems, and/or one or more tracking (or mapping and navigation) systems as described herein, or the like. In some cases, the IA ecosystem may perform analysis of data obtained by the one or more sensors, the one or more imaging systems, and/or the one or more tracking (or mapping and navigation) systems, as discussed herein, to generate recommendations or to facilitate physician/user plans for the procedure (or task). The procedure (or task) may then be performed based on sensor data, imaging data, tracking data, recommendations, and/or physician/user plans obtained or arising from the Pre-Operative Planning Stage 390a.

During the procedure itself, at the Intra-Operative Adjustments Stage 390b, the IA ecosystem may continue to collect sensor data, imaging data, and/or tracking data from the one or more sensors, the one or more imaging systems, and/or the one or more tracking (or mapping and navigation) systems, and may adjust device configurations, settings, and/or implementations in real-time or near-real-time (e.g., within milliseconds or seconds, etc.) based on any updates or changes to the sensor data, imaging data, tracking data, and/or recommendations obtained during the Intra-Operative Adjustments Stage 390b. The IA ecosystem may, even at the Intra-Operative Adjustments Stage 390b, collect sensor data, imaging data, and/or tracking data without a surgical step being particularly involved in collecting the sensor data, imaging data, and/or tracking data.

Following a predetermined time period after the procedure (or task) (e.g., 30 days, 60 days, and/or 90 days, or the like), the Post-Operative Monitoring Stage 390c may be performed. At the Post-Operative Monitoring Stage 390c, the IA ecosystem may collect sensor data from the one or more sensors, the one or more imaging systems, and/or the tracking (or mapping and navigation) systems, and may once again analyze the sensor data, imaging data, and/or tracking data to determine whether any aspect of the procedure (or task) may be optimized or enhanced, and how, and may provide recommendations accordingly. In particular, the IA ecosystem may determine based on the sensor data, imaging data, tracking data, and/or recommendations obtained or arising from the Post-Operative Monitoring Stage 390c whether there has been a change or a difference in the sensor data, imaging data, and/or tracking data, and, if so, whether the change or difference is indicative of a positive change (e.g., an expected, successful procedure (or task), or the like) or a negative change (e.g., where an issue arises from the procedure (or task), or the like). The operations of the Post-Operative Monitoring Stage 390c may be performed repeatedly over a predetermined period (e.g., every day for a week, or the like), which may also be repeated the following one or more months. Based on the sensor data, imaging data, and/or tracking data results and recommendations obtained during the Post-Operative Monitoring Stage 390c, the process may loop back to the Pre-Operative Planning Stage 390a, the Intra-Operative Adjustments Stage 390b, and the Post-Operative Monitoring Stage 390c during a follow-on procedure/task (or correction procedure/tasks), or the like.

Figure 4A:
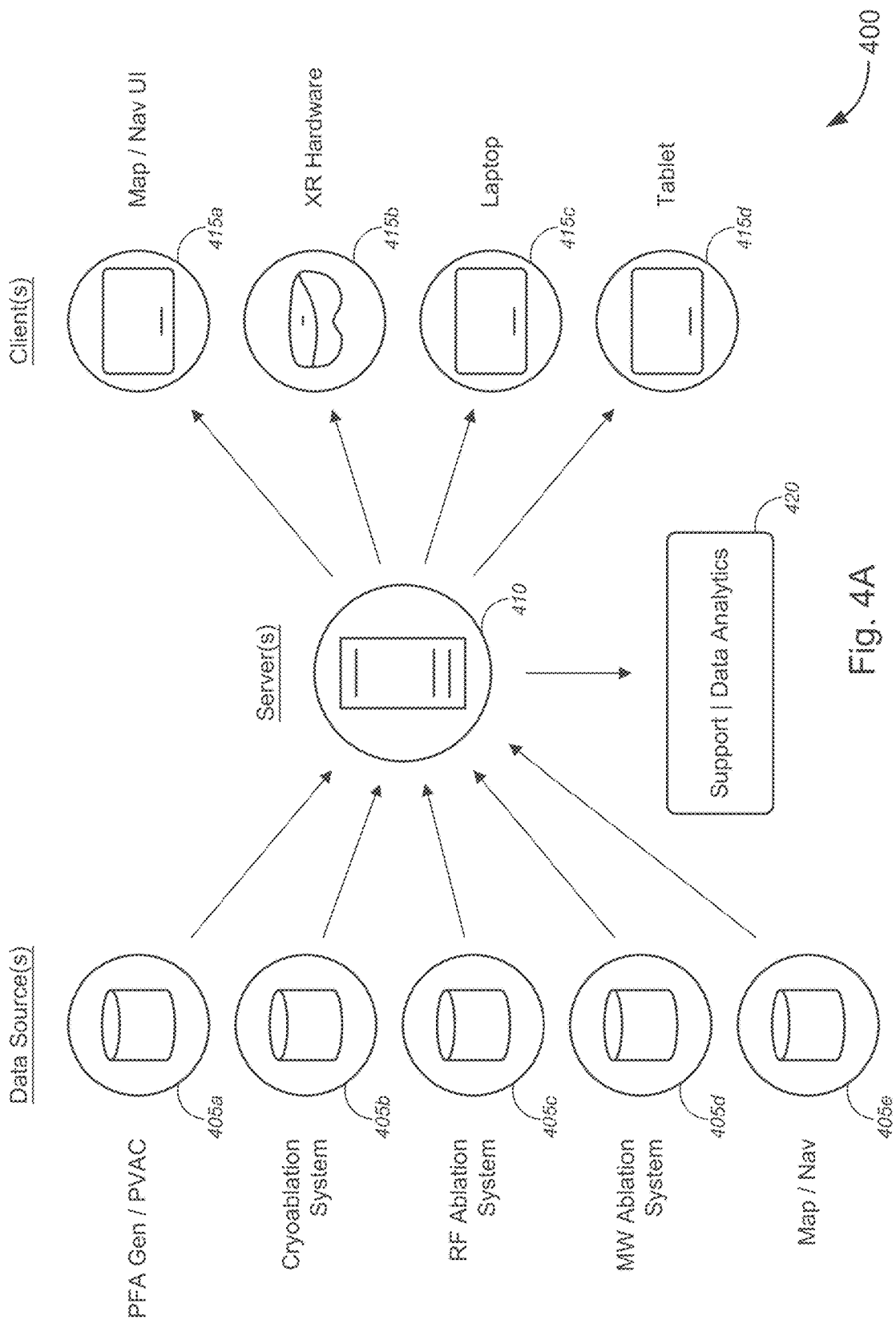
Figure 4B:
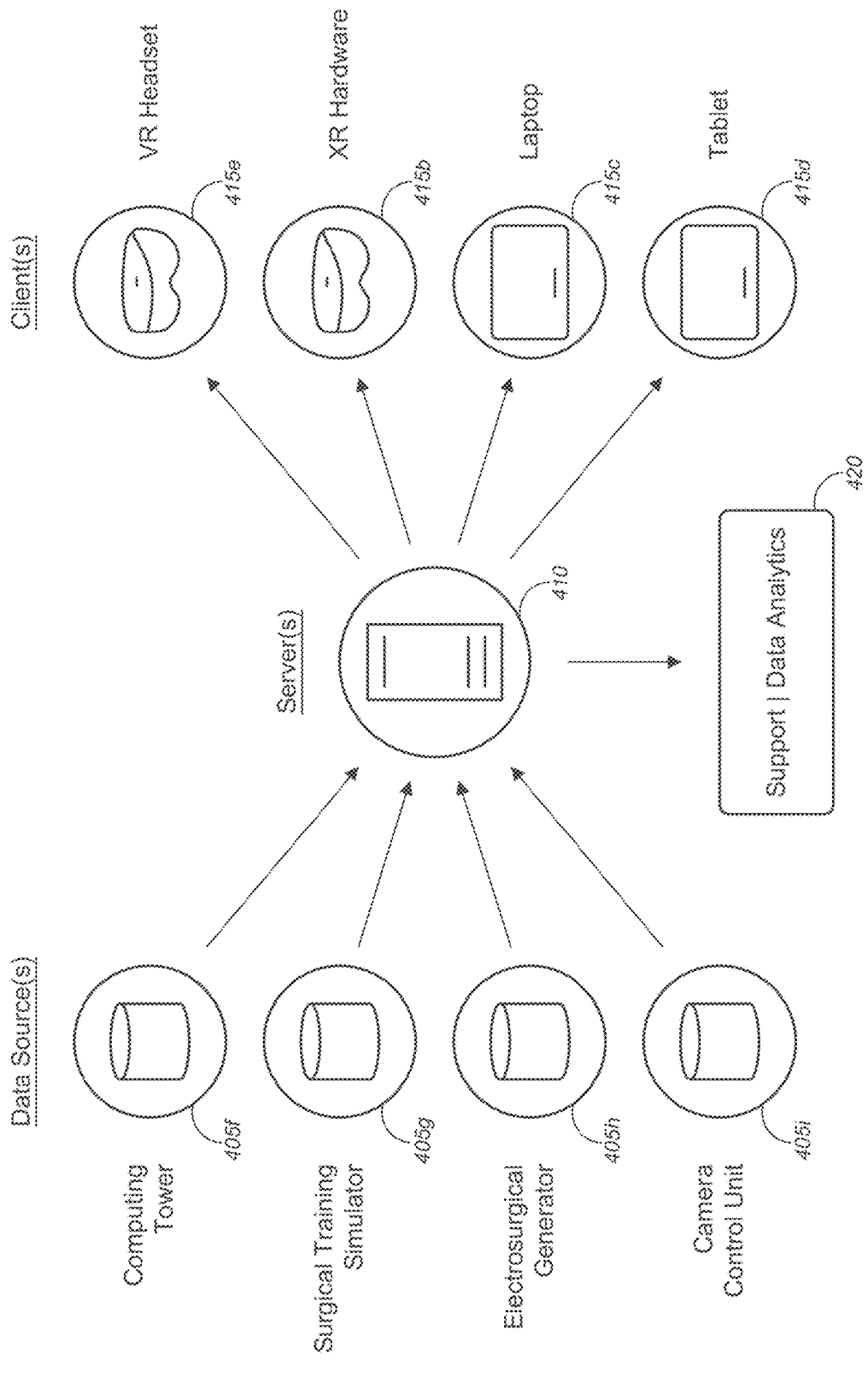

FIGS. 4A-4C (collectively, "FIG. 4") are schematic diagrams illustrating various non-limiting examples 400, 400', and 400" of example networks of interconnected components for various implementations of an IA ecosystem and an example data management flow of the IA ecosystem, in accordance with various embodiments.

With reference to the non-limiting example of FIG. 4A, system 400, which may be configured for implementations involving ablation of cardiac arrhythmias (e.g., atrial fibrillation, flutter, etc.) or the like, might comprise one or more data sources 405a-405e (collectively, "data sources 405" or the like), a server(s) 410, one or more client devices 415a-415d (collectively, "client devices 415" or the like), and a support and/or data analytics system 420. In some embodiments, the one or more data sources 405 might include, without limitation, at least one of pulsed field ablation ("PFA") (also referred to as "irreversible electroporation" or the like; e.g., PulseSelect PFA, or the like) generator and/or pulmonary vein ablation catheter 405a, cryoballoon catheter/system or cryoablation catheter/system 405b (e.g., Nimbus or Nitron Arctic Front Advance™ ("AFA") catheter, Arctic Front Advance Pro™ ("AFA Pro") cryoablation catheter, Freezor™ MAX cryoablation catheter, or the like), radiofrequency ("RF") ablation catheter/system 405c (e.g., EPIX generator (which utilizes a temperature feedback look to ablate faster and safer than traditional non- and irrigated RF catheters) and/or Diamond Temp ("DT") ablation system, or the like; which might include RF ablation catheters including, but not limited to, RF Contact™ ablation catheter, RF Conduct™ MC ablation catheter, RF Conduct™ MCXL ablation catheter, RF Marin™ MC ablation catheter, RF Marin™ MCXL ablation catheter, RF Marin™ 5 Fr ablation catheter, RF Enhancr™ II ablation catheter, or the like), microwave ("MW") ablation system 405d (e.g., Evident™ MW ablation system, or the like), or mapping and navigation system 405e (which might include a general mapping and navigation system or a procedure-specific system such as an atrial fibrillation solutions ("AFS") mapping and navigation system, or the like), and/or the like.

In some cases, the one or more data sources might include one or more first data sources including, without limitation, PFA generator and/or pulmonary vein ablation catheter 405a, and/or the like. In some instances, the one or more data sources might include one or more second data sources including, without limitation, cryoballoon catheter/system or cryoablation catheter/system 405b, and/or the like. In some cases, the one or more data sources might include one or more third data sources including, without limitation, RF ablation catheter/system 405c, and/or the like. In some instances, the one or more data sources might include one or more fourth data sources including, without limitation, microwave ("MW") ablation system 405d, and/or the like. In some cases, the one or more data sources might include one or more fifth data sources including, without limitation, mapping and navigation system 405e, and/or the like.

In some instances, the server(s) 410 might correspond to system hub or aggregator (such as system hub/computing system 105a, 105b, or 240 of FIGS. 1 and 2A-2C, or the like). According to some embodiments, the one or more client devices 415 might include, but are not limited to, at least one of mapping and navigation user interface ("UI") 415a, extended reality ("XR") hardware 415b, a laptop computer 415c, or a tablet computer 415d, and/or the like.

In operation, data obtained by the one or more data sources 405 may be sent to the server(s) 410, which either directly relays the data to the one or more client devices 415 or pre-processes the data prior to sending to the one or more client devices 415. In some embodiments, a message broker system (such as, but not limited to, RabbitMQ, or the like), which is an intermediary computer program module that translate messages in the messaging protocol of the sender device to the messaging protocol of the receiver device, may be used to relay the data from the one or more data sources 405 to the server(s) 410. The server(s) 410 also (whether sequentially, simultaneously, or concurrently) sends the data to the support and/or data analytics system 420 for deeper analysis of the data, in some cases, utilizing AI functionalities to determine patterns, trends, and/or the like. Although specific equipment and corresponding energy modalities are described above with reference to the embodiments of FIG. 4A (e.g., PulseSelect PFA, which is a pulse field ablation/electroporation catheter and generator system; Nimbus or Nitron AFA, each of which is a capital console for cryotherapy systems; EPIX generator or DiamondTemp ("DT") ablation system, which is a temperature (or contact force)-titered RF catheter-based system in which a feedback loop of data from temperature (or contact/proximity) sensors on various locations on the tip of the catheter provides real-time or near-real-time (e.g., milliseconds or seconds, etc.) tracking of temperature (or contact force) changes over time due to conditions changing or encountered (e.g., blood flow, catheter tip being pushed into tissue, tissue properties like scarring, etc.) and corresponding adjustment of power delivery to the ablation system; or the like, and corresponding energy modalities, namely, electroporation, cryoablation, RF, or the like), the various embodiments are not so limited, and any suitable equipment and their corresponding energy modalities—including, but not limited to, electroporation, cryoablation, phased RF, heating with RF, laser, radiation, microwave, or high intensity focused ultrasound, and the like—may be used for ablation or other medical procedures.

Turning to the non-limiting example of FIG. 4B, system 400', which may be configured for implementations using a surgical robot or the like, might comprise one or more data sources 405f-405i (collectively, "data sources 405'" or the like), a server(s) 410, one or more client devices 415b-415e (collectively, "client devices 415'" or the like), and a support and/or data analytics system 420. In some embodiments, the one or more data sources 405' might include, without limitation, at least one of computing tower 405f, surgical training simulator 405g, electrosurgical generator 405h, or camera control unit 405i, and/or the like. In some instances, the server(s) 410 might correspond to system hub or aggregator (such as system hub/computing system 105a, 105b, or 240 of FIGS. 1 and 2A-2C, or the like). According to some embodiments, the one or more client devices 415' might include, but are not limited to, at least one of virtual reality ("VR") headset 415e, XR hardware 415b, a laptop computer 415c, or a tablet computer 415d, and/or the like.

In operation, data obtained by the one or more data sources 405' may be sent to the server(s) 410, which either directly relays the data to the one or more client devices 415' or pre-processes the data prior to sending to the one or more client devices 415'. The server(s) 410 also (whether sequentially, simultaneously, or concurrently) sends the data to the support and/or data analytics system 420 for deeper analysis of the data, in some cases, utilizing AI functionalities to, e.g., determine patterns, trends, and/or the like.

Referring to the non-limiting example 400" of FIG. 4C, an embodiment of data management for the IA ecosystem is depicted, in which data streams 425 (which may contain the data from the one or more data sources 405 or 405' of FIG. 4A or 4B, or the like) may be combined as comprehensive procedure data 430 by a system hub or aggregator (similar to system hub or computing systems or server(s) 105a, 105b, 240, or 410 of FIGS. 1, 2A-2C, 4A, and 4B, or the like). In some embodiments, the comprehensive procedure data 430 might include, without limitation, at least one of navigation data 435, mapping data 440, generator data 445, lesion set data 450, anatomy data 455, location or gaze heatmap 460, biometrics data 465, user and support data 470, or time series data 475, and/or the like. The system hub or aggregator might output the comprehensive procedure data 430 to a user experience ("UX") device 480, or the like. In some cases, the system hub or aggregator might also output the comprehensive procedure data 430 to a data analytics or AI system (such as data analytics or AI system 160a, 160b, 305, 365, or 420 of FIG. 1, 3A, 3B, 4A, or 4C, or the like).

Although particular examples are described with reference to the example networks of interconnected components for various implementations of an IA ecosystem and an example data management flow of the IA ecosystem of FIGS. 4A-4C, the various embodiments are not so limited, and the IA ecosystem may utilize any combination of components or may aggregate any combination of data as appropriate or as desired to implement desired operations or procedures using the IA ecosystem.

Figure 5B:
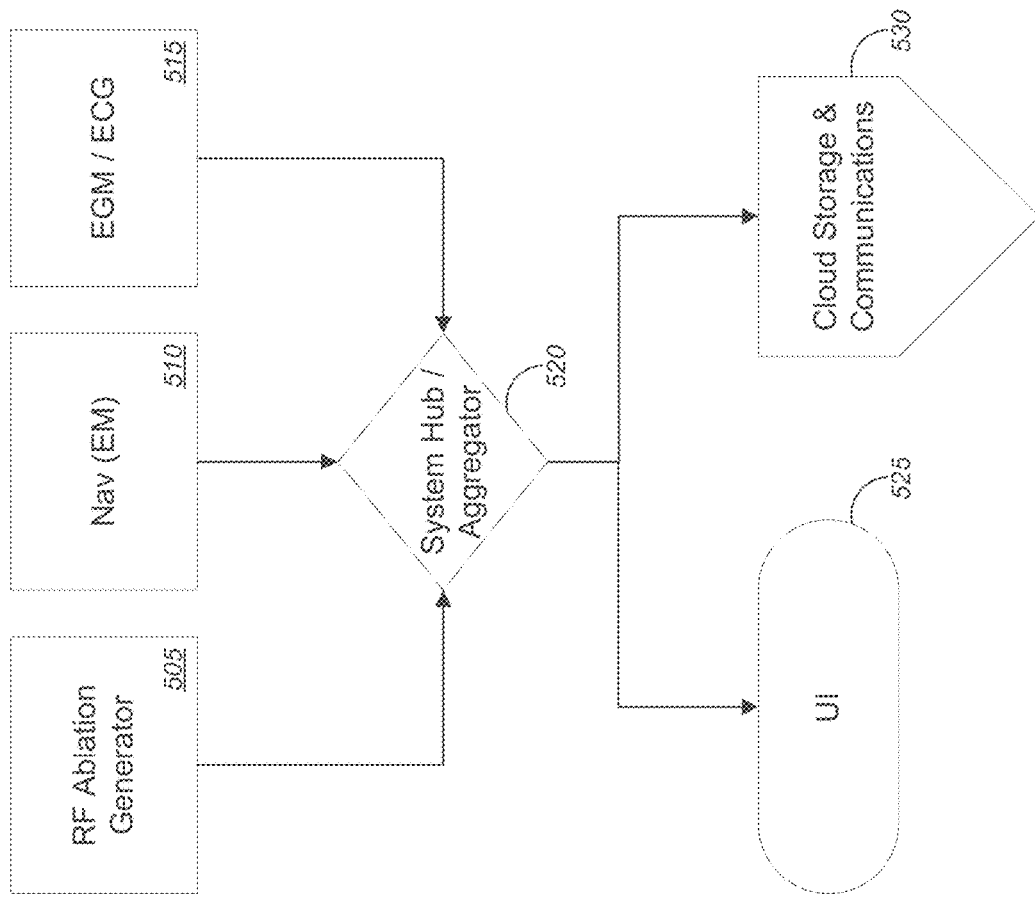
FIGS. 5A-5C are schematic diagrams illustrating various non-limiting examples of data structure or data flow using an IA ecosystem, in accordance with various embodiments.
Figure 5A:
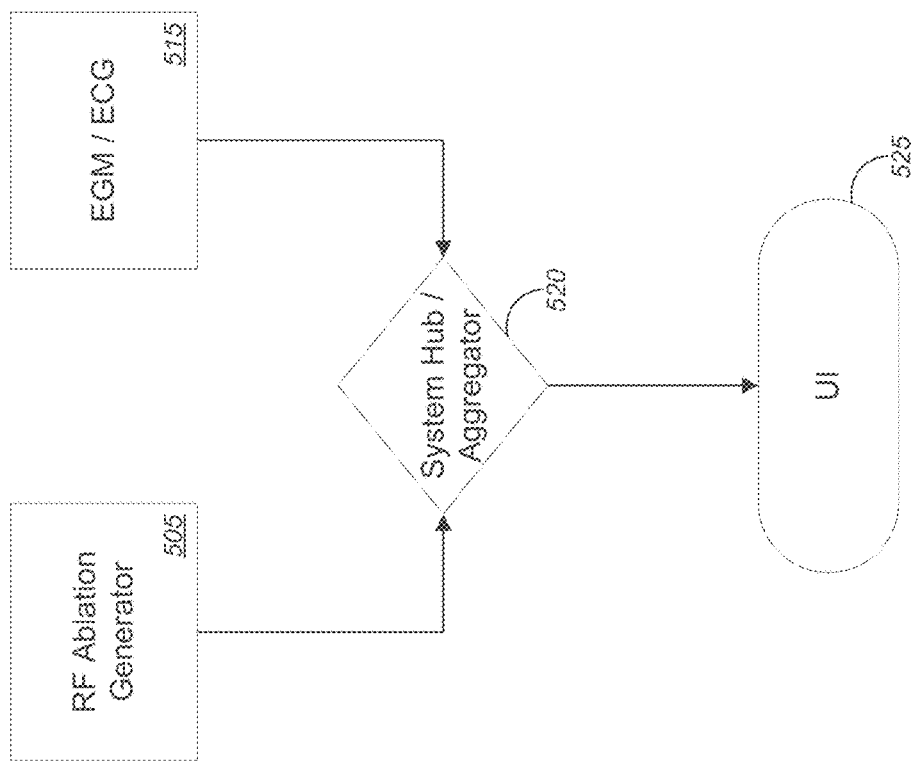
Figure 5C:
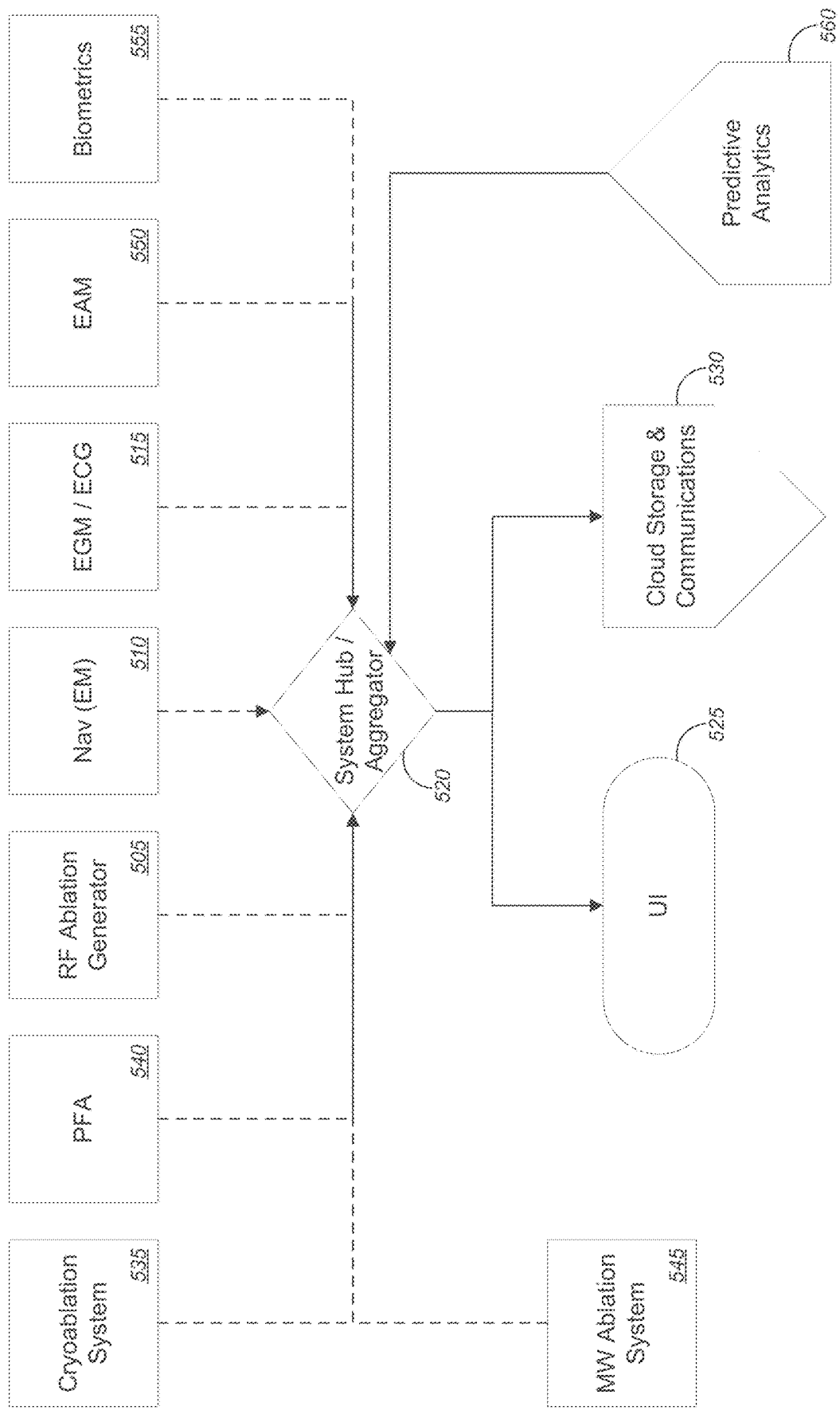

FIGS. 5A-5C (collectively, "FIG. 5") are schematic diagrams illustrating various non-limiting examples 500, 500', and 500" of data structure or data flow using an IA ecosystem, in accordance with various embodiments.

With reference to the non-limiting example 500 of FIG. 5A, data from a radiofrequency ("RF") ablation generator 505 (e.g., Diamond Temp ("DT") ablation system generator or DT generator, or the like) and from an electrogram ("EGM") or electrocardiogram ("ECG") 515 monitoring of a patient may be received, collected, or aggregated by system hub or aggregator 520. The system hub or aggregator 520 might process the received, collected, or aggregated data, and might generate user experience ("UX") data that may be presented to a healthcare or medical professional via a user interface ("UI") or UX device 525.

Alternatively, as shown in the non-limiting example 500' of FIG. 5B, data from each of an RF ablation generator 505, an electromagnetic ("EM") navigation system 510, and an EGM or ECG 515 monitoring of a patient may be received, collected, or aggregated by system hub or aggregator 520. The system hub or aggregator 520 might process the received, collected, or aggregated data, and might generate user experience ("UX") data that may be presented to a healthcare or medical professional via a user interface ("UI") or UX device 525. Sequentially, simultaneously, or concurrently, the system hub or aggregator 520 might send the received, collected, or aggregated data and/or the UX data to cloud storage and communications system 530 for storing in the cloud and/or for relaying to other computing systems or devices, and the like.

In another alternative, as shown in the non-limiting example 500" of FIG. 5C, data from each of one or more of an RF ablation generator 505, an EM navigation system 510, an EGM or ECG 515 monitoring of a patient, a cryoballoon catheter/system or cryoablation catheter/system 535 (e.g., a Nimbus or Nitron Arctic Front Advance™ ("AFA") catheter system, Arctic Front Advance Pro™ ("AFA Pro") cryoablation catheter, Freezor™ MAX cryoablation catheter, or the like), a pulsed field ablation ("PFA") system 540 (e.g., PulseSelect PFA, or the like), a microwave ("MW") ablation system 545 (e.g., Evident™ MW ablation system, or the like), an electroanatomic mapping ("EAM") system 550, or a biometrics system 555, and the like, may be received, collected, or aggregated by system hub or aggregator 520. In some cases, data from at least one of an RF ablation generator 505, a cryoballoon catheter system or cryoablation catheter system 535, or a PFA system 540, and the like, and data from at least one of an EM navigation system 510, an EGM or ECG 515 monitoring of a patient, an EAM system 550, or a biometrics system, and the like, may be received, collected, or aggregated by system hub or aggregator 520. The system hub or aggregator 520 might process the received, collected, or aggregated data, and might generate user experience ("UX") data that may be presented to a healthcare or medical professional via a user interface ("UI") or UX device 525. Sequentially, simultaneously, or concurrently, the system hub or aggregator 520 might send the received, collected, or aggregated data and/or the UX data to cloud storage and communications system 530 for storing in the cloud and/or for relaying to other computing systems or devices, and the like. In some cases, the cloud storage and communications system 530 might relay the received, collected, or aggregated data to a data analytics or artificial intelligence ("AI") system, such as predictive analytics system 560, which might perform deep learning analysis on the received, collected, or aggregated data to, e.g., identify trends, patterns, and/or the like, and/or to identify regions of interest or regions of focus, and might send resultant data (continually, periodically, or randomly) back to the system hub or aggregator 520 (in some cases, in real-time or near-real-time) to generate updated UX data that may be presented (in some cases, also in real-time or near-real-time) to the healthcare or medical professional via UI or UX device 525.

Although particular example applications are provided above (such as particular atrial fibrillation ablation systems and particular patient sensor, navigation, or mapping systems, or the like), the various embodiments are not so limited, and the IA ecosystem may utilize any type of device, instrument, or equipment as appropriate or as desired to perform any suitable medical procedure or application (not limited to atrial fibrillation therapy or even heart procedures), and may also utilize any type of patient sensor or monitor, as well as any type of navigation or mapping system, as appropriate or as desired. Also, although specific equipment and corresponding energy modalities are described above with reference to the embodiments of FIGS. 5A-5C (e.g., PulseSelect PFA, Nimbus or Nitron AFA, EPIX generator or DT ablation system, or the like, and corresponding energy modalities, namely, electroporation, cryoablation, RF, or the like), the various embodiments are not so limited, and any suitable equipment and their corresponding energy modalities—including, but not limited to, electroporation, cryoablation, phased RF, heating with RF, laser, radiation, microwave, or high intensity focused ultrasound, and the like—may be used for ablation or other medical procedures.

Figure 6A:
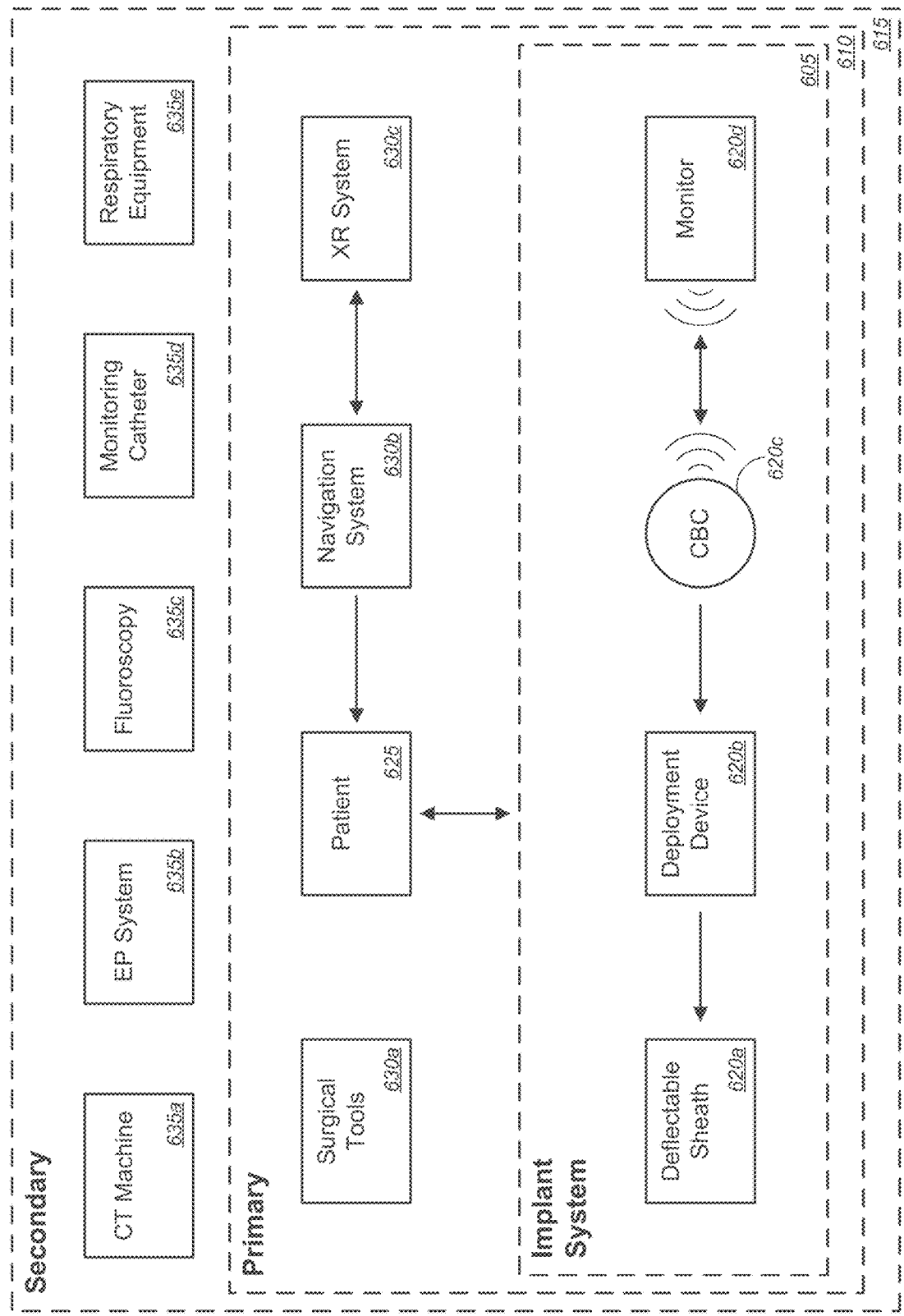
FIGS. 6A and 6B are schematic diagrams illustrating various non-limiting examples of system and method for implementing cardiac bionic construct ("CBC") implantation or deployment using an IA ecosystem, in accordance with various embodiments.
Figure 6B:
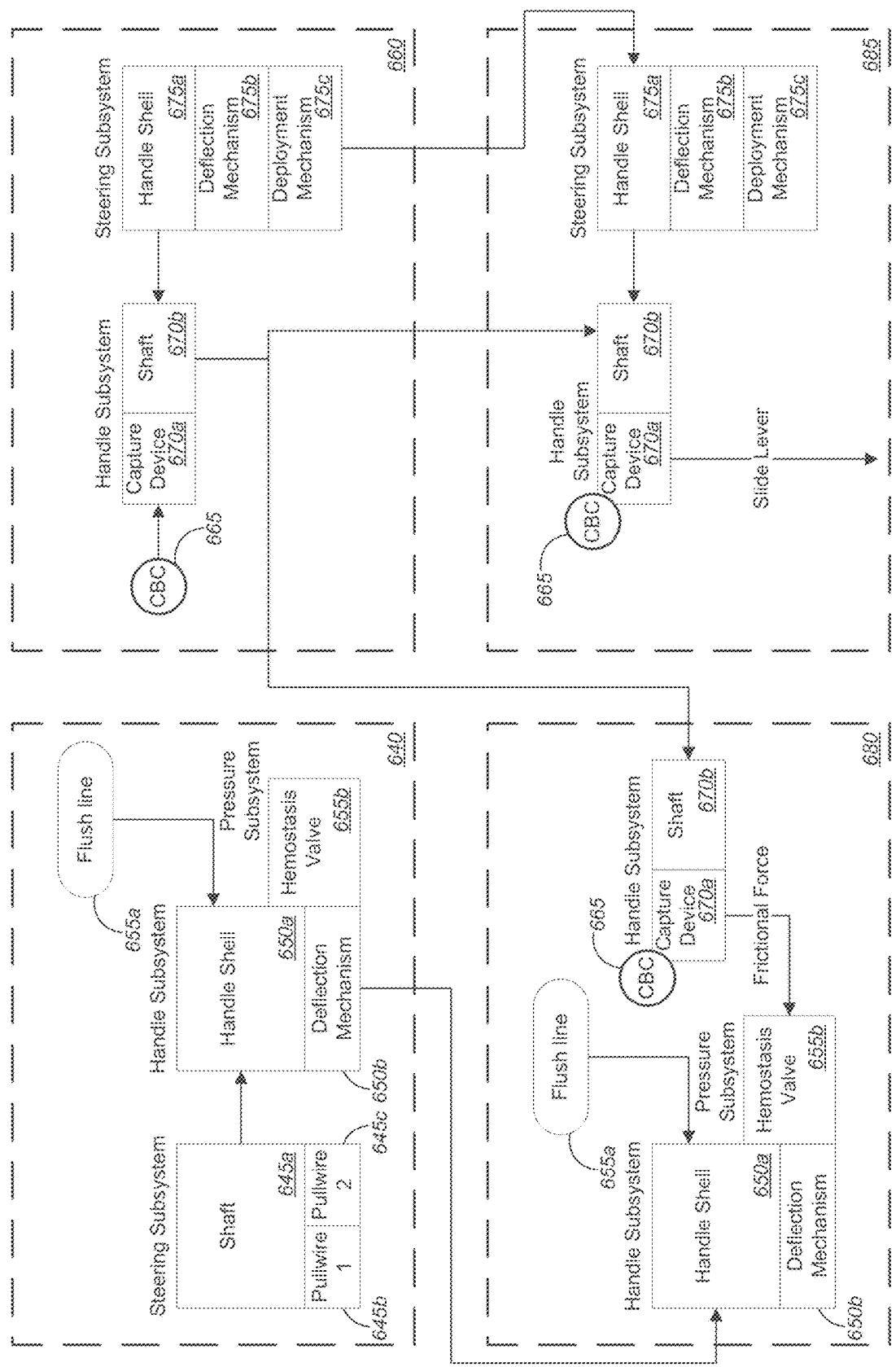

FIGS. 6A and 6B (collectively, "FIG. 6") are schematic diagrams illustrating various non-limiting examples 600 and 600' of system and method for implementing cardiac bionic construct ("CBC") implantation or deployment using an IA ecosystem, in accordance with various embodiments. Herein, cardiac bionic construct or CBC refers to engineered tissue with sensors on it for use in cardiac applications. An example of a CBC may include, but is not limited to, a heart patch(es) with sensors that allow for visualization of the CBC during deployment, movement tracking, detection of electrical signals, detection of hormonal responses (e.g., paracrine effect, etc.), or the like, after deployment and attachment of the CBC to an exterior or interior surface of the heart to aid in healing infarcts, or the like. Another example of bionic constructs in general may include, without limitation, a patch(es) for application or attachment to the skin of a patient for wound healing, or a wearable device with sensors that combines the therapy with the sensor(s) and delivery of the therapy specific to a cardiac application, or the like.

FIG. 6 describes a non-limiting example of a complete system architecture for a CBC implant. There are specific needs to tie together the devices, sensors, map data, navigation data, visualization data, and even long-term data of the device since it is an implant. The delivery, navigation, and visualization of the CBC is also depicted in FIG. 6.

With reference to the non-limiting example 600 of FIG. 6A, there are three hierarchies to the system organization: (1) the implant system 605; (2) the primary equipment 610; and (3) the secondary equipment 615. In some embodiments, the implant system 605 might include, without limitation, a deflectable or steerable sheath (with dilator) 620a, a deployment device 620b, a CBC implant 620c, and/or a monitor 620d. The monitor 620d might communicate wirelessly with the CBC implant 620c (as denoted in FIG. 6A by the double-headed arrow and the wave symbols between the CBC implant 620c and the monitor 620d, or the like).

In some cases, the primary equipment 610 might include, but is not limited to, one or more surgical tools 630a, a navigation system 630b, and/or an extended reality ("XR") system 630c, or the like. According to some embodiments, the one or more surgical tools 630a might, in general, include, without limitation, at least one of one or more graspers (e.g., forceps, or the like), one or more clamps or occluders, one or more needle drivers or needle holders, one or more retractors, one or more distractors, positioners or stereotactic devices, one or more mechanical cutters (e.g., scalpels, lancets, drill bits, rasps, trocars, harmonic scalpels, surgical scissors, rongeurs, or the like), one or more dilators or specula, one or more suction tips or tubes, one or more sealing devices (e.g., surgical staplers, or the like), one or more irrigation or injection needles, tips, or tubes, one or more powered devices (e.g., drills, dermatomes, or the like), one or more scopes or probes (e.g., fiber optic endoscopes, tactile probes, or the like), one or more optical, electrical, or mechanical device carriers or appliers, one or more ultrasound tissue disruptors, cryotomes, or cutting laser guides, or one or more measurement devices (e.g., rulers, calipers, or the like), and/or the like. Alternatively, or additionally, the one or more surgical tools 630a might, specific to CBC implantation, include, without limitation, an introducer, a guidewire, a transseptal needle, a syringe and manifold system, a high-density mapping catheter (e.g., Achieve™ or Achieve Advance™ mapping catheter, or the like), and/or the like.

In some cases, the one or more surgical tools might include one or more first surgical tools including, without limitation, at least one of one or more graspers (e.g., forceps, or the like), one or more clamps or occluders, one or more needle drivers or needle holders, one or more retractors, one or more distractors, positioners or stereotactic devices, one or more mechanical cutters (e.g., scalpels, lancets, drill bits, rasps, trocars, harmonic scalpels, surgical scissors, rongeurs, or the like), one or more irrigation or injection needles, tips, or tubes, one or more dilators or specula, or one or more suction tips or tubes, and/or the like.

In some instances, the one or more surgical tools might include one or more second surgical tools including, without limitation, at least one of one or more powered devices (e.g., drills, dermatomes, or the like), one or more scopes or probes (e.g., fiber optic endoscopes, tactile probes, or the like), one or more optical, electrical, or mechanical device carriers or appliers, one or more ultrasound tissue disruptors, cryotomes, or cutting laser guides, and/or the like. In some cases, the one or more surgical tools might include one or more third surgical tools including, without limitation, at least one of one or more sealing devices (e.g., surgical staplers, or the like) or one or more measurement devices (e.g., rulers, calipers, or the like), and/or the like.

In some instances, the navigation system 630b might include mapping and navigation systems including, but not limited to, at least one of an electroanatomic mapping ("EAM") system, an electromagnetic ("EM") mapping and/or navigation system, a radiofrequency identification ("RFID") mapping and/or navigation system, an impedance-based mapping and/or navigation system, an ultrasound ("US") mapping and/or navigation system, an optical mapping and/or navigation system, a high-density mapping catheter, one or more patient patches, or navigation hardware and software, and/or the like. According to some embodiments, the XR system 630c might include, without limitation, at least one of an XR headset, a set of XR goggles, a pair of XR-enabled eyewear, an XR-enabled smartphone mounted in a headset, an XR helmet, a mixed reality ("MR") headset, a set of MR goggles, a pair of MR-enabled eyewear, an MR-enabled smartphone mounted in a headset, an MR helmet, a virtual reality ("VR") headset, a set of VR goggles, a pair of VR-enabled eyewear, a VR-enabled smartphone mounted in a headset, a VR helmet, an augmented reality ("AR") headset, a set of AR goggles, a pair of AR-enabled eyewear, an AR-enabled smartphone mounted in a headset, or an AR helmet, and/or the like. In some instances, the XR system 630c might generate one or more XR experiences including, but not limited to, at least three or more of the one or more XR images, one or more XR sounds, one or more XR haptic or tactile responses, one or more XR simulated smells, or one or more XR simulated tastes, and/or the like, in some cases, based at least in part on the mapping performed by the navigation system 630b.

In some cases, the one or more XR devices might include one or more first XR devices including, without limitation, at least one of an XR headset, a set of XR goggles, a pair of XR-enabled eyewear, or an XR-enabled smartphone mounted in a headset, an XR helmet, and/or the like. In some instances, the one or more XR devices might include one or more second XR devices including, without limitation, at least one of a MR headset, a set of MR goggles, a pair of MR-enabled eyewear, an MR-enabled smartphone mounted in a headset, an MR helmet, and/or the like. In some cases, the one or more XR devices might include one or more third XR devices including, without limitation, at least one of a VR headset, a set of VR goggles, a pair of VR-enabled eyewear, a VR-enabled smartphone mounted in a headset, or a VR helmet, and/or the like. In some instances, the one or more XR devices might include one or more fourth XR devices including, without limitation, at least one of an AR headset, a set of AR goggles, a pair of AR-enabled eyewear, an AR-enabled smartphone mounted in a headset, or an AR helmet, and/or the like.

According to some embodiments, the one or more XR images might be dynamic images, which might include an overlay of data models depicting at least one of electrical pulses, blood flow, tissue movement, damage, stress, and/or the like, and thus may not be a still frame in 3D.

In some embodiments, the secondary equipment 615 might include, without limitation, at least one of a computed tomography ("CT") machine, an electrophysiology ("EP") system 635b, a fluoroscopy system 635c, a monitoring catheter 635d, or respiratory equipment 635e, and/or the like.

For implantation within the body of a patient 625, the CBC implant 620c might be implanted using the deployment device 620b via the deflectable or steerable sheath 620a into the heart of the patient 625. The deflectable or steerable sheath 620a (e.g., FlexCath Advance steerable sheath, or the like) is configured to provide deflection (e.g., between 0 and 180 degrees, or more) to control the angle of insertion into the heart, while the dilator facilitates introduction of the sheath into the vasculature of the heart. Prior to using the deployment device 620b or the deflectable or steerable sheath 620a, the patient 625 might be anesthetized and connected to the respiratory equipment 635e, while being monitored by at least one of the CT machine 635a, the EP system 635b, the fluoroscopy system 635c, or the monitoring catheter 635d, and/or the like. The navigation system 630b tracks the position and movement of the one or more surgical tools, as well as those of the deflectable or steerable sheath 620a, the deployment device 620b, and/or the CBC 620c, as the healthcare or medical professional—who is guided by data presented via the XR system 630c, including the tracking data, patient date, imaging data, and/or the like—performs the operation, using the surgical tools, the deflectable or steerable sheath 620a, and the deployment device 620b to implant the CBC 620c into the heart of the patient 625.

Merely by way of example, in some cases, a CBC 620c may be customized with the following features: (a) CBC-Monitor telemetry (including, without limitation, one of Bluetooth™ communication, capacitive intrabody coupling, galvanic coupling, Internet of things ("IoT") communication, cellular communication, radio-frequency ("rf") communication, or telemetry AB/C, and/or the like); (b) CBC fixation (including, but not limited to, hook tines, liquid adhesive dispense, or corkscrew tines, and/or the like); (c) CBC to navigation signal (including, without limitation, wireless electrodes to monitor, electrodes triangulated to external patch, or visibility before deployment (wired), and/or the like); (d) deployment mechanism (including, but not limited to, slide, twist, slide-and-lock, or push button, and/or the like); (e) sheath deflection mechanism (including, without limitation, twist knob or back and forth lever, and/or the like); and (f) CBC to deployment attachment (including, but not limited to, pleated fold, vertical roll, wrap with sleeve, or memory matrix, and/or the like); or the like.

According to some embodiments, to select a particular non-limiting design for the CBC implant, down selection was performed based on the following criteria: (i) ability to meet stakeholder needs; (ii) cost; (iii) predicted reliability of final system; (iv) predicted safety of final system; (v) ability to meet certain system conditions and project timelines; and/or the like. Rankings were applied to each concept criteria and scores were summed, both unweighted and weighted by criteria importance. The result of such selection was a CBC implant with the following features: (A) Bluetooth as a means of telemetry between the CBC implant 620c and the monitor 620d; (B) hook tines (e.g., ones that are distributed in a density of 1 per square mm, or the like) for CBC to native tissue fixation mechanism; (C) an external patch for triangulation of electrodes signals from the CBC 620c for navigation system 630b visibility after the CBC 620c is freed from the deployment device 620b; (D) a slide-and-lock deployment device mechanism; (E) a twist knob type sheath deflection steering mechanism that maintains its position via friction; and (F) a pleated fold design of the CBC 620c to facilitate attachment to a distal tip of the deployment device 620b.

Turning to the non-limiting example 600' of FIG. 6B, functional blocks are shown that depict stages of deployment of the CBC implant 620c. At block 640, a steering subsystem 645 (including, but not limited to, a shaft 645a, a first pullwire 645b, and a second pullwire 645c, or the like) may be coupled with a handle subsystem 650 (including, without limitation, a handle shell 650a and a deflection mechanism 650b)—particularly, with the shaft 645a coupled with the handle shell 650a. A pressure subsystem (including, but not limited to, a flush line 655a and a hemostasis valve 655b) may also be coupled with the handle subsystem—particularly, with the flush line 655a coupled with the handle shell 650a. The deflection mechanism 650b—which might provide the mechanism for controlling the amount of deflection of the deflectable or steerable sheath 620a—and the hemostasis valve 655b—which might allow for introduction, withdrawing, or swapping of catheters and guide wires, while preventing air ingress and minimizing blood loss—may both be part of, integrated with, or affixed to the handle shell 650a. With such configuration, the sheath may be navigated to a target location (e.g., the heart of the patient 625, or the like).

At block 660, CBC implant 665 (such as CBC implant 620c, or the like) may be captured by a capture device 670a of a handle subsystem 670 (which might include, without limitation, the capture device 670a and a shaft 670b, or the like). A handle shell 675a of a steering subsystem 675 (which might include, but is not limited to, the handle shell 675a, a deflection mechanism 675b, and a deployment mechanism 675c, or the like) may be coupled with the shaft 670b of the handle subsystem 670, in some cases, using frictional force. With such configuration, the CBC 665 may be attached to the deployment device.

At block 680, the handle subsystem 670 (with the captured or attached CBC 665) may be coupled with the handle subsystem 650 via the hemostasis valve 655b. With such configuration, the deployment device may be inserted through the sheath.

At block 685, using the steering subsystem 675 and the handle subsystem 670, the device tip (i.e., capture device 670a) with the CBC 665 may be exposed to the heart of the patient 625. By actuating the slide lever of the capture device 670a, the CBC 665 may be deployed. The healthcare or medical professional may then verify attachment of the CBC 665 in the heart of the patient 625.

Although particular example applications are provided above (such as particular equipment for CBC implantation in the heart of the patient, or the like), the various embodiments are not so limited, and the IA ecosystem may utilize any type of device, instrument, or equipment as appropriate or as desired to perform any suitable medical procedure or application (not limited to CBC implantation in the heart of the patient; e.g., implantation of other devices in the heart (e.g., pacemaker, or the like) or in other parts of the body of the patient (e.g., insulin pumps, insulin monitors, drug delivery systems, implantable health monitors, or the like), and may also utilize any type of patient sensor or monitor, as well as any type of navigation or mapping system, as appropriate or as desired.

Figure 7A:
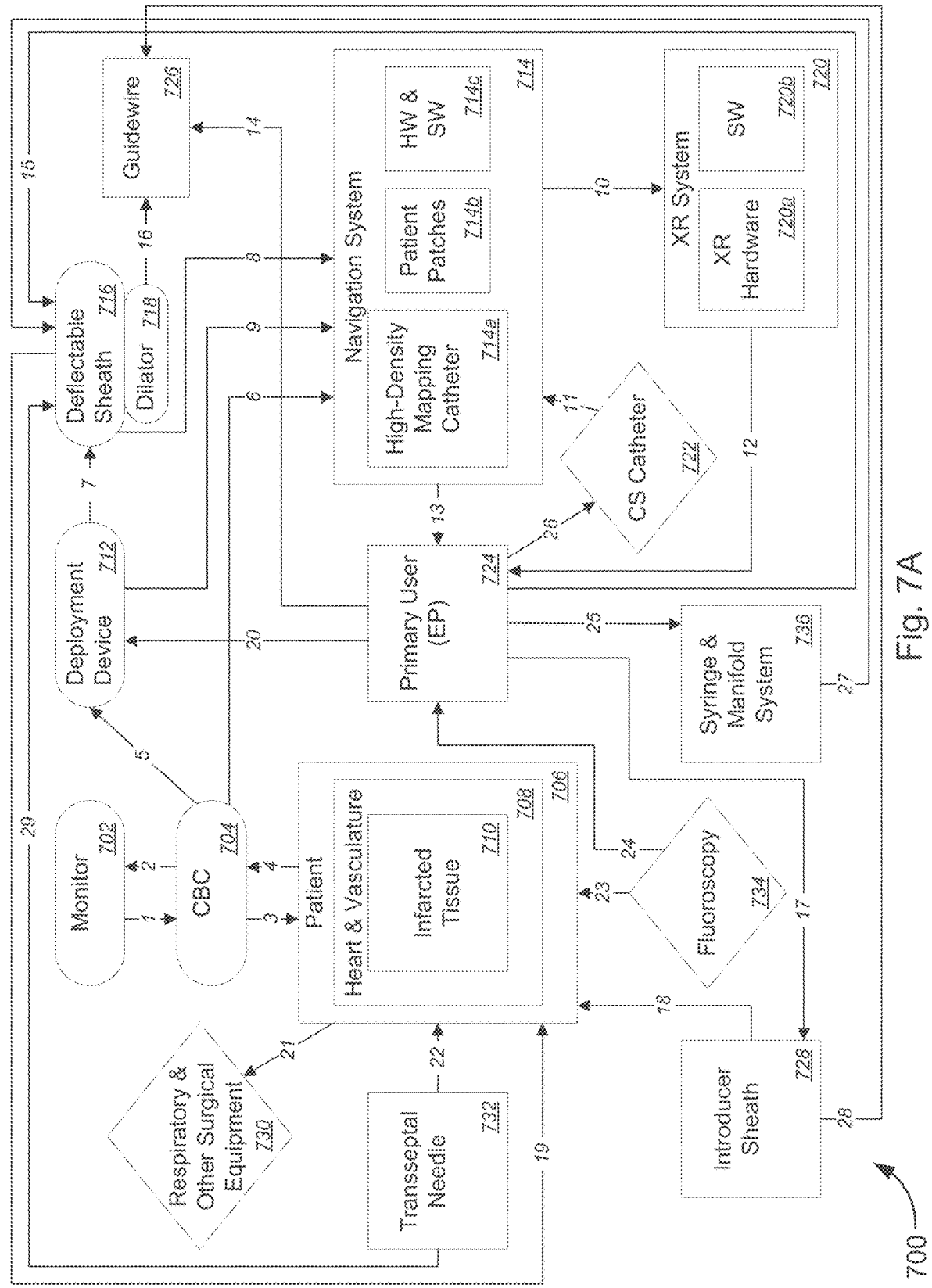
FIGS. 7A and 7B are schematic diagrams illustrating various system flows illustrating various non-limiting examples of implementing a heart procedure or performing information exchange using an IA ecosystem, in accordance with various embodiments.
Figure 7B:
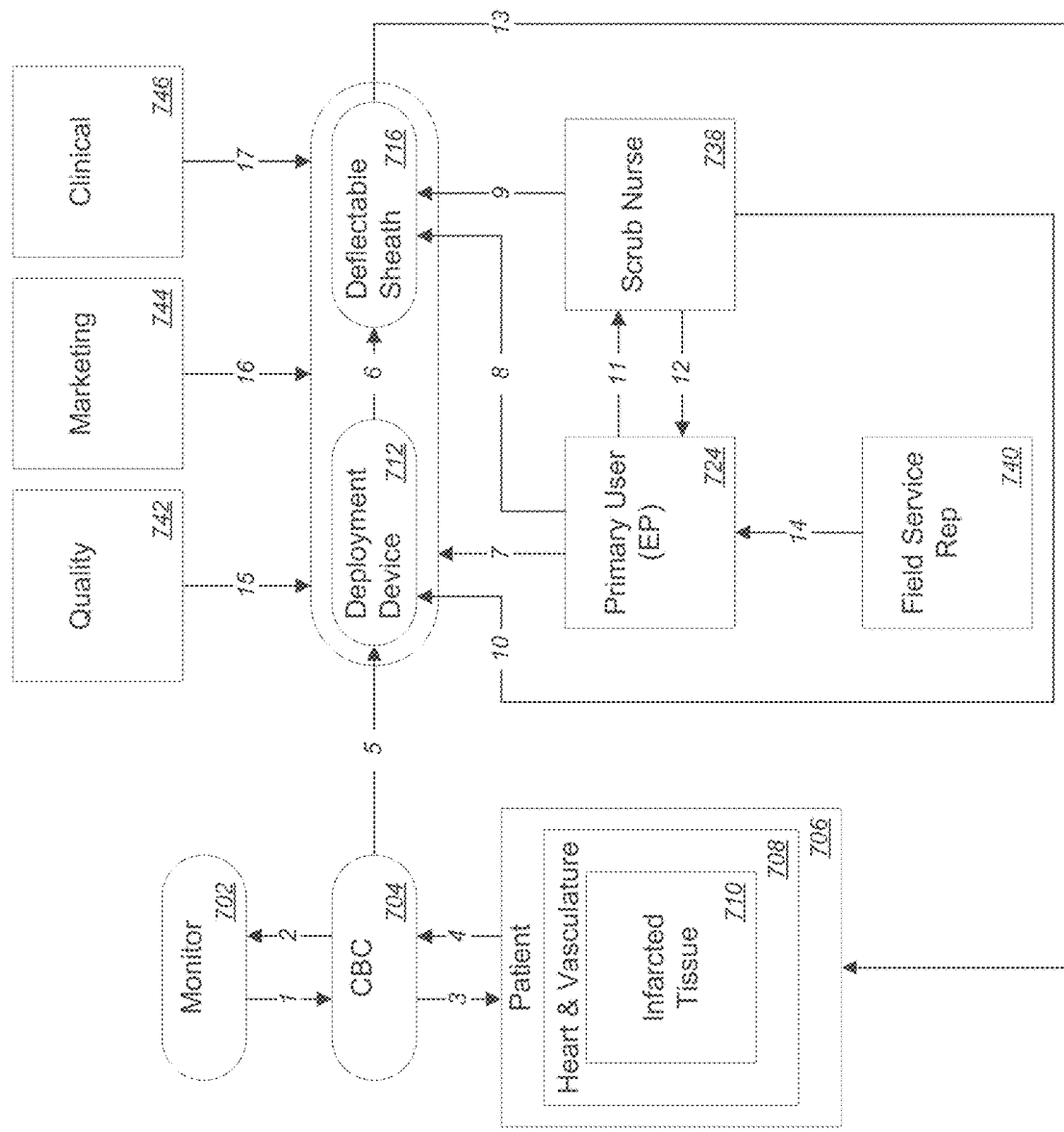

FIGS. 7A and 7B (collectively, "FIG. 7") are schematic diagrams illustrating various system flows illustrating various non-limiting examples 700 and 700' of implementing a heart procedure or performing information exchange using an IA ecosystem, in accordance with various embodiments. Process steps in FIG. 7 are denoted by numbered arrows corresponding to the process step numbers.

With reference to the non-limiting example 700 of FIG. 7A, monitor 702, which is a telemetry device, might interact with sensors (including, but not limited to, electrical, pressure, and/or temperature sensors, or the like) on a cardiac bionic construct ("CBC") implant 704. At Step #1, the monitor 702 might send messages to the CBC implant 704 for sensor activation. At Step #2, the CBC sensors might wirelessly send data (e.g., electrical, pressure, and/or temperature data, or the like) to the monitor 702. At Step #3, the CBC implant 704 might be implanted into the patient 706, over dead or damaged endocardial tissue (i.e., within the heart and vasculature 708, in the infarcted tissue 710, or the like). At Step #4, the patient 706 might accept the CBC implant 704 and the native anatomy might merge with the CBC implant 704, engrafting over time.

For the implantation process itself, at Step #5, the CBC implant 704 may be securely connected to a distal tip of a deployment device 712. At Step #6, the CBC implant 704 might connect with and send signals (including, but not limited to electrical sensor data, or the like) to navigation system 714 (which might include, without limitation, a high-density mapping catheter 714a (e.g., Achieve™ or Achieve Advance™ mapping catheter, or the like), an electroanatomic mapping ("EAM") system, an electromagnetic ("EM") mapping and/or navigation system, a radiofrequency identification ("RFID") mapping and/or navigation system, an impedance-based mapping and/or navigation system, an ultrasound ("US") mapping and/or navigation system, an optical mapping and/or navigation system, one or more patient patches, and hardware ("HW") and software ("SW"), or the like) for visualization of the CBC implant 704 within the anatomy of the patient 706, in some cases, via impedance triangulation, or the like.

In some cases, the one or more navigation systems might include one or more first navigation systems including, without limitation, a high-density mapping catheter 714a, a RFID mapping and/or navigation system, an impedance-based mapping and/or navigation system, a US mapping and/or navigation system, an optical mapping and/or navigation system, or one or more patient patches, and/or the like.

In some instances, the one or more navigation systems might include one or more second navigation systems including, without limitation, at least one of an EAM system, an EM mapping and/or navigation system, and/or the like.

In some cases, the one or more navigation systems might include one or more third navigation systems including, without limitation, HW and SW, and/or the like.

At Step #7, the deployment device 712 may be inserted into, and may physically interact with, a deflectable or steerable sheath 716. At Step #8, the deflectable or steerable sheath might send signals (including, but not limited to, electrical sensor data from tip electrodes of the deflectable or steerable sheath 716, or the like) to the navigation system 714 for visualization of the deflectable or steerable sheath 716 within the anatomy of the patient 706, in some cases, via impedance triangulation, or the like. At Step #9, the deployment device might likewise send signals (including, but not limited to, electrical sensor data from tip electrodes of the deployment device 712, or the like) to the navigation system 714 for visualization of the deployment device 712 within the anatomy of the patient 706, in some cases, via impedance triangulation, or the like. At Step #10, the navigation system 714 might send visual information to extended reality ("XR") system 720 (which might include, without limitation, XR hardware 720a and software 720b, or the like) for an augmented reality ("AR") or XR view of the heart 708 of the patient 706.

At Step #10, a coronary sinus ("CS") catheter 722 (e.g., Torqr™ CS diagnostic catheter, Marinr™ CS mapping catheter, or the like) might send signals (including, but not limited to, electrode data, or the like) to the navigation system 714 for visualization of the CS catheter 722 within the anatomy of the patient 706, in some cases, via impedance triangulation, or the like. At Step #12, a primary user 724 (such as a medical or healthcare professional including, without limitation, a doctor, surgeon, an electrophysiologist ("EP"), or the like) might wear an XR headset (which may be part of the XR hardware 720a of the XR system 720), to view three-dimensional ("3D") images or videos or four-dimensional ("4D") images or videos (i.e., 3D images or videos plus at least one of real-time updates, dynamic modeling, or data streaming, and/or the like) of the heart 708 during the procedure. At Step #13, the primary user 724 might interpret information from the navigation system 714 throughout the procedure.

At Step #14, the primary user 724 might manipulate a guidewire 726 into the anatomy for safe wiring of devices. At Step #15, the primary user 724 might manipulate the deflectable or steerable sheath 716 with respect to an introducer sheath 728 (deployable via dilator 718) and the deployment device 712, both axially and rotationally. At Step #16, the primary user 724 might manipulate the deployment device 712 with respect to the CBC 704 and deflectable or steerable sheath 716, both axially and rotationally for a successful introduction and deployment of the CBC implant 704. At Step #17, the primary user 724 might place the introducer sheath 728 (which, in some cases, might have a (French) size of 18 Fr, or the like) at a femoral access site of the patient 706. At Step #18, the dilator 718 (within the deflectable or steerable sheath 716) may be tracked over the guidewire 726 for safe introduction of the introducer sheath 728 into the anatomy. At Step #19, the deflectable or steerable sheath 716 may be inserted into the patient 706 and may be navigated throughout the four chambers of the heart 708, as needed. The deflectable or steerable sheath 716 provides the length to reach the target implant location, while also providing refined steering capabilities. At Step #20, the introducer sheath 728 may be inserted into the patient 706 and may be statically seated with the right femoral vein. At Step #21, all other surgical equipment 730 (including, but not limited to, respirators, heart monitors, and anesthesia machines, or the like) may continually monitor the patient 706 via direct lines or with the help of secondary users (including, but not limited to, nurses, scrub technicians, or the like).

At Step #22, a transseptal needle 732 may be used to perform a puncture within the patient's interatrial septum to reach the left side of the heart 708, if needed. At Step #23, a fluoroscopy machine 734 might emit X-rays to the patient 706 for supplementary visualization of the anatomy and radiopaque devices within (such as a radiopaque marker in the deflectable or steerable sheath 716, or the like). At Step #24, the primary user 724 might interpret the images from fluoroscopy to help guide treatment decisions. At Step #25, the primary user 724 might control a syringe and manifold system 736 to maintain a flush and clear embolus. At Step #26, the primary user 724 might place the monitoring catheter in the CS catheter 722 for monitoring baseline atrial and ventricular signals throughout the procedure. At Step #27, the syringe and manifold system might be connected to the deflectable or steerable sheath 716 for aspiration and flushing to prevent clot formation. At Step #28, the guidewire 726 may be inserted into the introducer sheath 728 for tracking in the deflectable or steerable sheath 716. At Step #29, the transseptal needle 732 may be inserted into the deflectable or steerable sheath 716 to perform the transseptal puncture (both must be compatible to prevent skiving). In this manner, the CBC 704 may be implanted in the infarcted tissue 710 of the heart 708 of the patient 706.

Turning to the non-limiting example 700' of FIG. 7B, monitor 702, which is a telemetry device, might interact with sensors (including, but not limited to, electrical, pressure, and/or temperature sensors, or the like) on a CBC implant 704. At Step #1, the monitor 702 might send messages to the CBC implant 704 for sensor activation. At Step #2, the CBC sensors might wirelessly send data (e.g., electrical, pressure, and/or temperature data, or the like) to the monitor 702. At Step #3, the CBC implant 704 might be implanted into the patient 706, over dead or damaged endocardial tissue (i.e., within the heart and vasculature 708, in the infarcted tissue 710, or the like). At Step #4, the patient 706 might accept the CBC implant 704 and the native anatomy might merge with the CBC implant 704, engrafting over time.

For the implantation process itself, at Step #5, the CBC implant 704 may be securely connected to a distal tip of a deployment device 712. At Step #6, the deployment device 712 may be inserted into, and may physically interact with, a deflectable or steerable sheath 716. At Step #7, the primary user 724 might manipulate the deflectable or steerable sheath 716 with respect to an introducer sheath (deployable via dilator) and the deployment device 712, both axially and rotationally. At Step #8, the primary user 724 might manipulate the deployment device 712 with respect to the CBC 704 and deflectable or steerable sheath 716, both axially and rotationally for a successful introduction and deployment of the CBC implant 704.

At Step #9, a scrub nurse 738 may help in manipulating the deflectable or steerable sheath 716 with respect to the introducer sheath and the deployment device 712, both axially and rotationally. The scrub nurse 738 may also keep track of hospital inventory of the deflectable or steerable sheath 716, may organize purchasing of the deflectable or steerable sheath 716, may dispose of the deflectable or steerable sheath 716 after use, may report any issues with the deflectable or steerable sheath 716, and may return the deflectable or steerable sheath 716 to the manufacturer (if needed). In some cases, the tracking of hospital inventory of the deflectable or steerable sheath 716 may be performed by XR tool tracking, image recognition, and/or the like. At Step #10, the scrub nurse 738 may help in manipulating the deployment device 712 with respect to the CBC implant 704 and the deflectable or steerable sheath 716, both axially and rotationally, for a successful introduction and deployment of the CBC implant 704. The scrub nurse 738 may also keep track of hospital inventory of the deployment device 712, may organize purchasing of the deployment device 712, may dispose of the deployment device 712 after use, may report any issues with the deployment device 712, and may return the deployment device 712 to the manufacturer (if needed). At Step #11, the primary user 724 may communicate verbally with the scrub nurse, giving instructions. At Step #12, the scrub nurse 738 may communicate verbally with the primary user 724, with confirmations of messages as well as providing status updates regarding the patient 706. In some instances, the XR/AI system can anonymize people and/or data sheets being viewed for privacy, security, and/or the like.

At Step #13, the deflectable or steerable sheath 716 may be inserted into the patient 706 and may be navigated throughout the four chambers of the heart 708, as needed. The deflectable or steerable sheath 716 provides the length to reach the target implant location, while also providing refined steering capabilities. At Step #14, a field service representative (or rep) 740 of the manufacturer may watch the manipulations of the deflectable or steerable sheath 716 and the deployment device 712 by the primary user 724, noting any problems and answering any questions. At Step #15, a quality group 742 of the manufacturer may track issues and complaints regarding the deflectable or steerable sheath—deployment device system during use. At Step #16, a marketing group 744 of the manufacturer may track issues and/or positive feedback of the deflectable or steerable sheath—deployment device system during use for post-market validation of stakeholder needs. At Step #17, a clinical group 746 of the manufacturer might track clinical performance and might gather clinical data for any internal or external sponsored research studies to support procedural device performance and efficacy.

Although particular example applications are provided above (such as particular system and components for implementing CBC implantation in the heart of a patient, or the like), the various embodiments are not so limited, and the IA ecosystem may utilize any type of device, instrument, or equipment as appropriate or as desired to perform any suitable medical procedure or application (not limited to CBC implantation or even heart procedures), and may also utilize any type of patient sensor or monitor, as well as any type of navigation or mapping system, as appropriate or as desired.

Figure 8A:
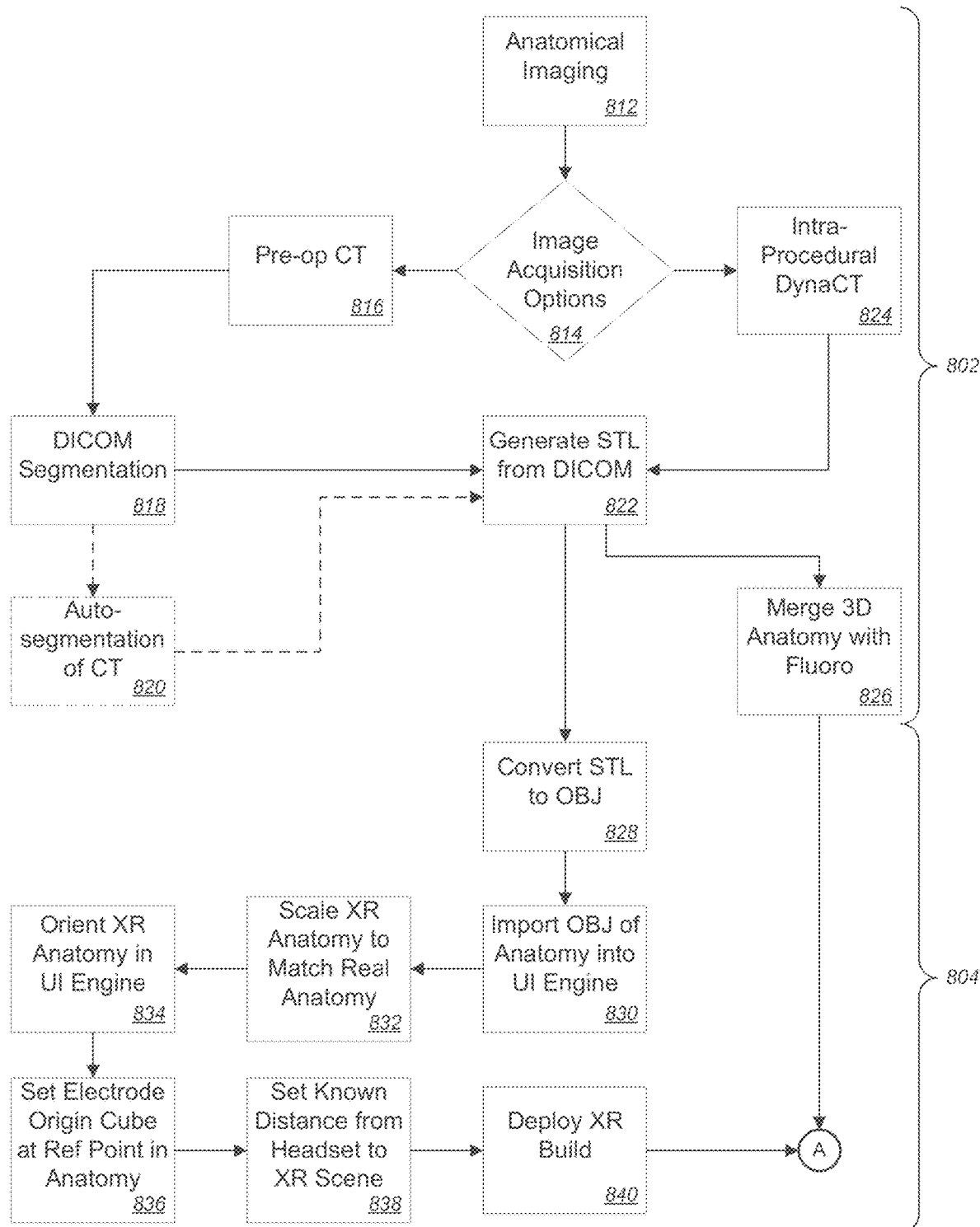
FIGS. 8A and 8B is a flow diagram illustrating a method illustrating a non-limiting example of a preclinical workflow for implementing an IA ecosystem, in accordance with various embodiments.
Figure 8B:
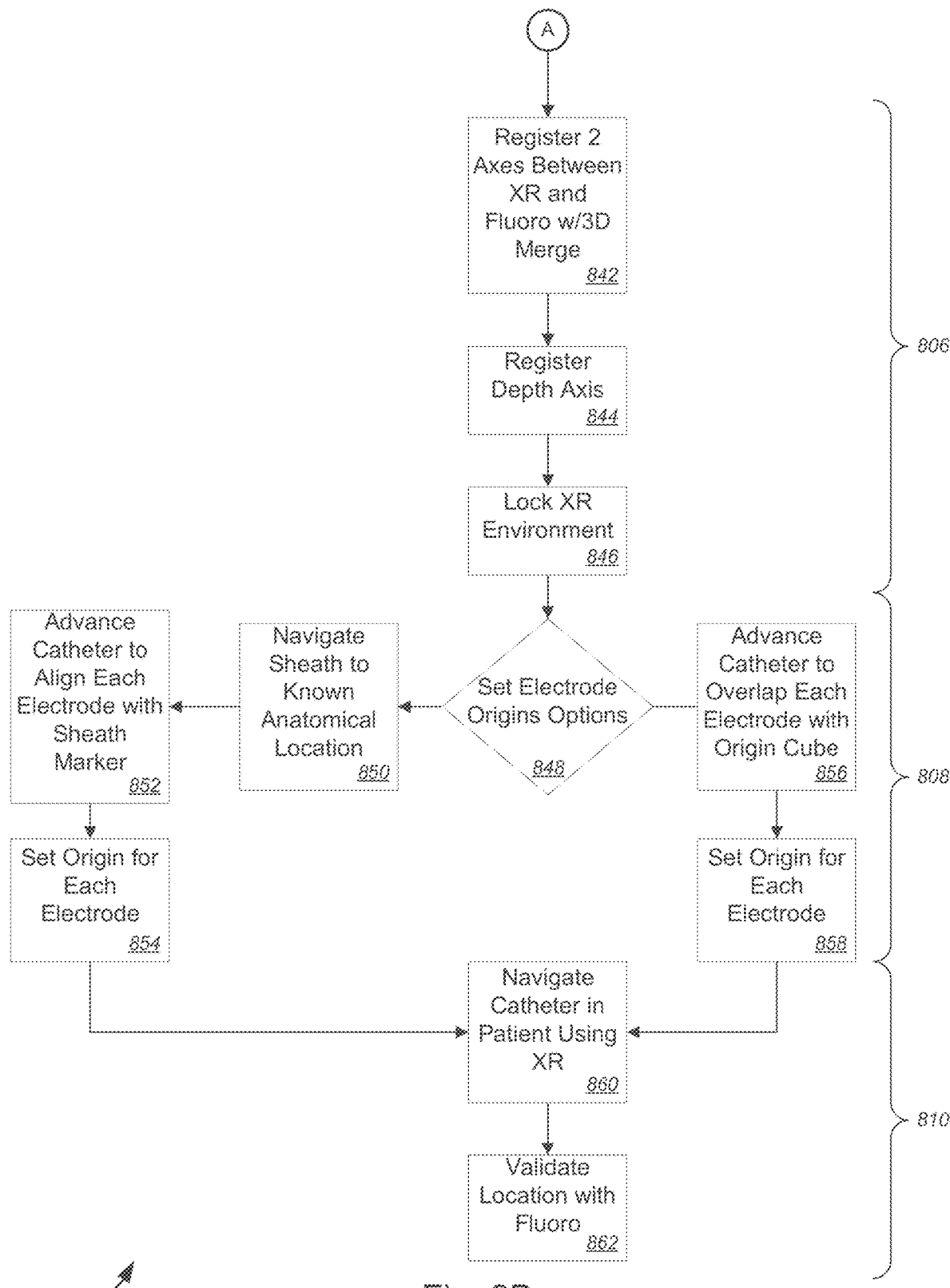

FIGS. 8A and 8B (collectively, "FIG. 8") is a flow diagram illustrating a method 800 illustrating a non-limiting example of a preclinical workflow for implementing an IA ecosystem, in accordance with various embodiments.

In the non-limiting embodiment of FIG. 8, the preclinical workflow for implementing an IA ecosystem might comprise preclinical process steps including, without limitation, anatomical image acquisition 802, extended reality ("XR") integration 804, XR/fluoroscopy (or "fluoro") registration 806, navigation origin calibration 808, and anatomical navigation position validation 810, and/or the like.

With regard to anatomical image acquisition 802, method 800 might begin with initiation or selection of anatomical imaging (at block 812). At block 814, method 800 might comprise providing image acquisition options, which might include, but are not limited to, pre-procedural computed tomography ("CT") imaging or intra-procedural CT imaging, and/or the like. For example, if a user selects the pre-procedural CT option, then the process would continue to block 816, where pre-procedural CT would be implemented. The process would continue onto block 818, at which method 800 might comprise implementing digital imaging and communications in medicine ("DICOM") segmentation, which, in some cases, would involve implementing auto-segmentation of CT images (at optional block 820). Herein, DICOM refers to the standard for communication and management of medical imaging information and related data. The process would then continue onto block 822, where a stereolithography ("STL") file (which is also referred to as "STL model" or ".stl file" or the like) is generated from a DICOM file after DICOM segmentation performed (at block 820) for pre-procedural CT. Herein, stereolithography generally refers to a form of 3D printing technology used for creating models, prototypes, patterns, and components, or the like, while STL file may refer to a standard 3D image format that describes surface geometry of a 3D structure (and although STL files once arose from use in stereolithography implementations, STL files are not limited to such, and can be used for any 3D rendering or the like). Rather than STL files, alternative 3D file formats may be used, including, but not limited to, filmbox ("FBX") format, which is a 3D data interchange format used to provide interoperability between digital content creation applications (e.g., 3D editors, 3D graphics engines, etc.); graphics language transmission format ("glTF"), which is a standard file format for 3D scenes and models; or graphics language binary ("GLB") format, which is a binary file format representation of 3D models saved in glTF; OBJ file format (described below); or the like.

Alternatively, if the user selects the intra-procedural CT imaging option (such as, but not limited to, intra-procedural Dyna-CT, or the like), then the process would continue from block 814 to block 824, where intra-procedural CT would be implemented, in some cases, including implementing a fluoroscopy sweep for three-dimensional ("3D") anatomy images. Herein fluoroscopy (or "fluoro") sweep refers to, rather than using a 2D fluoro shot, utilizing biplanar fluoro to sweep across the anatomy to obtain a stack of 2D images that are subsequently compiled into a single 3D model, with pertinent anatomy segmented, that is used as an input model into a XR headset, displaying registered 3D model of anatomy with catheter navigation. Knowing the catheter electrode spacing and size, the model can touch off on landmarks until the model is locked in XR and no more fluoro is needed. The process would continue onto block 822, at which method 800 might comprise generating a STL file from a DICOM file that is produced during the intra-procedural CT (at block 824). At block 826, method 800 might comprise merging 3D anatomy images (e.g., from the STL file) with fluoroscopy images. The process would then continue onto the process at block 842 in FIG. 8B, corresponding to the start of XR/Fluoro registration 806, following the circular marker denoted, "A," thereby skipping XR integration 804. Alternatively, the process would continue onto the process at block 828, corresponding to the start of XR integration 804.

For XR integration 804—which may be used to merge devices and anatomy and to orient the devices and anatomy (whether individually or merged) in 3D space—method 800 might comprise, at block 828, converting the STL file (which is generated at block 822) to an OBJ file (which is also referred to as "OBJ model," "Wavefront OBJ file" or ".obj file" or the like). Herein, OBJ file generally refers to a standard 3D image format that can be exported and opened by various commercial 3D image editing programs. As mentioned above, other 3D file formats (including, but not limited to, FBX format, glTF, or GLB format, or the like) may be used instead of an OBJ file format. At block 830, method 800 might comprise importing the OBJ file of the anatomy into a user interface ("UI") engine (which might include, but is not limited to, a 3D content engine, a cross-platform 3D content engine (e.g., Unity™ engine, Unreal® engine, or the like), an XR engine, a VR engine, an AR engine, a MR engine, and/or the like). In some embodiments, the UI engine combines together rendering functionalities, user interface functionalities, user control functionalities, realistic physics functionalities (e.g., gravity, directionality, etc.), and/or the like, for integrating XR models, images, or experiences. Method 800, at block 832, might comprise scaling the XR anatomy to match real anatomy, in some cases, based on the fluoroscopy measurements. Method 800 might further comprise orienting the XR anatomy in the UI engine (at block 834), in some cases, in the same position as one of the fluoroscopy angles. At block 836, method 800 might comprise setting an electrode origin cube at a reference point in the anatomy (e.g., at the left superior pulmonary vein ("LSPV"), at left inferior pulmonary vein ("LIPV"), or at some other anatomical location, or the like)). Method 800 might further comprise, at block 838, setting a known distance from the user's headset to the XR scene. Method 800 might further comprise deploying the XR build (at block 840). The process would then continue onto the process at block 842 in FIG. 8B, corresponding to the start of XR/Fluoro registration 806, following the circular marker denoted, "A."

With reference to XR/Fluoro registration and calibration 806, method 800, at block 842, might comprise registering two axes between the XR build and the fluoroscopy image with 3D merge, in some cases, using anatomical structures (e.g., on pulmonary veins ("PVs"), left atrial appendage ("LAA"), etc.). Method 800 might further comprise registering the depth axis (at block 844), in some cases, by measuring between a display screen and a headset based on known programmed distances, or the like. Method 800 might further comprise, at block 846, locking the XR environment.

For navigation origin calibration 808, method 800, at block 848, might comprise providing options for setting electrode origin, including, but not limited to, setting the electrode origin based on a sheath marker, or setting the electrode origin based on origin cube, or the like. For example, if the user selects the option to set the electrode origin based on a sheath marker, then the process would continue onto block 850, where method 800 might comprise navigating a sheath (with a radiopaque marker, or the like) to a known anatomical location while under fluoroscopy (similar to origin cube in XR environment, or the like). At block 852, method 800 might comprise advancing a catheter to align (in some cases, line-to-line) with the sheath marker. Method 800 might further comprise setting the origin for each electrode after (line-to-line) alignment with the sheath marker (at block 854). In such cases, the electrode must be fully outside the sheath. Alternatively, if the user selects the option to set the electrode origin based on origin cube, then the process would continue onto block 856, where method 800 might comprise advancing a catheter to overlap each electrode with the origin cube. Method 800 might further comprise setting the origin for each electrode after overlapping with the origin cube (at block 858). In either alternative, after setting the origin for each electrode (at block 854 or block 858), the process would continue onto block 860, corresponding to the start of anatomical navigation position validation 810.

Referring to anatomical navigation position validation 810, method 800, at block 860 might comprise navigating the catheter in the patient (e.g., in the left atrium ("LA"), or the like) using XR. At block 862, method 800 might comprise validating the location with fluoroscopy.

Although the method 800 of FIG. 8 has been described with examples of heart structures or parts, the various embodiments are not so limited, and method 800 may be applicable to imaging of other anatomical regions. Also, although specific references are made to file types (e.g., STL, OBJ, etc.), the various embodiments are not so limited, and the method 800 may utilize or convert any suitable file types (including, but not limited to, STL, OBJ, FBX, etc.). Further, although method 800 of FIG. 8 has referred to the use of fluoroscopy, the various embodiments are not so limited, and method 800 may instead utilize other imaging techniques, including, without limitation, ultrasound ("US") imaging, electroanatomic mapping ("EAM"), magnetic resonance imaging ("MRI"), and/or the like.

FIGS. 9A-9H (collectively, "FIG. 9") are schematic diagrams illustrating various non-limiting examples 900, 900', 900", 900''', 900'''', 900''''', 900'''''', and 900''''''' of process stacks for implementing an IA ecosystem, in accordance with various embodiments.

Figure 9A:
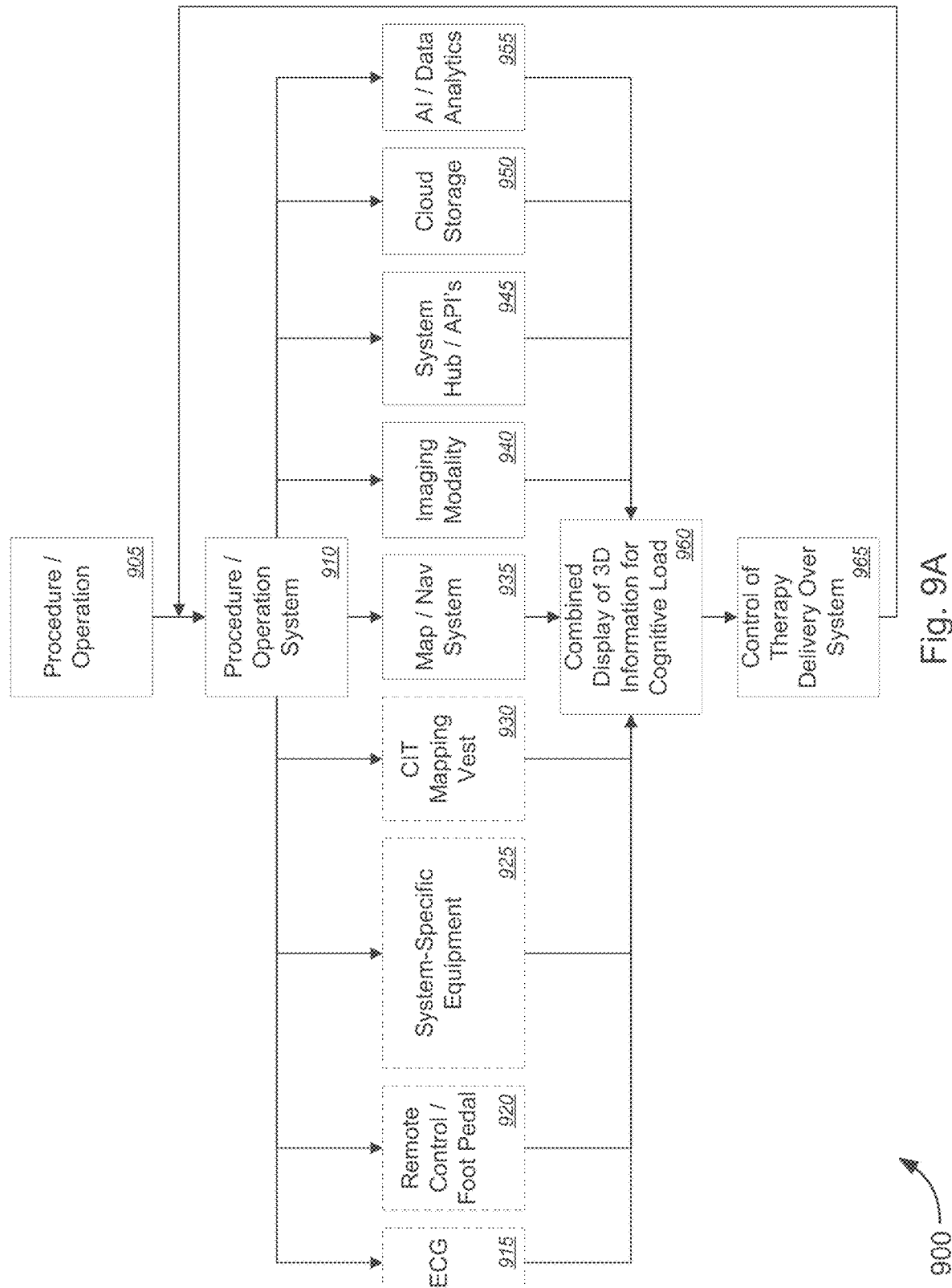

With reference to the non-limiting example 900 of FIG. 9A, a general process stack for implementing an IA ecosystem might begin with a selection of a procedure or operation (at block 905). In response to such selection, a corresponding procedure or operation system may be implemented (at block 910). The IA ecosystem might utilize, in conjunction with the procedure or operation system, a number of devices or equipment, sensors, imaging systems, and other systems (collectively, "sub-systems" or the like), including, but not limited to, at least one, two, or three of an electrocardiogram ("ECG") monitor (at optional block 915), a remote control and/or foot pedal (at optional block 920), system-specific equipment (at optional block 925), a mapping vest (e.g., CardioInsight™ ("CIT") mapping vest, or the like) (at optional block 930), a mapping and/or navigation system (at block 935), imaging modality (at block 940), a system hub and/or application programming interfaces ("API's") (at block 945), cloud storage (at block 950), or artificial intelligence ("AI") and/or data analytics (at block 955), and/or the like. In some cases, the mapping vest (e.g., CIT mapping vest, or the like) might be a single-use, disposable, multi-electrode vest that gathers cardiac electrophysiological data from the surface of the patient's body, with such data being combined with imaging data taken of the patient to produce and display simultaneous, bi-atrial and bi-ventricular 3D cardiac maps, or the like. Data from these sub-systems may be combined to generate a combined display of three-dimensional ("3D") information or four-dimensional ("4D") information (i.e., 3D information plus at least one of real-time updates, dynamic modeling, or data streaming, and/or the like) for cognitive load (at block 960). Such 3D or 4D information may be used to control therapy delivery over the system (at block 965). The process at blocks 910-965 may be repeated as necessary or as desired.

Figure 9B:
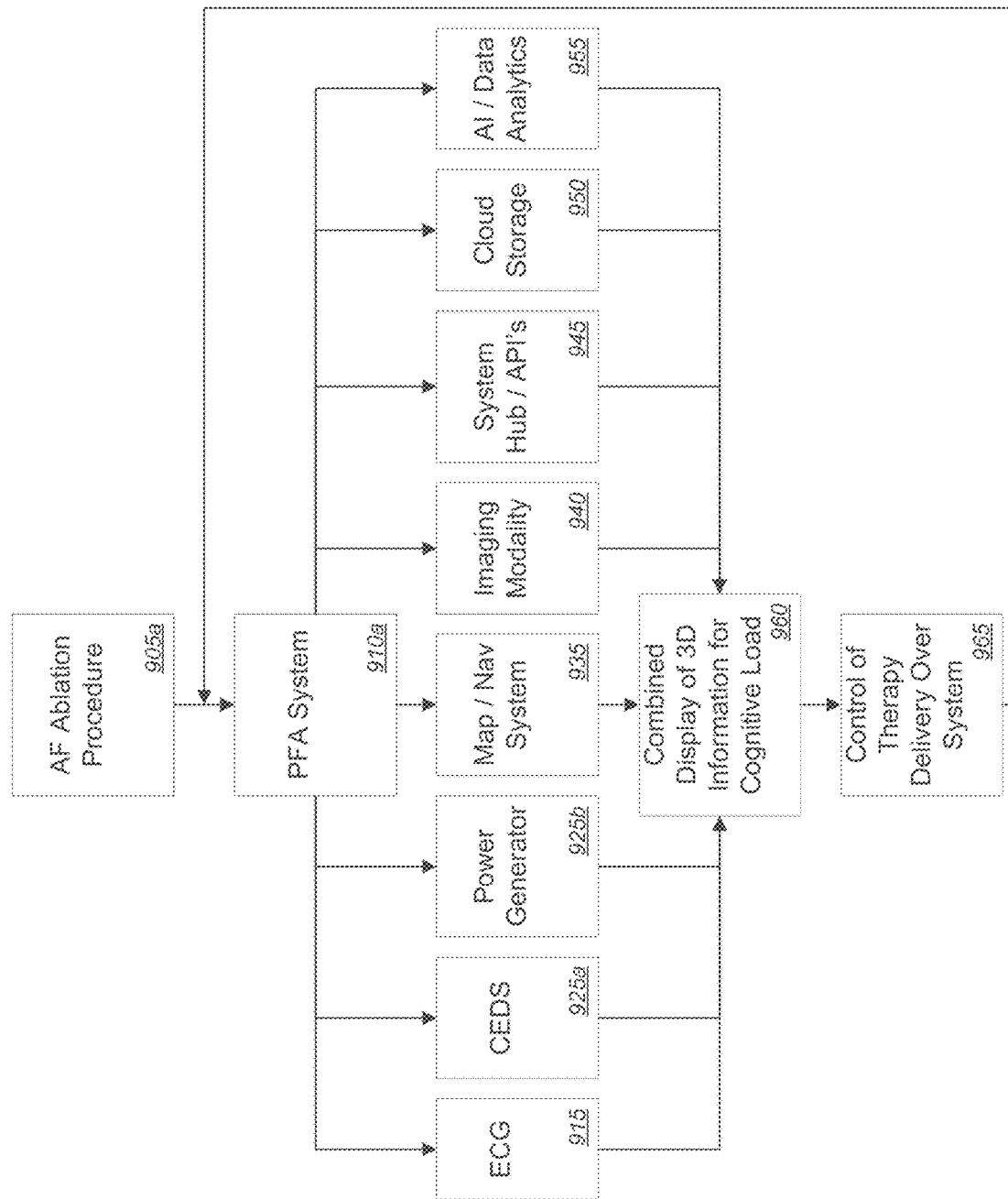
Figure 9C:
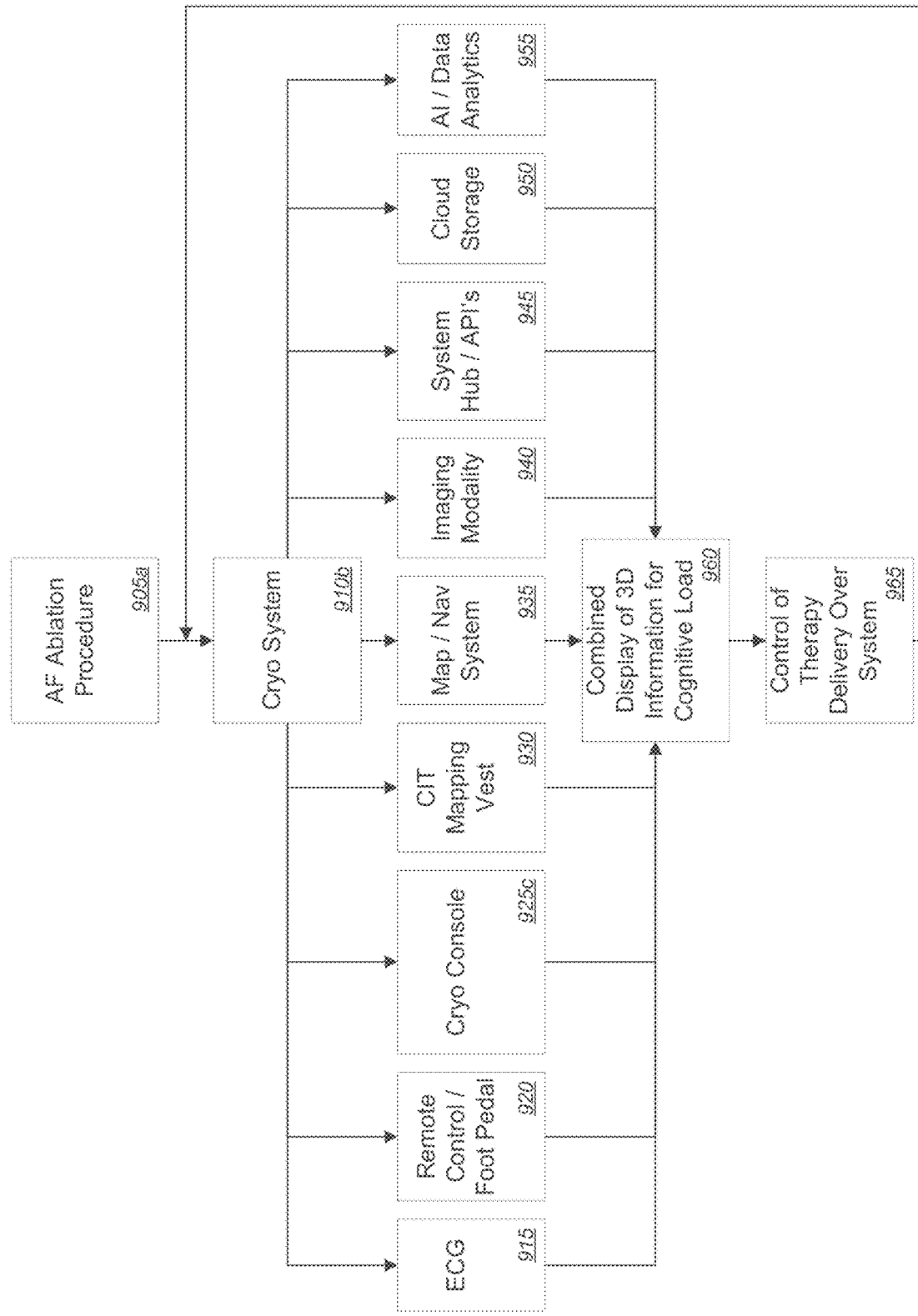
Figure 9E:
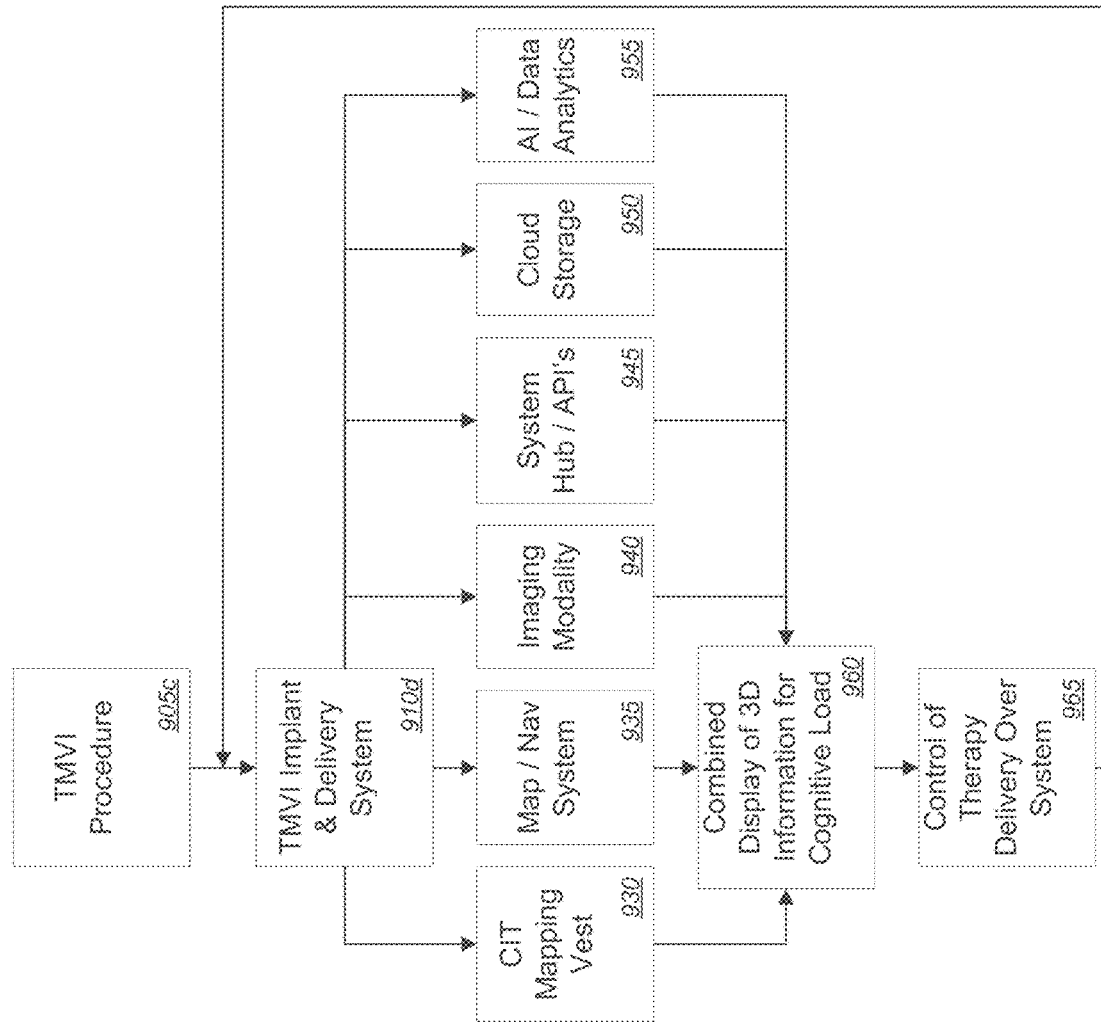
Figure 9F:
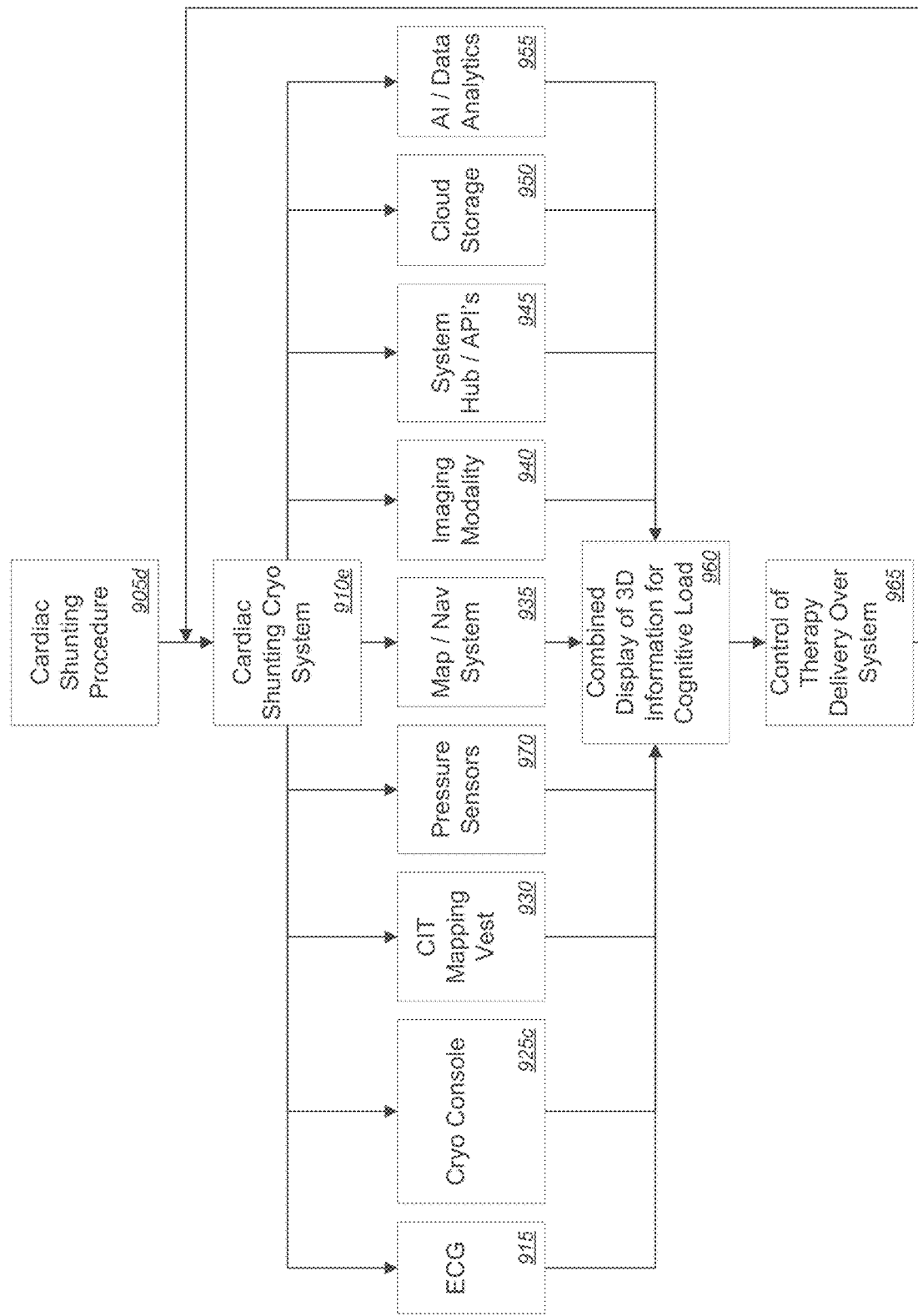
Figure 9G:
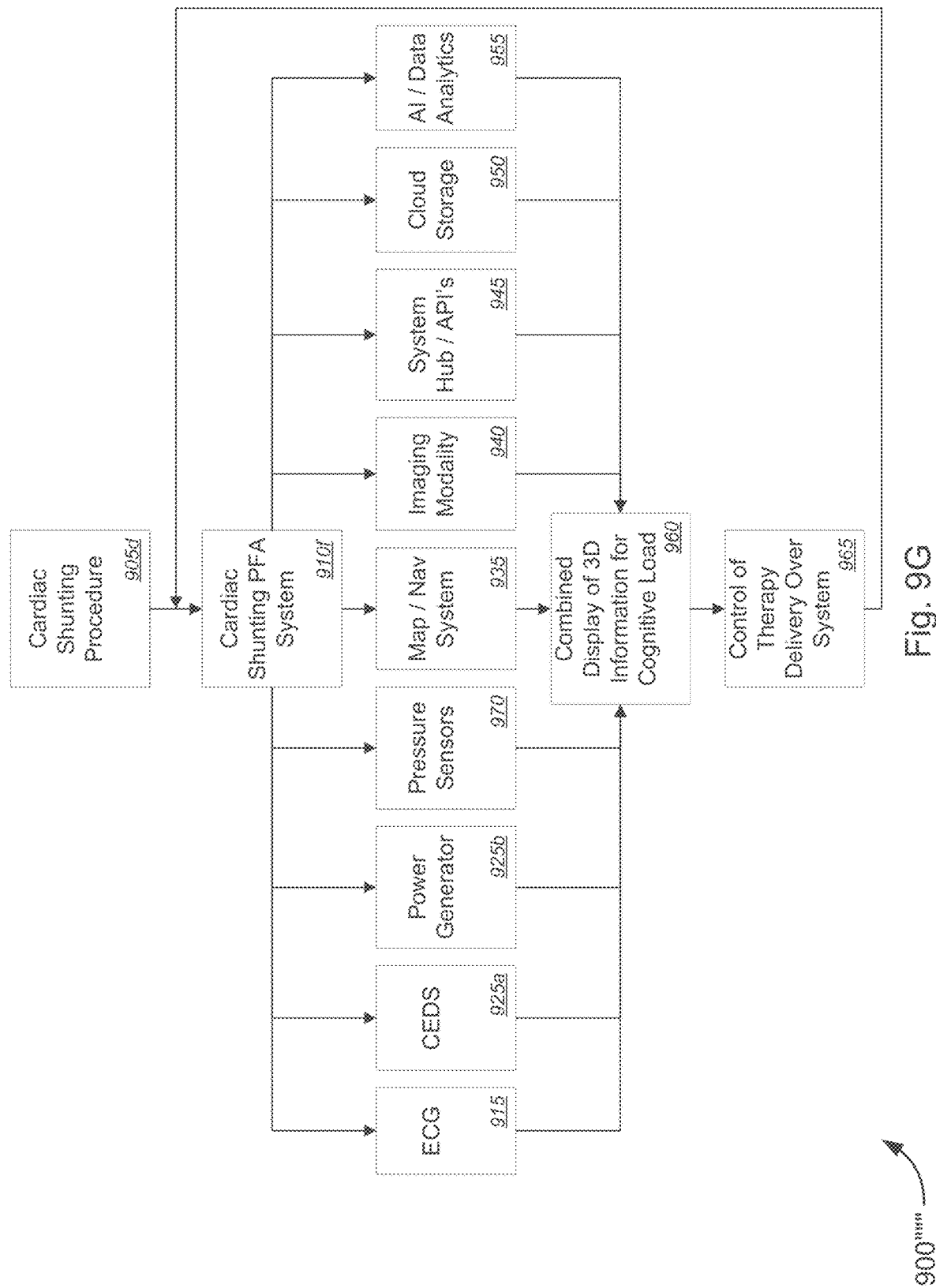
Figure 9H:
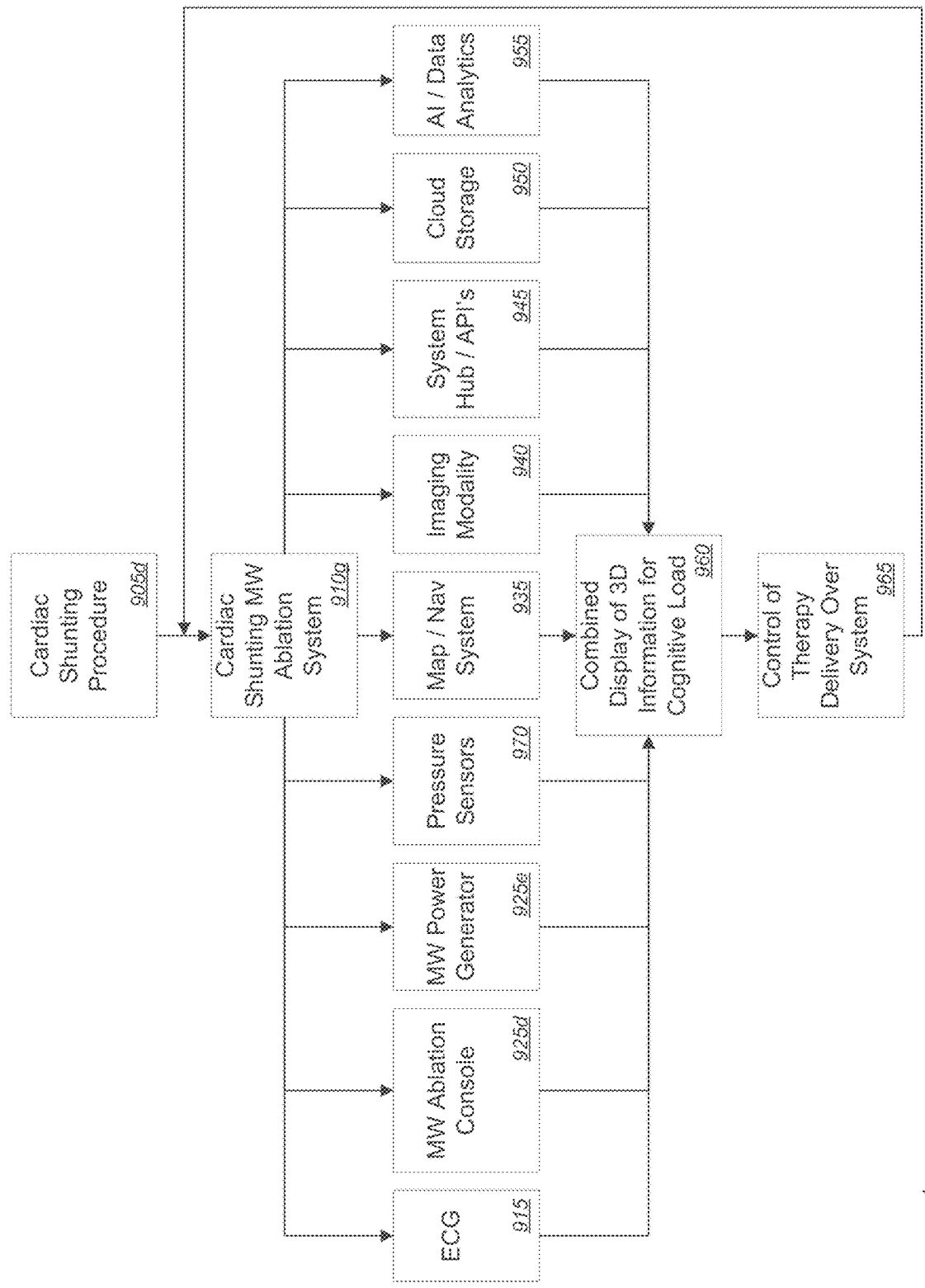

FIGS. 9B-9H depict some non-limiting specific implementations, including, but not limited to, atrial fibrillation ("AF") ablation using a pulsed field ablation ("PFA") system (FIG. 9B) or using a cryoablation system (FIG. 9C), a transcatheter aortic valve implant ("TAVI") procedure (FIG. 9D), a transcatheter mitral valve implant ("TMVI") procedure (FIG. 9E), and cardiac shunting procedures (FIGS. 9F-9H).

Referring to the non-limiting example 900' of FIG. 9B, a process stack for implementing an IA ecosystem for AF ablation might begin with a selection of an AF ablation procedure (at block 905a). In response to such selection, a PFA system may be selected for implementation (at block 910a). The IA ecosystem might utilize, in conjunction with the PFA system, a number of devices or equipment, sensors, imaging systems, and other systems (collectively, "PFA sub-systems" or the like), including, but not limited to, at least one, two, or three of an ECG monitor (at block 915), system-specific equipment including a catheter electrode distribution system ("CEDS") (at block 925a) and a power generator (at block 925b), a mapping and/or navigation system (at block 935), imaging modality (at block 940), a system hub and/or application programming interfaces ("API's") (at block 945), cloud storage (at block 950), or artificial intelligence ("AI") and/or data analytics (at block 955), and/or the like. In some embodiments, the CEDS might be external, yet communicatively coupled, to the (PFA) power generator. Alternatively, the CEDS might be integrated or incorporated within the (PFA) power generator. Data from these PFA sub-systems may be combined to generate a combined display of three-dimensional ("3D") information or four-dimensional ("4D") information (i.e., 3D information plus at least one of real-time updates, dynamic modeling, or data streaming, and/or the like) for cognitive load (at block 960). Such 3D or 4D information may be used to control therapy delivery over the system (at block 965). The process at blocks 910a-965 may be repeated as necessary or as desired.

Table 1 below illustrates a specific non-limiting example combination(s) of sensors, imaging systems, tracking (or mapping and navigation) systems, and devices (e.g., robotic devices or the like) for each of the Pre-Operative Planning Stage, the Intra-Operative Adjustment Stage, and the Post-Operative Monitory Stage (as described above with respect to FIG. 3C) while implementing an IA ecosystem for an AF ablation procedure using a PFA system. The various embodiments, however, are not limited to these items nor their specific combinations and can include any combination of items listed for sensors, imaging systems, tracking (or mapping and navigation) systems, and devices, e.g., as described below with respect to FIG. 13, or the like.

As shown in Table 1 above, for the AF ablation procedure using PFA, the IA ecosystem may utilize, for an integrated diagnostics system during the Pre-Operative Planning Stage, one or a combination of an electromechanical wave imaging ("EWI") ultrasound system, biometric input (including, but not limited to, information regarding at least one of age, weight, height, gender, race, etc.), and/or morphology inputs (such as cardiac history including, without limitation, persistent versus paroxysmal, etc.), and/or the like. In some cases, the IA ecosystem may perform analysis of data obtained by these sensors, imaging systems, and/or tracking (or mapping and navigation) systems as well as user input to generate recommendations or to facilitate physician/user plans for the AF ablation procedure using PFA. The AF ablation procedure using PFA may then be performed based on sensor data, imaging data, tracking data, recommendations, and/or physician/user plans obtained or arising from the Pre-Operative Planning Stage.

During the Intra-Operative Adjustment Stage, the IA ecosystem may combine (1) imaging device(s) including one or a combination of an EWI ultrasound system and/or an ICE system, with (2) navigation/mapping system(s) including one or a combination of a radio frequency identification ("RFID")-based tracking system merged with a 3D AR and/or EWI, with (3) sensor device(s) including one or a combination of a contactless optical-based tracking system, an infrared ("IR")-based tracking system for sensing temperature, a blood pressure sensor, a heart rate sensor, a motion sensor (e.g., to track motion from phrenic damage, or the like), a respiratory rate sensor, a fiducial tracking sensor to track motion of fiducials to maintain imaging/mapping/navigation alignment, a surgical tool object recognition system, robotic collision detection system, tracking system for tracking traffic flow in a room, and/or user fatigue and/or cognitive overload detector, and/or the like, with (4) integrated robotics including a soft-tissue intra-luminal robotic ("ILR") system (where an intra-luminal device refers to a device that is configured to be introduced into a lumen in the body of a patient or subject, where a lumen refers to the cavity or channel within a tubular organ, such as a blood vessel (e.g., artery, vein, or capillary), esophagus, trachea,

TABLE 1

Combination List of Systems and Devices for implementing IA ecosystem for AF ablation using a PFA system

| Pre-Op Stage | Intra-Op Stage | | | | | Post-Op Stage Monitoring/ |
|---|---|---|---|---|---|---|
| Integrated Diagnostics | Imaging Devices | Navigation/ Mapping | Sensor Devices | Integrated Robotics | AI/Data Analytics | Analytics Feedback |
| EWI, Biometric Input, Morphology Inputs | EWI, ICE | RFID + 3D AR/ EWI | Contactless Optical, IR Temp, Blood Pressure, Heart Rate, Motion, Respiratory Rate, Fiducials Alignment, Tool Object Recognition, Collision Detection, Room Traffic Flow, Fatigue/Overload | ILR + AR and Haptics Feedback, Eye Tracking, Trajectory Coordinate Tracking | Merging Imaging and Other Sensor Data | Output of Acute and Chronic Outcomes + Feedback Loop | and intestine, etc.), eye tracking system for tracking physicians with XR headset relative to robotics for cognitive load and safety shut offs, and/or trajectory coordinate tracking of physical catheters relative to digital twins for replay, approach angle, etc., to relate back to outcomes, with (5) intra-operative AI and/or data analytics (i.e., real-time or near-real-time predictive and prescriptive analytics, etc.) that merges imaging and other sensor data to adjust device configurations, settings, and/or implementations in real-time (or near-real-time (e.g., within milliseconds or seconds, etc.)) based on any updates or changes to the sensor data, imaging data, tracking data, and/or recommendations obtained during the Intra-Operative Adjustments Stage. The ILR system may combine an intra-luminal robotic device with AR assistance and haptics feedback, particularly, for ablations that are in the realm of seconds and/or navigating to pulmonary vein isolation ("PVI") plus ("PVI+"), with complex targets outside of the pulmonary vein.

In some embodiments, the merged imaging and other sensor data for the intra-operative AI and/or data analytics may include, without limitation, the following combinations: (a) electrogram ("EGM") sensor data combined with ablation catheter itself and capital equipment time series data from sensors for temperature, voltage, current, and/or waveforms; (b) combination of ablation catheter and capital equipment data for electrical field proximity to targets with predictive analytics from electroanatomic mapping ("EAM") system data merge and previous post-operative feedback loops; (c) auto-segmentation of anatomical imaging, object/feature recognition, trajectory recommendation to target and real-time tracking, 3D XR with catheter electrode proximity to location or gap, electrical field growth, tagging of therapy, predictive arrhythmia change to titer therapy dosage, proximity to adjacent anatomy (e.g., esophagus and phrenic nerve, etc.) with warnings to recommend approach and to titer therapy, and provide device and size recommendations; (d) XR headset eye tracking and robotic coordinates for safety, efficiency, and relationships with digital twins (e.g., "back-up camera" following moving anatomy that has real-time or near-real-time distance and auditory feedback until "docked"); or (e) facial and/or text recognition to anonymize people and/or documents; etc.

In one non-limiting example, (1) EWI may be combined with (2) RFID merged with 3D AR, with (3) an optical-based tracking system(s), with (4) ILR system, with (5) AI and/or data analytics. In an alternative example, (1) EWI may be combined with (2) RFID merged with EWI, with (3) an optical-based tracking system(s), with (4) ILR system, with (5) AI and/or data analytics. In an alternative example, (1) EWI may be combined with (2) RFID merged with 3D AR, with (3) an IR-based tracking system(s), with (4) ILR system, with (5) AI and/or data analytics. In an alternative example, (1) EWI may be combined with (2) RFID merged with EWI, with (3) an IR-based tracking system(s), with (4) ILR system, with (5) AI and/or data analytics. In an alternative example, (1) EWI may be combined with (2) RFID merged with 3D AR, with (3) a blood pressure sensor(s) and/or a heart rate sensor(s), with (4) ILR system, with (5) AI and/or data analytics. In an alternative example, (1) EWI may be combined with (2) RFID merged with EWI, with (3) a blood pressure sensor(s) and/or a heart rate sensor(s), with (4) ILR system, with (5) AI and/or data analytics. In an alternative example, (1) EWI may be combined with (2) RFID merged with 3D AR, with (3) a respiratory rate sensor(s), with (4) ILR system, with (5) AI and/or data analytics. In an alternative example, (1) EWI may be combined with (2) RFID merged with EWI, with (3) a respiratory rate sensor(s), with (4) ILR system, with (5) AI and/or data analytics. In an alternative example, (1) EWI may be combined with (2) RFID merged with 3D AR, with (3) an object/person motion/collision tracking system(s), with (4) ILR system, with (5) AI and/or data analytics. In an alternative example, (1) EWI may be combined with (2) RFID merged with EWI, with (3) an object/person motion/collision tracking system(s), with (4) ILR system, with (5) AI and/or data analytics. In an alternative example, (1) EWI may be combined with (2) RFID merged with 3D AR, with (3) a user fatigue and/or cognitive overload detector(s), with (4) ILR system, with (5) AI and/or data analytics. In an alternative example, (1) EWI may be combined with (2) RFID merged with EWI, with (3) a user fatigue and/or cognitive overload detector(s), with (4) ILR system, with (5) AI and/or data analytics.

In another non-limiting example, (1) ICE may be combined with (2) RFID merged with 3D AR, with (3) an optical-based tracking system(s), with (4) ILR system, with (5) AI and/or data analytics. In an alternative example, (1) ICE may be combined with (2) RFID merged with EWI, with (3) an optical-based tracking system(s), with (4) ILR system, with (5) AI and/or data analytics. In an alternative example, (1) ICE may be combined with (2) RFID merged with 3D AR, with (3) an IR-based tracking system(s), with (4) ILR system, with (5) AI and/or data analytics. In an alternative example, (1) ICE may be combined with (2) RFID merged with EWI, with (3) an IR-based tracking system(s), with (4) ILR system, with (5) AI and/or data analytics. In an alternative example, (1) ICE may be combined with (2) RFID merged with 3D AR, with (3) a blood pressure sensor(s) and/or a heart rate sensor(s), with (4) ILR system, with (5) AI and/or data analytics. In an alternative example, (1) ICE may be combined with (2) RFID merged with EWI, with (3) a blood pressure sensor(s) and/or a heart rate sensor(s), with (4) ILR system, with (5) AI and/or data analytics. In an alternative example, (1) ICE may be combined with (2) RFID merged with 3D AR, with (3) a respiratory rate sensor(s), with (4) ILR system, with (5) AI and/or data analytics. In an alternative example, (1) ICE may be combined with (2) RFID merged with EWI, with (3) a respiratory rate sensor(s), with (4) ILR system, with (5) AI and/or data analytics. In an alternative example, (1) ICE may be combined with (2) RFID merged with 3D AR, with (3) an object/person motion/collision tracking system(s), with (4) ILR system, with (5) AI and/or data analytics. In an alternative example, (1) ICE may be combined with (2) RFID merged with EWI, with (3) an object/person motion/collision tracking system(s), with (4) ILR system, with (5) AI and/or data analytics. In an alternative example, (1) ICE may be combined with (2) RFID merged with 3D AR, with (3) a user fatigue and/or cognitive overload detector(s), with (4) ILR system, with (5) AI and/or data analytics. In an alternative example, (1) ICE may be combined with (2) RFID merged with EWI, with (3) a user fatigue and/or cognitive overload detector(s), with (4) ILR system, with (5) AI and/or data analytics.

During the Post-Operative Monitory Stage, the IA ecosystem may utilize the output of acute and chronic outcomes assessed per inputs from the Integrated Diagnostics, the Imaging Devices, Navigation/Mapping, and/or Sensor Devices (to track transient ischemic attack ("TIA"), stroke, and/or arrhythmia recurrence, or the like). A feedback loop may be used to continually enhance predictive and prescriptive recommendations in real-time or near-real-time, with playback of trajectories and/or ablations, descriptive analytics, suggested morphologies from similar patients, literature, etc. In this manner, the combinations during all three stages (i.e., the Pre-Operative Planning Stage, the Intra-Operative Adjustment Stage, and the Post-Operative Monitory Stage) may achieve personalized trajectories and titered therapy for long term efficacy with minimal safety risk, while providing the user with efficient application of the therapy (i.e., reduced or consistent time and increased throughput) and extended career longevity (with no or low fluoro).

Stage, the Intra-Operative Adjustment Stage, and the Post-Operative Monitory Stage (as described above with respect to FIG. 3C) while implementing an IA ecosystem for an AF ablation procedure using a cryo system. The various embodiments, however, are not limited to these items nor their specific combinations and can include any combination of items listed for sensors, imaging systems, tracking (or mapping and navigation) systems, and devices, e.g., as described below with respect to FIG. 13, or the like.

TABLE 2

Combination List of Systems and Devices for implementing IA ecosystem for AF ablation using a cryo system

| Pre-Op Stage | Intra-Op Stage | | | | | Post-Op Stage Monitoring/ |
| --- | --- | --- | --- | --- | --- | --- |
| Integrated Diagnostics | Imaging Devices | Navigation/ Mapping | Sensor Devices | Integrated Robotics | AI/Data Analytics | Analytics Feedback |
| CT + EAM, Cuff BP, MRI Biometric Input, Morphology Inputs | Fluoro, MRI, ICE | EM + Impedance, EP Mapping Cathether, Proximity Mapping Catheter | ECG Patches, Esophagus Temperature Probe, Breathing Accelerometer | None for PVI and/or Minutes-Long Ablation Aided by Cryoadhesion | Merging Imaging and Other Sensor Data | Output of Acute and Chronic Outcomes + Feedback Loop |

Turning to the non-limiting example 900" of FIG. 9C, a process stack for implementing an IA ecosystem for AF ablation might begin with a selection of an AF ablation procedure (at block 905a). In response to such selection, a cryoablation system may be selected for implementation (at block 910b). The IA ecosystem might utilize, in conjunction with the cryoablation system, a number of devices or equipment, sensors, imaging systems, and other systems (collectively, "cryoablation" or "cryo sub-systems" or the like), including, but not limited to, at least one, two, or three of an ECG monitor (at block 915), a remote control and/or foot pedal (at block 920), system-specific equipment including a cryo or cryoablation console (at block 925c), a cardio insight ("CIT") mapping vest (at block 930), a mapping and/or navigation system (at block 935), imaging modality (at block 940), a system hub and/or application programming interfaces ("API's") (at block 945), cloud storage (at block 950), or artificial intelligence ("AI") and/or data analytics (at block 955), and/or the like. In some cases, the cryo or cryoablation console might store and control delivery of liquid refrigerant (e.g., $N_2O$, or the like) through a coaxial umbilical to a cryoablation catheter, or the like, might recover the refrigerant vapor from the catheter under constant vacuum, and might safely and efficiently dispose of the refrigerant through a scavenging system. Data from these cryo or cryoablation sub-systems may be combined to generate a combined display of three-dimensional ("3D") information or four-dimensional ("4D") information (i.e., three-dimensional ("3D") information plus at least one of real-time updates, dynamic modeling, or data streaming, and/or the like) for cognitive load (at block 960). Such 3D or 4D information may be used to control therapy delivery over the system (at block 965). The process at blocks 910b-965 may be repeated as necessary or as desired.

Table 2 below illustrates a specific non-limiting example combination(s) of sensors, imaging systems, tracking (or mapping and navigation) systems, and devices (e.g., robotic devices or the like) for each of the Pre-Operative Planning As shown in Table 2 above, for the AF ablation procedure using cryo, the IA ecosystem may utilize, for an integrated diagnostics system during the Pre-Operative Planning Stage, one or a combination of a computed tomography ("CT") system, a cardio insight ("CIT") vest-based electroanatomic mapping ("EAM") system, a sphygmomanometer or cuff blood pressure ("BP") detector, a magnetic resonance imaging ("MRI") system, biometric input (including, but not limited to, information regarding at least one of age, weight, height, gender, race, etc.), and/or morphology inputs (such as cardiac history including, without limitation, persistent versus paroxysmal, etc.), and/or the like. In some cases, the IA ecosystem may perform analysis of data obtained by these sensors, imaging systems, and/or tracking (or mapping and navigation) systems as well as user input to generate recommendations or to facilitate physician/user plans for the AF ablation procedure using cryo. The AF ablation procedure using cryo may then be performed based on sensor data, imaging data, tracking data, recommendations, and/or physician/user plans obtained or arising from the Pre-Operative Planning Stage.

During the Intra-Operative Adjustment Stage, the IA ecosystem may combine (1) imaging device(s) including one or a combination of a fluoroscopy ("Fluoro") system, a MRI system, and/or an ICE system, with (2) navigation/mapping system(s) including one or a combination of an electromagnetic ("EM") mapping and/or navigation system merged with an impedance-based mapping and/or navigation system, an electrophysiology ("EP") mapping catheter, and/or a proximity mapping catheter, with (3) sensor device(s) including one or a combination of an electrocardiogram ("ECG") sensor patch(es), an esophagus temperature probe, and/or a breathing accelerometer (for monitoring phrenic nerve, or the like), and/or the like, without (4) integrated robotics for PVI and/or minutes-long ablation aided by cryoadhesion, with (5) intra-operative AI and/or data analytics (i.e., real-time or near-real-time predictive and prescriptive analytics, etc.) that merges imaging and other sensor data to adjust device configurations, settings, and/or implementations in real-time (or near-real-time (e.g., within milliseconds or seconds, etc.)) based on any updates or changes to the sensor data, imaging data, tracking data, and/or recommendations obtained during the Intra-Operative Adjustments Stage.

In some embodiments, the merged imaging and other sensor data for the intra-operative AI and/or data analytics may include, without limitation, the following combinations: (a) electrogram ("EGM") sensor data combined with mapping catheter itself and capital equipment time series data from sensors for cryo flow, pressure, and/or temperature; (b) combination of mapping catheter and capital equipment data with time-to-isolation with temperature waveforms from the capital equipment with predictive analytics from EAM system data merge and previous post-operative feedback loops; (c) auto-segmentation of anatomical imaging, object/feature recognition, trajectory recommendation to target and real-time tracking, 3D XR with balloon contact location or gap, ice or temperature growth, tagging of therapy, predictive arrhythmia change to titer therapy dosage, proximity to adjacent anatomy (e.g., esophagus and phrenic nerve, etc.) with warnings to recommend approach and to titer therapy, and provide device and size recommendations; or (d) facial and/or text recognition to anonymize people and/or documents; etc.

In one non-limiting example, (1) Fluoro may be combined with (2) EM merged with impedance, with (3) an ECG patch(es), with (4) ILR system, with (5) AI and/or data analytics. In an alternative example, (1) Fluoro may be combined with (2) EP mapping catheter, with (3) an ECG patch(es), with (5) AI and/or data analytics. In an alternative example, (1) Fluoro may be combined with (2) proximity mapping catheter, with (3) an ECG patch(es), with (5) AI and/or data analytics. In an alternative example, (1) Fluoro may be combined with (2) EM merged with impedance, with (3) an Esophagus temperature probe(s), with (5) AI and/or data analytics. In an alternative example, (1) Fluoro may be combined with (2) EP mapping catheter, with (3) an Esophagus temperature probe(s), with (5) AI and/or data analytics. In an alternative example, (1) Fluoro may be combined with (2) proximity mapping catheter, with (3) an Esophagus temperature probe(s), with (5) AI and/or data analytics. In an alternative example, (1) Fluoro may be combined with (2) EM merged with impedance, with (3) a breathing accelerometer, with (5) AI and/or data analytics. In an alternative example, (1) Fluoro may be combined with (2) EP mapping catheter, with (3) a breathing accelerometer, with (5) AI and/or data analytics. In an alternative example, (1) Fluoro may be combined with (2) proximity mapping catheter, with (3) a breathing accelerometer, with (5) AI and/or data analytics.

In another non-limiting example, (1) Mill may be combined with (2) EM merged with impedance, with (3) an ECG patch(es), with (4) ILR system, with (5) AI and/or data analytics. In an alternative example, (1) MRI may be combined with (2) EP mapping catheter, with (3) an ECG patch(es), with (5) AI and/or data analytics. In an alternative example, (1) MRI may be combined with (2) proximity mapping catheter, with (3) an ECG patch(es), with (5) AI and/or data analytics. In an alternative example, (1) MRI may be combined with (2) EM merged with impedance, with (3) an Esophagus temperature probe(s), with (5) AI and/or data analytics. In an alternative example, (1) MRI may be combined with (2) EP mapping catheter, with (3) an Esophagus temperature probe(s), with (5) AI and/or data analytics. In an alternative example, (1) Mill may be combined with (2) proximity mapping catheter, with (3) an Esophagus temperature probe(s), with (5) AI and/or data analytics. In an alternative example, (1) Mill may be combined with (2) EM merged with impedance, with (3) a breathing accelerometer, with (5) AI and/or data analytics. In an alternative example, (1) MRI may be combined with (2) EP mapping catheter, with (3) a breathing accelerometer, with (5) AI and/or data analytics. In an alternative example, (1) MRI may be combined with (2) proximity mapping catheter, with (3) a breathing accelerometer, with (5) AI and/or data analytics.

In yet another non-limiting example, (1) ICE may be combined with (2) EM merged with impedance, with (3) an ECG patch(es), with (4) ILR system, with (5) AI and/or data analytics. In an alternative example, (1) ICE may be combined with (2) EP mapping catheter, with (3) an ECG patch(es), with (5) AI and/or data analytics. In an alternative example, (1) ICE may be combined with (2) proximity mapping catheter, with (3) an ECG patch(es), with (5) AI and/or data analytics. In an alternative example, (1) ICE may be combined with (2) EM merged with impedance, with (3) an Esophagus temperature probe(s), with (5) AI and/or data analytics. In an alternative example, (1) ICE may be combined with (2) EP mapping catheter, with (3) an Esophagus temperature probe(s), with (5) AI and/or data analytics. In an alternative example, (1) ICE may be combined with (2) proximity mapping catheter, with (3) an Esophagus temperature probe(s), with (5) AI and/or data analytics. In an alternative example, (1) ICE may be combined with (2) EM merged with impedance, with (3) a breathing accelerometer, with (5) AI and/or data analytics. In an alternative example, (1) ICE may be combined with (2) EP mapping catheter, with (3) a breathing accelerometer, with (5) AI and/or data analytics. In an alternative example, (1) ICE may be combined with (2) proximity mapping catheter, with (3) a breathing accelerometer, with (5) AI and/or data analytics.

During the Post-Operative Monitory Stage, the IA ecosystem may utilize the output of acute and chronic outcomes assessed per inputs from the Integrated Diagnostics, the Imaging Devices, Navigation/Mapping, and/or Sensor Devices (to track transient ischemic attack ("TIA"), stroke, and/or arrhythmia recurrence, or the like). A feedback loop may be used to continually enhance predictive and prescriptive recommendations in real-time or near-real-time, with playback of trajectories and/or ablations, descriptive analytics, suggested morphologies from similar patients, literature, etc. In this manner, the combinations during all three stages (i.e., the Pre-Operative Planning Stage, the Intra-Operative Adjustment Stage, and the Post-Operative Monitory Stage) may achieve personalized trajectories and titered therapy for long term efficacy with minimal safety risk, while providing the user with efficient application of the therapy (i.e., reduced or consistent time and increased throughput) and extended career longevity (with no or low fluoro).

With reference to the non-limiting example 900''' of FIG. 9D, a process stack for implementing an IA ecosystem for TAVI might begin with a selection of a TAVI procedure (at block 905b). In response to such selection, a TAVI implant and delivery system may be selected for implementation (at block 910c). The IA ecosystem might utilize, in conjunction with the TAVI implant and delivery system, a number of devices or equipment, sensors, imaging systems, and other systems (collectively, "TAVI sub-systems" or the like), including, but not limited to, at least one, two, or three of a cardio insight ("CIT") mapping vest (at block 930), a mapping and/or navigation system (at block 935), imaging modality (at block 940), a system hub and/or application programming interfaces ("API's") (at block 945), cloud storage (at block 950), or artificial intelligence ("AI") and/or data analytics (at block 955), and/or the like. Data from these TAVI sub-systems may be combined to generate a combined display of three-dimensional ("3D") information or four-dimensional ("4D") information (i.e., three-dimensional ("3D") information plus at least one of real-time updates, dynamic modeling, or data streaming, and/or the like) for cognitive load (at block 960). Such 3D or 4D information may be used to control therapy delivery over the system (at block 965). The process at blocks 910c-965 may be repeated as necessary or as desired.

Table 3 below illustrates a specific non-limiting example combination(s) of sensors, imaging systems, tracking (or mapping and navigation) systems, and devices (e.g., robotic devices or the like) for each of the Pre-Operative Planning Stage, the Intra-Operative Adjustment Stage, and the Post-Operative Monitory Stage (as described above with respect to FIG. 3C) while implementing an IA ecosystem for an aortic valve replacement or repair procedure using a TAVI implant and delivery system. The various embodiments, however, are not limited to these items nor their specific combinations and can include any combination of items listed for sensors, imaging systems, tracking (or mapping and navigation) systems, and devices, e.g., as described below with respect to FIG. 15, or the like.

During the Intra-Operative Adjustment Stage, the IA ecosystem may combine (1) imaging device(s) including one or a combination of a Fluoro system merged with an EWI ultrasound system (e.g., for placement of a pacemaker or CRT device to treat left bundle branch block ("LBBB"), which is a condition that interferes with the contraction of the left ventricle; or the like), with (2) navigation/mapping system(s) including one or a combination of an EM system, an impedance-based system, a RFID-based tracking system, and/or an optical-based tracking system merged with a 3D AR and/or EWI or Fluoro, with (3) sensor device(s) including one or a combination of a contactless optical-based tracking system, an IR-based tracking system for sensing temperature, a blood pressure sensor, a heart rate sensor, a respiratory rate sensor, a fiducial tracking sensor to track motion of fiducials to maintain imaging/mapping/navigation alignment, a surgical tool object recognition system, robotic collision detection system, tracking system for tracking traffic flow in a room, and/or user fatigue and/or cognitive overload detector, and/or the like, with (4) integrated robotics including a soft-tissue ILR system, eye tracking system for tracking physicians with XR headset relative to robotics for cognitive load and safety shut offs, and/or trajectory coordinate tracking of physical catheters relative to digital twins for replay, approach angle, etc., to relate back to

TABLE 3

Combination List of Systems and Devices for implementing IA ecosystem for TAVR/TAVr using TAVI

| Pre-Op Stage | Intra-Op Stage | | | | | Post-Op Stage Monitoring/ |
|---|---|---|---|---|---|---|
| Integrated Diagnostics | Imaging Devices | Navigation/ Mapping | Sensor Devices | Integrated Robotics | AI/Data Analytics | Analytics Feedback |
| CT, MRI, TTE, Biometric Input, Morphology Inputs | Fluoro + EWI for LBB Block | EM, Impedance, RFID, Optical + 3D AR, EWI, Fluoro | Contactless Optical, IR Temp, Blood Pressure, Heart Rate, Respiratory Rate, Fiducials Alignment, Tool Object Recognition, Collision Detection, Room Traffic Flow, Fatigue/Overload | ILR + AR and Haptics Feedback, Eye Tracking, Trajectory Coordinate Tracking | Merging Imaging and Other Sensor Data | Output of Acute and Chronic Outcomes + Feedback Loop |

As shown in Table 3 above, for the TAVR/TAVr using TAVI, the IA ecosystem may utilize, for an integrated diagnostics system during the Pre-Operative Planning Stage, one or a combination of a CT system, a MRI system, a transthoracic echocardiography ("TTE") system, biometric input (including, but not limited to, information regarding at least one of age, weight, height, gender, race, etc.), and/or morphology inputs (such as cardiac history including, without limitation, persistent versus paroxysmal, etc.), and/or the like. In some cases, the IA ecosystem may perform analysis of data obtained by these sensors, imaging systems, and/or tracking (or mapping and navigation) systems as well as user input to generate recommendations or to facilitate physician/user plans for the TAVR/TAVr using TAVI. The TAVR/TAVr using TAVI may then be performed based on sensor data, imaging data, tracking data, recommendations, and/or physician/user plans obtained or arising from the Pre-Operative Planning Stage.

outcomes, with (5) intra-operative AI and/or data analytics (i.e., real-time or near-real-time predictive and prescriptive analytics, etc.) that merges imaging and other sensor data to adjust device configurations, settings, and/or implementations in real-time (or near-real-time (e.g., within milliseconds or seconds, etc.)) based on any updates or changes to the sensor data, imaging data, tracking data, and/or recommendations obtained during the Intra-Operative Adjustments Stage. The ILR system may combine an intra-luminal robotic device with AR assistance and haptics feedback, particularly, for valve releases that are in the realm of seconds and/or navigating to complex targets (e.g., releasing device in flow with moving leaflets, etc.). With respect to LBBB, EWI when used with TAVI may be used to track LBBB in real-time (or near-real-time) so that the valve can be moved to a location that avoids causing an arrhythmia, prior to deployment of the device, and so that the system can determine whether or not the device needs to be placed at all.

Taking this a step further, understanding when LBBB is acute during the procedure and/or when or why it would resolve naturally over time without a pacemaker implant may be useful for generating recommendations for implementing the procedure. The IA ecosystem is thus very useful for addressing at least this issue by capitalizing on its ability to obtain the data, to merge the data, and to use an AI feedback loop to provide recommendations pertaining to this LBBB issue as well as any issues arising during other types of procedures. In some cases, real-time (or near-real-time) doppler sensor data for perivalvular leaks, effective orifice area, etc., before the valve is fully released, may be used by the IA ecosystem to facilitate optimal positioning, or repositioning, of the valve, in some cases with the use of a "back-up camera" following moving anatomy that has real-time or near-real-time distance and auditory feedback until "docked."

In some embodiments, the merged imaging and other sensor data for the intra-operative AI and/or data analytics may include, without limitation, the following combinations: (a) capital equipment time series data from sensors for coordinates, flows, and/or pressures; (b) combination of delivery system and capital equipment data for proximity to targets with predictive analytics from EAM system data merge and previous post-operative feedback loops; (c) auto-segmentation of anatomical imaging, object/feature recognition, trajectory recommendation to target and real-time tracking, 3D XR with catheter electrode proximity to location or gap, electrical field growth, tagging of therapy, predictive arrhythmia change to titer therapy dosage, proximity to adjacent anatomy (e.g., esophagus and phrenic nerve, etc.) with warnings to recommend approach and to titer therapy, and provide device and size recommendations; (d) XR headset eye tracking and robotic coordinates for safety, efficiency, and relationships with digital twins (e.g., "back-up camera" following moving anatomy that has real-time or near-real-time distance and auditory feedback until "docked"); or (e) facial and/or text recognition to anonymize people and/or documents; etc.

In one non-limiting example, (1) Fluoro merged with EWI ultrasound may be combined with (2) an EM-based tracking system(s) merged with 3D AR and EWI, with (3) an Optical-based tracking system(s), with (4) ILR system, with (5) AI and/or data analytics. In an alternative example, (1) Fluoro merged with EWI ultrasound may be combined with (2) an impedance-based tracking system(s) merged with 3D AR and EWI, with (3) an Optical-based tracking system(s), with (4) ILR system, with (5) AI and/or data analytics. In an alternative example, (1) Fluoro merged with EWI ultrasound may be combined with (2) RFID merged with 3D AR and EWI, with (3) an Optical-based tracking system(s), with (4) ILR system, with (5) AI and/or data analytics. In an alternative example, (1) Fluoro merged with EWI ultrasound may be combined with (2) an optical-based tracking system(s) merged with 3D AR and EWI, with (3) an Optical-based tracking system(s), with (4) ILR system, with (5) AI and/or data analytics. In an alternative example, (1) Fluoro merged with EWI ultrasound may be combined with (2) an EM-based tracking system(s) merged with 3D AR and EWI, with (3) an IR-based tracking system(s), with (4) ILR system, with (5) AI and/or data analytics. In an alternative example, (1) Fluoro merged with EWI ultrasound may be combined with (2) an impedance-based tracking system(s) merged with 3D AR and EWI, with (3) an IR-based tracking system(s), with (4) ILR system, with (5) AI and/or data analytics. In an alternative example, (1) Fluoro merged with EWI ultrasound may be combined with (2) RFID merged with 3D AR and EWI, with (3) an IR-based tracking system(s), with (4) ILR system, with (5) AI and/or data analytics. In an alternative example, (1) Fluoro merged with EWI ultrasound may be combined with (2) an optical-based tracking system(s) merged with 3D AR and EWI, with (3) an IR-based tracking system(s), with (4) ILR system, with (5) AI and/or data analytics. In an alternative example, (1) Fluoro merged with EWI ultrasound may be combined with (2) an EM-based tracking system(s) merged with 3D AR and EWI, with (3) a blood pressure sensor(s) and/or a heart rate sensor(s), with (4) ILR system, with (5) AI and/or data analytics. In an alternative example, (1) Fluoro merged with EWI ultrasound may be combined with (2) an impedance-based tracking system(s) merged with 3D AR and EWI, with (3) a blood pressure sensor(s) and/or a heart rate sensor(s), with (4) ILR system, with (5) AI and/or data analytics. In an alternative example, (1) Fluoro merged with EWI ultrasound may be combined with (2) RFID merged with 3D AR and EWI, with (3) a blood pressure sensor(s) and/or a heart rate sensor(s), with (4) ILR system, with (5) AI and/or data analytics. In an alternative example, (1) Fluoro merged with EWI ultrasound may be combined with (2) an optical-based tracking system(s) merged with 3D AR and EWI, with (3) a blood pressure sensor(s) and/or a heart rate sensor(s), with (4) ILR system, with (5) AI and/or data analytics.

In an alternative example, (1) Fluoro merged with EWI ultrasound may be combined with (2) an EM-based tracking system(s) merged with 3D AR and EWI, with (3) a respiratory rate sensor(s), with (4) ILR system, with (5) AI and/or data analytics. In an alternative example, (1) Fluoro merged with EWI ultrasound may be combined with (2) an impedance-based tracking system(s) merged with 3D AR and EWI, with (3) a respiratory rate sensor(s), with (4) ILR system, with (5) AI and/or data analytics. In an alternative example, (1) Fluoro merged with EWI ultrasound may be combined with (2) RFID merged with 3D AR and EWI, with (3) a respiratory rate sensor(s), with (4) ILR system, with (5) AI and/or data analytics. In an alternative example, (1) Fluoro merged with EWI ultrasound may be combined with (2) an optical-based tracking system(s) merged with 3D AR and EWI, with (3) a respiratory rate sensor(s), with (4) ILR system, with (5) AI and/or data analytics. In an alternative example, (1) Fluoro merged with EWI ultrasound may be combined with (2) an EM-based tracking system(s) merged with 3D AR and EWI, with (3) an object/person motion/collision tracking system(s), with (4) ILR system, with (5) AI and/or data analytics. In an alternative example, (1) Fluoro merged with EWI ultrasound may be combined with (2) an impedance-based tracking system(s) merged with 3D AR and EWI, with (3) an object/person motion/collision tracking system(s), with (4) ILR system, with (5) AI and/or data analytics. In an alternative example, (1) Fluoro merged with EWI ultrasound may be combined with (2) RFID merged with 3D AR and EWI, with (3) an object/person motion/collision tracking system(s), with (4) ILR system, with (5) AI and/or data analytics. In an alternative example, (1) Fluoro merged with EWI ultrasound may be combined with (2) an optical-based tracking system(s) merged with 3D AR and EWI, with (3) an object/person motion/collision tracking system(s), with (4) ILR system, with (5) AI and/or data analytics. In an alternative example, (1) Fluoro merged with EWI ultrasound may be combined with (2) an EM-based tracking system(s) merged with 3D AR and EWI, with (3) a user fatigue and/or cognitive overload detector(s), with (4) ILR system, with (5) AI and/or data analytics. In an alternative example, (1) Fluoro merged with EWI ultrasound may be combined with (2) an impedance-based tracking system(s) merged with 3D AR and EWI, with (3) a user fatigue and/or cognitive overload detector(s), with (4) ILR system, with (5) AI and/or data analytics. In an alternative example, (1) Fluoro merged with EWI ultrasound may be combined with (2) RFID merged with 3D AR and EWI, with (3) a user fatigue and/or cognitive overload detector(s), with (4) ILR system, with (5) AI and/or data analytics. In an alternative example, (1) Fluoro merged with EWI ultrasound may be combined with (2) an optical-based tracking system(s) merged with 3D AR and EWI, with (3) a user fatigue and/or cognitive overload detector(s), with (4) ILR system, with (5) AI and/or data analytics.

In another non-limiting example, (1) Fluoro merged with EWI ultrasound may be combined with (2) an EM-based tracking system(s) merged with 3D AR and Fluoro, with (3) an Optical-based tracking system(s), with (4) ILR system, with (5) AI and/or data analytics. In an alternative example, (1) Fluoro merged with EWI ultrasound may be combined with (2) an impedance-based tracking system(s) merged with 3D AR and Fluoro, with (3) an Optical-based tracking system(s), with (4) ILR system, with (5) AI and/or data analytics. In an alternative example, (1) Fluoro merged with EWI ultrasound may be combined with (2) RFID merged with 3D AR and Fluoro, with (3) an Optical-based tracking system(s), with (4) ILR system, with (5) AI and/or data analytics. In an alternative example, (1) Fluoro merged with EWI ultrasound may be combined with (2) an optical-based tracking system(s) merged with 3D AR and Fluoro, with (3) an Optical-based tracking system(s), with (4) ILR system, with (5) AI and/or data analytics. In an alternative example, (1) Fluoro merged with EWI ultrasound may be combined with (2) an EM-based tracking system(s) merged with 3D AR and Fluoro, with (3) an IR-based tracking system(s), with (4) ILR system, with (5) AI and/or data analytics. In an alternative example, (1) Fluoro merged with EWI ultrasound may be combined with (2) an impedance-based tracking system(s) merged with 3D AR and Fluoro, with (3) an IR-based tracking system(s), with (4) ILR system, with (5) AI and/or data analytics. In an alternative example, (1) Fluoro merged with EWI ultrasound may be combined with (2) RFID merged with 3D AR and Fluoro, with (3) an IR-based tracking system(s), with (4) ILR system, with (5) AI and/or data analytics. In an alternative example, (1) Fluoro merged with EWI ultrasound may be combined with (2) an optical-based tracking system(s) merged with 3D AR and Fluoro, with (3) an IR-based tracking system(s), with (4) ILR system, with (5) AI and/or data analytics. In an alternative example, (1) Fluoro merged with EWI ultrasound may be combined with (2) an EM-based tracking system(s) merged with 3D AR and Fluoro, with (3) a blood pressure sensor(s) and/or a heart rate sensor(s), with (4) ILR system, with (5) AI and/or data analytics. In an alternative example, (1) Fluoro merged with EWI ultrasound may be combined with (2) an impedance-based tracking system(s) merged with 3D AR and Fluoro, with (3) a blood pressure sensor(s) and/or a heart rate sensor(s), with (4) ILR system, with (5) AI and/or data analytics. In an alternative example, (1) Fluoro merged with EWI ultrasound may be combined with (2) RFID merged with 3D AR and Fluoro, with (3) a blood pressure sensor(s) and/or a heart rate sensor(s), with (4) ILR system, with (5) AI and/or data analytics. In an alternative example, (1) Fluoro merged with EWI ultrasound may be combined with (2) an optical-based tracking system(s) merged with 3D AR and Fluoro, with (3) a blood pressure sensor(s) and/or a heart rate sensor(s), with (4) ILR system, with (5) AI and/or data analytics.

In an alternate example, (1) Fluoro merged with EWI ultrasound may be combined with (2) an EM-based tracking system(s) merged with 3D AR and Fluoro, with (3) a respiratory rate sensor(s), with (4) ILR system, with (5) AI and/or data analytics. In an alternative example, (1) Fluoro merged with EWI ultrasound may be combined with (2) an impedance-based tracking system(s) merged with 3D AR and Fluoro, with (3) a respiratory rate sensor(s), with (4) ILR system, with (5) AI and/or data analytics. In an alternative example, (1) Fluoro merged with EWI ultrasound may be combined with (2) RFID merged with 3D AR and Fluoro, with (3) a respiratory rate sensor(s), with (4) ILR system, with (5) AI and/or data analytics. In an alternative example, (1) Fluoro merged with EWI ultrasound may be combined with (2) an optical-based tracking system(s) merged with 3D AR and Fluoro, with (3) a respiratory rate sensor(s), with (4) ILR system, with (5) AI and/or data analytics. In an alternative example, (1) Fluoro merged with EWI ultrasound may be combined with (2) an EM-based tracking system(s) merged with 3D AR and Fluoro, with (3) an object/person motion/collision tracking system(s), with (4) ILR system, with (5) AI and/or data analytics. In an alternative example, (1) Fluoro merged with EWI ultrasound may be combined with (2) an impedance-based tracking system(s) merged with 3D AR and Fluoro, with (3) an object/person motion/collision tracking system(s), with (4) ILR system, with (5) AI and/or data analytics. In an alternative example, (1) Fluoro merged with EWI ultrasound may be combined with (2) RFID merged with 3D AR and Fluoro, with (3) an object/person motion/collision tracking system(s), with (4) ILR system, with (5) AI and/or data analytics. In an alternative example, (1) Fluoro merged with EWI ultrasound may be combined with (2) an optical-based tracking system(s) merged with 3D AR and Fluoro, with (3) an object/person motion/collision tracking system(s), with (4) ILR system, with (5) AI and/or data analytics. In an alternative example, (1) Fluoro merged with EWI ultrasound may be combined with (2) an EM-based tracking system(s) merged with 3D AR and Fluoro, with (3) a user fatigue and/or cognitive overload detector(s), with (4) ILR system, with (5) AI and/or data analytics. In an alternative example, (1) Fluoro merged with EWI ultrasound may be combined with (2) an impedance-based tracking system(s) merged with 3D AR and Fluoro, with (3) a user fatigue and/or cognitive overload detector(s), with (4) ILR system, with (5) AI and/or data analytics. In an alternative example, (1) Fluoro merged with EWI ultrasound may be combined with (2) RFID merged with 3D AR and Fluoro, with (3) a user fatigue and/or cognitive overload detector(s), with (4) ILR system, with (5) AI and/or data analytics. In an alternative example, (1) Fluoro merged with EWI ultrasound may be combined with (2) an optical-based tracking system(s) merged with 3D AR and Fluoro, with (3) a user fatigue and/or cognitive overload detector(s), with (4) ILR system, with (5) AI and/or data analytics.

During the Post-Operative Monitory Stage, the IA ecosystem may utilize the output of acute and chronic outcomes assessed per inputs from the Integrated Diagnostics, the Imaging Devices, Navigation/Mapping, and/or Sensor Devices (to track transient ischemic attack ("TIA"), stroke, patient prosthetic mismatch, and/or arrhythmia resolution if left bundle branch block from stent pressing on it, or the like). A feedback loop may be used to continually enhance predictive and prescriptive recommendations in real-time or near-real-time, with playback of trajectories and/or ablations, descriptive analytics, suggested morphologies from similar patients, literature, etc. In this manner, the combinations during all three stages (i.e., the Pre-Operative Planning Stage, the Intra-Operative Adjustment Stage, and the Post-Operative Monitory Stage) may achieve personalized therapy and trajectories for long term efficacy with minimal safety risk, while providing the user with efficient application of the therapy (i.e., reduced or consistent time and increased throughput) and extended career longevity (with no or low fluoro).

Referring to the non-limiting example 900"" of FIG. 9E, a process stack for implementing an IA ecosystem for TMVI might begin with a selection of a TMVI procedure (at block 905b). In response to such selection, a TMVI implant and delivery system may be selected for implementation (at block 910d). The IA ecosystem might utilize, in conjunction with the TMVI implant and delivery system, a number of devices or equipment, sensors, imaging systems, and other systems (collectively, "TMVI sub-systems" or the like), including, but not limited to, at least one, two, or three of a cardio insight ("CIT") mapping vest (at block 930), a mapping and/or navigation system (at block 935), imaging modality (at block 940), a system hub and/or application programming interfaces ("API's") (at block 945), cloud storage (at block 950), or artificial intelligence ("AI") and/or data analytics (at block 955), and/or the like. Data from these TMVI sub-systems may be combined to generate a combined display of three-dimensional ("3D") information or four-dimensional ("4D") information (i.e., three-dimensional ("3D") information plus at least one of real-time updates, dynamic modeling, or data streaming, and/or the like) for cognitive load (at block 960). Such 3D or 4D information may be used to control therapy delivery over the system (at block 965). The process at blocks 910d-965 may be repeated as necessary or as desired.

Table 4 below illustrates a specific non-limiting example combination(s) of sensors, imaging systems, tracking (or mapping and navigation) systems, and devices (e.g., robotic devices or the like) for each of the Pre-Operative Planning Stage, the Intra-Operative Adjustment Stage, and the Post-Operative Monitory Stage (as described above with respect to FIG. 3C) while implementing an IA ecosystem for a mitral valve replacement or repair procedure using a TMVI implant and delivery system. The various embodiments, however, are not limited to these items nor their specific combinations and can include any combination of items listed for sensors, imaging systems, tracking (or mapping and navigation) systems, and devices, e.g., as described below with respect to FIG. 15, or the like.

TABLE 4

Combination List of Systems and Devices for implementing IA ecosystem for TMVR/TMVr using TMVI

| Pre-Op Stage | Intra-Op Stage | | | | | Post-Op Stage Monitoring/ |
|---|---|---|---|---|---|---|
| Integrated Diagnostics | Imaging Devices | Navigation/ Mapping | Sensor Devices | Integrated Robotics | AI/Data Analytics | Analytics Feedback |
| CT, MRI, TTE, Biometric Input, Morphology Inputs | TTE, TEE, ICE | EM, Impedance, RFID, Optical + 3D AR, EWI, ICE, TEE, TTE | Contactless Optical, IR Temp, Blood Pressure, Heart Rate, Respiratory Rate, Fiducials Alignment, Tool Object Recognition, Collision Detection, Room Traffic Flow, Fatigue/Overload | ILR + AR and Haptics Feedback, Eye Tracking, Trajectory Coordinate Tracking | Merging Imaging and Other Sensor Data | Output of Acute and Chronic Outcomes + Feedback Loop |

As shown in Table 4 above, for the TMVR/TMVr using TMVI, the IA ecosystem may utilize, for an integrated diagnostics system during the Pre-Operative Planning Stage, one or a combination of a CT system, a MRI system, a TTE system, biometric input (including, but not limited to, information regarding at least one of age, weight, height, gender, race, etc.), and/or morphology inputs (such as cardiac history including, without limitation, persistent versus paroxysmal, etc.), and/or the like. In some cases, the IA ecosystem may perform analysis of data obtained by these sensors, imaging systems, and/or tracking (or mapping and navigation) systems as well as user input to generate recommendations or to facilitate physician/user plans for the TMVR/TMVr using TMVI. The TMVR/TMVr using TMVI may then be performed based on sensor data, imaging data, tracking data, recommendations, and/or physician/user plans obtained or arising from the Pre-Operative Planning Stage.

During the Intra-Operative Adjustment Stage, the IA ecosystem may combine (1) imaging device(s) including one or a combination of a TTE system, a transesophageal echocardiography ("TEE") system, and/or ICE, with (2) navigation/mapping system(s) including one or a combination of an EM system, an impedance-based system, a RFID-based tracking system, and/or an optical-based tracking system merged with a 3D AR and EWI/ICE/TEE/TTE, with (3) sensor device(s) including one or a combination of a contactless optical-based tracking system, an IR-based tracking system for sensing temperature, a blood pressure sensor, a heart rate sensor, a respiratory rate sensor, a fiducial tracking sensor to track motion of fiducials to maintain imaging/mapping/navigation alignment, a surgical tool object recognition system, robotic collision detection system, tracking system for tracking traffic flow in a room, and/or user fatigue and/or cognitive overload detector, and/or the like, with (4) integrated robotics including a soft-tissue ILR system, eye tracking system for tracking physicians with XR headset relative to robotics for cognitive load and safety shut offs, and/or trajectory coordinate tracking of physical catheters relative to digital twins for replay, approach angle, etc., to relate back to outcomes, with (5) intra-operative AI and/or data analytics (i.e., real-time or near-real-time AI and/or data analytics (i.e., real-time or near-real-time predictive and prescriptive analytics, etc.) that merges imaging and other sensor data to adjust device configurations, settings, and/or implementations in real-time (or near-real-time (e.g., within milliseconds or seconds, etc.)) based on any updates or changes to the sensor data, imaging data, tracking data, and/or recommendations obtained during the Intra-Operative Adjustments Stage. The ILR system may combine an intra-luminal robotic device with AR assistance and haptics feedback, particularly, for valve releases that are in the realm of seconds and/or navigating to complex targets (e.g., releasing device in flow with moving leaflets, etc.). Similar to TAVR/TAVr, the IA ecosystem may utilize sensor data to compensate, in real-time or near-real-time, for motion of the beating left ventricle and moving leaflets, which data may be used as another feedback loop for the AI and/or robotics when implementing the procedure.

In some embodiments, the merged imaging and other sensor data for the intra-operative AI and/or data analytics may include, without limitation, the following combinations: (a) capital equipment time series data from sensors for coordinates, flows, and/or pressures; (b) combination of delivery system and capital equipment data for proximity to targets with predictive analytics from imaging system data merge and previous post-operative feedback loops; (c) auto-segmentation of anatomical imaging, object/feature recognition, trajectory recommendation to target and real-time tracking, 3D XR with catheter electrode proximity to location or gap, electrical field growth, tagging of therapy, predictive arrhythmia change to titer therapy dosage, proximity to adjacent anatomy (e.g., esophagus and phrenic nerve, etc.) with warnings to recommend approach and to titer therapy, and provide device and size recommendations; (d) XR headset eye tracking and robotic coordinates for safety, efficiency, and relationships with digital twins (e.g., "back-up camera" following moving anatomy that has real-time or near-real-time distance and auditory feedback until "docked"); or (e) facial and/or text recognition to anonymize people and/or documents; etc.

In one non-limiting example, (1) TTE or TEE may be combined with (2) an EM-based tracking system(s) merged with 3D AR and EWI, with (3) an Optical-based tracking system(s), with (4) ILR system, with (5) AI and/or data analytics. In an alternative example, (1) TTE or TEE may be combined with (2) an impedance-based tracking system(s) merged with 3D AR and EWI, with (3) an Optical-based tracking system(s), with (4) ILR system, with (5) AI and/or data analytics. In an alternative example, (1) TTE or TEE may be combined with (2) RFID merged with 3D AR and EWI, with (3) an Optical-based tracking system(s), with (4) ILR system, with (5) AI and/or data analytics. In an alternative example, (1) TTE or TEE may be combined with (2) an optical-based tracking system(s) merged with 3D AR and EWI, with (3) an Optical-based tracking system(s), with (4) ILR system, with (5) AI and/or data analytics. In an alternative example, (1) TTE or TEE may be combined with (2) an EM-based tracking system(s) merged with 3D AR and EWI, with (3) an IR-based tracking system(s), with (4) ILR system, with (5) AI and/or data analytics. In an alternative example, (1) TTE or TEE may be combined with (2) an impedance-based tracking system(s) merged with 3D AR and EWI, with (3) an IR-based tracking system(s), with (4) ILR system, with (5) AI and/or data analytics. In an alternative example, (1) TTE or TEE may be combined with (2) RFID merged with 3D AR and EWI, with (3) an IR-based tracking system(s), with (4) ILR system, with (5) AI and/or data analytics. In an alternative example, (1) TTE or TEE may be combined with (2) an optical-based tracking system(s) merged with 3D AR and EWI, with (3) an IR-based tracking system(s), with (4) ILR system, with (5) AI and/or data analytics. In an alternative example, (1) TTE or TEE may be combined with (2) an EM-based tracking system(s) merged with 3D AR and EWI, with (3) a blood pressure sensor(s) and/or a heart rate sensor(s), with (4) ILR system, with (5) AI and/or data analytics. In an alternative example, (1) TTE or TEE may be combined with (2) an impedance-based tracking system(s) merged with 3D AR and EWI, with (3) a blood pressure sensor(s) and/or a heart rate sensor(s), with (4) ILR system, with (5) AI and/or data analytics. In an alternative example, (1) TTE or TEE may be combined with (2) RFID merged with 3D AR and EWI, with (3) a blood pressure sensor(s) and/or a heart rate sensor(s), with (4) ILR system, with (5) AI and/or data analytics. In an alternative example, (1) TTE or TEE may be combined with (2) an optical-based tracking system(s) merged with 3D AR and EWI, with (3) a blood pressure sensor(s) and/or a heart rate sensor(s), with (4) ILR system, with (5) AI and/or data analytics.

In an alternative example, (1) TTE or TEE may be combined with (2) an EM-based tracking system(s) merged with 3D AR and EWI, with (3) a respiratory rate sensor(s), with (4) ILR system, with (5) AI and/or data analytics. In an alternative example, (1) TTE or TEE may be combined with (2) an impedance-based tracking system(s) merged with 3D AR and EWI, with (3) a respiratory rate sensor(s), with (4) ILR system, with (5) AI and/or data analytics. In an alternative example, (1) TTE or TEE may be combined with (2) RFID merged with 3D AR and EWI, with (3) a respiratory rate sensor(s), with (4) ILR system, with (5) AI and/or data analytics. In an alternative example, (1) TTE or TEE may be combined with (2) an optical-based tracking system(s) merged with 3D AR and EWI, with (3) a respiratory rate sensor(s), with (4) ILR system, with (5) AI and/or data analytics. In an alternative example, (1) TTE or TEE may be combined with (2) an EM-based tracking system(s) merged with 3D AR and EWI, with (3) an object/person motion/collision tracking system(s), with (4) ILR system, with (5) AI and/or data analytics. In an alternative example, (1) TTE or TEE may be combined with (2) an impedance-based tracking system(s) merged with 3D AR and EWI, with (3) an object/person motion/collision tracking system(s), with (4) ILR system, with (5) AI and/or data analytics. In an alternative example, (1) TTE or TEE may be combined with (2) RFID merged with 3D AR and EWI, with (3) an object/person motion/collision tracking system(s), with (4) ILR system, with (5) AI and/or data analytics. In an alternative example, (1) TTE or TEE may be combined with (2) an optical-based tracking system(s) merged with 3D AR and EWI, with (3) an object/person motion/collision tracking system(s), with (4) ILR system, with (5) AI and/or data analytics. In an alternative example, (1) TTE or TEE may be combined with (2) an EM-based tracking system(s) merged with 3D AR and EWI, with (3) a user fatigue and/or cognitive overload detector(s), with (4) ILR system, with (5) AI and/or data analytics. In an alternative example, (1) TTE or TEE may be combined with (2) an impedance-based tracking system(s) merged with 3D AR and EWI, with (3) a user fatigue and/or cognitive overload detector(s), with (4) ILR system, with (5) AI and/or data analytics. In an alternative example, (1) TTE or TEE may be combined with (2) RFID merged with 3D AR and EWI, with (3) a user fatigue and/or cognitive overload detector(s), with (4) ILR system, with (5) AI and/or data analytics. In an alternative example, (1) TTE or TEE may be combined with (2) an optical-based tracking system(s) merged with 3D AR and EWI, with (3) a user fatigue and/or cognitive overload detector(s), with (4) ILR system, with (5) AI and/or data analytics.

In another non-limiting example, (1) TTE or TEE may be combined with (2) an EM-based tracking system(s) merged with 3D AR and ICE, with (3) an Optical-based tracking system(s), with (4) ILR system, with (5) AI and/or data analytics. In an alternative example, (1) TTE or TEE may be combined with (2) an impedance-based tracking system(s) merged with 3D AR and ICE, with (3) an Optical-based tracking system(s), with (4) ILR system, with (5) AI and/or data analytics. In an alternative example, (1) TTE or TEE may be combined with (2) RFID merged with 3D AR and ICE, with (3) an Optical-based tracking system(s), with (4) ILR system, with (5) AI and/or data analytics. In an alternative example, (1) TTE or TEE may be combined with (2) an optical-based tracking system(s) merged with 3D AR and ICE, with (3) an Optical-based tracking system(s), with (4) ILR system, with (5) AI and/or data analytics. In an alternative example, (1) TTE or TEE may be combined with (2) an EM-based tracking system(s) merged with 3D AR and ICE, with (3) an IR-based tracking system(s), with (4) ILR system, with (5) AI and/or data analytics. In an alternative example, (1) TTE or TEE may be combined with (2) an impedance-based tracking system(s) merged with 3D AR and ICE, with (3) an IR-based tracking system(s), with (4) ILR system, with (5) AI and/or data analytics. In an alternative example, (1) TTE or TEE may be combined with (2) RFID merged with 3D AR and ICE, with (3) an IR-based tracking system(s), with (4) ILR system, with (5) AI and/or data analytics. In an alternative example, (1) TTE or TEE may be combined with (2) an optical-based tracking system(s) merged with 3D AR and ICE, with (3) an IR-based tracking system(s), with (4) ILR system, with (5) AI and/or data analytics. In an alternative example, (1) TTE or TEE may be combined with (2) an EM-based tracking system(s) merged with 3D AR and ICE, with (3) a blood pressure sensor(s) and/or a heart rate sensor(s), with (4) ILR system, with (5) AI and/or data analytics. In an alternative example, (1) TTE or TEE may be combined with (2) an impedance-based tracking system(s) merged with 3D AR and ICE, with (3) a blood pressure sensor(s) and/or a heart rate sensor(s), with (4) ILR system, with (5) AI and/or data analytics. In an alternative example, (1) TTE or TEE may be combined with (2) RFID merged with 3D AR and ICE, with (3) a blood pressure sensor(s) and/or a heart rate sensor(s), with (4) ILR system, with (5) AI and/or data analytics. In an alternative example, (1) TTE or TEE may be combined with (2) an optical-based tracking system(s) merged with 3D AR and ICE, with (3) a blood pressure sensor(s) and/or a heart rate sensor(s), with (4) ILR system, with (5) AI and/or data analytics.

In an alternative example, (1) TTE or TEE may be combined with (2) an EM-based tracking system(s) merged with 3D AR and ICE, with (3) a respiratory rate sensor(s), with (4) ILR system, with (5) AI and/or data analytics. In an alternative example, (1) TTE or TEE may be combined with (2) an impedance-based tracking system(s) merged with 3D AR and ICE, with (3) a respiratory rate sensor(s), with (4) ILR system, with (5) AI and/or data analytics. In an alternative example, (1) TTE or TEE may be combined with (2) RFID merged with 3D AR and ICE, with (3) a respiratory rate sensor(s), with (4) ILR system, with (5) AI and/or data analytics. In an alternative example, (1) TTE or TEE may be combined with (2) an optical-based tracking system(s) merged with 3D AR and ICE, with (3) a respiratory rate sensor(s), with (4) ILR system, with (5) AI and/or data analytics. In an alternative example, (1) TTE or TEE may be combined with (2) an EM-based tracking system(s) merged with 3D AR and ICE, with (3) an object/person motion/collision tracking system(s), with (4) ILR system, with (5) AI and/or data analytics. In an alternative example, (1) TTE or TEE may be combined with (2) an impedance-based tracking system(s) merged with 3D AR and ICE, with (3) an object/person motion/collision tracking system(s), with (4) ILR system, with (5) AI and/or data analytics. In an alternative example, (1) TTE or TEE may be combined with (2) RFID merged with 3D AR and ICE, with (3) an object/person motion/collision tracking system(s), with (4) ILR system, with (5) AI and/or data analytics. In an alternative example, (1) TTE or TEE may be combined with (2) an optical-based tracking system(s) merged with 3D AR and ICE, with (3) an object/person motion/collision tracking system(s), with (4) ILR system, with (5) AI and/or data analytics. In an alternative example, (1) TTE or TEE may be combined with (2) an EM-based tracking system(s) merged with 3D AR and ICE, with (3) a user fatigue and/or cognitive overload detector(s), with (4) ILR system, with (5) AI and/or data analytics. In an alternative example, (1) TTE or TEE may be combined with (2) an impedance-based tracking system(s) merged with 3D AR and ICE, with (3) a user fatigue and/or cognitive overload detector(s), with (4) ILR system, with (5) AI and/or data analytics. In an alternative example, (1) TTE or TEE may be combined with (2) RFID merged with 3D AR and ICE, with (3) a user fatigue and/or cognitive overload detector(s), with (4) ILR system, with (5) AI and/or data analytics. In an alternative example, (1) TTE or TEE may be combined with (2) an optical-based tracking system(s) merged with 3D AR and ICE, with (3) a user fatigue and/or cognitive overload detector(s), with (4) ILR system, with (5) AI and/or data analytics.

In another non-limiting example, (1) TTE or TEE may be combined with (2) an EM-based tracking system(s) merged with 3D AR and TEE, with (3) an Optical-based tracking system(s), with (4) ILR system, with (5) AI and/or data analytics. In an alternative example, (1) TTE or TEE may be combined with (2) an impedance-based tracking system(s) merged with 3D AR and TEE, with (3) an Optical-based tracking system(s), with (4) ILR system, with (5) AI and/or data analytics. In an alternative example, (1) TTE or TEE may be combined with (2) RFID merged with 3D AR and TEE, with (3) an Optical-based tracking system(s), with (4) ILR system, with (5) AI and/or data analytics. In an alternative example, (1) TTE or TEE may be combined with (2) an optical-based tracking system(s) merged with 3D AR and TEE, with (3) an Optical-based tracking system(s), with (4) ILR system, with (5) AI and/or data analytics. In an alternative example, (1) TTE or TEE may be combined with (2) an EM-based tracking system(s) merged with 3D AR and TEE, with (3) an IR-based tracking system(s), with (4) ILR system, with (5) AI and/or data analytics. In an alternative example, (1) TTE or TEE may be combined with (2) an impedance-based tracking system(s) merged with 3D AR and TEE, with (3) an IR-based tracking system(s), with (4) ILR system, with (5) AI and/or data analytics. In an alternative example, (1) TTE or TEE may be combined with (2) RFID merged with 3D AR and TEE, with (3) an IR-based tracking system(s), with (4) ILR system, with (5) AI and/or data analytics. In an alternative example, (1) TTE or TEE may be combined with (2) an optical-based tracking system(s) merged with 3D AR and TEE, with (3) an IR-based tracking system(s), with (4) ILR system, with (5) AI and/or data analytics. In an alternative example, (1) TTE or TEE may be combined with (2) an EM-based tracking system(s) merged with 3D AR and TEE, with (3) a blood pressure sensor(s) and/or a heart rate sensor(s), with (4) ILR system, with (5) AI and/or data analytics. In an alternative example, (1) TTE or TEE may be combined with (2) an impedance-based tracking system(s) merged with 3D AR and TEE, with (3) a blood pressure sensor(s) and/or a heart rate sensor(s), with (4) ILR system, with (5) AI and/or data analytics. In an alternative example, (1) TTE or TEE may be combined with (2) RFID merged with 3D AR and TEE, with (3) a blood pressure sensor(s) and/or a heart rate sensor(s), with (4) ILR system, with (5) AI and/or data analytics. In an alternative example, (1) TTE or TEE may be combined with (2) an optical-based tracking system(s) merged with 3D AR and TEE, with (3) a blood pressure sensor(s) and/or a heart rate sensor(s), with (4) ILR system, with (5) AI and/or data analytics.

In an alternative example, (1) TTE or TEE may be combined with (2) an EM-based tracking system(s) merged with 3D AR and TEE, with (3) a respiratory rate sensor(s), with (4) ILR system, with (5) AI and/or data analytics. In an alternative example, (1) TTE or TEE may be combined with (2) an impedance-based tracking system(s) merged with 3D AR and TEE, with (3) a respiratory rate sensor(s), with (4) ILR system, with (5) AI and/or data analytics. In an alternative example, (1) TTE or TEE may be combined with (2) RFID merged with 3D AR and TEE, with (3) a respiratory rate sensor(s), with (4) ILR system, with (5) AI and/or data analytics. In an alternative example, (1) TTE or TEE may be combined with (2) an optical-based tracking system(s) merged with 3D AR and TEE, with (3) a respiratory rate sensor(s), with (4) ILR system, with (5) AI and/or data analytics. In an alternative example, (1) TTE or TEE may be combined with (2) an EM-based tracking system(s) merged with 3D AR and TEE, with (3) an object/person motion/collision tracking system(s), with (4) ILR system, with (5) AI and/or data analytics. In an alternative example, (1) TTE or TEE may be combined with (2) an impedance-based tracking system(s) merged with 3D AR and TEE, with (3) an object/person motion/collision tracking system(s), with (4) ILR system, with (5) AI and/or data analytics. In an alternative example, (1) TTE or TEE may be combined with (2) RFID merged with 3D AR and TEE, with (3) an object/person motion/collision tracking system(s), with (4) ILR system, with (5) AI and/or data analytics. In an alternative example, (1) TTE or TEE may be combined with (2) an optical-based tracking system(s) merged with 3D AR and TEE, with (3) an object/person motion/collision tracking system(s), with (4) ILR system, with (5) AI and/or data analytics. In an alternative example, (1) TTE or TEE may be combined with (2) an EM-based tracking system(s) merged with 3D AR and TEE, with (3) a user fatigue and/or cognitive overload detector(s), with (4) ILR system, with (5) AI and/or data analytics. In an alternative example, (1) TTE or TEE may be combined with (2) an impedance-based tracking system(s) merged with 3D AR and TEE, with (3) a user fatigue and/or cognitive overload detector(s), with (4) ILR system, with (5) AI and/or data analytics. In an alternative example, (1) TTE or TEE may be combined with (2) RFID merged with 3D AR and TEE, with (3) a user fatigue and/or cognitive overload detector(s), with (4) ILR system, with (5) AI and/or data analytics. In an alternative example, (1) TTE or TEE may be combined with (2) an optical-based tracking system(s) merged with 3D AR and TEE, with (3) a user fatigue and/or cognitive overload detector(s), with (4) ILR system, with (5) AI and/or data analytics.

In another non-limiting example, (1) TTE or TEE may be combined with (2) an EM-based tracking system(s) merged with 3D AR and TTE, with (3) an Optical-based tracking system(s), with (4) ILR system, with (5) AI and/or data analytics. In an alternative example, (1) TTE or TEE may be combined with (2) an impedance-based tracking system(s) merged with 3D AR and TTE, with (3) an Optical-based tracking system(s), with (4) ILR system, with (5) AI and/or data analytics. In an alternative example, (1) TTE or TEE may be combined with (2) RFID merged with 3D AR and TTE, with (3) an Optical-based tracking system(s), with (4) ILR system, with (5) AI and/or data analytics. In an alternative example, (1) TTE or TEE may be combined with (2) an optical-based tracking system(s) merged with 3D AR and TTE, with (3) an Optical-based tracking system(s), with (4) ILR system, with (5) AI and/or data analytics. In an alternative example, (1) TTE or TEE may be combined with (2) an EM-based tracking system(s) merged with 3D AR and TTE, with (3) an IR-based tracking system(s), with (4) ILR system, with (5) AI and/or data analytics. In an alternative example, (1) TTE or TEE may be combined with (2) an impedance-based tracking system(s) merged with 3D AR and TTE, with (3) an IR-based tracking system(s), with (4) ILR system, with (5) AI and/or data analytics. In an alternative example, (1) TTE or TEE may be combined with (2) RFID merged with 3D AR and TTE, with (3) an IR-based tracking system(s), with (4) ILR system, with (5) AI and/or data analytics. In an alternative example, (1) TTE or TEE may be combined with (2) an optical-based tracking system(s) merged with 3D AR and TTE, with (3) an IR-based tracking system(s), with (4) ILR system, with (5) AI and/or data analytics. In an alternative example, (1) TTE or TEE may be combined with (2) an EM-based tracking system(s) merged with 3D AR and TTE, with (3) a blood pressure sensor(s) and/or a heart rate sensor(s), with (4) ILR system, with (5) AI and/or data analytics. In an alternative example, (1) TTE or TEE may be combined with (2) an impedance-based tracking system(s) merged with 3D AR and TTE, with (3) a blood pressure sensor(s) and/or a heart rate sensor(s), with (4) ILR system, with (5) AI and/or data analytics. In an alternative example, (1) TTE or TEE may be combined with (2) RFID merged with 3D AR and TTE, with (3) a blood pressure sensor(s) and/or a heart rate sensor(s), with (4) ILR system, with (5) AI and/or data analytics. In an alternative example, (1) TTE or TEE may be combined with (2) an optical-based tracking system(s) merged with 3D AR and TTE, with (3) a blood pressure sensor(s) and/or a heart rate sensor(s), with (4) ILR system, with (5) AI and/or data analytics.

In an alternative example, (1) TTE or TEE may be combined with (2) an EM-based tracking system(s) merged with 3D AR and TTE, with (3) a respiratory rate sensor(s), with (4) ILR system, with (5) AI and/or data analytics. In an alternative example, (1) TTE or TEE may be combined with (2) an impedance-based tracking system(s) merged with 3D AR and TTE, with (3) a respiratory rate sensor(s), with (4) ILR system, with (5) AI and/or data analytics. In an alternative example, (1) TTE or TEE may be combined with (2) RFID merged with 3D AR and TTE, with (3) a respiratory rate sensor(s), with (4) ILR system, with (5) AI and/or data analytics. In an alternative example, (1) TTE or TEE may be combined with (2) an optical-based tracking system(s) merged with 3D AR and TTE, with (3) a respiratory rate sensor(s), with (4) ILR system, with (5) AI and/or data analytics. In an alternative example, (1) TTE or TEE may be combined with (2) an EM-based tracking system(s) merged with 3D AR and TTE, with (3) an object/person motion/collision tracking system(s), with (4) ILR system, with (5) AI and/or data analytics. In an alternative example, (1) TTE or TEE may be combined with (2) an impedance-based tracking system(s) merged with 3D AR and TTE, with (3) an object/person motion/collision tracking system(s), with (4) ILR system, with (5) AI and/or data analytics. In an alternative example, (1) TTE or TEE may be combined with (2) RFID merged with 3D AR and TTE, with (3) an object/person motion/collision tracking system(s), with (4) ILR system, with (5) AI and/or data analytics. In an alternative example, (1) TTE or TEE may be combined with (2) an optical-based tracking system(s) merged with 3D AR and TTE, with (3) an object/person motion/collision tracking system(s), with (4) ILR system, with (5) AI and/or data analytics. In an alternative example, (1) TTE or TEE may be combined with (2) an EM-based tracking system(s) merged with 3D AR and TTE, with (3) a user fatigue and/or cognitive overload detector(s), with (4) ILR system, with (5) AI and/or data analytics. In an alternative example, (1) TTE or TEE may be combined with (2) an impedance-based tracking system(s) merged with 3D AR and TTE, with (3) a user fatigue and/or cognitive overload detector(s), with (4) ILR system, with (5) AI and/or data analytics. In an alternative example, (1) TTE or TEE may be combined with (2) RFID merged with 3D AR and TTE, with (3) a user fatigue and/or cognitive overload detector(s), with (4) ILR system, with (5) AI and/or data analytics. In an alternative example, (1) TTE or TEE may be combined with (2) an optical-based tracking system(s) merged with 3D AR and TTE, with (3) a user fatigue and/or cognitive overload detector(s), with (4) ILR system, with (5) AI and/or data analytics.

In yet another non-limiting example, (1) ICE may be combined with (2) an EM-based tracking system(s) merged with 3D AR and EWI, with (3) an Optical-based tracking system(s), with (4) ILR system, with (5) AI and/or data analytics. In an alternative example, (1) ICE may be combined with (2) an impedance-based tracking system(s) merged with 3D AR and EWI, with (3) an Optical-based tracking system(s), with (4) ILR system, with (5) AI and/or data analytics. In an alternative example, (1) ICE may be combined with (2) RFID merged with 3D AR and EWI, with (3) an Optical-based tracking system(s), with (4) ILR system, with (5) AI and/or data analytics. In an alternative example, (1) ICE may be combined with (2) an optical-based tracking system(s) merged with 3D AR and EWI, with (3) an Optical-based tracking system(s), with (4) ILR system, with (5) AI and/or data analytics. In an alternative example, (1) ICE may be combined with (2) an EM-based tracking system(s) merged with 3D AR and EWI, with (3) an IR-based tracking system(s), with (4) ILR system, with (5) AI and/or data analytics. In an alternative example, (1) ICE may be combined with (2) an impedance-based tracking system(s) merged with 3D AR and EWI, with (3) an IR-based tracking system(s), with (4) ILR system, with (5) AI and/or data analytics. In an alternative example, (1) ICE may be combined with (2) RFID merged with 3D AR and EWI, with (3) an IR-based tracking system(s), with (4) ILR system, with (5) AI and/or data analytics. In an alternative example, (1) ICE may be combined with (2) an optical-based tracking system(s) merged with 3D AR and EWI, with (3) an IR-based tracking system(s), with (4) ILR system, with (5) AI and/or data analytics. In an alternative example, (1) ICE may be combined with (2) an EM-based tracking system(s) merged with 3D AR and EWI, with (3) a blood pressure sensor(s) and/or a heart rate sensor(s), with (4) ILR system, with (5) AI and/or data analytics. In an alternative example, (1) ICE may be combined with (2) an impedance-based tracking system(s) merged with 3D AR and EWI, with (3) a blood pressure sensor(s) and/or a heart rate sensor(s), with (4) ILR system, with (5) AI and/or data analytics. In an alternative example, (1) ICE may be combined with (2) RFID merged with 3D AR and EWI, with (3) a blood pressure sensor(s) and/or a heart rate sensor(s), with (4) ILR system, with (5) AI and/or data analytics. In an alternative example, (1) ICE may be combined with (2) an optical-based tracking system(s) merged with 3D AR and EWI, with (3) a blood pressure sensor(s) and/or a heart rate sensor(s), with (4) ILR system, with (5) AI and/or data analytics.

In an alternative example, (1) ICE may be combined with (2) an EM-based tracking system(s) merged with 3D AR and EWI, with (3) a respiratory rate sensor(s), with (4) ILR system, with (5) AI and/or data analytics. In an alternative example, (1) ICE may be combined with (2) an impedance-based tracking system(s) merged with 3D AR and EWI, with (3) a respiratory rate sensor(s), with (4) ILR system, with (5) AI and/or data analytics. In an alternative example, (1) ICE may be combined with (2) RFID merged with 3D AR and EWI, with (3) a respiratory rate sensor(s), with (4) ILR system, with (5) AI and/or data analytics. In an alternative example, (1) ICE may be combined with (2) an optical-based tracking system(s) merged with 3D AR and EWI, with (3) a respiratory rate sensor(s), with (4) ILR system, with (5) AI and/or data analytics. In an alternative example, (1) ICE may be combined with (2) an EM-based tracking system(s) merged with 3D AR and EWI, with (3) an object/person motion/collision tracking system(s), with (4) ILR system, with (5) AI and/or data analytics. In an alternative example, (1) ICE may be combined with (2) an impedance-based tracking system(s) merged with 3D AR and EWI, with (3) an object/person motion/collision tracking system(s), with (4) ILR system, with (5) AI and/or data analytics. In an alternative example, (1) ICE may be combined with (2) RFID merged with 3D AR and EWI, with (3) an object/person motion/collision tracking system(s), with (4) ILR system, with (5) AI and/or data analytics. In an alternative example, (1) ICE may be combined with (2) an optical-based tracking system(s) merged with 3D AR and EWI, with (3) an object/person motion/collision tracking system(s), with (4) ILR system, with (5) AI and/or data analytics. In an alternative example, (1) ICE may be combined with (2) an EM-based tracking system(s) merged with 3D AR and EWI, with (3) a user fatigue and/or cognitive overload detector(s), with (4) ILR system, with (5) AI and/or data analytics. In an alternative example, (1) ICE may be combined with (2) an impedance-based tracking system(s) merged with 3D AR and EWI, with (3) a user fatigue and/or cognitive overload detector(s), with (4) ILR system, with (5) AI and/or data analytics. In an alternative example, (1) ICE may be combined with (2) RFID merged with 3D AR and EWI, with (3) a user fatigue and/or cognitive overload detector(s), with (4) ILR system, with (5) AI and/or data analytics. In an alternative example, (1) ICE may be combined with (2) an optical-based tracking system(s) merged with 3D AR and EWI, with (3) a user fatigue and/or cognitive overload detector(s), with (4) ILR system, with (5) AI and/or data analytics.

In another non-limiting example, (1) ICE may be combined with (2) an EM-based tracking system(s) merged with 3D AR and ICE, with (3) an Optical-based tracking system(s), with (4) ILR system, with (5) AI and/or data analytics. In an alternative example, (1) ICE may be combined with (2) an impedance-based tracking system(s)

merged with 3D AR and ICE, with (3) an Optical-based tracking system(s), with (4) ILR system, with (5) AI and/or data analytics. In an alternative example, (1) ICE may be combined with (2) RFID merged with 3D AR and ICE, with (3) an Optical-based tracking system(s), with (4) ILR system, with (5) AI and/or data analytics. In an alternative example, (1) ICE may be combined with (2) an optical-based tracking system(s) merged with 3D AR and ICE, with (3) an Optical-based tracking system(s), with (4) ILR system, with (5) AI and/or data analytics. In an alternative example, (1) ICE may be combined with (2) an EM-based tracking system(s) merged with 3D AR and ICE, with (3) an IR-based tracking system(s), with (4) ILR system, with (5) AI and/or data analytics. In an alternative example, (1) ICE may be combined with (2) an impedance-based tracking system(s) merged with 3D AR and ICE, with (3) an IR-based tracking system(s), with (4) ILR system, with (5) AI and/or data analytics. In an alternative example, (1) ICE may be combined with (2) RFID merged with 3D AR and ICE, with (3) an IR-based tracking system(s), with (4) ILR system, with (5) AI and/or data analytics. In an alternative example, (1) ICE may be combined with (2) an optical-based tracking system(s) merged with 3D AR and ICE, with (3) an IR-based tracking system(s), with (4) ILR system, with (5) AI and/or data analytics. In an alternative example, (1) ICE may be combined with (2) an EM-based tracking system(s) merged with 3D AR and ICE, with (3) a blood pressure sensor(s) and/or a heart rate sensor(s), with (4) ILR system, with (5) AI and/or data analytics. In an alternative example, (1) ICE may be combined with (2) an impedance-based tracking system(s) merged with 3D AR and ICE, with (3) a blood pressure sensor(s) and/or a heart rate sensor(s), with (4) ILR system, with (5) AI and/or data analytics. In an alternative example, (1) ICE may be combined with (2) RFID merged with 3D AR and ICE, with (3) a blood pressure sensor(s) and/or a heart rate sensor(s), with (4) ILR system, with (5) AI and/or data analytics. In an alternative example, (1) ICE may be combined with (2) an optical-based tracking system(s) merged with 3D AR and ICE, with (3) a blood pressure sensor(s) and/or a heart rate sensor(s), with (4) ILR system, with (5) AI and/or data analytics.

In an alternative example, (1) ICE may be combined with (2) an EM-based tracking system(s) merged with 3D AR and ICE, with (3) a respiratory rate sensor(s), with (4) ILR system, with (5) AI and/or data analytics. In an alternative example, (1) ICE may be combined with (2) an impedance-based tracking system(s) merged with 3D AR and ICE, with (3) a respiratory rate sensor(s), with (4) ILR system, with (5) AI and/or data analytics. In an alternative example, (1) ICE may be combined with (2) RFID merged with 3D AR and ICE, with (3) a respiratory rate sensor(s), with (4) ILR system, with (5) AI and/or data analytics. In an alternative example, (1) ICE may be combined with (2) an optical-based tracking system(s) merged with 3D AR and ICE, with (3) a respiratory rate sensor(s), with (4) ILR system, with (5) AI and/or data analytics. In an alternative example, (1) ICE may be combined with (2) an EM-based tracking system(s) merged with 3D AR and ICE, with (3) an object/person motion/collision tracking system(s), with (4) ILR system, with (5) AI and/or data analytics. In an alternative example, (1) ICE may be combined with (2) an impedance-based tracking system(s) merged with 3D AR and ICE, with (3) an object/person motion/collision tracking system(s), with (4) ILR system, with (5) AI and/or data analytics. In an alternative example, (1) ICE may be combined with (2) RFID merged with 3D AR and ICE, with (3) an object/person motion/collision tracking system(s), with (4) ILR system, with (5) AI and/or data analytics. In an alternative example, (1) ICE may be combined with (2) an optical-based tracking system(s) merged with 3D AR and ICE, with (3) an object/person motion/collision tracking system(s), with (4) ILR system, with (5) AI and/or data analytics. In an alternative example, (1) ICE may be combined with (2) an EM-based tracking system(s) merged with 3D AR and ICE, with (3) a user fatigue and/or cognitive overload detector(s), with (4) ILR system, with (5) AI and/or data analytics. In an alternative example, (1) ICE may be combined with (2) an impedance-based tracking system(s) merged with 3D AR and ICE, with (3) a user fatigue and/or cognitive overload detector(s), with (4) ILR system, with (5) AI and/or data analytics. In an alternative example, (1) ICE may be combined with (2) RFID merged with 3D AR and ICE, with (3) a user fatigue and/or cognitive overload detector(s), with (4) ILR system, with (5) AI and/or data analytics. In an alternative example, (1) ICE may be combined with (2) an optical-based tracking system(s) merged with 3D AR and ICE, with (3) a user fatigue and/or cognitive overload detector(s), with (4) ILR system, with (5) AI and/or data analytics.

In another non-limiting example, (1) ICE may be combined with (2) an EM-based tracking system(s) merged with 3D AR and TEE, with (3) an Optical-based tracking system(s), with (4) ILR system, with (5) AI and/or data analytics. In an alternative example, (1) ICE may be combined with (2) an impedance-based tracking system(s) merged with 3D AR and TEE, with (3) an Optical-based tracking system(s), with (4) ILR system, with (5) AI and/or data analytics. In an alternative example, (1) ICE may be combined with (2) RFID merged with 3D AR and TEE, with (3) an Optical-based tracking system(s), with (4) ILR system, with (5) AI and/or data analytics. In an alternative example, (1) ICE may be combined with (2) an optical-based tracking system(s) merged with 3D AR and TEE, with (3) an Optical-based tracking system(s), with (4) ILR system, with (5) AI and/or data analytics. In an alternative example, (1) ICE may be combined with (2) an EM-based tracking system(s) merged with 3D AR and TEE, with (3) an IR-based tracking system(s), with (4) ILR system, with (5) AI and/or data analytics. In an alternative example, (1) ICE may be combined with (2) an impedance-based tracking system(s) merged with 3D AR and TEE, with (3) an IR-based tracking system(s), with (4) ILR system, with (5) AI and/or data analytics. In an alternative example, (1) ICE may be combined with (2) RFID merged with 3D AR and TEE, with (3) an IR-based tracking system(s), with (4) ILR system, with (5) AI and/or data analytics. In an alternative example, (1) ICE may be combined with (2) an optical-based tracking system(s) merged with 3D AR and TEE, with (3) an IR-based tracking system(s), with (4) ILR system, with (5) AI and/or data analytics. In an alternative example, (1) ICE may be combined with (2) an EM-based tracking system(s) merged with 3D AR and TEE, with (3) a blood pressure sensor(s) and/or a heart rate sensor(s), with (4) ILR system, with (5) AI and/or data analytics. In an alternative example, (1) ICE may be combined with (2) an impedance-based tracking system(s) merged with 3D AR and TEE, with (3) a blood pressure sensor(s) and/or a heart rate sensor(s), with (4) ILR system, with (5) AI and/or data analytics. In an alternative example, (1) ICE may be combined with (2) RFID merged with 3D AR and TEE, with (3) a blood pressure sensor(s) and/or a heart rate sensor(s), with (4) ILR system, with (5) AI and/or data analytics. In an alternative example, (1) ICE may be combined with (2) an optical-based tracking system(s) merged with 3D AR and TEE, with (3) a blood pressure sensor(s) and/or a heart rate sensor(s), with (4) ILR system, with (5) AI and/or data analytics.

In an alternative example, (1) ICE may be combined with (2) an EM-based tracking system(s) merged with 3D AR and TEE, with (3) a respiratory rate sensor(s), with (4) ILR system, with (5) AI and/or data analytics. In an alternative example, (1) ICE may be combined with (2) an impedance-based tracking system(s) merged with 3D AR and TEE, with (3) a respiratory rate sensor(s), with (4) ILR system, with (5) AI and/or data analytics. In an alternative example, (1) ICE may be combined with (2) RFID merged with 3D AR and TEE, with (3) a respiratory rate sensor(s), with (4) ILR system, with (5) AI and/or data analytics. In an alternative example, (1) ICE may be combined with (2) an optical-based tracking system(s) merged with 3D AR and TEE, with (3) a respiratory rate sensor(s), with (4) ILR system, with (5) AI and/or data analytics. In an alternative example, (1) ICE may be combined with (2) an EM-based tracking system(s) merged with 3D AR and TEE, with (3) an object/person motion/collision tracking system(s), with (4) ILR system, with (5) AI and/or data analytics. In an alternative example, (1) ICE may be combined with (2) an impedance-based tracking system(s) merged with 3D AR and TEE, with (3) an object/person motion/collision tracking system(s), with (4) ILR system, with (5) AI and/or data analytics. In an alternative example, (1) ICE may be combined with (2) RFID merged with 3D AR and TEE, with (3) an object/person motion/collision tracking system(s), with (4) ILR system, with (5) AI and/or data analytics. In an alternative example, (1) ICE may be combined with (2) an optical-based tracking system(s) merged with 3D AR and TEE, with (3) an object/person motion/collision tracking system(s), with (4) ILR system, with (5) AI and/or data analytics. In an alternative example, (1) ICE may be combined with (2) an EM-based tracking system(s) merged with 3D AR and TEE, with (3) a user fatigue and/or cognitive overload detector(s), with (4) ILR system, with (5) AI and/or data analytics. In an alternative example, (1) ICE may be combined with (2) an impedance-based tracking system(s) merged with 3D AR and TEE, with (3) a user fatigue and/or cognitive overload detector(s), with (4) ILR system, with (5) AI and/or data analytics. In an alternative example, (1) ICE may be combined with (2) RFID merged with 3D AR and TEE, with (3) a user fatigue and/or cognitive overload detector(s), with (4) ILR system, with (5) AI and/or data analytics. In an alternative example, (1) ICE may be combined with (2) an optical-based tracking system(s) merged with 3D AR and TEE, with (3) a user fatigue and/or cognitive overload detector(s), with (4) ILR system, with (5) AI and/or data analytics.

In another non-limiting example, (1) ICE may be combined with (2) an EM-based tracking system(s) merged with 3D AR and TTE, with (3) an Optical-based tracking system(s), with (4) ILR system, with (5) AI and/or data analytics. In an alternative example, (1) ICE may be combined with (2) an impedance-based tracking system(s) merged with 3D AR and TTE, with (3) an Optical-based tracking system(s), with (4) ILR system, with (5) AI and/or data analytics. In an alternative example, (1) ICE may be combined with (2) RFID merged with 3D AR and TTE, with (3) an Optical-based tracking system(s), with (4) ILR system, with (5) AI and/or data analytics. In an alternative example, (1) ICE may be combined with (2) an optical-based tracking system(s) merged with 3D AR and TTE, with (3) an Optical-based tracking system(s), with (4) ILR system, with (5) AI and/or data analytics. In an alternative example, (1) ICE may be combined with (2) an EM-based tracking system(s) merged with 3D AR and TTE, with (3) an IR-based tracking system(s), with (4) ILR system, with (5) AI and/or data analytics. In an alternative example, (1) ICE may be combined with (2) an impedance-based tracking system(s) merged with 3D AR and TTE, with (3) an IR-based tracking system(s), with (4) ILR system, with (5) AI and/or data analytics. In an alternative example, (1) ICE may be combined with (2) RFID merged with 3D AR and TTE, with (3) an IR-based tracking system(s), with (4) ILR system, with (5) AI and/or data analytics. In an alternative example, (1) ICE may be combined with (2) an optical-based tracking system(s) merged with 3D AR and TTE, with (3) an IR-based tracking system(s), with (4) ILR system, with (5) AI and/or data analytics. In an alternative example, (1) ICE may be combined with (2) an EM-based tracking system(s) merged with 3D AR and TTE, with (3) a blood pressure sensor(s) and/or a heart rate sensor(s), with (4) ILR system, with (5) AI and/or data analytics. In an alternative example, (1) ICE may be combined with (2) an impedance-based tracking system(s) merged with 3D AR and TTE, with (3) a blood pressure sensor(s) and/or a heart rate sensor(s), with (4) ILR system, with (5) AI and/or data analytics. In an alternative example, (1) ICE may be combined with (2) RFID merged with 3D AR and TTE, with (3) a blood pressure sensor(s) and/or a heart rate sensor(s), with (4) ILR system, with (5) AI and/or data analytics. In an alternative example, (1) ICE may be combined with (2) an optical-based tracking system(s) merged with 3D AR and TTE, with (3) a blood pressure sensor(s) and/or a heart rate sensor(s), with (4) ILR system, with (5) AI and/or data analytics.

In an alternative example, (1) ICE may be combined with (2) an EM-based tracking system(s) merged with 3D AR and TTE, with (3) a respiratory rate sensor(s), with (4) ILR system, with (5) AI and/or data analytics. In an alternative example, (1) ICE may be combined with (2) an impedance-based tracking system(s) merged with 3D AR and TTE, with (3) a respiratory rate sensor(s), with (4) ILR system, with (5) AI and/or data analytics. In an alternative example, (1) ICE may be combined with (2) RFID merged with 3D AR and TTE, with (3) a respiratory rate sensor(s), with (4) ILR system, with (5) AI and/or data analytics. In an alternative example, (1) ICE may be combined with (2) an optical-based tracking system(s) merged with 3D AR and TTE, with (3) a respiratory rate sensor(s), with (4) ILR system, with (5) AI and/or data analytics. In an alternative example, (1) ICE may be combined with (2) an EM-based tracking system(s) merged with 3D AR and TTE, with (3) an object/person motion/collision tracking system(s), with (4) ILR system, with (5) AI and/or data analytics. In an alternative example, (1) ICE may be combined with (2) an impedance-based tracking system(s) merged with 3D AR and TTE, with (3) an object/person motion/collision tracking system(s), with (4) ILR system, with (5) AI and/or data analytics. In an alternative example, (1) ICE may be combined with (2) RFID merged with 3D AR and TTE, with (3) an object/person motion/collision tracking system(s), with (4) ILR system, with (5) AI and/or data analytics. In an alternative example, (1) ICE may be combined with (2) an optical-based tracking system(s) merged with 3D AR and TTE, with (3) an object/person motion/collision tracking system(s), with (4) ILR system, with (5) AI and/or data analytics. In an alternative example, (1) ICE may be combined with (2) an EM-based tracking system(s) merged with 3D AR and TTE, with (3) a user fatigue and/or cognitive overload detector(s), with (4) ILR system, with (5) AI and/or data analytics. In an alternative example, (1) ICE may be combined with (2) an impedance-based tracking system(s) merged with 3D AR and TTE, with (3) a user fatigue and/or cognitive overload detector(s), with (4) ILR system, with (5) AI and/or data analytics. In an alternative example, (1) ICE may be combined with (2) RFID merged with 3D AR and TTE, with (3) a user fatigue and/or cognitive overload detector(s), with (4) ILR system, with (5) AI and/or data analytics. In an alternative example, (1) ICE may be combined with (2) an optical-based tracking system(s) merged with 3D AR and TTE, with (3) a user fatigue and/or cognitive overload detector(s), with (4) ILR system, with (5) AI and/or data analytics.

During the Post-Operative Monitory Stage, the IA ecosystem may utilize the output of acute and chronic outcomes assessed per inputs from the Integrated Diagnostics, the Imaging Devices, Navigation/Mapping, and/or Sensor Devices (to track transient ischemic attack ("TIA"), stroke, and/or patient prosthetic mismatch, or the like). A feedback loop may be used to continually enhance predictive and prescriptive recommendations in real-time or near-real-time, with playback of trajectories and/or ablations, descriptive analytics, suggested morphologies from similar patients, literature, etc. In this manner, the combinations during all three stages (i.e., the Pre-Operative Planning Stage, the Intra-Operative Adjustment Stage, and the Post-Operative Monitory Stage) may achieve personalized therapy and trajectories for long term efficacy with minimal safety risk, while providing the user with efficient application of the therapy (i.e., reduced or consistent time and increased throughput) and extended career longevity (with no or low fluoro).

Turning to the non-limiting example 900' of FIG. 9F, a process stack for implementing an IA ecosystem for a cardiac shunting procedure (e.g., atrial septal shunting procedure, or other shunting procedure in the heart, or the like) might begin with a selection of a cardiac shunting procedure (at block 905d). In response to such selection, a cardiac shunting cryoablation system (not unlike the cryoablation system 910b of FIG. 9C, or the like) may be selected for implementation (at block 910e). The IA ecosystem might utilize, in conjunction with the cardiac shunting cryoablation system, a number of devices or equipment, sensors, imaging systems, and other systems (collectively, "cardiac shunting cryo sub-systems" or the like), including, but not limited to, at least one, two, or three of an ECG monitor (at block 915), system-specific equipment including a cryo or cryoablation console (at block 925c), a cardio insight ("CIT") mapping vest (at block 930), one or more pressure sensors (at block 970), a mapping and/or navigation system (at block 935), imaging modality (at block 940), a system hub and/or application programming interfaces ("API's") (at block 945), cloud storage (at block 950), or artificial intelligence ("AI") and/or data analytics (at block 955), and/or the like. Data from these cardiac shunting cryo sub-systems may be combined to generate a combined display of three-dimensional ("3D") information or four-dimensional ("4D") information (i.e., three-dimensional ("3D") information plus at least one of real-time updates, dynamic modeling, or data streaming, and/or the like) for cognitive load (at block 960). Such 3D or 4D information may be used to control therapy delivery over the system (at block 965). The process at blocks 910e-970 may be repeated as necessary or as desired.

Referring to the non-limiting example 900'''' of FIG. 9G, a process stack for implementing an IA ecosystem for a cardiac shunting procedure (e.g., atrial septal shunting procedure, or other shunting procedure in the heart, or the like) might begin with a selection of a cardiac shunting procedure (at block 905d). In response to such selection, a cardiac shunting PFA system (not unlike the PFA system 910a of FIG. 9B, or the like) may be selected for implementation (at block 910f). The IA ecosystem might utilize, in conjunction with the cardiac shunting PFA system, a number of devices or equipment, sensors, imaging systems, and other systems (collectively, "cardiac shunting PFA sub-systems" or the like), including, but not limited to, at least one, two, or three of an ECG monitor (at block 915), system-specific equipment including a catheter electrode distribution system ("CEDS") (at block 925a) and a power generator (at block 925b), one or more pressure sensors (at block 970), a mapping and/or navigation system (at block 935), imaging modality (at block 940), a system hub and/or application programming interfaces ("API's") (at block 945), cloud storage (at block 950), or artificial intelligence ("AI") and/or data analytics (at block 955), and/or the like. In some embodiments, the CEDS might be external, yet communicatively coupled, to the (PFA) power generator. Alternatively, the CEDS might be integrated or incorporated within the (PFA) power generator. Data from these cardiac shunting PFA sub-systems may be combined to generate a combined display of three-dimensional ("3D") information or four-dimensional ("4D") information (i.e., three-dimensional ("3D") information plus at least one of real-time updates, dynamic modeling, or data streaming, and/or the like) for cognitive load (at block 960). Such 3D or 4D information may be used to control therapy delivery over the system (at block 965). The process at blocks 910f-970 may be repeated as necessary or as desired. PFA for cardiac shunting allows for selective ablation of cardiac tissue, and has the potential to reduce collateral damage. With the use of pulsed electric fields, the resultant lesions are contiguous and transmural in the shape of the field. Further, ablation by electroporation (the mechanism through which PFA ablates tissue) is force-independent (i.e., independent of physical force applied by the device and the tissue it is ablating). In addition, with PFA, ultra-rapid or fast deliveries enable one to achieve pulmonary vein isolation ("PVI"). Anatomically shaped tools may also allow PVI with minimal catheter placements.

With reference to the non-limiting example 900' of FIG. 9H, a process stack for implementing an IA ecosystem for a cardiac shunting procedure (e.g., atrial septal shunting procedure, or other shunting procedure in the heart, or the like) might begin with a selection of a cardiac shunting procedure (at block 905d). In response to such selection, a cardiac shunting microwave ("MW") ablation system may be selected for implementation (at block 910g). The IA ecosystem might utilize, in conjunction with the cardiac shunting MW ablation system, a number of devices or equipment, sensors, imaging systems, and other systems (collectively, "cardiac shunting MW ablation sub-systems" or the like), including, but not limited to, at least one, two, or three of an ECG monitor (at block 915), system-specific equipment including a MW ablation console (at block 925d) and a MW power generator (at block 925e), one or more pressure sensors (at block 970), a mapping and/or navigation system (at block 935), imaging modality (at block 940), a system hub and/or application programming interfaces ("API's") (at block 945), cloud storage (at block 950), or artificial intelligence ("AI") and/or data analytics (at block 955), and/or the like. In some embodiments, the MW power generator might be external, yet communicatively coupled, to the MW ablation console. Alternatively, the MW power generator might be integrated or incorporated within the MW ablation console. Data from these cardiac shunting MW ablation sub-systems may be combined to generate a combined display of three-dimensional ("3D") information or four-dimensional ("4D") information (i.e., three-dimensional ("3D") information plus at least one of real-time updates, dynamic modeling, or data streaming, and/or the like) for cognitive load (at block 960). Such 3D or 4D information may be used to control therapy delivery over the system (at block 965). The process at blocks 910g-970 may be repeated as necessary or as desired.

Table 5 below illustrates a specific non-limiting example combination(s) of sensors, imaging systems, tracking (or mapping and navigation) systems, and devices (e.g., robotic devices or the like) for each of the Pre-Operative Planning Stage, the Intra-Operative Adjustment Stage, and the Post-Operative Monitory Stage (as described above with respect to FIG. 3C) while implementing an IA ecosystem for a cardiac shunting procedure using one of a cryo system (FIG. 9F), a PFA system (FIG. 9G), or a MW ablation system (FIG. 9H). The various embodiments, however, are not limited to these items nor their specific combinations and can include any combination of items listed for sensors, imaging systems, tracking (or mapping and navigation) systems, and devices, e.g., as described below with respect to FIG. 17, or the like.

catheter, etc.), an imaging sensor(s) (including, but not limited to, ICE and/or IVUS, etc.), and/or a stroke or arrhythmia sensor(s) (including, but not limited to, ECG sensor(s) or electroencephalographic ("EEG") sensor(s), etc.), with (4) integrated robotics including a soft-tissue ILR system, with (5) intra-operative AI and/or data analytics that merges imaging and other sensor data to adjust device configurations, settings, and/or implementations in real-time (or near-real-time (e.g., within milliseconds or seconds, etc.)) based on any updates or changes to the sensor data, imaging data, tracking data, and/or recommendations obtained during the Intra-Operative Adjustments Stage.

In one non-limiting example, (1) ICE may be combined with (2) EP mapping catheter system, with (3) a pressure sensor(s), with (4) ILR system, with (5) AI and/or data analytics. In an alternative example, (1) ICE may be combined with (2) proximity mapping catheter system, with (3) a pressure sensor(s), with (4) ILR system, with (5) AI and/or data analytics. In an alternative example, (1) ICE may be combined with (2) EP mapping catheter system, with (3) an imaging sensor(s), with (4) ILR system, with (5) AI and/or data analytics. In an alternative example, (1) ICE may be

TABLE 5

Combination List of Systems and Devices for implementing IA ecosystem for cardiac shunting using one of a cryo system, a PFA system, or a MW ablation system

| Pre-Op Stage | Intra-Op Stage | | | | | Post-Op Stage Monitoring/ |
| --- | --- | --- | --- | --- | --- | --- |
| Integrated Diagnostics | Imaging Devices | Navigation/ Mapping | Sensor Devices | Integrated Robotics | AI/Data Analytics | Analytics Feedback |
| Echo, Cuff BP, CT, CMR | ICE, IVUS, Fluoro | EP Mapping Cathether, Proximity Mapping Catheter | Pressure Sensor, Imaging Sensor, Arrhythmia Sensor | Soft-Tissue ILR System | Merging Imaging and Other Sensor Data | Echo, Cuff BP, ECG, Impedance, CMR |

As shown in Table 5 above, for the cardiac shunting procedures via any one of the cryo system, the PFA system, or the MW ablation system, the IA ecosystem may utilize, for an integrated diagnostics system during the Pre-Operative Planning Stage, one or a combination of an echocardiography ("Echo") system (including, but not limited to, TEE system, ICE system, TTE system, etc.), a cuff BP detector, a CT system, and/or a MRI or cardiac MRI ("CMR") system, and/or the like. In some cases, the IA ecosystem may perform analysis of data obtained by these sensors, imaging systems, and/or tracking (or mapping and navigation) systems to generate recommendations or to facilitate physician/user plans for the cardiac shunting procedure. The cardiac shunting procedure may then be performed based on sensor data, imaging data, tracking data, recommendations, and/or physician/user plans obtained or arising from the Pre-Operative Planning Stage.

During the Intra-Operative Adjustment Stage, the IA ecosystem may combine (1) imaging device(s) including one or a combination of an ICE system, an intravascular ultrasound ("IVUS"), and/or a Fluoro system, with (2) navigation/mapping system(s) including one or a combination of an electrophysiology ("EP") mapping catheter system and/or a proximity mapping catheter system, with (3) sensor device(s) including one or a combination of a pressure sensor(s) (including, but not limited to, Swan-Ganz combined with (2) proximity mapping catheter system, with (3) an imaging sensor(s), with (4) ILR system, with (5) AI and/or data analytics. In an alternative example, (1) ICE may be combined with (2) EP mapping catheter system, with (3) an arrhythmia sensor(s), with (4) ILR system, with (5) AI and/or data analytics. In an alternative example, (1) ICE may be combined with (2) proximity mapping catheter system, with (3) an arrhythmia sensor(s), with (4) ILR system, with (5) AI and/or data analytics.

In another non-limiting example, (1) IVUS may be combined with (2) EP mapping catheter system, with (3) a pressure sensor(s), with (4) ILR system, with (5) AI and/or data analytics. In an alternative example, (1) IVUS may be combined with (2) proximity mapping catheter system, with (3) a pressure sensor(s), with (4) ILR system, with (5) AI and/or data analytics. In an alternative example, (1) IVUS may be combined with (2) EP mapping catheter system, with (3) an imaging sensor(s), with (4) ILR system, with (5) AI and/or data analytics. In an alternative example, (1) IVUS may be combined with (2) proximity mapping catheter system, with (3) an imaging sensor(s), with (4) ILR system, with (5) AI and/or data analytics. In an alternative example, (1) IVUS may be combined with (2) EP mapping catheter system, with (3) an arrhythmia sensor(s), with (4) ILR system, with (5) AI and/or data analytics. In an alternative example, (1) IVUS may be combined with (2) proximity mapping catheter system, with (3) an arrhythmia sensor(s), with (4) ILR system, with (5) AI and/or data analytics.

In yet another non-limiting example, (1) Fluoro may be combined with (2) EP mapping catheter system, with (3) a pressure sensor(s), with (4) ILR system, with (5) AI and/or data analytics. In an alternative example, (1) Fluoro may be combined with (2) proximity mapping catheter system, with (3) a pressure sensor(s), with (4) ILR system, with (5) AI and/or data analytics. In an alternative example, (1) Fluoro may be combined with (2) EP mapping catheter system, with (3) an imaging sensor(s), with (4) ILR system, with (5) AI and/or data analytics. In an alternative example, (1) Fluoro may be combined with (2) proximity mapping catheter system, with (3) an imaging sensor(s), with (4) ILR system, with (5) AI and/or data analytics. In an alternative example, (1) Fluoro may be combined with (2) EP mapping catheter system, with (3) an arrhythmia sensor(s), with (4) ILR system, with (5) AI and/or data analytics. In an alternative example, (1) Fluoro may be combined with (2) proximity mapping catheter system, with (3) an arrhythmia sensor(s), with (4) ILR system, with (5) AI and/or data analytics.

During the Post-Operative Monitory Stage, the IA ecosystem may utilize one or a combination of an Echo system, a cuff BP detector, an ECG sensor, an impedance-based mapping and/or navigation system, and/or a CMR system, and/or the like. Collecting sensor data from these sensors, imaging systems, and/or tracking (or mapping and navigation) systems, the IA ecosystem may once again analyze the sensor data, imaging data, and/or tracking data to determine whether any aspect of the cardiac shunting procedure may be optimized or enhanced, and how, and may provide recommendations accordingly. In particular, the IA ecosystem may determine based on the sensor data, imaging data, tracking data, and/or recommendations obtained or arising from the Post-Operative Monitoring Stage whether there has been a change or a difference in the sensor data, imaging data, and/or tracking data, and, if so, whether the change or difference is indicative of a positive change (e.g., an expected, successful cardiac shunting procedure, or the like) or a negative change (e.g., where an issue arises from the cardiac shunting procedure, or the like). The operations of the Post-Operative Monitoring Stage may be performed repeatedly over a predetermined period (e.g., every day for a week, or the like), which may also be repeated the following one or more months. Based on the sensor data, imaging data, and/or tracking data results and recommendations obtained during the Post-Operative Monitoring Stage, the process may loop back to the Pre-Operative Planning Stage, the Intra-Operative Adjustments Stage, and the Post-Operative Monitoring Stage during a follow-on cardiac shunting procedure (or correction cardiac shunting procedure), or the like. In this manner, the combinations during all three stages (i.e., the Pre-Operative Planning Stage, the Intra-Operative Adjustment Stage, and the Post-Operative Monitory Stage) may achieve personalized septal hole size and location for optimized heart failure with preserved ejection fraction ("HFpEF") outcomes with minimized adverse events.

Figure 10:
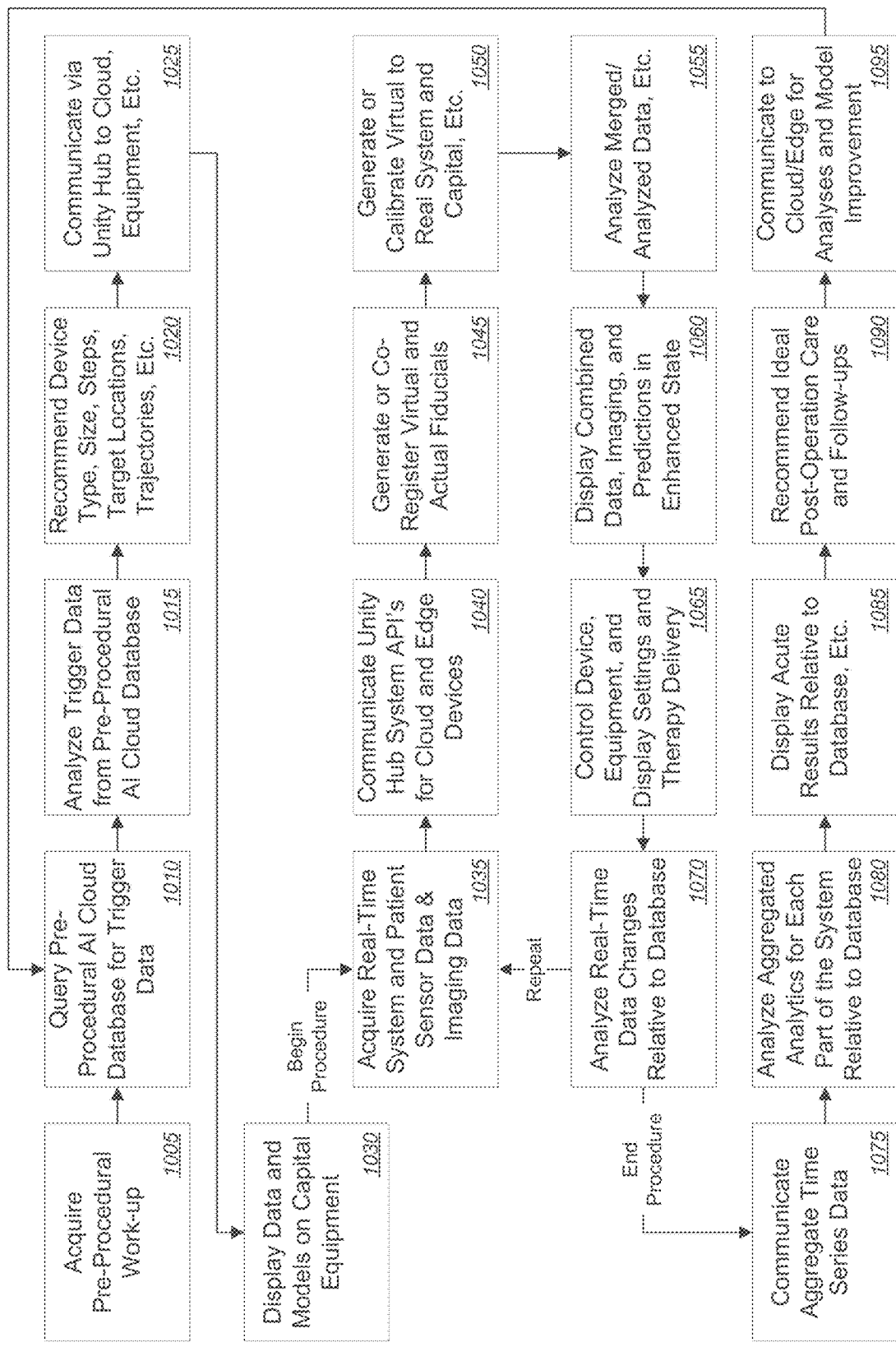
FIG. 10 is a flow diagram illustrating a method for implementing an IA ecosystem, in accordance with various embodiments.

FIG. 10 is a flow diagram illustrating a method 1000 for implementing an IA ecosystem, in accordance with various embodiments.

In the non-limiting embodiment of FIG. 10, method 1000 might comprise, at block 1005, acquiring pre-procedural work-up, in some cases, including, but not limited to, ultrasound, computed tomography ("CT"), magnetic resonance imaging ("MRI"), electrocardiogram ("ECG"), lifestyle, biometrics, or electroanatomic mapping ("EAM"), and/or the like. In some cases, for atrial fibrillation ("AF") procedures (e.g., pulsed field ablation ("PFA")-based or cryo-based, etc.), the pre-procedural work-up might include, without limitation, CT-based and/or cardio insight ("CIT") vest-based EAM, and/or the like. In some instances, for transcatheter aortic valve implant ("TAVI") therapy or transcatheter mitral valve implant ("TMVI") therapy, the pre-procedural work-up might include, but is not limited to, ultrasound, pressure catheters, CT-based and/or cardio insight ("CIT") vest-based EAM, and/or the like. In some cases, for cardiac shunting procedures (e.g., atrial septal shunting procedures, or other shunting procedures in the heart, or the like), the pre-procedural work-up might include, without limitation, ultrasound, CT, Mill, lifestyle, biometrics, EAM, and/or the like.

At block 1010, method 1000 might comprise querying a pre-procedural artificial intelligence ("AI") cloud database for trigger data, including, but not limited to, data regarding paroxysmal triggers (i.e., convulsive triggers, triggers that suddenly increase or recur, etc.), data regarding persistent triggers, and/or data regarding anatomical morphology prognosis. In some instances, for TAVI therapy, the trigger data might include, without limitation, aortic morphology, including, but not limited to, stenosis, regurgitation, aortic dilation, or bicuspid, and/or the like. In some cases, for TMVI therapy, the trigger data might include, without limitation, mitral morphology, including, but not limited to, infarct location, chordae rupture, ischemic, left atrium ("LA") size, or septum location, and/or the like. In some instances, for cardiac shunting procedures, the trigger data might include, but is not limited to, data regarding disease triggers and/or data regarding anatomical morphology prognosis, or the like.

Method 1000, at block 1015, might comprise analyzing the trigger data from pre-procedural AI cloud database. In some cases, for AF procedures, analyzing the trigger data might include, without limitation, feature recognition of likely targets, including, but not limited to, pulmonary veins, atrial posterior wall, roofline, mitral isthmus, left atrial appendage, and/or the like. In some instances, for TAVI therapy, analyzing the trigger data might include, but is not limited to, feature recognition of likely targets, including, without limitation, left bundle branch, aortic arch, coronary artery ostia, stenosis, or tortuosity, and/or the like. In some cases, for TMVI therapy, analyzing the trigger data might include, but is not limited to, feature recognition of likely targets, including, without limitation, transseptal location, mitral annulus, outflow tract, left atrial appendage, or prior implanted prosthesis or device, and/or the like. In some instances, for cardiac shunting procedures, analyzing the trigger data might include, but is not limited to, feature recognition of likely targets, including, without limitation, atrial or interatrial septum, septum primum, fossa ovalis, patent foramen ovale (or unfused fossa ovalis), annulus ovalis (i.e., oval margin of the fossa ovalis in the right atrium), pulmonary valve, outflow tract, or coronary vessels or vasculature, and/or the like.

Method 1000 might further comprise, at block 1020, recommending, predicting, or prescribing at least one of device type, size, procedural steps, target locations, trajectories, or statistical success rates of similar patients and procedures, and/or the like. In some cases, for PFA-based AF procedures, such recommendations might include, without limitation, pulmonary vein ablation catheter ("PVAC"), introducer sheath (e.g., 10 F sized introducer sheath, or the like), array size, array orientation, or proximity to target, and/or the like. In some instances, for cryo-based AF procedures, such recommendations might include, but are not limited to, Arctic Front Advance™ ("AFA") cryoablation catheter, introducer sheath (e.g., 12F sized introducer sheath, or the like), balloon size, compliance, or interface to contact, and/or the like. In some cases, for TAVI therapy, such recommendations might include, without limitation, core valve size, delivery system, interface to contact, or conduction triggers, and/or the like. In some instances, for TMVI therapy, such recommendations might include, but are not limited to, TMVI valve size, delivery system, interface to contact, or conduction trigger, and/or the like. In some cases, for cardiac shunting procedures, such recommendations might include, without limitation, cryoablation catheter, cryoballoon catheter, introducer sheath, balloon size, compliance, or interface to contact, and/or the like.

At block 1025, method 1000 might comprise communicating the analyses and/or recommendations via, e.g., unity hub or similar system to cloud or edge data system, equipment, capital equipment, etc. Herein, 3D engine refers a platform (e.g., Unity® engine hub or Unreal Engine® hub, or the like) for creating and operating interactive, real-time 3D ("RT3D") content that integrates 3D models for a "scene" and software code (e.g., C#, C++, etc.) that breathes life into features including, but not limited to, coloration, animation, user interfaces, collision detection, and/or other physics-based elements (e.g., the electric field for PFA, ice growth for cryoablation, cardiac electrical wave propagation, blood flow/pressure/velocity, etc.). The unity hub refers to a standalone application that streamlines searching, downloading, and managing 3D engine projects and installations. The unity hub is the integration point of the real-world devices with the AR world, but can add data-related features to enhance the UI via AI or other algorithms, or the like. Herein, capital equipment refers to equipment that is associated with therapy delivery (e.g., mapping and navigation equipment, ablation generators, etc.). In some cases, the capital equipment may provide information to/from the XR unity hub. Method 1000 might further comprise displaying data and models on capital equipment, in some cases, projecting slaved imaged on at least one of one or more operating room ("OR") screens, one or more tablets, one or more extended reality ("XR") headsets, or one or more XR spatial projections, and/or the like (block 1030). In some cases, the capital equipment might include, without limitation, a PFA console (for PFA-based AF procedures), a cryo or cryoablation console (for cryo-based AF procedures), or imaging modality and navigation (for TAVI therapy or TMVI therapy), and/or the like.

The processes at blocks 1005-1030 might correspond to pre-procedural processes.

At block 1035, method 1000 might comprise acquiring system data (e.g., PVAC data for PFA-based AF procedures, AFA catheter data for cryo-based AF procedures, and/or the like), patient sensor data, and imaging data, one or more of which might be real-time or near-real-time data (where "near-real-time" herein refers to within milliseconds or seconds, or the like). For example, auto-segmentation of an anatomy is beneficial in minutes compared to manual segmentation, but may need to be an order of magnitude better (i.e., faster) to drive real change—hence, "near-real-time" or millisecond or second data acquisition times. Also, when ablating, one may be moving the catheter across a posterior wall with a point-by-point or line catheter (e.g., the DiamondTemp catheter, or the like) while ablating with high power, so one needs to see the movement and interaction with minimal lag. Another example may involve the delivery of a heart valve where the heart valve is released into the blood flow and moving leaflets, where one cannot afford to have a noticeable lag. In some embodiments, the system data and patient sensor data might include, without limitation, data regarding phrenic activation, respiration data, ECG data, or esophageal temperature navigation coordinates, and/or the like. According to some embodiments, the imaging data might include, but is not limited to, CIT-based EAM data, electromechanical wave imaging ("EWI") data, or ultrasound data, and/or the like. In some cases, for TAVI therapy, the system data and patient sensor data might include, without limitation, left bundle branch block ("LBBB") activation, respiration, ECG, or navigation coordinates through aorta to aortic annulus, and/or the like, while the imaging data might further include fluoro data. In some instances, for TMVI therapy, the system data and patient sensor data might include, without limitation, LA conduction activation, respiration, ECG, chordae or papillary behavior, or navigation coordinates relative to transseptal puncture ("TS") mitral annulus, and/or the like, while the imaging data might further include fluoro data. In some cases, for cardiac shunting procedures, the system data and patient sensor data might include, but are not limited to, doppler flow, pressures, respiration, ECG, neurological events, or navigation coordinates, and/or the like, while the imaging data might include, without limitation, CIT-based EAM data, EWI data, or ultrasound data, and/or the like.

Method 1000, at block 1040, might comprise communicating unity hub system application programming interfaces ("API's") for cloud and edge devices, in some cases, as the acquired data are merged. Method 1000 might further comprise generating or co-registering virtual and actual fiducials, in some cases, via at least one of digital imaging and communications in medicine ("DICOM") files, headset mapping and/or photogrammetry, skin patches, reflective infrared markers, impedance, electromagnetic, or radio frequency identifiers ("RFIDs"), and/or the like (block 1045). Herein, the term fiducials refers to an object that is placed in the field of view of an imaging system that appears in the produced image as a point of reference or a measure, and/or to landmarks (whether anatomical or other) that are employed to co-register the digital world with the real world.

Method 1000 might further comprise, at block 1050, generating or calibrating virtual to real (or physical or non-digital) device and capital, target anatomy, adjacent structures, tissue selectivity, safety shut-offs (e.g., no delivery without focused eye gaze), etc. In some embodiments, for the AF procedures, the real (or physical or non-digital) device might include a PVAC catheter or an AFA catheter. According to some embodiments, for TAVI therapy, the real device might include a TAVI delivery system, while the target anatomy might include, but is not limited to, target anatomy of aortic annulus, adjacent structures like left bundle branch, coronaries, or mitral valve, etc., and the safety shut-offs might include no delivery without focused eye gaze to ensure proper valve anchoring, sealing before releasing, or LBBB conduction, and/or the like. In some cases, for TMVI therapy, the real device might include a TMVI delivery system, while the target anatomy might include, but is not limited to, target anatomy of mitral annulus, adjacent structures like chordae and left atrial appendage, etc., and the safety shut-offs might include no delivery without focused eye gaze to ensure proper valve anchoring, or sealing before releasing, and/or the like. In some instances, for cardiac shunting procedures, the real device or capital equipment might include a cryo or a cryoablation system or console, cryoballoon catheter, or the like.

At block 1055, method 1000 might comprise analyzing merged or analyzed data, predictions, prescriptions, real-time electroanatomic mapping ("EAM") changes, jet velocities, effective orifice areas, pressure drops, and/or the like, as it relates to device location (e.g., PVAC location, AFA catheter location, TAVI delivery system and valve location, TMVI delivery system and valve location, cryoballoon location, etc.) and therapy delivery. Method 1000, at block 1060, might comprise displaying combined data, imaging, and predictions in enhanced state, in some cases or preferably, via XR spatial projections or headset. Herein, enhanced state refers to the state in which information that is presented to the user (such as the combined data, imaging, and predictions, or the like, as preferably displayed via the XR spatial projections or headset) exceed what would normally be perceived by the unaided human eye alone. In some cases, the enhanced state may refer to enhancements to the unaided human senses in addition to visual enhancements as described above, including, but not limited to, auditory enhancements (e.g., surround sound, voice commands, auditory information presentation, etc.), haptic-like feedback (e.g., haptic feedback for robotic or instrument control when interacting with objects or tissue, etc.), or the like.

Method 1000 might further comprise controlling device, robotics, capital equipment settings, therapy delivery through system interaction, including, but not limited to, voice commands, eye gaze, virtual buttons, virtual triggers, electrocardiogram ("ECG") gating, AI algorithm, etc., by one or more team members within the operating room or remotely (block 1065). In some cases, for PFA-based AF procedures, the capital equipment settings might comprise PFA console settings including, without limitation, temperature, time, energy setting, or impedance, and/or the like. In some instances, for cryo-based AF procedures, the capital equipment settings might comprise cryo or cryoablation console settings including, but not limited to, temperature, time, or tank level, and/or the like. In some cases, for TAVI therapy or TMVI therapy, the capital equipment settings might comprise map, navigation, and/or display settings including, without limitation, time, flow, location, heart rate, respiration, cognitive ischemic events, or embolic protection, and/or the like. In some instances, for cardiac shunting procedures, the capital equipment settings might comprise cryo or cryoablation console settings including, but not limited to, temperature, time, or tank level, and/or the like, as well as map, navigation, and/or display settings including, without limitation, time, flow, location, heart rate, or respiration, and/or the like.

Method 1000 might further comprise, at block 1070, analyzing data changes—including, without limitation, at least one of EAM changes via CIT vest and/or EWI, phrenic injury to respiration, biometric data, genetic data, or cellular data, and/or the like, relative to database. Herein, the data may be similar, if not identical, at least in type to the data (or type of data) described with respect to the other embodiments as shown, e.g., in FIGS. 1-9 and 11-17. In some instances, the data changes might be real-time or near-real-time data. In some cases, for TAVI therapy or TMVI therapy, the data changes being analyzed might include, but are not limited to, at least one of flow, pressure, effective orifice area ("EOA"), EAM, or biometrics (in some instances, for patient prosthetic mismatch, etc.), and/or the like. In some instances, for cardiac shunting procedures, the data changes being analyzed might include, without limitation, at least one of pressure, flow, EAM changes via CIT vest, ultrasound, EWI, stroke detection (including, but not limited to, transient ischemic attacks ("TIAs"), other ischemic stroke manifestations, hemorrhagic stroke manifestations, and/or the like), biometrics, and/or the like, relative to database.

Based on the analysis (at block 1070), method 1000 either might continue onto the process at block 1075 or might return to the process at block 1035. The processes at blocks 1035-1070 might correspond to intra-procedural processes.

At block 1075, method 1000 might comprise communicating aggregate time series data via the hub system to cloud or edge data system, equipment, capital equipment, etc.

Method 1000, at block 1080, might comprise analyze the aggregated analytics for each part of the system relative to database. In some instances, for PFA-based AF procedures, the aggregated analytics for each part of the system might include, without limitation, at least one, two, or three of time to isolate, LA dwell time, procedure time, transseptal location, energy settings used, voltage and current of each electrode, selection and/or deselection of each electrode, pulse width, inter-phase delay, inter-pulse delay, pulse cycle length, number and/or location of each ablation (contact and proximity), arrhythmia source locations, reconnections over time, phrenic nerve response, esophageal temperature, or time series change in EAM, and/or the like. In some cases, the one or more aggregated analytics might include one or more first aggregated analytics including, without limitation, at least one, two, or three of time to isolate, LA dwell time, procedure time, and/or the like.

In some instances, the one or more aggregated analytics might include one or more second aggregated analytics including, without limitation, at least one, two, or three of transseptal location, number and/or location of each ablation (contact and proximity), arrhythmia source locations, and/or the like.

In some cases, the one or more aggregated analytics might include one or more third aggregated analytics including, without limitation, at least one, two, or three of energy settings used, voltage and current of each electrode, selection and/or deselection of each electrode, pulse width, inter-phase delay, inter-pulse delay, pulse cycle length, reconnections over time, and/or the like.

In some instances, the one or more aggregated analytics might include one or more fourth aggregated analytics including, without limitation, at least one, two, or three of phrenic nerve response, esophageal temperature, or time series change in EAM, and/or the like.

In some cases, for cryo-based AF procedures, the aggregated analytics for each part of the system might include, without limitation, at least one, two, or three of time to isolate, LA dwell time, procedure time, transseptal location, energy settings used, size of balloon, pressure of balloon, number and/or location of each ablation (contact), arrhythmia source locations, reconnections over time, phrenic nerve response, esophageal temperature, or time series change in EAM, and/or the like. In some cases, the one or more aggregated analytics might include one or more first aggregated analytics including, without limitation, at least one, two, or three of time to isolate, LA dwell time, or procedure time, and/or the like. In some instances, the one or more aggregated analytics might include one or more second aggregated analytics including, without limitation, at least one, two, or three of transseptal location, number and/or location of each ablation (contact), or arrhythmia source locations, and/or the like. In some cases, the one or more aggregated analytics might include one or more third aggregated analytics including, without limitation, at least one, two, or three of energy settings used, size of balloon, pressure of balloon, or reconnections over time, and/or the like. In some instances, the one or more aggregated analytics might include one or more fourth aggregated analytics including, without limitation, at least one, two, or three of phrenic nerve response, esophageal temperature, or time series change in EAM, and/or the like.

In some instances, for TAVI therapy, the aggregated analytics for each part of the system might include, without limitation, at least one, two, or three of time to delivery, aortic or left ventricle ("LV") dwell time, procedure time, aortic location, orientation and/or location of each valve (if multiple valves used), arrhythmia source locations, regurgitation locations, regurgitation severity, peri-valvular leakage locations, peri-valvular severity, time series change in EAM, time series change in pressures, time series change in flows, or coronary openings, and/or the like. In some cases, the one or more aggregated analytics might include one or more first aggregated analytics including, without limitation, at least one, two, or three of time to delivery, aortic or left ventricle ("LV") dwell time, or procedure time, and/or the like. In some instances, the one or more aggregated analytics might include one or more second aggregated analytics including, without limitation, at least one, two, or three of aortic location, orientation and/or location of each valve (if multiple valves used), arrhythmia source locations, regurgitation locations, or peri-valvular leakage locations, and/or the like. In some cases, the one or more aggregated analytics might include one or more third aggregated analytics including, without limitation, at least one, two, or three of regurgitation severity, peri-valvular severity, or coronary openings, and/or the like. In some instances, the one or more aggregated analytics might include one or more fourth aggregated analytics including, without limitation, at least one, two, or three of time series change in EAM, time series change in pressures, or time series change in flows, and/or the like.

In some cases, for TMVI therapy, the aggregated analytics for each part of the system might include, without limitation, at least one, two, or three of time to delivery, LA dwell time, procedure time, transseptal location, orientation and/or location of each valve (if multiple valves used), arrhythmia source locations, regurgitation locations, regurgitation severity, peri-valvular leakage locations, peri-valvular severity, time series change in EAM, time series change in pressures, or time series change in flows, and/or the like. In some cases, the one or more aggregated analytics might include one or more first aggregated analytics including, without limitation, at least one, two, or three of time to delivery, LA dwell time, or procedure time, and/or the like. In some instances, the one or more aggregated analytics might include one or more second aggregated analytics including, without limitation, at least one, two, or three of transseptal location, orientation and/or location of each valve (if multiple valves used), arrhythmia source locations, regurgitation locations, or peri-valvular leakage locations, and/or the like. In some cases, the one or more aggregated analytics might include one or more third aggregated analytics including, without limitation, at least one or both of regurgitation severity or peri-valvular severity, and/or the like. In some instances, the one or more aggregated analytics might include one or more fourth aggregated analytics including, without limitation, at least one, two, or three of time series change in EAM, time series change in pressures, or time series change in flows, and/or the like.

In some instances, for cardiac shunting procedures, the aggregated analytics for each part of the system might include, without limitation, at least one, two, or three of time to isolate, LA dwell time, procedure time, transseptal location, energy settings used, voltage and current of each electrode, selection and/or deselection of each electrode, pulse width, inter-phase delay, inter-pulse delay, pulse cycle length, number and/or location of each ablation (contact and proximity), size of balloon, pressure of balloon, number and/or location of each ablation (contact), reconnections over time, phrenic nerve response, esophageal temperature, time series change in EAM, time series change in pressures, or time series change in flows, and/or the like. In some cases, the one or more aggregated analytics might include one or more first aggregated analytics including, without limitation, at least one, two, or three of time to isolate, LA dwell time, or procedure time, and/or the like. In some instances, the one or more aggregated analytics might include one or more second aggregated analytics including, without limitation, at least one, two, or three of transseptal location, number and/or location of each ablation (contact and proximity), or number and/or location of each ablation (contact), and/or the like. In some cases, the one or more aggregated analytics might include one or more third aggregated analytics including, without limitation, at least one, two, or three of energy settings used, voltage and current of each electrode, selection and/or deselection of each electrode, pulse width, inter-phase delay, inter-pulse delay, pulse cycle length, size of balloon, pressure of balloon, or reconnections over time, and/or the like. In some instances, the one or more aggregated analytics might include one or more fourth aggregated analytics including, without limitation, at least one, two, or three of phrenic nerve response, esophageal temperature, time series change in EAM, time series change in pressures, or time series change in flows, and/or the like.

Method 1000 might further comprise, at block 1085, displaying acute results relative to database, predict long term success, three-dimensional ("3D") replays, four-dimensional ("4D") replays (i.e., 3D replays plus at least one of real-time updates, dynamic modeling, or data streaming, and/or the like), statistical dashboards, etc., in paper, two-dimensional ("2D") digital, interactive 3D digital, and/or extended reality ("XR") format, or the like. Method 1000 might further comprise recommending ideal post-procedural care and follow-ups for value-based healthcare (block 1090). Herein, value-based healthcare refers to a framework for restructuring healthcare systems with the principal goals of health outcomes per unit costs (i.e., value) for patients. At block 1095, method 1000 might comprise communicating, de-identifying, and sending back to the cloud or edge data system for analyses and model improvement. Method 1000 might return to the process at block 1010. The processes at blocks 1075-1095 might correspond to post-procedural processes.

FIGS. 11A-11E (collectively, "FIG. 11") are flow diagrams illustrating another method 1100 for implementing an IA ecosystem, in accordance with various embodiments. Method 1100 of FIG. 11A continues onto FIG. 11B following the circular marker denoted, "A," continues onto FIG. 11C following the circular marker denoted, "B," or continues onto FIG. 11D following the circular marker denoted, "C."

While the techniques and procedures are depicted and/or described in a certain order for purposes of illustration, it should be appreciated that certain procedures may be reordered and/or omitted within the scope of various embodiments. Moreover, while the method 1100 illustrated by FIG. 11 can be implemented by or with (and, in some cases, are described below with respect to) the systems, examples, or embodiments 100, 200, 200', 200", 300, 300', 300", 400, 400', 400", 500, 500', 500", 600, 600', 700, 700', 800, 900, 900', 900", 900''', 900'''', 900''''', 900'''''', 900''''''', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10, respectively (or components thereof), such methods may also be implemented using any suitable hardware (or software) implementation. Similarly, while each of the systems, examples, or embodiments 100, 200, 200', 200'', 300, 300', 300'', 400, 400', 400'', 500, 500', 500'', 600, 600', 700, 700', 800, 900, 900', 900'', 900''', 900'''', 900''''', 900'''''', 900''''''', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10, respectively (or components thereof), can operate according to the method 1100 illustrated by FIG. 11 (e.g., by executing instructions embodied on a computer readable medium), the systems, examples, or embodiments 100, 200, 200', 200'', 300, 300', 300'', 400, 400', 400'', 500, 500', 500'', 600, 600', 700, 700', 800, 900, 900', 900'', 900''', 900'''', 900''''', 900'''''', 900''''''', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10 can each also operate according to other modes of operation and/or perform other suitable procedures.

Figure 11A:
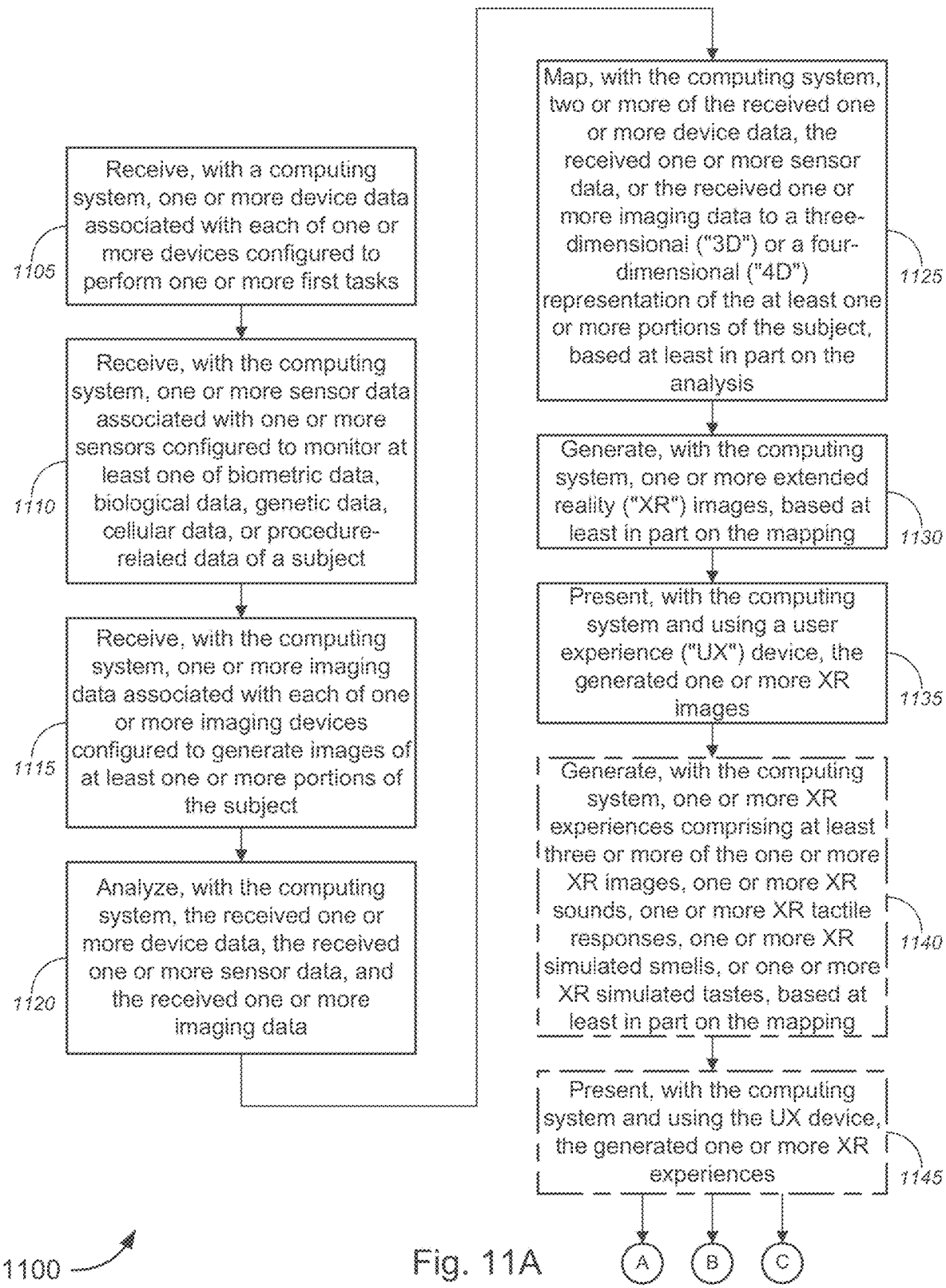

In the non-limiting embodiment of FIG. 11A, method 1100 might comprise receiving, with a computing system, one or more device data associated with each of one or more devices configured to perform one or more first tasks (block 1105); receiving, with the computing system, one or more sensor data associated with one or more sensors configured to monitor at least one of biometric data, biological data, genetic data, cellular data, or procedure-related data of a subject (block 1110); and receiving, with the computing system, one or more imaging data associated with each of one or more imaging devices configured to generate images of at least one or more portions of the subject (block 1115). In some cases, at least one of the received one or more device data, the received one or more sensor data, and the received one or more imaging data might be real-time or near-real-time data that is received by the computing system in real-time or near-real-time.

In some embodiments, the computing system might include, without limitation, at least one of an XR computing system, a medical procedure computing system, a hub computing system, a three-dimensional ("3D") graphical processing unit, a cluster computing system, a four-dimensional ("4D"; with 4D being as defined above, e.g., with respect to FIGS. 1, 7, 9, and 10, or the like) graphics computing system, a server computer, a cloud computing system, or a distributed computing system, and/or the like.

According to some embodiments, the one or more devices might include, but are not limited, at least one of one or more catheters, one or more catheter interconnect or interface cables, one or more valves, one or more balloons, one or more leads, one or more pacemakers, one or more defibrillators, one or more neuromodulation devices, one or more neurostimulation devices, one or more rigid robotic devices, one or more soft robotic devices, one or more stents, one or more needles, one or more grafts, one or more occluders, one or more shunts, one or more orthopedic screws, one or more orthopedic plates, one or more orthopedic rods, one or more vertebral sponges, one or more therapeutic delivery devices, one or more implant delivery devices, one or more diagnostic devices, one or more diagnostic catheters, one or more implant devices, one or more surgical tools, one or more biologics, one or more drug pumps, one or more genes, one or more cells, one or more organs, one or more organelles, one or more delivery pharmaceuticals, one or more biopsy tools, one or more excision tools, one or more ablation tools, one or more monitoring devices, one or more cameras, one or more imaging tools, one or more fiducials, one or more staples, one or more anchors, one or more meshes, one or more vascular cannulae, one or more circulatory pumps, one or more valve repair devices, one or more embolic protection devices, one or more cardiomyoplasty tools, one or more vascular closure tools, one or more septal closure tools, one or more ventricular closure tools, one or more lasers, one or more plaque removal tools, one or more guide wires, one or more introducers, one or more sheaths, one or more pillcams, one or more clips, one or more capsules, one or more microbiomes, one or more microbes of bacterial vectors, one or more microbes of viral vectors, one or more microbes of prion vectors, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment, and/or the like.

In some cases, the one or more devices might include one or more first devices including, without limitation, at least one of one or more catheters, one or more valves, one or more balloons, one or more leads, one or more stents, one or more needles, one or more grafts, one or more occluders, one or more shunts, one or more orthopedic screws, one or more orthopedic plates, one or more orthopedic rods, one or more vertebral sponges, one or more diagnostic catheters, one or more surgical tools, one or more drug pumps, one or more biopsy tools, one or more excision tools, one or more staples, one or more anchors, one or more meshes, one or more vascular cannulae, one or more circulatory pumps, one or more valve repair devices, one or more embolic protection devices, one or more cardiomyoplasty tools, one or more vascular closure tools, one or more septal closure tools, one or more ventricular closure tools, one or more plaque removal tools, one or more guide wires, one or more introducers, one or more sheaths, one or more clips, or one or more capsules, and/or the like.

In some instances, the one or more devices might include one or more second devices including, without limitation, at least one of one or more catheter interconnect or interface cables, one or more rigid robotic devices, one or more soft robotic devices, one or more diagnostic devices, one or more monitoring devices, one or more cameras, one or more imaging tools, one or more fiducials, one or more lasers, one or more pillcams, or one or more ablation tools, and/or the like.

In some cases, the one or more devices might include one or more third devices including, without limitation, at least one of one or more pacemakers, one or more defibrillators, one or more neuromodulation devices, one or more neurostimulation devices, one or more therapeutic delivery devices, one or more implant delivery devices, one or more implant devices, an ICD device, an EV-ICD, a miniature leadless implant, or one or more implantable sensors, and/or the like.

In some instances, the one or more devices might include one or more fourth devices including, without limitation, at least one of one or more biologics, one or more genes, one or more cells, one or more organs, one or more organelles, one or more delivery pharmaceuticals, one or more microbiomes, one or more microbes of bacterial vectors, one or more microbes of viral vectors, or one or more microbes of prion vectors, and/or the like.

In some cases, the one or more devices might include one or more fifth devices including, without limitation, at least one of a PVAC, one or more energy delivery tools, a CEDS, a PFA system, a PFA console, an electroporation system, an electroporation control console, a cryoballoon or a cryoablation catheter, a cryoablation console, a RF ablation-based system, an RF ablation control console, a MW ablation-based system, a MW ablation control console, a laser ablation-based system, a laser ablation control console, a radiation ablation-based system, a radiation ablation control console, a microwave ablation-based system, a HIFU system, a HIFU control console, or one or more capital equipment, and/or the like.

In some embodiments, the one or more sensors might include, without limitation, at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography (EOG) sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some cases, the one or more sensors might include one or more first sensors including, without limitation, at least one of one or more blood velocity sensors, one or more blood volume sensors, one or more blood pressure sensors, one or more heart rate sensors, one or more pulse sensors, one or more oxygen sensors, one or more $CO_2$ sensors, one or more hormonal sensors, one or more fluid levels, one or more biomarker sensors, one or more genetic sensors, one or more blood chemistry sensors, one or more tissue matrix sensors, one or more bacteria sensors, one or more respiration sensors, one or more emotional stress sensors, one or more sleep sensors, one or more ischemia sensors, one or more HCT level sensors, one or more brainwave sensors, or one or more pain sensors, and/or the like.

In some instances, the one or more sensors might include one or more second sensors including, without limitation, at least one of one or more gas sensors, one or more optical sensors, one or more impedance sensors, one or more ultrasound sensors, one or more flow sensors, one or more electrical sensors, one or more voltage sensors, one or more amperage sensors, one or more wattage sensors, one or more chemical sensors, one or more pH sensors, one or more motion sensors, one or more proximity sensors, one or more light sensors, one or more sound sensors, one or more laser sensors, one or more doppler sensors, one or more mechanical sensors, one or more IR sensors, one or more UV sensors, one or more moisture sensors, one or more humidity sensors, one or more temperature sensors, one or more pressure sensors, one or more force sensors, one or more strain sensors, one or more stress sensors, one or more olfactory sensors, one or more viscosity sensors, one or more EMI sensors, one or more vibration sensors, one or more sound wave sensors, one or more magnetic sensors, one or more visible light sensors, or one or more radiation sensors, and/or the like.

In some cases, the one or more sensors might include one or more third sensors including, without limitation, at least one of one or more diagnostic sensors, one or more surgical sensors, one or more wearable sensors, one or more DIC sensors, one or more cameras, one or more perfusion sensors, one or more EMG sensors, one or more EOG sensors, one or more cardiac hemodynamics sensors, one or more photographic plate sensors, one or more polymer-metal sensors, one or more electrochemical sensors, one or more biometric sensors, or one or more EEG sensors, and/or the like.

In some instances, the one or more sensors might include one or more fourth sensors including, without limitation, at least one of one or more surgeon fatigue sensors or one or more compliance sensors, and/or the like. In some cases, the one or more sensors might include one or more fifth sensors including, without limitation, at least one of one or more CCDs or one or more photo diode arrays, and/or the like.

In some instances, the one or more sensors might include one or more sixth sensors including, without limitation, at least one of one or more tissue contractility sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, or one or more metabolic process sensors, and/or the like.

In some cases, the one or more sensors might include one or more seventh sensors including, without limitation, at least one of one or more chronically implanted sensors, and/or the like. In some instances, the one or more sensors might include one or more eighth sensors including, without limitation, at least one of one or more contactless optical sensors, one or more fiducial alignment sensors, one or more tool recognition sensors, one or more collision detection sensors, one or more room traffic flow sensors, one or more motion sensors, one or more blood pressure sensors, one or more heart rate sensors, one or more respiratory rate sensors, one or more IR-based temperature sensors, one or more surgeon fatigue sensors, or one or more cognitive overload sensors, and/or the like.

According to some embodiments, the one or more imaging devices might include, but are not limited to, at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

In some cases, the one or more imaging devices might include one or more first imaging devices including, without limitation, at least one of a MRI system, a DTI system, a MRA system, an ASL system, a MEG system, a MRS system, a DSC MRI system, a BOLD system, or a FLAIR system, and/or the like.

In some instances, the one or more imaging devices might include one or more second imaging devices including, without limitation, at least one of a CT system, a SPECT system, a CTA system, a PET system, or an OCT system, and/or the like.

In some cases, the one or more imaging devices might include one or more third imaging devices including, without limitation, at least one of a US system, a TEE system, an ICE system, a TTE system, an IVUS system, or an EWI system, and/or the like.

In some instances, the one or more imaging devices might include one or more fourth imaging devices including, without limitation, at least one of a neuro-endoscopy system, an OIS system, an endoscopy system, a bioluminescent system, a triboluminescence system, an image fusion system, or a microscope, and/or the like.

In some cases, the one or more imaging devices might include one or more fifth imaging devices including, without limitation, an EEG system, and/or the like.

In some instances, the one or more imaging devices might include one or more sixth imaging devices including, without limitation, at least one of a fluoroscopy system, an X-ray system, a 3D scanning system, an IR system, or a UV system, and/or the like.

In some embodiments, the one or more first tasks might include, without limitation, at least one of a surgical procedure, a left atrial appendage ("LAA") procedure, a tissue ablation procedure, a transcatheter aortic valve repair ("TAVr") procedure, a transcatheter aortic valve replacement ("TAVR") procedure (e.g., with the Evolut™ PRO+TAVR system, or the like), a transcatheter mitral valve repair ("TMVr") procedure, a transcatheter mitral valve replacement ("TMVR") procedure (e.g., with the Intrepid™ TMVR system, or the like), a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, an implant procedure, a home care ventilation procedure, a lung cancer procedure, an aneurysm flow diversion procedure, a deep brain stimulation procedure, a shunt procedure, a bone grafting procedure, an insulin pump installation procedure, a continuous glucose monitoring system installation procedure, a colon disease procedure, a gastroparesis therapy, a hernia surgery, a bowel control therapy, a microwave ablation procedure, a reflux testing and treatment, a weight-loss surgery, a bone conduction hearing therapy, a sinus surgery, a thyroid surgery, a treatment for ear infections, a balloon angioplasty, a stenting procedure, an atrial septal defect ("ASD") treatment procedure, a cardiac shunt treatment procedure, a heart bypass surgery, a cardiac mapping procedure, a cardiac resynchronization therapy ("CRT") device installation procedure, a catheter ablation procedure, an endovascular repair procedure, a heart monitor installation procedure, an implantable cardioverter defibrillator ("ICD") device installation procedure, an extravascular ICD ("EV-ICD") device installation procedure, a minimally invasive endovascular repair procedure, a pacemaker installation procedure, a miniature leadless implant installation procedure, an implantable sensor installation procedure, a remote monitoring device installation procedure, a surgical heart valve repair and replacement procedure, a transcatheter pulmonary valve ("TPV") therapy (e.g., Melody™ TPV therapy, Harmony™ TPV therapy, or the like), a varicose vein therapy, a ventricular assist device ("VAD") installation procedure, an intra-aortic balloon pump ("IABP") implantation procedure, a heart transplant operation, a back surgery, a bone tumor treatment, a drug pump installation procedure, a spinal cord stimulation procedure, a targeted drug delivery procedure, a balloon kyphoplasty procedure, a cervical disc replacement procedure, a cervical fusion procedure, a sacroiliac joint fusion procedure, a sacral neuromodulation procedure, or a percutaneous tibial neuromodulation procedure, and/or the like.

In some cases, the one or more tasks might include one or more first tasks including, without limitation, at least one of a surgical procedure, a TAVr procedure, a TAVR procedure (e.g., with the Evolut™ PRO+TAVR system, or the like), a TMVr procedure, a TMVR procedure (e.g., with the Intrepid™ TMVR system, or the like), a TPVr procedure, a TPVR procedure, a TTVr procedure, a TTVR procedure, a mitral clip repair procedure, a minimally invasive endovascular repair procedure, a surgical heart valve repair and replacement procedure, a TPV therapy (e.g., Melody™ TPV therapy, Harmony™ TPV therapy, or the like), or an endovascular repair procedure, and/or the like.

In some instances, the one or more tasks might include one or more second tasks including, without limitation, at least one of a LAA procedure, a lung cancer procedure, an aneurysm flow diversion procedure, a deep brain stimulation procedure, a bone grafting procedure, a colon disease procedure, a gastroparesis therapy, a hernia surgery, a bowel control therapy, a reflux testing and treatment, a weight-loss surgery, a bone conduction hearing therapy, a sinus surgery, a thyroid surgery, a treatment for ear infections, a balloon angioplasty, an ASD treatment procedure, a cardiac shunt treatment procedure, a heart bypass surgery, a varicose vein therapy, a heart transplant operation, a back surgery, a bone tumor treatment, a spinal cord stimulation procedure, a targeted drug delivery procedure, a balloon kyphoplasty procedure, a cervical disc replacement procedure, a cervical fusion procedure, a sacroiliac joint fusion procedure, a sacral neuromodulation procedure, or a percutaneous tibial neuromodulation procedure, and/or the like.

In some cases, the one or more tasks might include one or more third tasks including, without limitation, at least one of an implant procedure, an insulin pump installation procedure, a continuous glucose monitoring system installation procedure, a CRT device installation procedure, a heart monitor installation procedure, an ICD device installation procedure, an EV-ICD device installation procedure, a pacemaker installation procedure, a miniature leadless implant installation procedure, an implantable sensor installation procedure, a remote monitoring device installation procedure, a VAD installation procedure, an IABP implantation procedure, or a drug pump installation procedure, and/or the like.

In some instances, the one or more tasks might include one or more fourth tasks including, without limitation, at least one of a tissue ablation procedure, a shunt procedure, a microwave ablation procedure, a stenting procedure, a cardiac mapping procedure, a catheter ablation procedure, or a home care ventilation procedure, and/or the like.

According to some embodiments, the subject might include, but is not limited to, one of a human patient, a large animal, a small animal, an organ, an organelle, one or more organs on a chip, one or more tissue constructs, one or more cells, one or more microbes of bacterial vectors, one or more microbes of viral vectors, one or more microbes of prion vectors, one or more genes, deoxyribonucleic acid ("DNA"), ribonucleic acid ("RNA"), one or more hormones, one or more biochemicals, one or more molecules, one or more tissues, one or more blood vessels, or one or more bones, and/or the like.

In some cases, the one or more subjects might include one or more first subjects including, without limitation, at least one of a human patient, a large animal, or a small animal, and/or the like.

In some instances, the one or more subjects might include one or more second subjects including, without limitation, at least one of an organ, an organelle, one or more organs on a chip, one or more tissue constructs, one or more cells, one or more molecules, one or more tissues, one or more blood vessels, or one or more bones, and/or the like.

In some cases, the one or more subjects might include one or more third subjects including, without limitation, at least one of one or more microbes of bacterial vectors, one or more microbes of viral vectors, one or more microbes of prion vectors, and/or the like.

In some instances, the one or more subjects might include one or more fourth subjects including, without limitation, at least one of one or more genes, DNA, RNA, one or more hormones, one or more biochemicals, and/or the like.

Any one of (or a combination of two or more of) the above-mentioned first through seventh sensors along with first through sixth imaging devices may be used, in conjunction with any one of (or combination of two or more of) the tracking systems (as described below) for any of the first through fourth tasks performed by corresponding first through fifth devices on corresponding first through fourth subjects. Specific non-limiting example combinations of these systems and devices are described above with respect to FIG. 9, in terms of specific example procedures in the context of pre-operative planning, intra-operative adjustments, and post-operative monitoring (as described above with respect to FIG. 3C, or the like).

At block 1120, method 1100 might comprise analyzing, with the computing system, the received one or more device data, the received one or more sensor data, and the received one or more imaging data. Method 1100 might further comprise, at block 1125, mapping, with the computing system, two or more of the received one or more device data, the received one or more sensor data, or the received one or more imaging data to a three-dimensional ("3D") or four-dimensional ("4D") representation (i.e., three-dimensional ("3D") representation plus at least one of real-time updates, dynamic modeling, or data streaming, and/or the like) of the at least one or more portions of the subject, based at least in part on the analysis.

Method 1100 might further comprise generating, with the computing system, one or more extended reality ("XR") images, based at least in part on the mapping (block 1130); and presenting, with the computing system and using a user experience ("UX") device, the generated one or more XR images (block 1135). In some embodiments, the one or more XR images might include, without limitation, at least one of one or more augmented reality ("AR") images, one or more AR videos, one or more virtual reality ("VR") images, one or more VR videos, one or more mixed reality ("MR") images, one or more MR videos, one or more XR images, or one or more XR videos, and/or the like.

According to some embodiments, the UX device might include, but is not limited to, at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

In some cases, the UX device might include one or more first UX devices including, without limitation, at least one of a headset, UX glasses, a supplement to existing glasses, UX contact lenses, or a HUD device, and/or the like.

In some instances, the UX device might include one or more second UX devices including, without limitation, at least one of a viewing window or a microscope, and/or the like.

In some cases, the UX device might include one or more third UX devices including, without limitation, at least one of headphones or a 3D spatial sound system, and/or the like.

In some instances, the UX device might include one or more fourth UX devices including, without limitation, at least one of an olfactory simulation system, a taste simulation system, a sensory neuro-perception system, a sensory conversion system, or a haptic feedback system, and/or the like.

In some cases, the UX device might include one or more fifth UX devices including, without limitation, at least one of a telemonitoring system, a rigid robotic device control and sensory feedback system, a soft robotic device control and sensory feedback system, a control system for nanostructures, a control system for cells, a control system for genes, or a nanoparticle reconstruction system, and/or the like.

In some instances, the UX device might include one or more sixth UX devices including, without limitation, at least one of an eye control system, a voice control system, a remote control system, a gesture-based control system, a sign language-based control system, a body-part-based control system, a joystick, a mouse, a blow-based control system, a neuro-interface system, or a peripheral nerve-computer interface system, and/or the like.

In some cases, the UX device might include one or more seventh UX devices including, without limitation, at least one of a 2D screen display, a 3D refractive display, a parallel reality system, a projection system, a fan-based display, a water-based display, an ionized air-based display, an ionized laser-based display, a smoke-based display, a sand-based display, a particulate-based display, a 3D printed reconstruction system, or a customized view generation system, and/or the like.

In some instances, the UX device might include one or more eighth UX devices including, without limitation, at least one of a ghosting and prediction system, a master-slave control system, or an annotation system, and/or the like.

In some embodiments, the generated one or more XR images might be presented to provide one or more uses including, without limitation, a guide for a medical professional, a navigation tool during a medical procedure, a proximity detection tool during a medical procedure, a 3D or 4D visualization view of the at least one or more portions of the subject, a heads-up display of the one or more device data, a heads-up display of biological data of the subject, a heads-up display of chemical data of the subject, a heads-up display of physiological data of the subject, or a heads-up display of procedure-related data of the subject, and/or the like. In some cases, the one or more uses might include one or more first uses including, without limitation, at least one of a guide for a medical professional, a navigation tool during a medical procedure, or a proximity detection tool during a medical procedure, and/or the like.

In some instances, the one or more uses might include one or more second uses including, without limitation, at least one of a 3D or 4D visualization view of the at least one or more portions of the subject, a heads-up display of the one or more device data, a heads-up display of biological data of the subject, a heads-up display of chemical data of the subject, a heads-up display of physiological data of the subject, or a heads-up display of procedure-related data of the subject, and/or the like.

Any one of (or a combination of two or more of) the aforementioned UX devices may be used by a user for the first through second uses above, based on computer analysis of data obtained from the above-mentioned first through seventh sensors along with first through sixth imaging devices, in conjunction with any one of (or combination of two or more of) the first through sixth tracking systems (as described below) for any of the first through fourth tasks performed by corresponding first through fifth devices on corresponding first through fourth subjects. Specific non-limiting example combinations of these systems and devices are described above with respect to FIG. 9, in terms of specific example procedures in the context of pre-operative planning, intra-operative adjustments, and post-operative monitoring (as described above with respect to FIG. 3C, or the like).

At optional block 1140, method 1100 might comprise generating, with the computing system, one or more XR experiences comprising at least three or more of the one or more XR images, one or more XR sounds, one or more XR haptic or tactile responses, one or more XR simulated smells, or one or more XR simulated tastes, based at least in part on the mapping. According to some embodiments, the one or more XR images might be dynamic images, which might include an overlay of data models depicting at least one of electrical pulses, blood flow, tissue movement, damage, stress, and/or the like, and thus may not be a still frame in 3D. Method 1100, at optional block 1145, might comprise presenting, with the computing system and using the UX device, the generated one or more XR experiences. Method 1100 might continue onto the process at optional block 1150 in FIG. 11B following the circular marker denoted, "A," might continue onto the process at optional block 1155 in FIG. 11C following the circular marker denoted, "B," or might continue onto the process at optional block 1160 in FIG. 11D following the circular marker denoted, "C."

At optional block 1150 in FIG. 11B (following the circular marker denoted, "A"), method 1100 might comprise tracking, with the computing system, the one or more devices, in some cases, using one or more tracking systems including, but not limited to, at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In some cases, the one or more tracking systems might include one or more first tracking systems including, without limitation, at least one of an electropotential-based tracking system, an impedance-based tracking system, an accelerometer-based tracking system, an IR-based tracking system, an ultrasonic sound-based tracking system, a piezoelectric-based tracking system, or an acoustic-based tracking system, and/or the like.

In some instances, the one or more tracking systems might include one or more second tracking systems including, without limitation, at least one of an electromagnetic-based tracking system, a magnetic anomaly detection-based tracking system, or an MRI-based tracking system, and/or the like.

In some cases, the one or more tracking systems might include one or more third tracking systems including, without limitation, at least one of a RFID-based tracking system, a Bluetooth-based tracking system, a wireless-based tracking system, or a near-field communications-based tracking system, and/or the like.

In some instances, the one or more tracking systems might include one or more fourth tracking systems including, without limitation, at least one of an optical-based tracking system, a laser-based tracking system, an US imaging-based tracking system, a computer vision-based tracking system, a fluoroscopy-based tracking system, a SLAM-based tracking system, or a feature identification-based tracking system, and/or the like.

In some cases, the one or more tracking systems might include one or more fifth tracking systems including, without limitation, at least one of a GPS-based tracking system or a radar-based tracking system, and/or the like.

In some instances, the one or more tracking systems might include one or more sixth tracking systems including, without limitation, at least one of a machine learning-based tracking system, a predictive tracking system, or a prescriptive tracking system, and/or the like.

At optional block 1155 in FIG. 11C (following the circular marker denoted, "B"), method 1100 might comprise generating, with the computing system, one or more models that are used for analyzing or visualizing at least one of the received one or more device data, the received one or more sensor data, and the received one or more imaging data, and/or the like.

At optional block 1160 in FIG. 11D (following the circular marker denoted, "C"), method 1100 might comprise receiving, with the computing system, one or more inputs from a user. Method 1100 might further comprise, at optional block 1165, analyzing, with the computing system, the one or more inputs from the user to determine whether the one or more inputs comprise at least one command such as at least one of one or more voice commands, one or more eye-tracking-based commands, one or more gesture-based commands, one or more touch-based commands, or one or more entered commands, and/or the like.

Based on a determination that the one or more inputs comprise at least one command such as at least one of one or more voice commands, one or more eye-tracking-based commands, one or more gesture-based commands, or one or more entered commands, method 1100 might further comprise identifying, with the computing system, which at least one device among the one or more devices is intended to be controlled based on the one or more inputs (at optional block 1170); generating, with the computing system, one or more instructions for controlling the identified at least one device based at least in part on the one or more inputs (at optional block 1175); and sending, with the computing system, the generated one or more instructions to the identified at least one device (at optional block 1180).

Figure 11E:
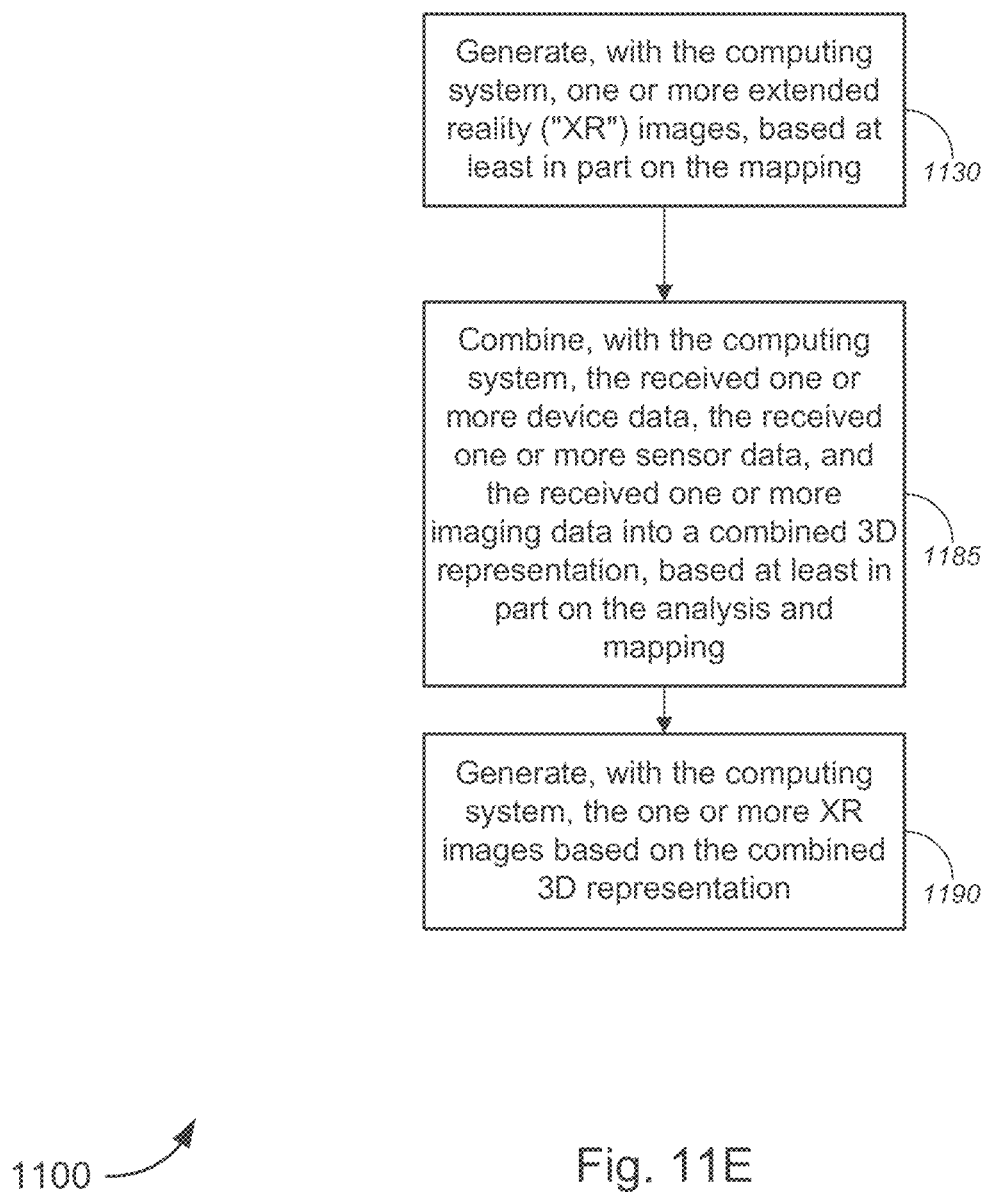

With reference to the non-limiting embodiment of FIG. 11E, generating the one or more XR images (at block 1130) might comprise combining, with the computing system, the received one or more device data, the received one or more sensor data, and the received one or more imaging data into a combined 3D or 4D representation, based at least in part on the analysis and mapping (block 1185); and generating, with the computing system, the one or more XR images based on the combined 3D or 4D representation (block 1190).

Figure 12A:
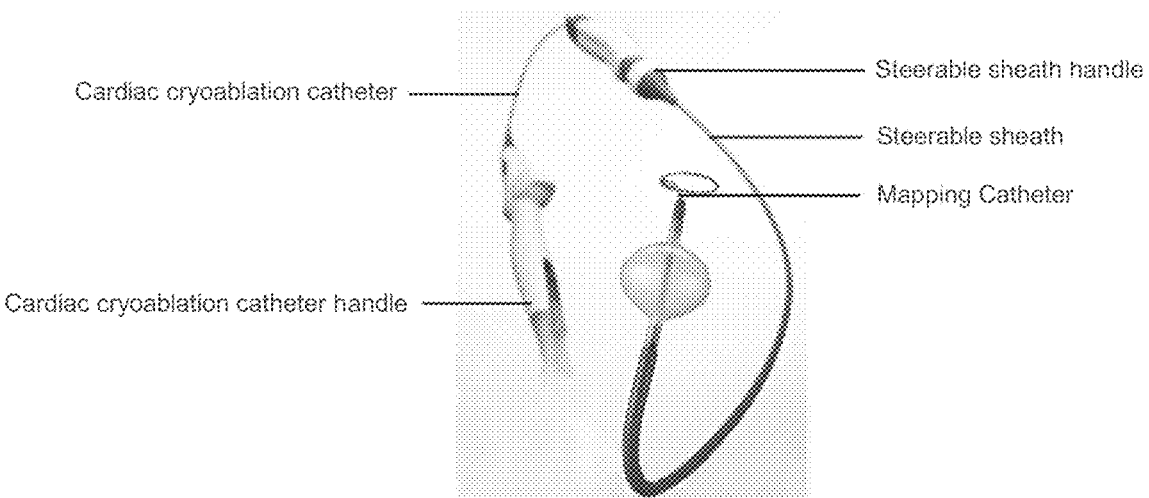
FIGS. 12A-12Y are schematic diagrams or images illustrating various non-limiting examples related to implementing a cardiac arrhythmia procedure using an IA ecosystem, in accordance with various embodiments.
Figure 12B:
Figure 12C:
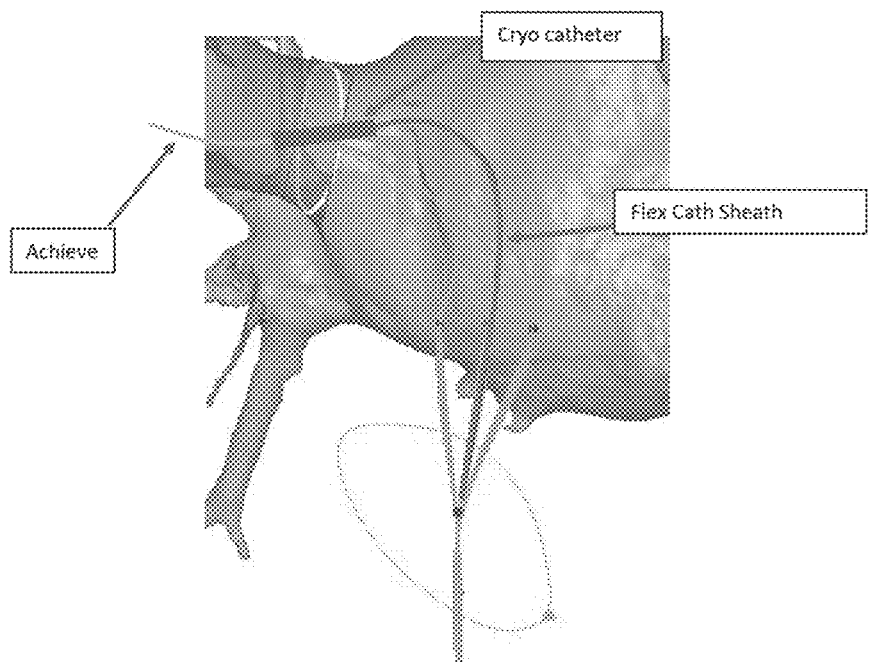
Figure 12D:
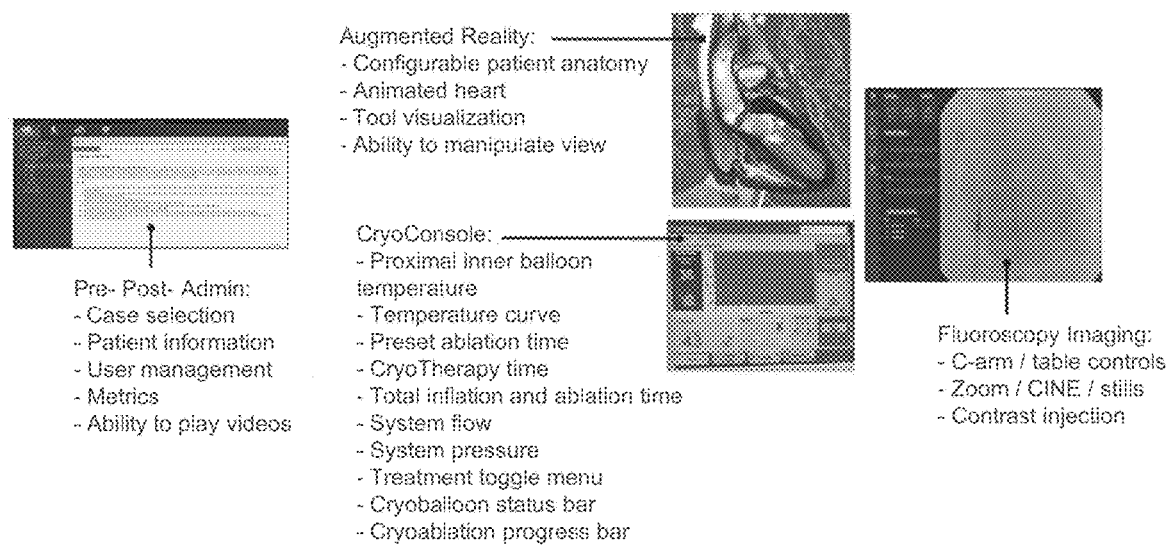
Figure 12F:
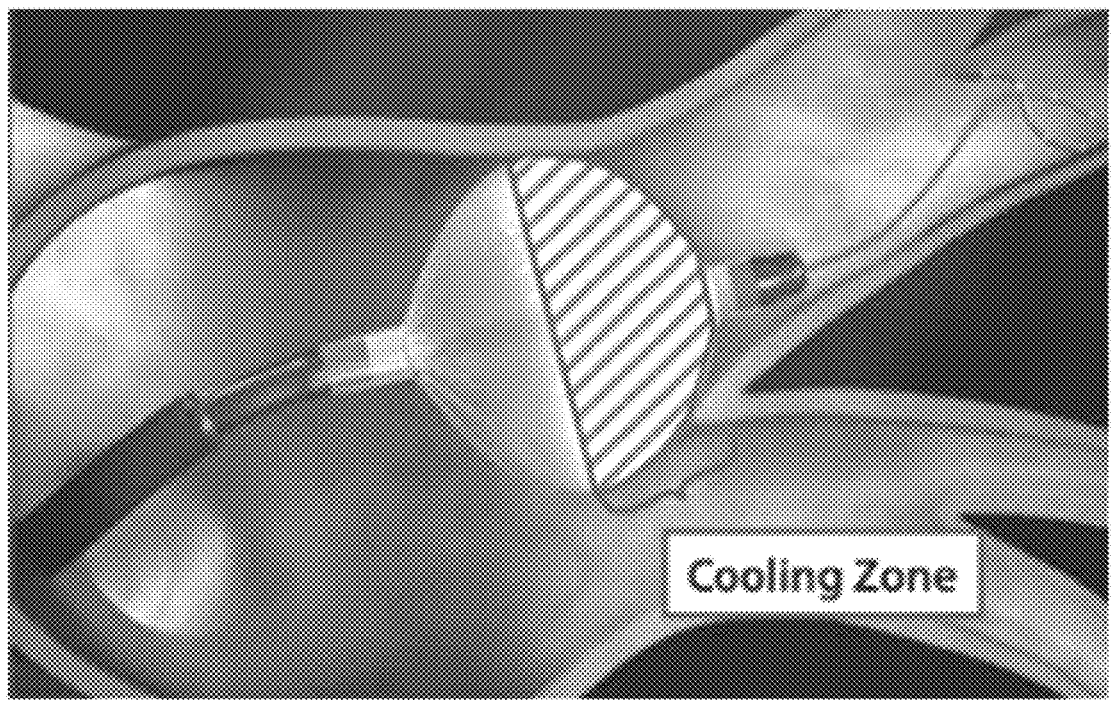
Figure 12G:
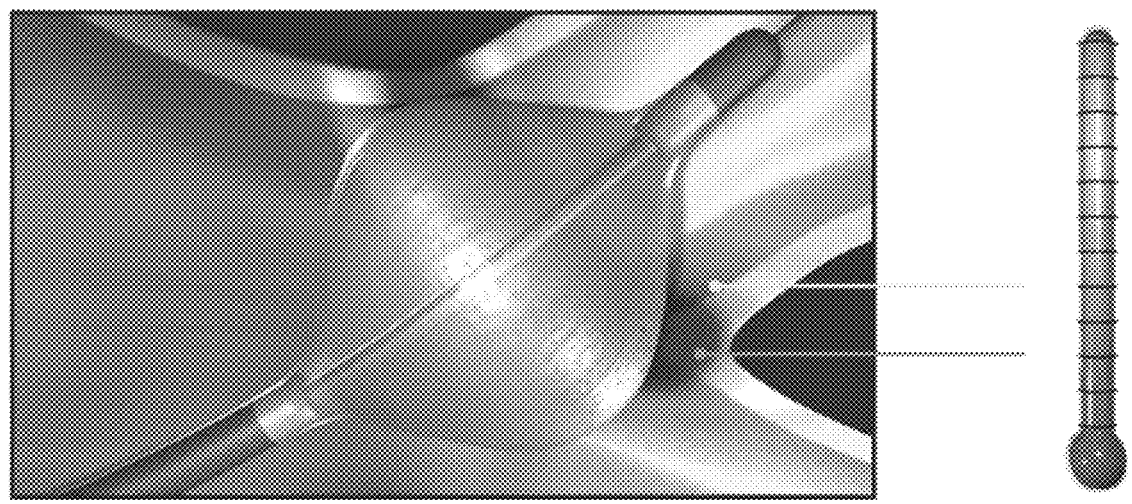
Figure 12H:
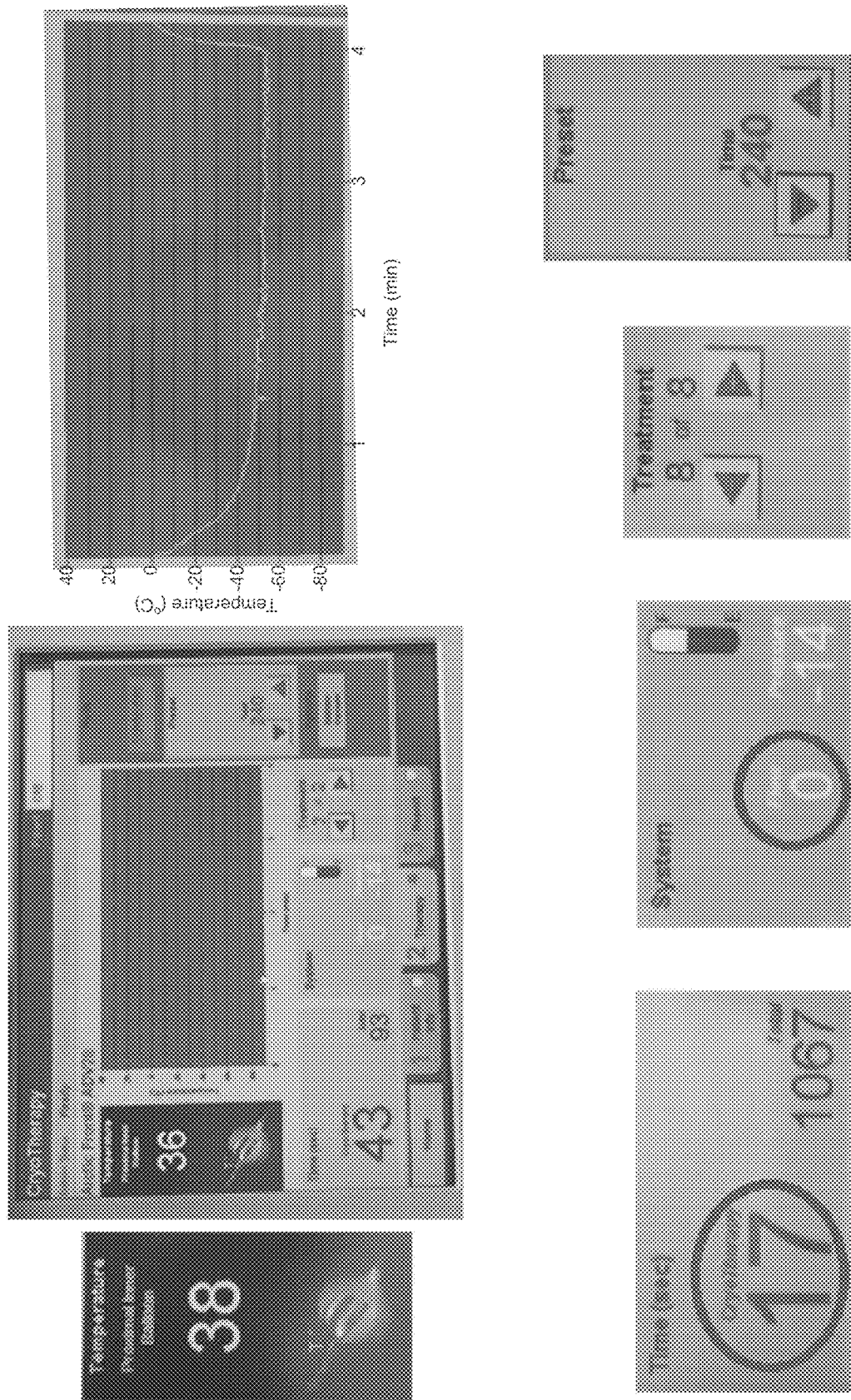
Figure 12I:
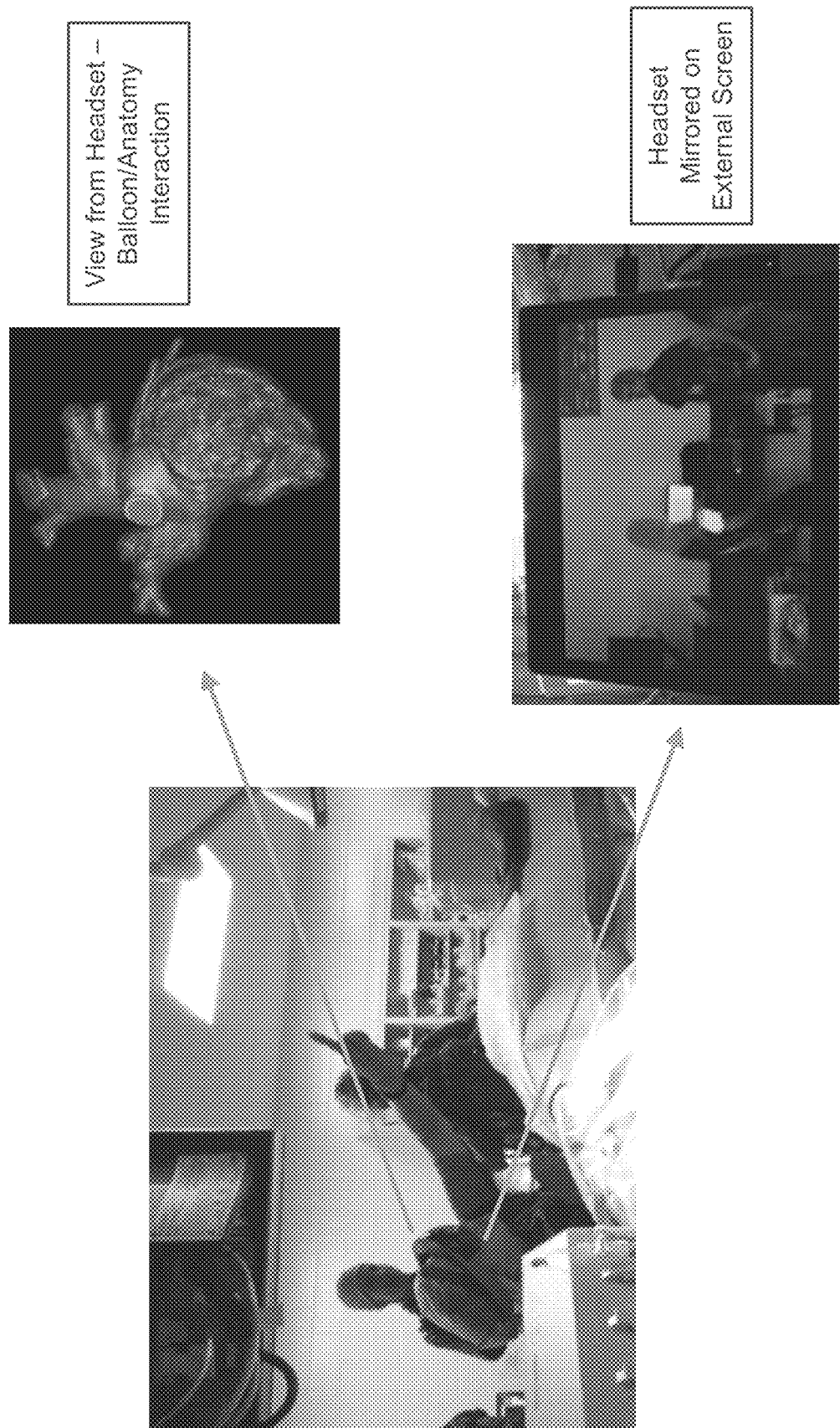
Figure 12M:
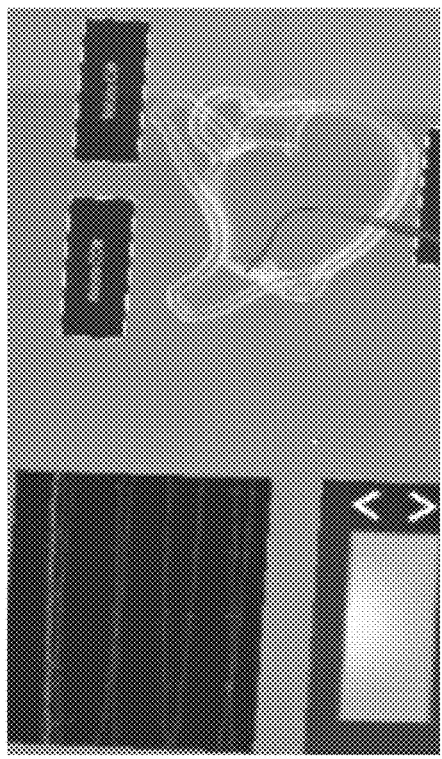
Figure 12N:
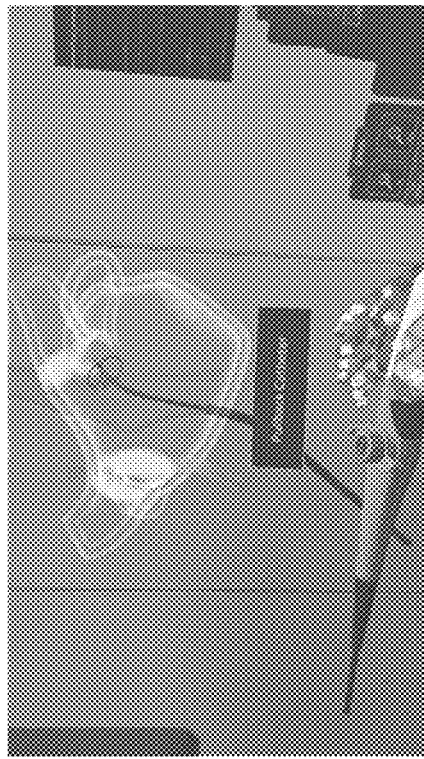
Figure 12K:
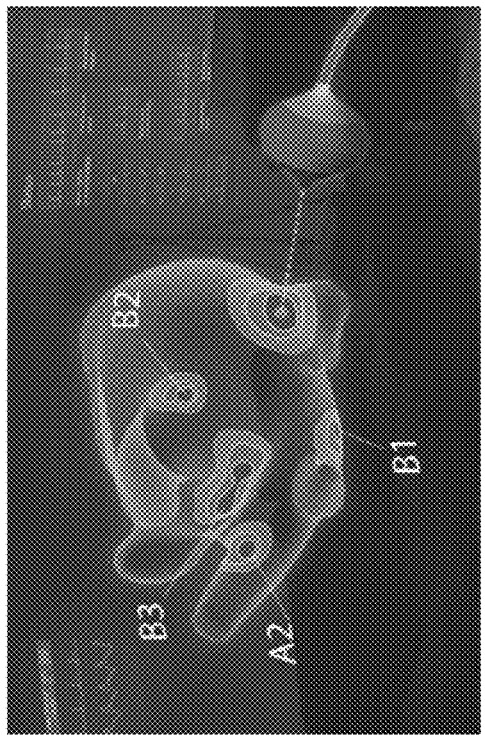
Figure 12L:
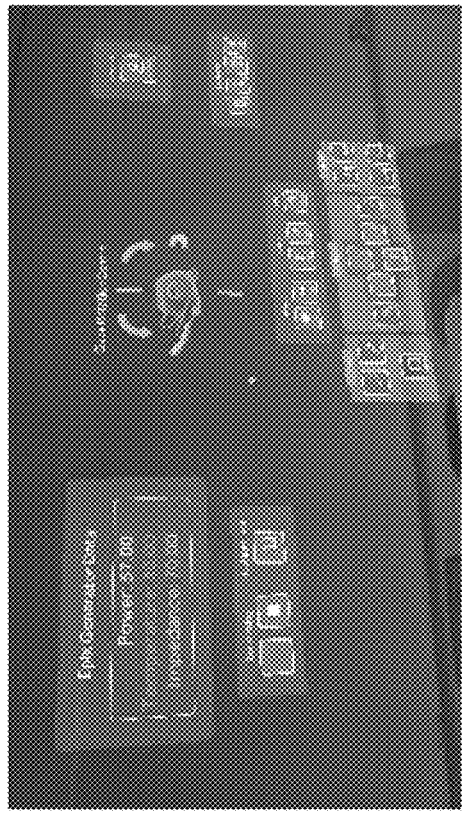
Figure 12O:
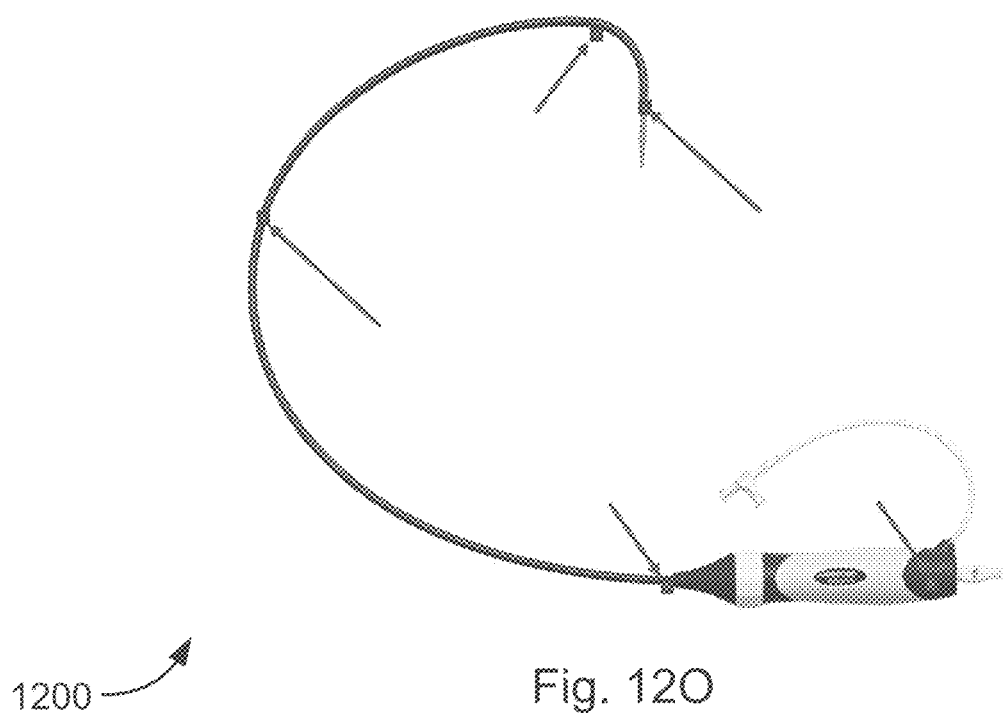
Figure 12P:
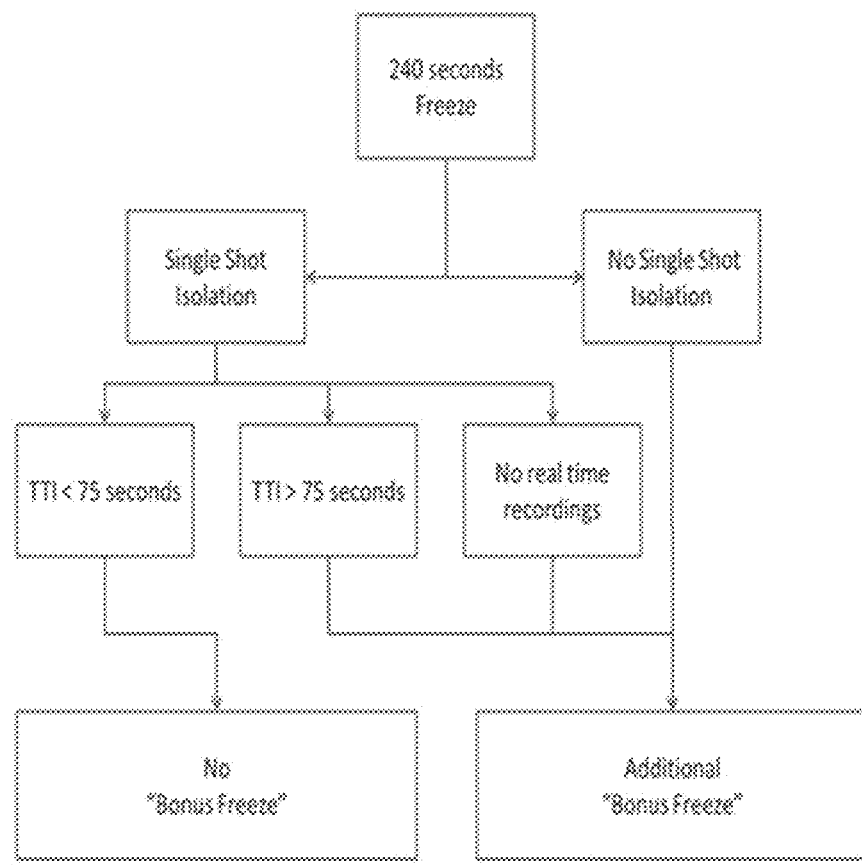
Figure 12Q:
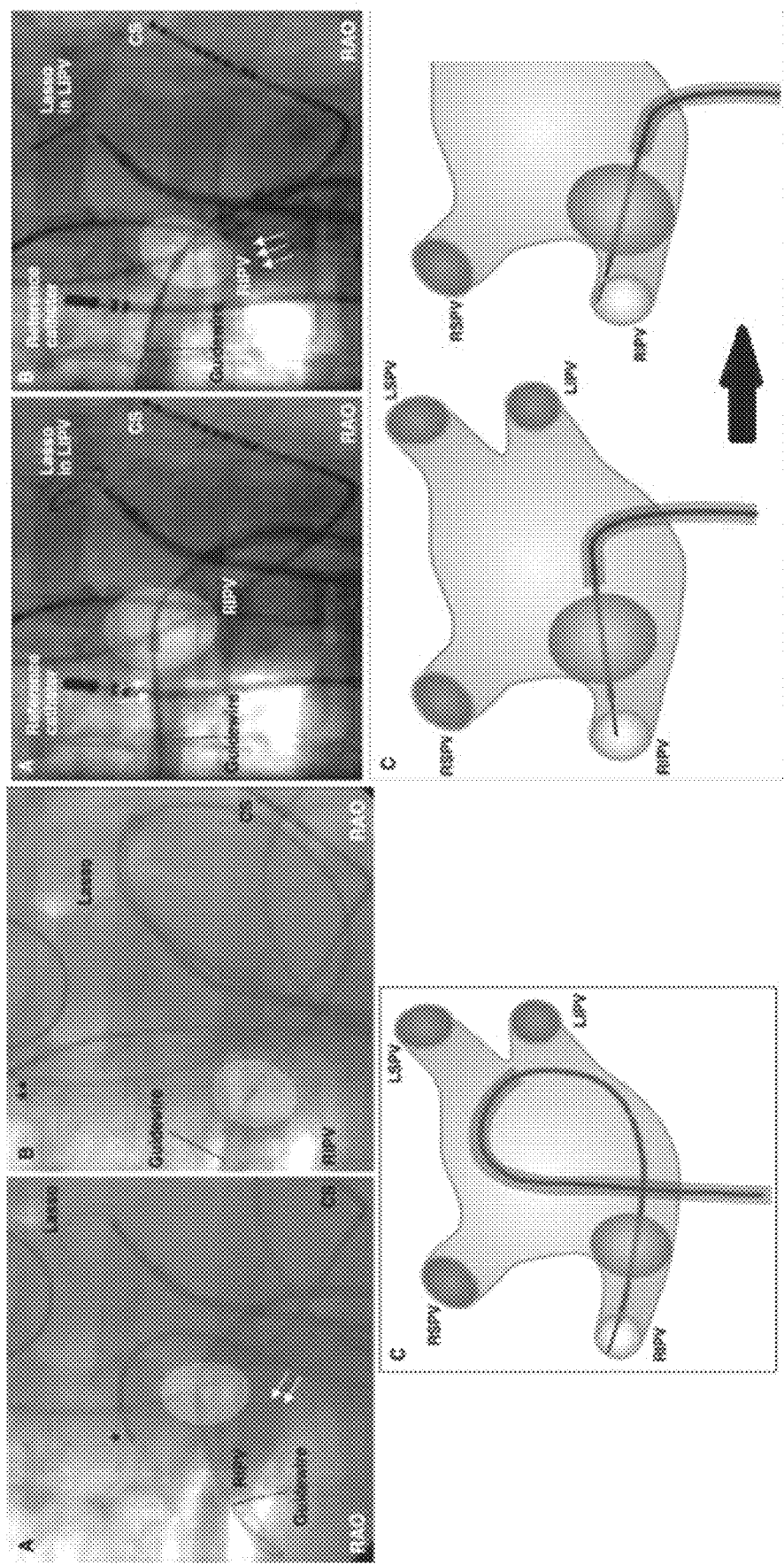
Figure 12R:
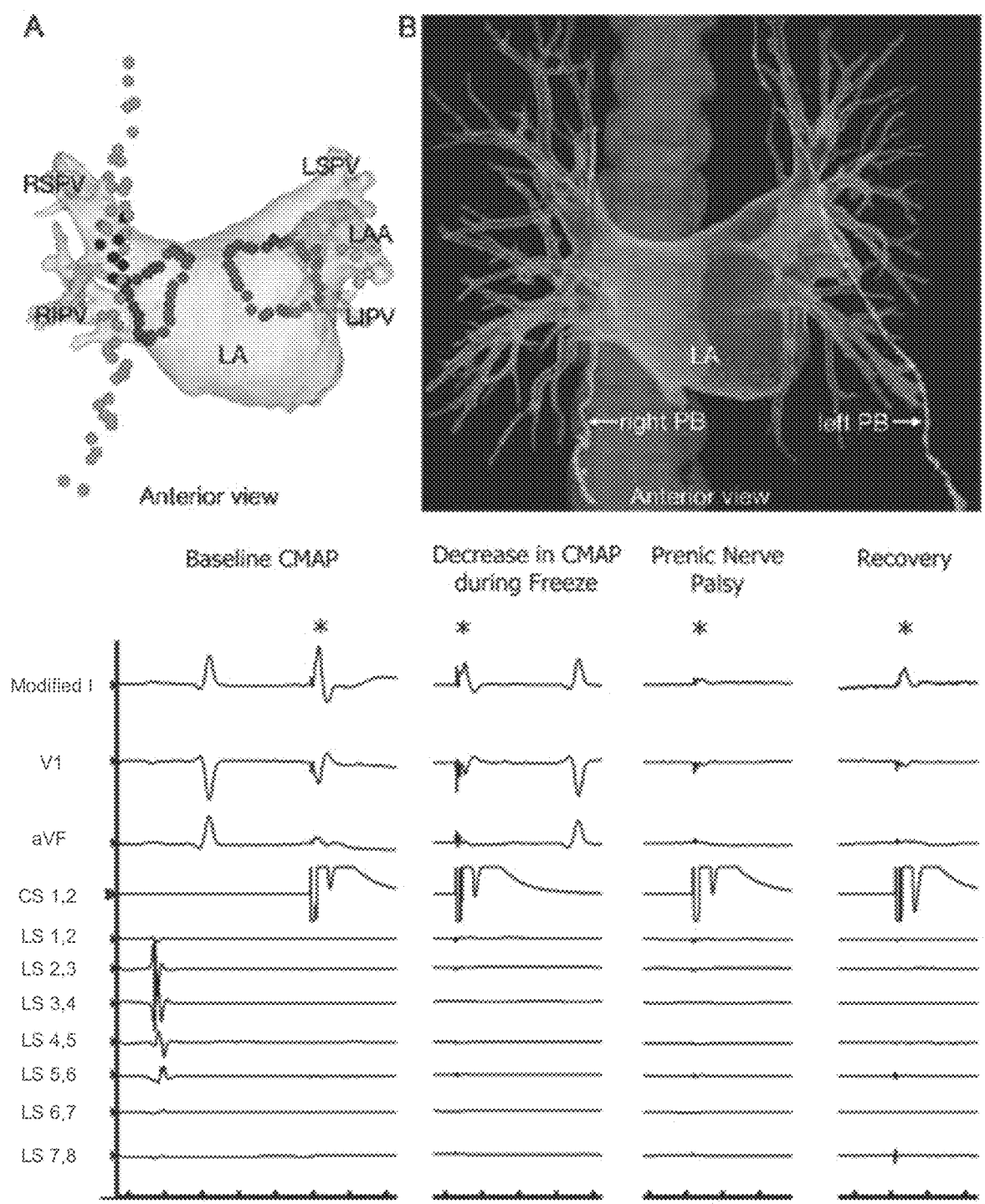
Figure 12S:
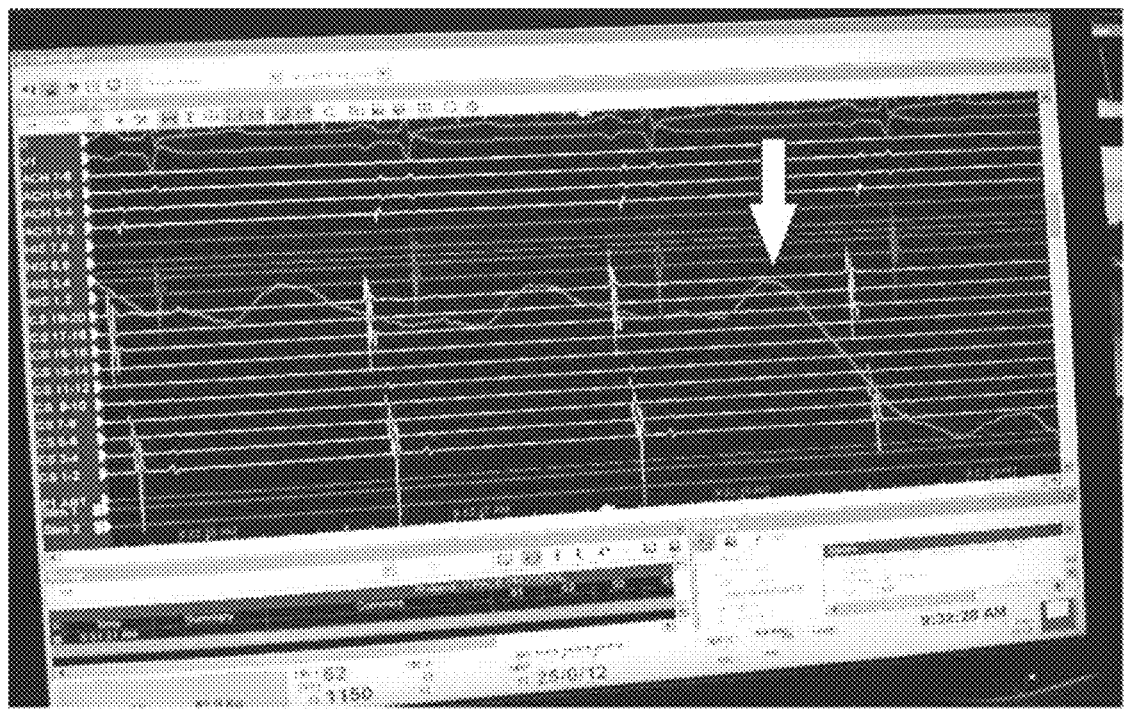
Figure 12T:
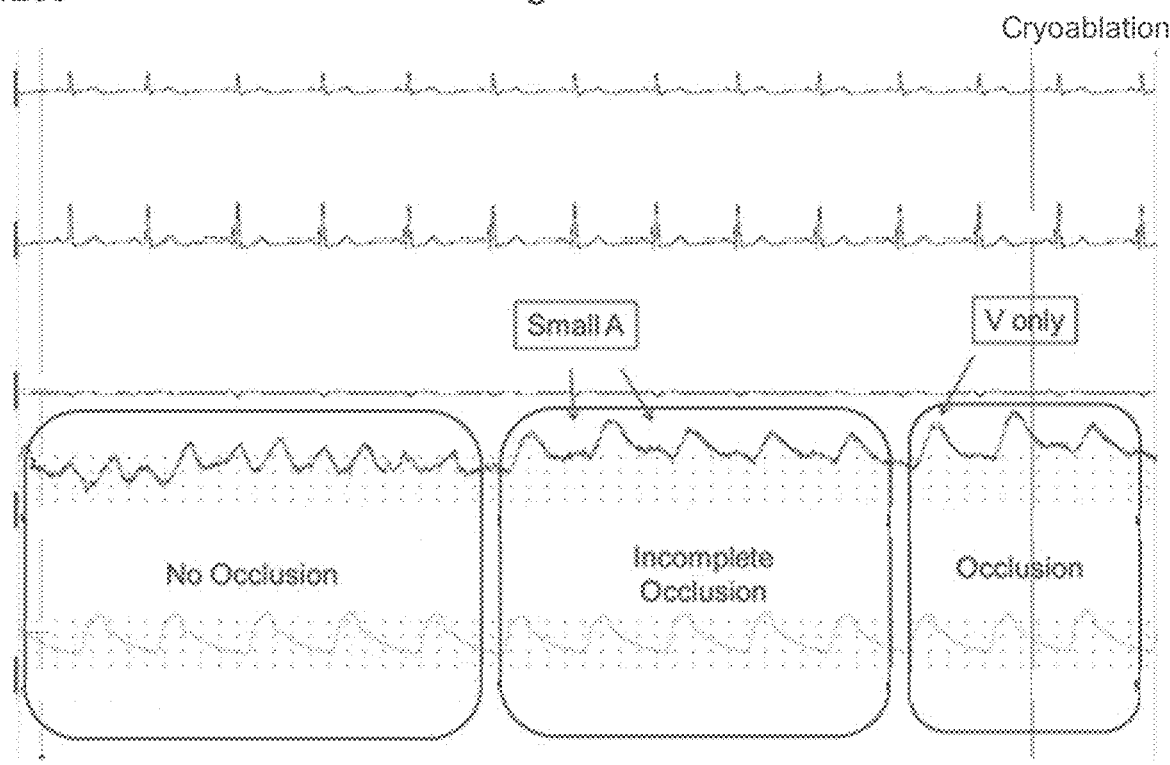
Figure 12V:
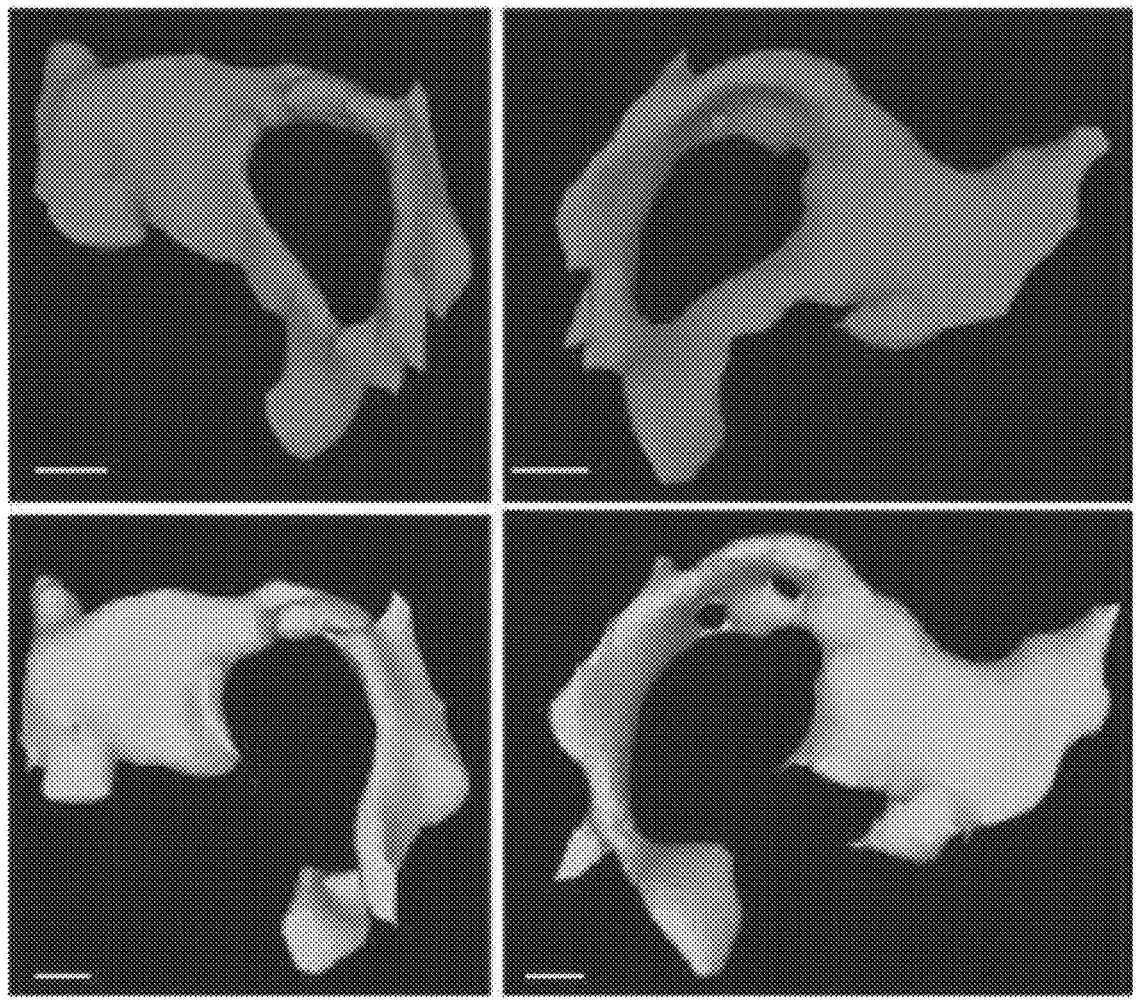
Figure 12Y:
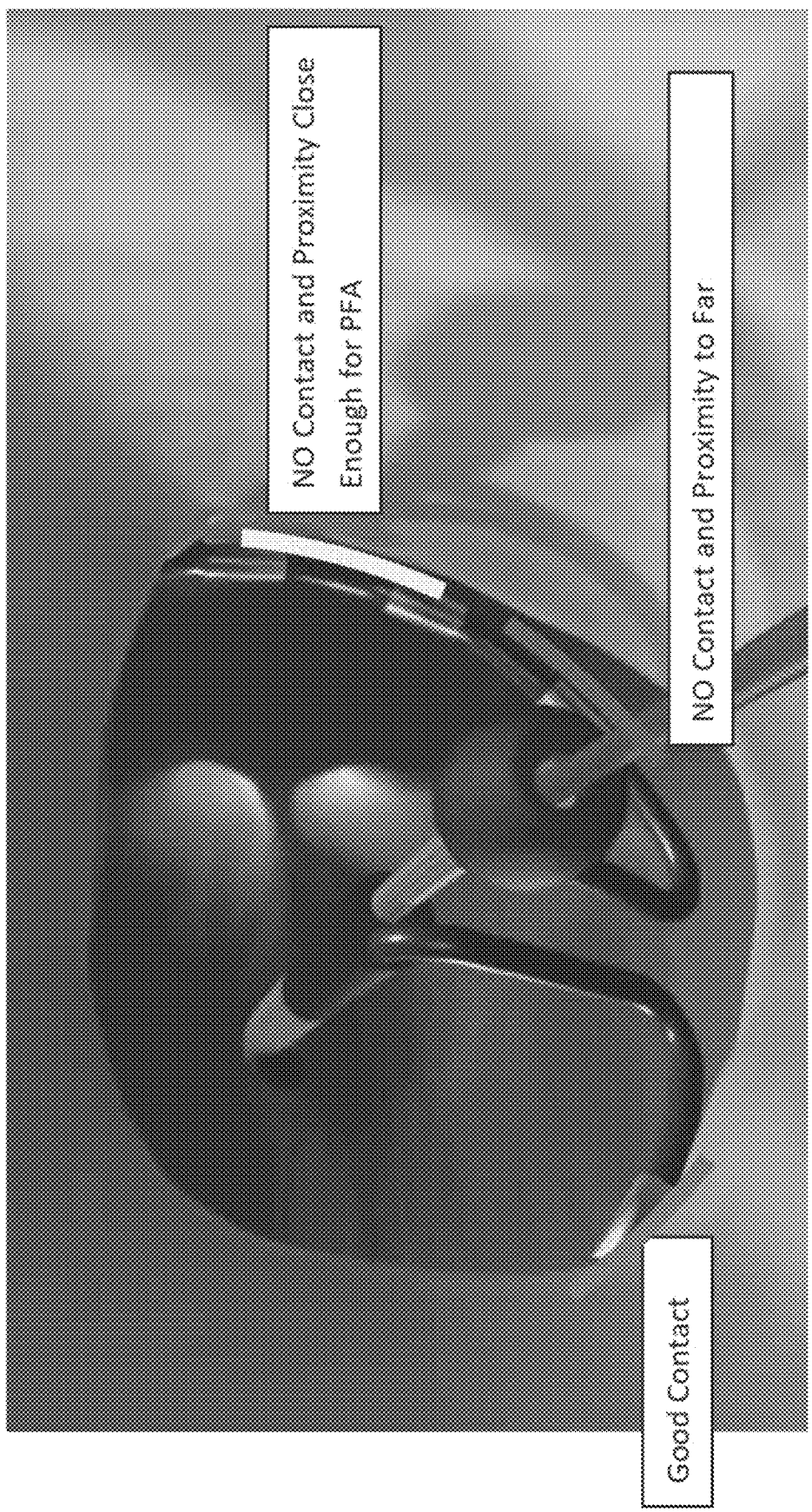

FIGS. 12A-12Y (collectively, "FIG. 12") are schematic diagrams or images illustrating various non-limiting examples 1200 related to implementing a cardiac arrhythmia procedure using an IA ecosystem, in accordance with various embodiments.

In some embodiments for implementing a cardiac arrhythmia procedure, several attributes of an ablation procedure should be considered to achieve the safest and most efficacious outcome. However, the system goes beyond just what is present in mechanical devices. For example, the Cryo Console controls the flow, houses the user interface, and conveys safety warnings, etc. Herein, Cryo Console refers to a system (not unlike the generator for delivering RF therapy) that is configured to deliver cryo therapy; that includes a compressed tank of gas, multiple valves, and sensor; and that causes the gas to flow through the catheter to the cryoballoon where the pressure change causes the cryoballoon to rapidly cool. The Cryo Console has a myriad of sensors to track temperature, which the Cryo Console uses to display temperature waveforms, timing to minimal temperature flows, background information on reliability of the capital equipment before potential breakdown or before required maintenance, and/or the like. The Cryo Console also utilizes decision-making and/or interfacing UI as well as background information that provides warnings and solutions for issues with the capital equipment and the catheter that can be communicated to the user during a procedure, compiled for a study, or used while fixing the system. If the mechanical portions of the system could communicate in a sophisticated manner, the cryoablation procedure could address several pains, gains, and jobs to be done: reduce procedure time, eliminate fluoro, reduce LA dwell time (emboli), improve catheter reliability, efficacy, safety, user experience, learning curve, unmet patient populations, non-users, single physician procedures, etc.

The integration of augmented and mixed reality (AR & MR) can be taken a step further when the entire system can be incorporated. For instance, a heads-up display could not only overlay the anatomy, the devices, and predictive paths, but could also provide several other features. These options can be viewed together, in part, and/or overlaid—for example, the 3D AR version on top of the patient, fluoro or echo image, patient history, console user interface, etc. Warnings such as leaks, tank levels, etc. can also be displayed. Not only could these details be displayed, but they can be activated with gestures on the AR headset (e.g., HoloLens or similar AR system, or the like) or can be voice activated. In this manner, the need for a second operator, hand buttons, and foot pedals may be eliminated. The view could also show adjacent structures (e.g., the phrenic nerve and esophagus, etc.), communicate with devices measuring diaphragm movement, emboli, and/or esophagus temperature, and send out a warning. Similarly, metrics to titrate the dosage can be displayed. Additionally, several metrics can be recorded to train, educate, and track learning curves. Further, these metrics when coupled with artificial intelligence can customize the predictive algorithms for specific patient anatomies, physician preferences, and use conditions for intra-procedural device warnings and future product development.

With reference to the non-limiting example of FIG. 12A, mechanical parts of a cryoballoon system is shown (namely, an Arctic Front Advance™ ("AFA") cryoablation catheter coupled to an AFA cryoablation catheter handle that is used to control or manipulate the AFA cryoablation catheter, a FlexCath steerable sheath coupled to a FlexCath steerable sheath handle that is used to control or manipulate the FlexCath steerable sheath, which is used to steer or guide the AFA cardiac cryoablation catheter (in this case) with an Achieve™ mapping catheter affixed to the distal end of the AFA cryoablation catheter to a predetermined portion of the heart of a patient. FIG. 12B depicts a cryoablation console (e.g., CryoFlex™ console, CryoConsole™ cardiac cryoablation system, or the like) that is used to control the flow, to house the user interface, and to convey safety warnings, or the like. The cryoablation console is also used to store and control delivery of the liquid refrigerant (e.g., $N_2O$, or the like) through a coaxial umbilical to the catheter, to recover the refrigerant vapor from the catheter under constant vacuum, and to safely and efficiently dispose of the refrigerant through a scavenging system.

The non-limiting example of FIG. 12C depicts a display projected in an augmented or extended reality navigation system that may be used to improve a user's ability to steer to the target anatomy with an approach that will assist the user in achieving optimal pulmonary vein ("PV") occlusion, while reducing the likelihood of catheter mechanical failures. As shown in FIG. 12C, various predictive curved trajectories may be displayed or presented relative to the transseptal puncture and anatomy for the final position for each of the interacting devices.

FIG. 12D depicts a non-limiting set of options that can be viewed together, in part, and/or overlaid, for example, as a 3D AR or XR version on top of imaging data (e.g., fluoro or echo image data), patient history, console user interface, and/or the like. In other words, these options represent potential views that may be presented in an AR or XR system display. FIG. 12E depicts non-limiting examples of potential views of EKG data and/or CardioInsight mapping data that may be additionally or alternatively presented in an AR or XR system display. FIG. 12F depicts a non-limiting example of a potential cooling zone contact view that may be additionally or alternatively presented in an AR or XR system display, where a cooling zone region is annotated over top of the image of the cryoablation balloon showing specifically the cooling zone of the cryoballoon in relation to the portion of the heart anatomy. FIG. 12G depicts a non-limiting example of a potential cooling or lesion view, which can be used to highlight ice formations in the target tissue of the heart, that may be additionally or alternatively presented in an AR or XR system display. FIG. 12H depicts various potential console views and controls (e.g., potential console temperature view and control, potential console temperature curve view and control, potential console preset time view and control, potential console therapy time view and control, potential console flow and pressure view and control, potential console treatment tracker view and control, and/or the like) that may be additionally or alternatively presented in an AR or XR system display.

FIG. 12I depicts a summary of a successful real-time ablation of pre-clinical cryoablation and a transcatheter aortic valve replacement ("TAVR") procedure using a novel 3D XR navigation in patient-specific anatomy using XR in a live swine model, resulting in reduction of fluoro time and contrast exposure, real-time feedback to the user on interaction between therapy delivery system and target anatomy (e.g., contact, distance, angle, lesion annotation, and/or the like), and validation of XR positioning via fluoro, and/or the like.

The system also provides for catheter imaging and navigation. Since the trajectory of a catheter relates directly to the efficacy of the therapy, the ability to visualize, navigate, and ultimately predict is critical. In addition to the optimal trajectories, the XR system can give feedback on where occlusion, contact, and/or proximity is optimal or not relative to therapy delivery (as shown in FIG. 12C). The XR system can detect balloon position via collision meshes on the anatomical image (e.g., CT, 3D Echo, or real time MR or XR, or the like) as well as with sensors on the balloon or electrode surface (as shown, e.g., in FIGS. 12J, 12K, 12M, and 12N, or the like). FIG. 12J depicts a real-time example of cryoballoon predictive trajectory and contact/ablation, with real-time distance to target annotation being displayed in the XR display, and with annotations of contact or ablated portions of the target tissue also being displayed in the XR display. In some cases, the pulsed field ablation ("PFA") electrical field (which is non-contact) at various settings can be visualized in the XR display before ablation as well as post-ablation (as shown, e.g., in FIG. 12M, or the like). In some instances, the radiofrequency ("RF") ablation (e.g., Diamond Temp ("DT") ablation, or the like) data can also be integrated in a similar way to display point for point by point contact information in the XR display. There is significant data that the Cryoballoon system (including focal and linear catheters like cryolinear, pRF/Genius/PFA console and EPIX/cEP catheters, or the like) does or could gather, and such as performance information, which may be embedded in the Bin files, could be analyzed and displayed for better use by medical professionals (e.g., physicians, nursing staff, and/or the like). Herein, Bin files refers to a file type that is used to gather or store data (including, but not limited to, temperature data, pressure data, flow data, time data, etc.) on the console for every ablation. In some cases, the encrypted data in the Bin files may be pulled from the console for decryption and analysis for clinical studies or for repairing the console. In some embodiments, machine learning algorithms may be used on time series data included among the encrypted data. According to some embodiments, the encrypted data and/or the Bin files may be streamed, and, in some cases, used live or in real-time (or near-real-time) to inform a procedure in progress. Some of these metrics include, without limitation, time, temperature, power, voltage, current, irrigation flow rate, impedance, and/or the like. A non-limiting example of an XR UI of the Diamond Temp data can be seen, e.g., in FIG. 12L.

In order to enable the XR system to coordinate the above movements, each of the devices may need to have active sensors on it. For example, the Achieve™ mapping catheter currently has 8 electrodes that can be employed for navigation, while the cryoballoon glacier project added two electrodes to the balloon tip, and electrodes (or potential locations of sensor tags, such as RFID tags, or the like) to generate the relative coordinates of the FlexCath Sheath™ or other steerable sheath are shown, e.g., in FIG. 12O.

In some embodiments, several data analytics, particularly visualized in real-time for actionable decision-making by a medical professional, can be employed for on the therapy delivery. For example, time-to-isolation ("TTI") is a good surrogate for lesion assessment to identify pulmonary vein isolation ("PVI"), but it is an indirect measure that does not tell the medical professional any information at the site of the lesion, such as location of a gap. First, some mapping catheters are only effective about two-thirds of the time overall and half for right inferior pulmonary vein ("RIPV"), which is the most difficult-to-maneuver position with the highest reconnection rate. Second, this leads to a difficulty in titrating the dosage of the treatment, and thus will increase procedure time, fluoro exposure, carcinogenic contrast, and collateral damage, etc. Third, device performance and reliability degrade with the number and type of maneuvers, which will increase with poor maneuvering and/or TTI. The various embodiments address critical unmet user needs, and thus lead to increased market share, while at the same time building a cadence of AFS technologies and devices. FIG. 12P depicts a typical decision tree for titrating dosage depending on TTI, while FIG. 12Q depicts two extremely different maneuvers to reach the RIPV, with fluoroscopy shown.

Alternatively, adjacent structures can be monitored in real-time and ablation dosages titrated accordingly (as shown, e.g., in FIGS. 12R and 12S, or the like). For example, as opposed to lengthy post-procedural processing by hand, occlusion, ice ball formation, and/or lesion formation, or the like, can be tracked and displayed relative to phrenic nerve palsy (such as by CMAP, or the like), and the dosage can be titrated in an optimal manner (e.g., as shown in FIG. 12R, or the like). Furthermore, not only could EGM signals such as the Achieve™ EGM signals be monitored in XR space, and deep learning could be used help to titrate with predictions of TTI, but additional data streams employed for fluoroless ablation/navigation can be incorporated, such as pressure traces and echo, or the like. This could be done in a system similar to a crowd sources application (like Human Diagnosis Project (Human DX), which uses machine learning technology to consider the data, to send the case to specialists who offer diagnoses, and then to sort and combine each curated finding to create a single diagnosis, or the like). FIG. 12R depicts phrenic nerve visualization on a 3D CT scan (as well as phrenic nerve data) that may be displayed in an XR system. FIG. 12S depicts an EGM readout from Achieve™ integrated with pressure traces for occlusion that may also be displayed in an XR system.

According to some embodiments, any type of data driven algorithm with an input, transfer functions, and output that could be employed (such as End Tidal $CO_2$, CMAP, pressure waveforms, doppler jet size/velocity, etc.) to predict balloon occlusion, lesion growth, PVI, and/or the like, can be analyzed with DL and displayed by the XR system. For example, FIG. 12T depicts pressure waveforms employed for occlusion detection that may be displayed in an XR system.

In some embodiments, magnetic resonance imaging ("MRI")-based ablation enables the visualization of ablation in a real-time setting. Delivery sheaths that are MRI safe exist today, and RF based ablation catheters are under development. However, a MRI safe and fully visualized cryoballoon is not yet available. One of the needs of the Cryoballoon procedure is to make it easier for a medical professional to assess the ablation by monitoring the freeze zone and tissue changes throughout the procedure. MRI based cryo-ablation may increase the success rate and reduce complications by allowing medical professionals to monitor the ablation in an acute setting. In addition to an MRI safe cryoballoon, the various embodiments describe the integration of a mixed or extended reality and deep learning platform since an MRI compatible balloon still has several challenges before it can be widely adopted and commercialized. In a similar manner that a catheter can be navigated in real time with CT-fluoro, a XR system can track the balloon and anatomy for occlusion. However, with the addition of MRI, it could also track the ice ball growth and lesion growth within the same XR display. For instance, FIG. 12U depicts a MRI-compatible cryoballoon showing ice formation and lesion growth. With some vision and physics-based algorithms, the system can learn to identify lesion formation, predict its growth, and even make recommendations. With the incorporation of deep learning, real-time MRI modeling of adjacent structures like the phrenic nerve and esophagus can be implemented and displayed in the XR system.

FIG. 12V depicts a non-limiting example of a 3D reconstruction of a lesion at multiple time points for XR display and AI interpretation. The system allows real-time catheter navigation, confirmation of catheter tip-tissue contact and vessel occlusion by cryo-balloon, real-time monitoring of a freeze zone, and intra-procedural assessment of lesion formation and collateral damage. FIG. 12W depicts non-limiting examples depicting potential focal cryo-catheter ice growth data that may be displayed in an XR system, where ice volume growth during ablation can be measured and displayed in the XR system and where a 3D rendering of ice volume could be visualized in the XR system.

According to some embodiments, a soft balloon (such as shown, e.g., in FIG. 12X, or the like) may be implemented to conform to varying anatomy and to detect contact, the soft balloon having the ability to change length and diameter as a function of flow and pressure. Since it is a low pressure compliant balloon, it can conform to PVI and PVI+ anatomy. In some cases, an MR balloon and collision mesh can be programmed with physics-based algorithms (e.g., flow, pressure, balloon material type, balloon material thickness, etc.) to change in size and shape as the console controls these inputs. In some instances, the collision mesh can detect PVI and PVI+ contact, and can change shape to show conformance and the associated metrics. Furthermore, with electrodes on the balloon, the collision mesh can be further refined, and is therefore more accurate. This could also allow for haptic and other feedback such as contact pressure, temperature, location, etc., to a greater accuracy. In some embodiments, these applications can also be applied to other AFS catheters such as PVAC Gold/PFA (e.g., as shown in FIG. 12Y, or the like) and diamond temp/EPIX.

FIGS. 13A-13D (collectively, "FIG. 13") are flow diagrams illustrating a method 1300 for implementing a cardiac arrhythmia procedure using an IA ecosystem, in accordance with various embodiments. Herein, the purpose of the arrhythmia procedure is to provide effective heart rhythm, and the IA ecosystem facilitates implementation of such procedure. In some embodiments, the cardiac arrhythmia procedure may include, without limitation, at least one of an atrial fibrillation procedure, a defibrillator implantation procedure, a pacemaker implantation procedure, an ablation-based procedure, and/or the like. In some cases, the implantation-based procedures (e.g., defibrillator implantation procedure or pacemaker implantation procedure, etc.) aims to utilize the implanted device to control or otherwise provide effective heart rhythm. The ablation-based procedures (e.g., ablation using energy modalities, including, but not limited to, electroporation, cryoablation, phased RF, heating with RF, laser, radiation, microwave, or high intensity focused ultrasound, and/or the like) aim to destroy or isolate tissue to prevent arrhythmogenic issues (i.e., issues related to the cause of cardiac arrhythmia, which is an alteration in rhythm of the heartbeat either in time (which can be further broken down into cardiac waveform that reflects how calcium transport in and out of the cells affect the rhythm) or force, and/or a malfunction of the heart's electrical system, or the like).

While the techniques and procedures are depicted and/or described in a certain order for purposes of illustration, it should be appreciated that certain procedures may be reordered and/or omitted within the scope of various embodiments. Moreover, while the method 1300 illustrated by FIG. 13 can be implemented by or with (and, in some cases, are described below with respect to) the systems, examples, or embodiments 100, 200, 200', 200", 300, 300', 300", 400, 400', 400", 500, 500', 500", 600, 600', 700, 700', 800, 900, 900', 900", 900'", 900"", 900""', 900"""-, and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10, respectively (or components thereof), such methods may also be implemented using any suitable hardware (or software) implementation. Similarly, while each of the systems, examples, or embodiments 100, 200, 200', 200", 300, 300', 300", 400, 400', 400", 500, 500', 500", 600, 600', 700, 700', 800, 900, 900', 900", 900'", 900"", 900""', 900"""', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10, respectively (or components thereof), can operate according to the method 1300 illustrated by FIG. 13 (e.g., by executing instructions embodied on a computer readable medium), the systems, examples, or embodiments 100, 200, 200', 200", 300, 300', 300", 400, 400', 400", 500, 500', 500", 600, 600', 700, 700', 800, 900, 900', 900", 900'", 900"", 900""', 900""", and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10 can each also operate according to other modes of operation and/or perform other suitable procedures.

Figure 13A:
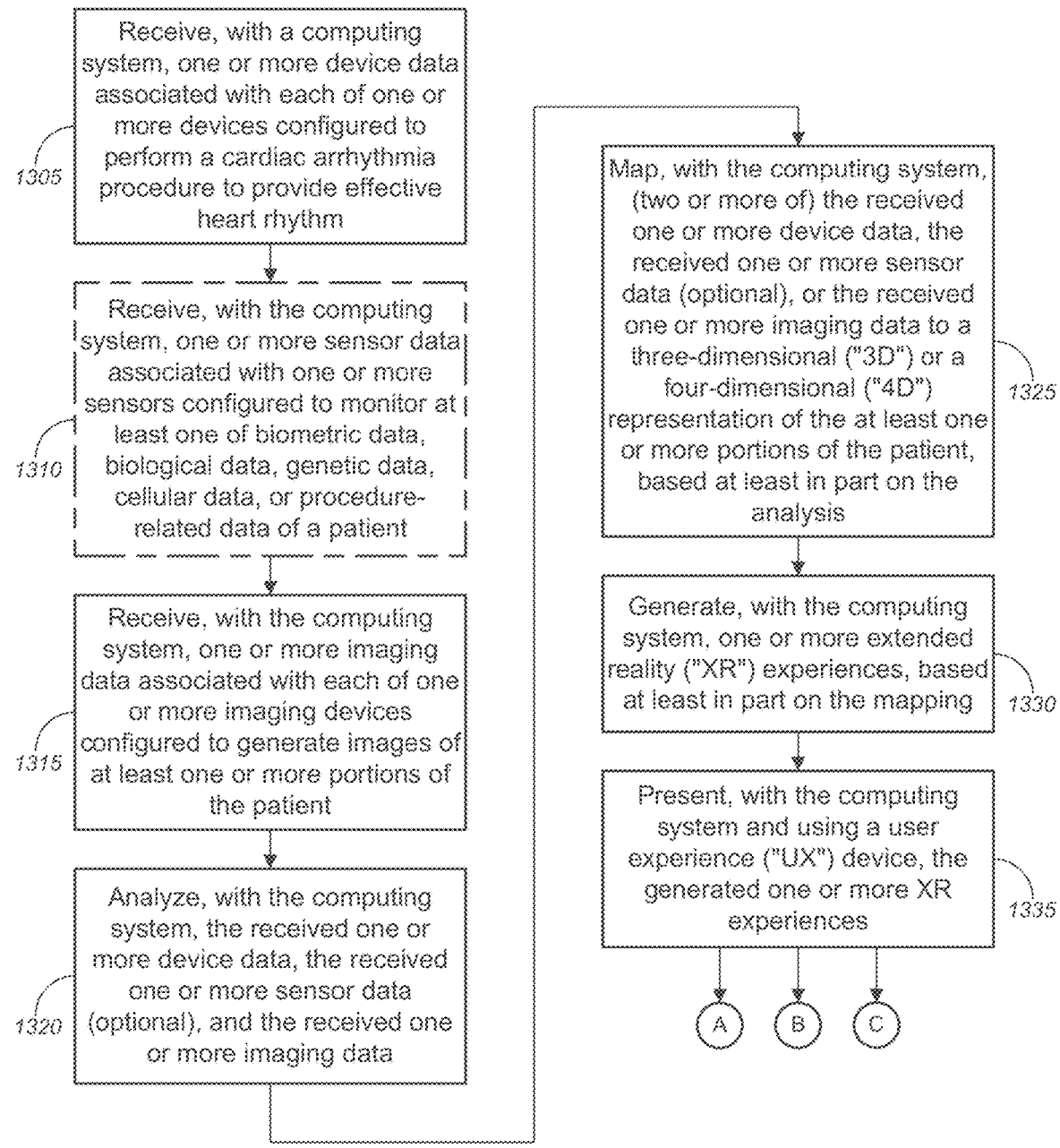

In the non-limiting embodiment of FIG. 13A, method 1300 might comprise receiving, with a computing system, one or more device data associated with each of one or more devices configured to perform a cardiac arrhythmia procedure to provide effective heart rhythm (block 1305); receiving, with the computing system, one or more sensor data associated with one or more sensors configured to monitor at least one of biometric data, biological data, genetic data, cellular data, or procedure-related data of a patient (optional block 1310); and receiving, with the computing system, one or more imaging data associated with each of one or more imaging devices configured to generate images of at least one or more portions of the patient (block 1315). In some cases, at least one of the received one or more device data, the received one or more sensor data, and the received one or more imaging data might be real-time or near-real-time data that is received by the computing system in real-time or near-real-time.

In some embodiments, the computing system might include, without limitation, at least one of an XR computing system, a medical procedure computing system, a hub computing system, a three-dimensional ("3D") graphical processing unit, a cluster computing system, a four-dimensional ("4D") graphics computing system, a server computer, a cloud computing system, or a distributed computing system, and/or the like. In some instances, the patient might include, but is not limited to, one of a human patient, a large animal, or a small animal, and/or the like.

According to some embodiments, the one or more devices might include, but are not limited to, at least one of one or more catheters, one or more catheter interconnect or interface cables, one or more balloons, one or more leads, one or more pacemakers, one or more defibrillators, one or more neuromodulation devices, one or more neurostimulation devices, one or more rigid robotic devices, one or more soft robotic devices, one or more needles, one or more occluders, one or more diagnostic catheters, one or more surgical tools, one or more biologics, one or more drug pumps, one or more genes, one or more cells, one or more organs, one or more organelles, one or more delivery pharmaceuticals, one or more ablation tools, one or more monitoring devices, one or more cameras, one or more imaging tools, one or more fiducials, one or more vascular cannulae, one or more cardiomyoplasty tools, one or more vascular closure tools, one or more septal closure tools, one or more ventricular closure tools, one or more lasers, one or more guide wires, one or more introducers, one or more sheaths, one or more microbes of bacterial vectors, one or more microbes of viral vectors, one or more microbes of prion vectors, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter or system (e.g., CryoFlex™ surgical ablation system, or the like), a cryoablation console (e.g., CryoFlex™ console, CryoConsole™ cardiac cryoablation system, or the like), a radio frequency ("RF") ablation-based system (e.g., Cardioblate™ irrigated RF ("IRF") surgical ablation system, Cardioblate™ IRF 68000 Generator, or the like), an RF ablation control console, a microwave ("MW") ablation-based system (e.g., Evident™ MW ablation system, or the like), a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment, and/or the like.

In some cases, the one or more devices might include one or more first devices including, without limitation, at least one of one or more catheters, one or more balloons, one or more leads, one or more needles, one or more occluders, one or more diagnostic catheters, one or more surgical tools, one or more drug pumps, one or more vascular cannulae, one or more cardiomyoplasty tools, one or more vascular closure tools, one or more septal closure tools, one or more ventricular closure tools, one or more guide wires, one or more introducers, or one or more sheaths, and/or the like.

In some instances, the one or more devices might include one or more second devices including, without limitation, at least one of one or more catheter interconnect or interface cables, one or more rigid robotic devices, one or more soft robotic devices, one or more monitoring devices, one or more cameras, one or more imaging tools, one or more fiducials, one or more lasers, or one or more ablation tools, and/or the like.

In some cases, the one or more devices might include one or more third devices including, without limitation, at least one of one or more pacemakers, one or more defibrillators, one or more neuromodulation devices, one or more neurostimulation devices, an ICD device, an EV-ICD, a miniature leadless implant, or one or more implantable sensors, and/or the like.

In some instances, the one or more devices might include one or more fourth devices including, without limitation, at least one of one or more biologics, one or more genes, one or more cells, one or more organs, one or more organelles, one or more delivery pharmaceuticals, one or more microbes of bacterial vectors, one or more microbes of viral vectors, or one or more microbes of prion vectors, and/or the like.

In some cases, the one or more devices might include one or more fifth devices including, without limitation, at least one of a PVAC, one or more energy delivery tools, a CEDS, a PFA system, a PFA console, an electroporation system, an electroporation control console, a cryoballoon or a cryoablation catheter or system (e.g., CryoFlex™ surgical ablation system, or the like), a cryoablation console (e.g., CryoFlex™ console, CryoConsole™ cardiac cryoablation system, or the like), a RF ablation-based system (e.g., Cardioblate™ IRF surgical ablation system, Cardioblate™ IRF 68000 Generator, or the like), an RF ablation control console, a MW ablation-based system (e.g., Evident™ MW ablation system, or the like), a MW ablation control console, a laser ablation-based system, a laser ablation control console, a radiation ablation-based system, a radiation ablation control console, a microwave ablation-based system, a HIFU system, a HIFU control console, or one or more capital equipment, and/or the like.

In some embodiments, the one or more sensors might include, without limitation, at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography ("EOG") sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some cases, the one or more sensors might include one or more first sensors including, without limitation, at least one of one or more blood velocity sensors, one or more blood volume sensors, one or more blood pressure sensors, one or more heart rate sensors, one or more pulse sensors, one or more oxygen sensors, one or more $CO_2$ sensors, one or more hormonal sensors, one or more fluid levels, one or more biomarker sensors, one or more genetic sensors, one or more blood chemistry sensors, one or more tissue matrix sensors, one or more bacteria sensors, one or more respiration sensors, one or more emotional stress sensors, one or more sleep sensors, one or more ischemia sensors, one or more HCT level sensors, one or more brainwave sensors, or one or more pain sensors, and/or the like.

In some instances, the one or more sensors might include one or more second sensors including, without limitation, at least one of one or more gas sensors, one or more optical sensors, one or more impedance sensors, one or more ultrasound sensors, one or more flow sensors, one or more electrical sensors, one or more voltage sensors, one or more amperage sensors, one or more wattage sensors, one or more chemical sensors, one or more pH sensors, one or more motion sensors, one or more proximity sensors, one or more light sensors, one or more sound sensors, one or more laser sensors, one or more doppler sensors, one or more mechanical sensors, one or more IR sensors, one or more UV sensors, one or more moisture sensors, one or more humidity sensors, one or more temperature sensors, one or more pressure sensors, one or more force sensors, one or more strain sensors, one or more stress sensors, one or more olfactory sensors, one or more viscosity sensors, one or more EMI sensors, one or more vibration sensors, one or more sound wave sensors, one or more magnetic sensors, one or more visible light sensors, or one or more radiation sensors, and/or the like.

In some cases, the one or more sensors might include one or more third sensors including, without limitation, at least one of one or more diagnostic sensors, one or more surgical sensors, one or more wearable sensors, one or more DIC sensors, one or more cameras, one or more perfusion sensors, one or more EMG sensors, one or more EOG sensors, one or more cardiac hemodynamics sensors, one or more photographic plate sensors, one or more polymer-metal sensors, one or more electrochemical sensors, one or more biometric sensors, or one or more EEG sensors, and/or the like. In some instances, the one or more sensors might include one or more fourth sensors including, without limitation, at least one of one or more surgeon fatigue sensors or one or more compliance sensors, and/or the like. In some cases, the one or more sensors might include one or more fifth sensors including, without limitation, at least one of one or more CCDs or one or more photo diode arrays, and/or the like.

In some instances, the one or more sensors might include one or more sixth sensors including, without limitation, at least one of one or more tissue contractility sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, or one or more metabolic process sensors, and/or the like. In some cases, the one or more sensors might include one or more seventh sensors including, without limitation, at least one of one or more chronically implanted sensors, and/or the like. In some instances, the one or more sensors might include one or more eighth sensors including, without limitation, at least one of one or more contactless optical sensors, one or more IR-based temperature sensors, one or more blood pressure sensors, one or more heart rate sensors, one or more motion sensors, one or more respiratory rate sensors, one or more fiducial alignment sensors, one or more tool recognition sensors, one or more collision detection sensors, one or more room traffic flow sensors, one or more surgeon fatigue sensors, one or more cognitive overload sensors, and/or the like.

According to some embodiments, the one or more imaging devices might include, but are not limited to, at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

In some cases, the one or more imaging devices might include one or more first imaging devices including, without limitation, at least one of a MRI system, a DTI system, a MRA system, an ASL system, a MEG system, a MRS system, a DSC MRI system, a BOLD system, or a FLAIR system, and/or the like. In some instances, the one or more imaging devices might include one or more second imaging devices including, without limitation, at least one of a CT system, a SPECT system, a CTA system, a PET system, or an OCT system, and/or the like. In some cases, the one or more imaging devices might include one or more third imaging devices including, without limitation, at least one of a US system, a TEE system, an ICE system, a TTE system, an IVUS system, or an EWI system, and/or the like. In some instances, the one or more imaging devices might include one or more fourth imaging devices including, without limitation, at least one of a neuro-endoscopy system, an OIS system, an endoscopy system, a bioluminescent system, a triboluminescence system, an image fusion system, or a microscope, and/or the like. In some cases, the one or more imaging devices might include one or more fifth imaging devices including, without limitation, an EEG system, and/or the like. In some instances, the one or more imaging devices might include one or more sixth imaging devices including, without limitation, at least one of a fluoroscopy system, an X-ray system, a 3D scanning system, an IR system, or a UV system, and/or the like.

In some embodiments, the cardiac arrhythmia procedure might include, without limitation, at least one of a surgical procedure, a left atrial appendage ("LAA") procedure, a tissue ablation procedure, an atrial fibrillation ("AF") procedure, a balloon angioplasty, a cardiac mapping procedure, a catheter ablation procedure, a heart monitor installation procedure, an implantable cardioverter defibrillator ("ICD") device installation procedure, an extravascular ICD ("EV-ICD") device installation procedure, a pacemaker installation procedure, a miniature leadless implant installation procedure, an implantable sensor installation procedure, a remote monitoring device installation procedure, a cryoballoon or cryoablation catheter procedure, a pulsed field ablation ("PFA") procedure, an electroporation procedure, a radio frequency ("RF") ablation procedure, a microwave ("MW") ablation procedure, a laser ablation procedure, a radiation ablation procedure, a microwave ablation-based procedure, or a high intensity focused ultrasound ("HIFU") procedure, and/or the like.

In some cases, the cardiac arrhythmia procedure might include one or more first procedures including, without limitation, at least one of a surgical procedure, an AF procedure, a cryoballoon or cryoablation catheter procedure, a PFA procedure, an electroporation procedure, a RF ablation procedure, a MW ablation procedure, a laser ablation procedure, a radiation ablation procedure, or a HIFU procedure, and/or the like.

In some instances, the cardiac arrhythmia procedure might include one or more second procedures including, without limitation, at least one of a LAA procedure, a balloon angioplasty, and/or the like.

In some cases, the cardiac arrhythmia procedure might include one or more third procedures including, without limitation, at least one of a heart monitor installation procedure, an ICD device installation procedure, an EV-ICD device installation procedure, a pacemaker installation procedure, a miniature leadless implant installation procedure, an implantable sensor installation procedure, a remote monitoring device installation procedure, and/or the like.

In some instances, the cardiac arrhythmia procedure might include one or more fourth procedures including, without limitation, at least one of a tissue ablation procedure, a shunt procedure, a microwave-base ablation procedure, a stenting procedure, a cardiac mapping procedure, a catheter ablation procedure, or a home care ventilation procedure, and/or the like.

Any one of (or a combination of two or more of) the above-mentioned first through seventh sensors along with first through sixth imaging devices may be used, in conjunction with any one of (or combination of two or more of) the tracking systems (as described below) for any of the first through fourth procedures performed by corresponding first through fifth devices on patients (or subjects). Specific non-limiting example combinations of these systems and devices are described above with respect to FIG. 9 (e.g., FIGS. 9B and 9C, or the like), in terms of specific example procedures in the context of pre-operative planning, intra-operative adjustments, and post-operative monitoring (as described above with respect to FIG. 3C, or the like).

At block 1320, method 1300 might comprise analyzing, with the computing system, the received one or more device data, the received one or more sensor data (optional), and the received one or more imaging data. Method 1300 might further comprise, at block 1325, mapping, with the computing system, (two or more of) the received one or more device data, the received one or more sensor data (optional), or the received one or more imaging data to a three-dimensional ("3D") or four-dimensional ("4D") representation (i.e., three-dimensional ("3D") representation plus at least one of real-time updates, dynamic modeling, or data streaming, and/or the like) of the at least one or more portions of the patient, based at least in part on the analysis.

Method 1300 might further comprise generating, with the computing system, one or more extended reality ("XR") experiences, based at least in part on the mapping (block 1330); and presenting, with the computing system and using a user experience ("UX") device, the generated one or more XR experiences (block 1335). In some embodiments, the one or more XR experiences might include, without limitation, at least one of one or more augmented reality ("AR") images, one or more AR videos, one or more virtual reality ("VR") images, one or more VR videos, one or more mixed reality ("MR") images, one or more MR videos, one or more XR images, or one or more XR videos, and/or the like. In some cases, generating the one or more XR experiences might comprise generating, with the computing system, one or more XR experiences comprising at least three or more of the one or more XR images, one or more XR sounds, one or more XR haptic or tactile responses, one or more XR simulated smells, or one or more XR simulated tastes, based at least in part on the mapping. According to some embodiments, the one or more XR images might be dynamic images, which might include an overlay of data models depicting at least one of electrical pulses, blood flow, tissue movement, damage, stress, and/or the like, and thus may not be a still frame in 3D.

According to some embodiments, the UX device might include, but is not limited to, at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

In some cases, the UX device might include one or more first UX devices including, without limitation, at least one of a headset, UX glasses, a supplement to existing glasses, UX contact lenses, or a HUD device, and/or the like. In some instances, the UX device might include one or more second UX devices including, without limitation, at least one of a viewing window or a microscope, and/or the like. In some cases, the UX device might include one or more third UX devices including, without limitation, at least one of headphones or a 3D spatial sound system, and/or the like. In some instances, the UX device might include one or more fourth UX devices including, without limitation, at least one of an olfactory simulation system, a taste simulation system, a sensory neuro-perception system, a sensory conversion system, or a haptic feedback system, and/or the like. In some cases, the UX device might include one or more fifth UX devices including, without limitation, at least one of a telemonitoring system, a rigid robotic device control and sensory feedback system, a soft robotic device control and sensory feedback system, a control system for nanostructures, a control system for cells, a control system for genes, or a nanoparticle reconstruction system, and/or the like.

In some instances, the UX device might include one or more sixth UX devices including, without limitation, at least one of an eye control system, a voice control system, a remote control system, a gesture-based control system, a sign language-based control system, a body-part-based control system, a joystick, a mouse, a blow-based control system, a neuro-interface system, or a peripheral nerve-computer interface system, and/or the like. In some cases, the UX device might include one or more seventh UX devices including, without limitation, at least one of a 2D screen display, a 3D refractive display, a parallel reality system, a projection system, a fan-based display, a water-based display, an ionized air-based display, an ionized laser-based display, a smoke-based display, a sand-based display, a particulate-based display, a 3D printed reconstruction system, or a customized view generation system, and/or the like. In some instances, the UX device might include one or more eighth UX devices including, without limitation, at least one of a ghosting and prediction system, a master-slave control system, or an annotation system, and/or the like.

In some embodiments, the generated one or more XR images might be presented to provide one or more uses including, without limitation, a guide for a medical professional, a navigation tool during the cardiac arrhythmia procedure, a proximity detection tool during the cardiac arrhythmia procedure, a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient, and/or the like. In some cases, the one or more uses might include one or more first uses including, without limitation, at least one of a guide for a medical professional, a navigation tool during the cardiac arrhythmia procedure, or a proximity detection tool during the cardiac arrhythmia procedure, and/or the like.

In some instances, the one or more uses might include one or more second uses including, without limitation, at least one of a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient, and/or the like.

Any one of (or a combination of two or more of) the aforementioned UX devices may be used by a user for the first through second uses above, based on computer analysis of data obtained from the above-mentioned first through seventh sensors along with first through sixth imaging devices, in conjunction with any one of (or combination of two or more of) the first through sixth tracking systems (as described below) for any of the first through fourth procedures performed by corresponding first through fifth devices on patients (or subjects). Specific non-limiting example combinations of these systems and devices are described above with respect to FIG. 9 (e.g., FIGS. 9B and 9C, or the like), in terms of specific example procedures in the context of pre-operative planning, intra-operative adjustments, and post-operative monitoring (as described above with respect to FIG. 3C, or the like).

Method 1300 might continue onto the process at optional block 1340 in FIG. 13B following the circular marker denoted, "A," might continue onto the process at optional block 1345 in FIG. 13C following the circular marker denoted, "B," or might continue onto the process at optional block 1350 in FIG. 13D following the circular marker denoted, "C."

At optional block 1340 in FIG. 13B (following the circular marker denoted, "A"), method 1300 might comprise tracking, with the computing system, the one or more devices, in some cases, using one or more tracking systems including, but not limited to, at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In some cases, the one or more tracking systems might include one or more first tracking systems including, without limitation, at least one of an electropotential-based tracking system, an impedance-based tracking system, an accelerometer-based tracking system, an IR-based tracking system, an ultrasonic sound-based tracking system, a piezoelectric-based tracking system, or an acoustic-based tracking system, and/or the like. In some instances, the one or more tracking systems might include one or more second tracking systems including, without limitation, at least one of an electromagnetic-based tracking system, a magnetic anomaly detection-based tracking system, or an MRI-based tracking system, and/or the like. In some cases, the one or more tracking systems might include one or more third tracking systems including, without limitation, at least one of a RFID-based tracking system, a Bluetooth-based tracking system, a wireless-based tracking system, or a near-field communications-based tracking system, and/or the like.

In some instances, the one or more tracking systems might include one or more fourth tracking systems including, without limitation, at least one of an optical-based tracking system, a laser-based tracking system, an US imaging-based tracking system, a computer vision-based tracking system, a fluoroscopy-based tracking system, a SLAM-based tracking system, or a feature identification-based tracking system, and/or the like. In some cases, the one or more tracking systems might include one or more fifth tracking systems including, without limitation, at least one of a GPS-based tracking system or a radar-based tracking system, and/or the like. In some instances, the one or more tracking systems might include one or more sixth tracking systems including, without limitation, at least one of a machine learning-based tracking system, a predictive tracking system, or a prescriptive tracking system, and/or the like.

At optional block 1345 in FIG. 13C (following the circular marker denoted, "B"), method 1300 might comprise generating, with the computing system, one or more models that are used for analyzing or visualizing at least one of the received one or more device data, the received one or more sensor data (optional), or the received one or more imaging data, and/or the like.

At optional block 1350 in FIG. 13D (following the circular marker denoted, "C"), method 1300 might comprise receiving, with the computing system, one or more inputs from a user. Method 1300 might further comprise, at optional block 1355, analyzing, with the computing system, the one or more inputs from the user to determine whether the one or more inputs comprise at least one command such as at least one of one or more voice commands, one or more eye-tracking-based commands, one or more gesture-based commands, one or more touch-based commands, or one or more entered commands, and/or the like.

Based on a determination that the one or more inputs comprise at least one command such as at least one of one or more voice commands, one or more eye-tracking-based commands, one or more gesture-based commands, or one or more entered commands, method 1300 might further comprise identifying, with the computing system, which at least one device among the one or more devices is intended to be controlled based on the one or more inputs (at optional block 1360); generating, with the computing system, one or more instructions for controlling the identified at least one device based at least in part on the one or more inputs (at optional block 1365); and sending, with the computing system, the generated one or more instructions to the identified at least one device (at optional block 1370).

FIGS. 14A-14M (collectively, "FIG. 14") are schematic diagrams or images illustrating various non-limiting examples 1400 related to implementing a cardiac blood flow procedure using an IA ecosystem, in accordance with various embodiments.

Figure 14A:
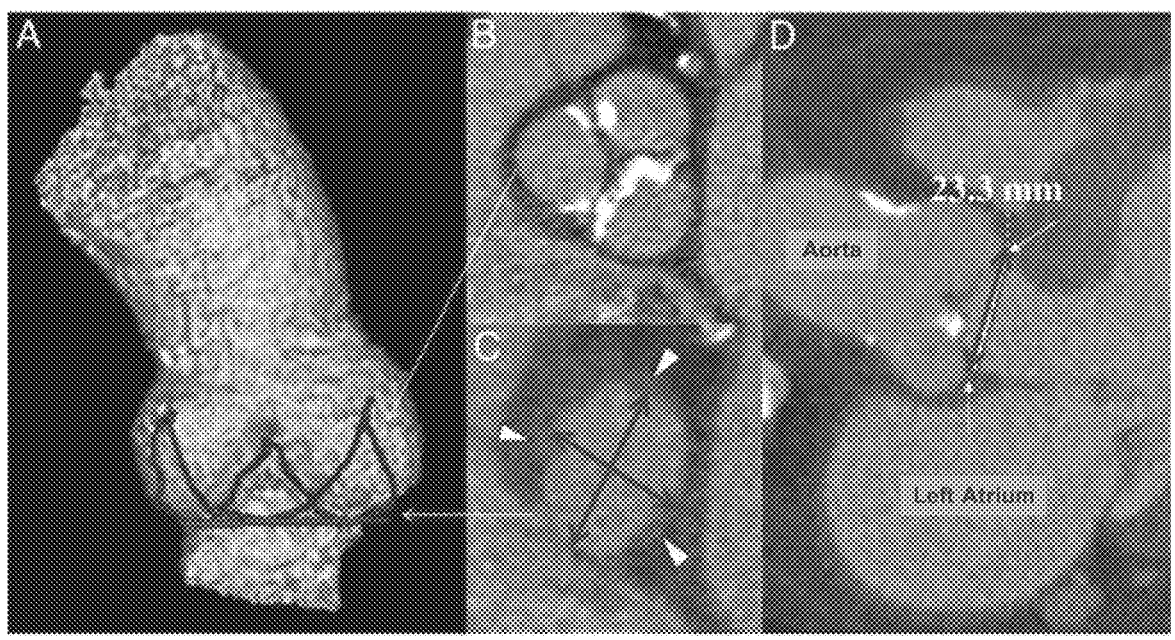
Figure 14B:
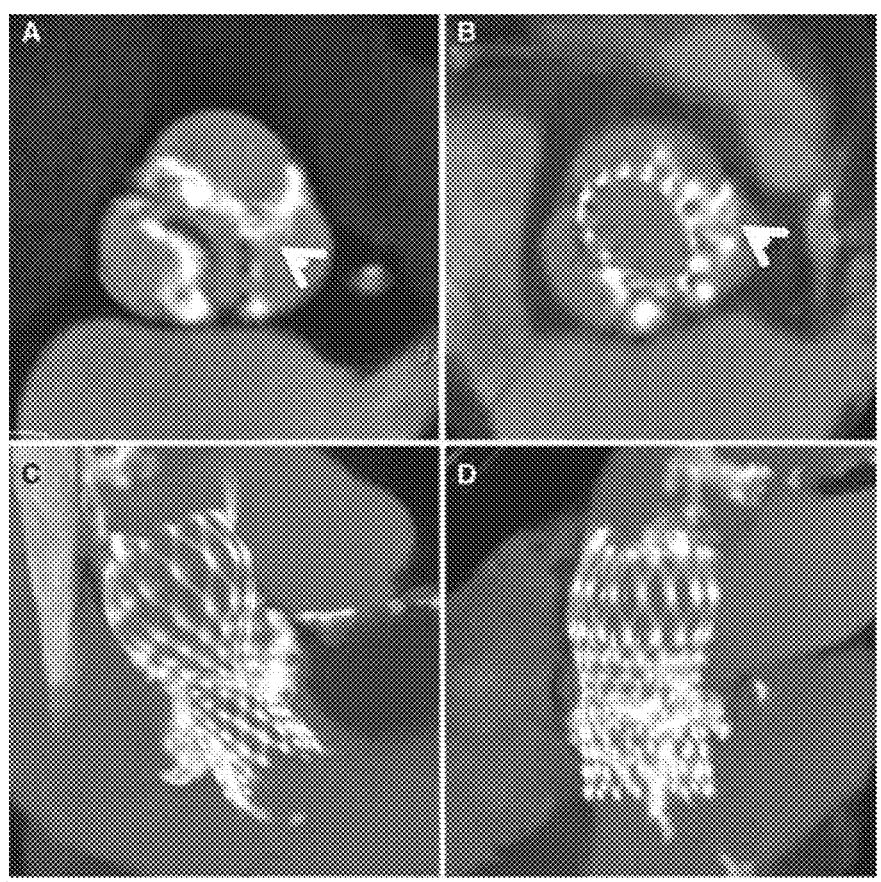
Figure 14C:
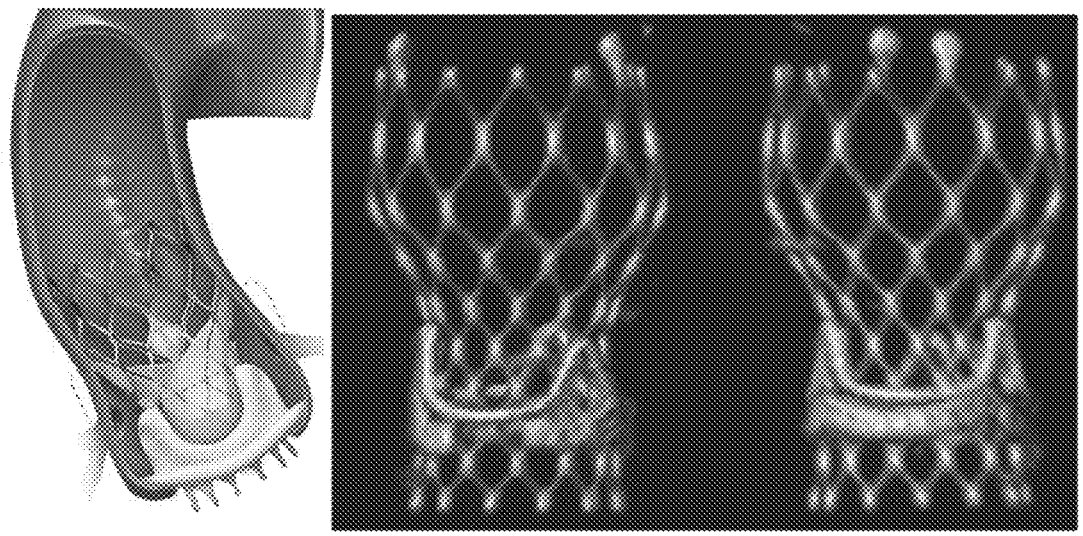
Figure 14D:
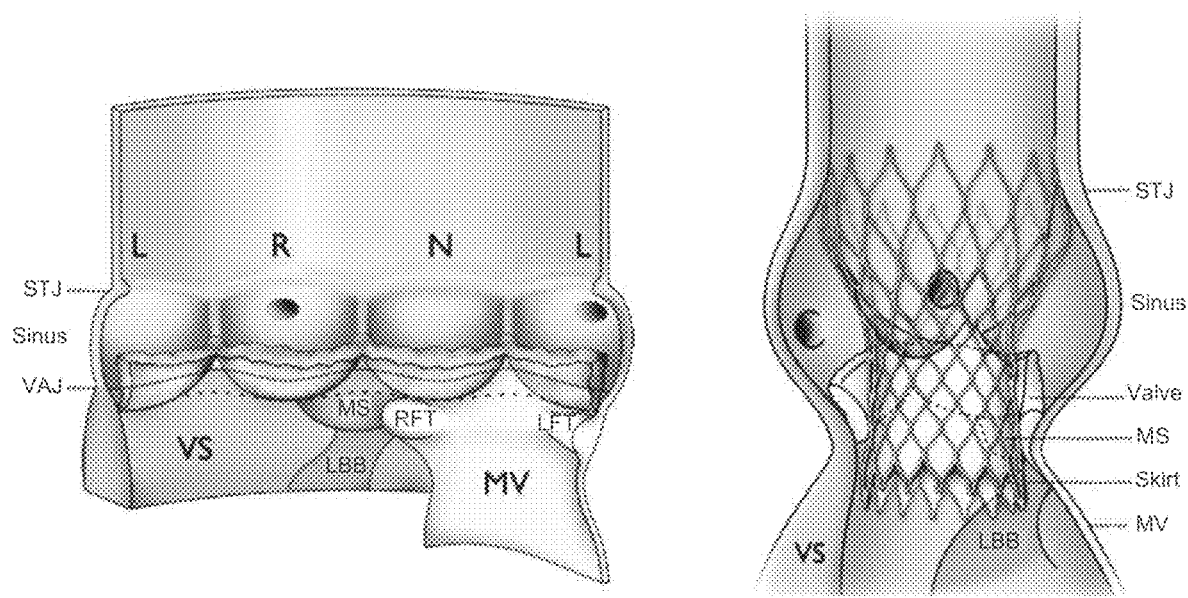

Conventionally, maneuvering, placing, and securing a transcatheter aortic or mitral valve implant (i.e., TAVI or TMVI, or the like) can be challenging. Often, CT data and 3D printed models are employed, especially for complex and pediatric cases. However, the current state of the art techniques typically employ 3D fluoroscopy for TAVI and echography for TMVI. Typically, TAVI is delivered transfemorally or transapically, while TMVI is delivered transseptally, much like the cryoballoon catheter. FIG. 14A depicts the saddle and elliptical annuli for TMVI and TAVI. FIG. 14B depicts issues related to calcification pattern and implant location potentially leading to valve durability and increased mortality. FIG. 14C depicts valve-in-valve placement. FIG. 14D depicts left bundle branch block or mitral valve impingement due to sizing (i.e., force) and placement height. The data underlying the depictions in FIGS. 14A-14D may be used as input for an XR system to visualize, via the XR display, placement of a cardiac valve or conduit to provide effective blood flow.

Figure 14E:
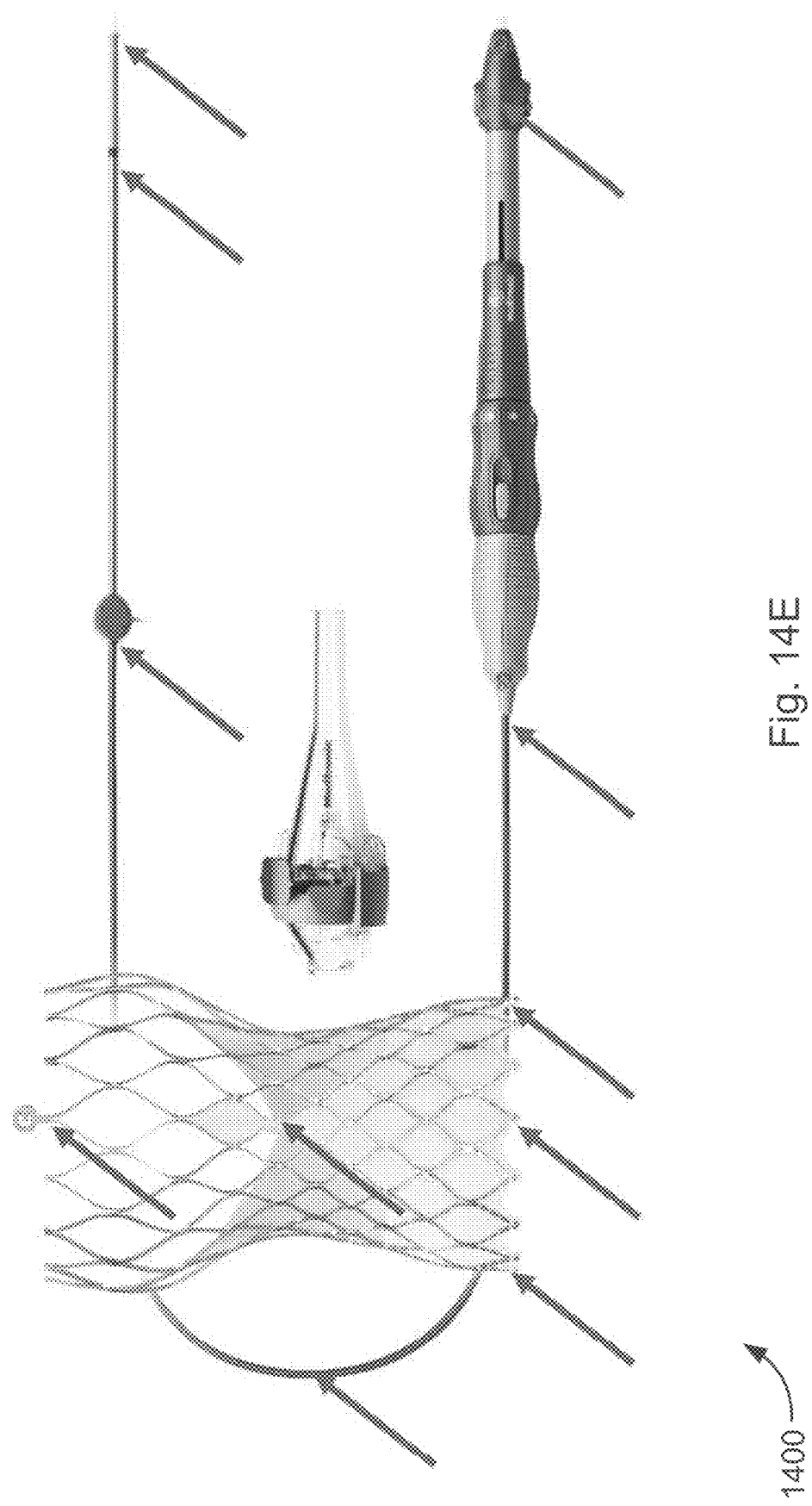

According to some embodiments, it is feasible to employ RFID tags (or other sensors or sensor tags) for navigation of a cardiac valve implant or the like. Prototypes for this are also currently being built, but have not been extended to the transcatheter delivery systems yet. Not only can the RFID tags (or other sensors or sensor tags) be placed on the implant, tip, shaft, or handle, their location can be employed to generate a 3D rendering of the device. For example, FIG. 14E depicts a visualization of an implant and delivery system with RFID tags (or other sensors or sensor tags).

Now that the system can be navigated and visualized in 3D, it can be integrated with a mixed or extended reality system (like Hololens, or the like) for improved functionality. One of the most useful features of the mixed or extended reality system is its hands-free nature (and such a benefit is not limited to particular procedures such as TAVI/TMVI, but rather to any procedure utilizing the IA ecosystem). Since medical professionals will likely have their hands full during a procedure, they simply need to make vocal commands (or hand gestures) to bring up various pieces of information. This would address some of the current limitations where the screens for navigation, heart rate, blood pressure, etc., are separate and controlled independently. With the incorporation of the MR or XR integrated 3D display with the TAVI/TMVI with deep learning, real-time tracking, prediction, and recommendations can be given. The optimal path is dependent on the interaction of all the parts of the system with the anatomy which can be displayed by MR or XR system and guided by deep learning whether it is a cryoballoon to a pulmonary vein or a TMVI to a mitral valve, or the like. All of these factors can be viewed, toggled on-off, and the deep learning algorithms can sort through and simplify.

Additionally, adjacent structures can be monitored in real-time and placement predictions can be made before and after implant accordingly, e.g., for paravalvular leakage (as shown, e.g., in FIG. 14F, or the like). Additionally, the deep learning algorithms can predict future PV-leak outcomes (as shown, e.g., in FIG. 14G, or the like). Furthermore, not only can calcification be visualized in a real-time MR or XR system, but it could also predict shape and placement outcomes for each valve size, and thus recommend if a device should be resheathed (see, e.g., FIG. 14B, or the like).

Figure 14H:
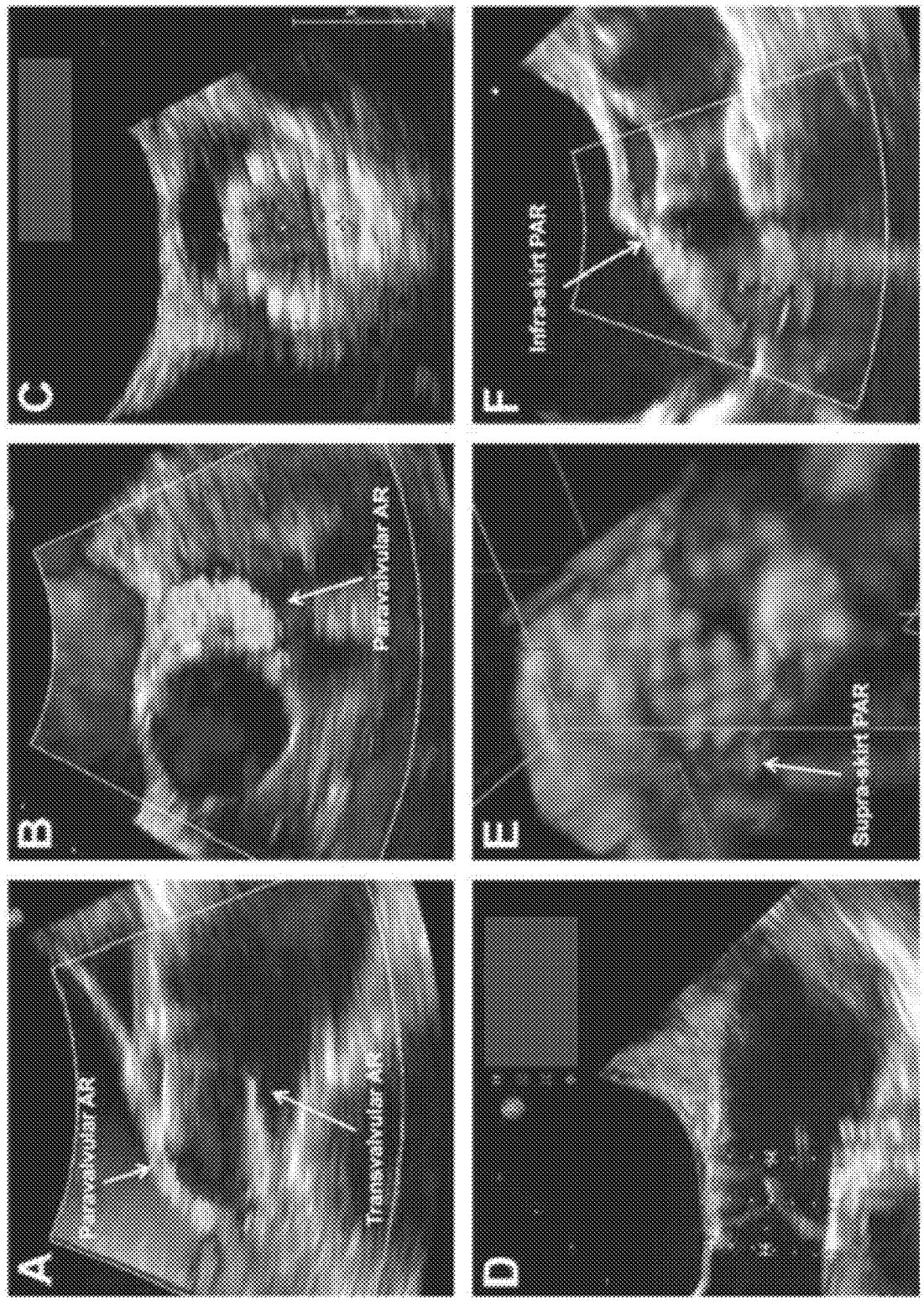
Figure 141:
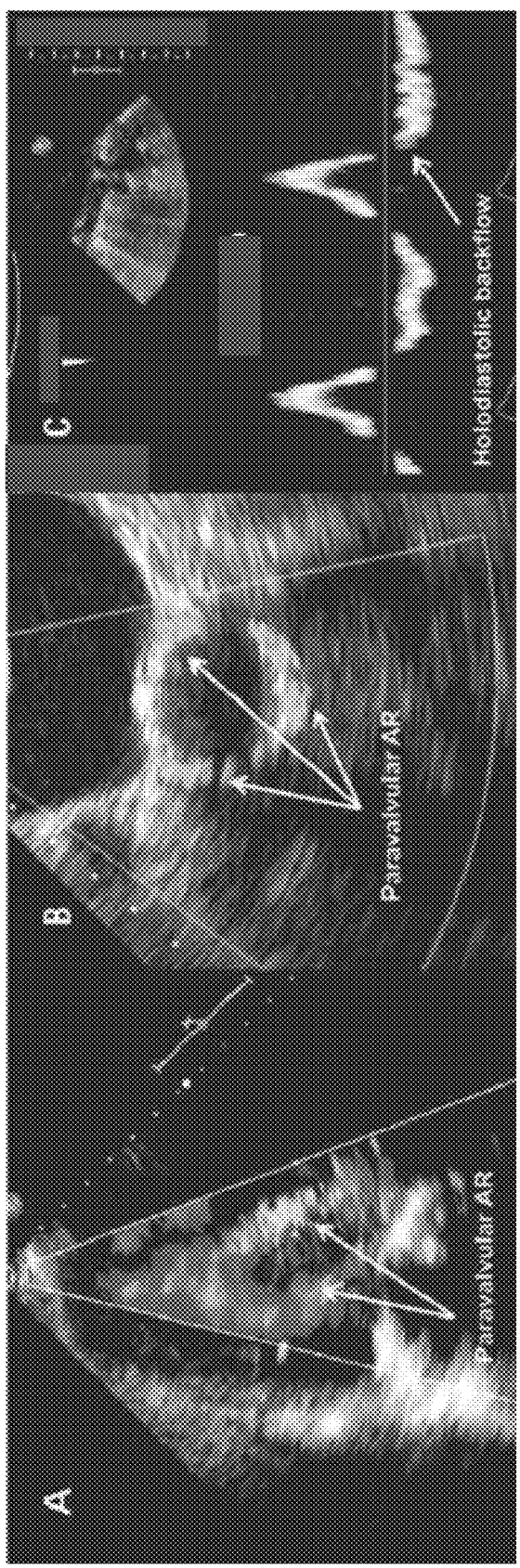
Figure 14J:
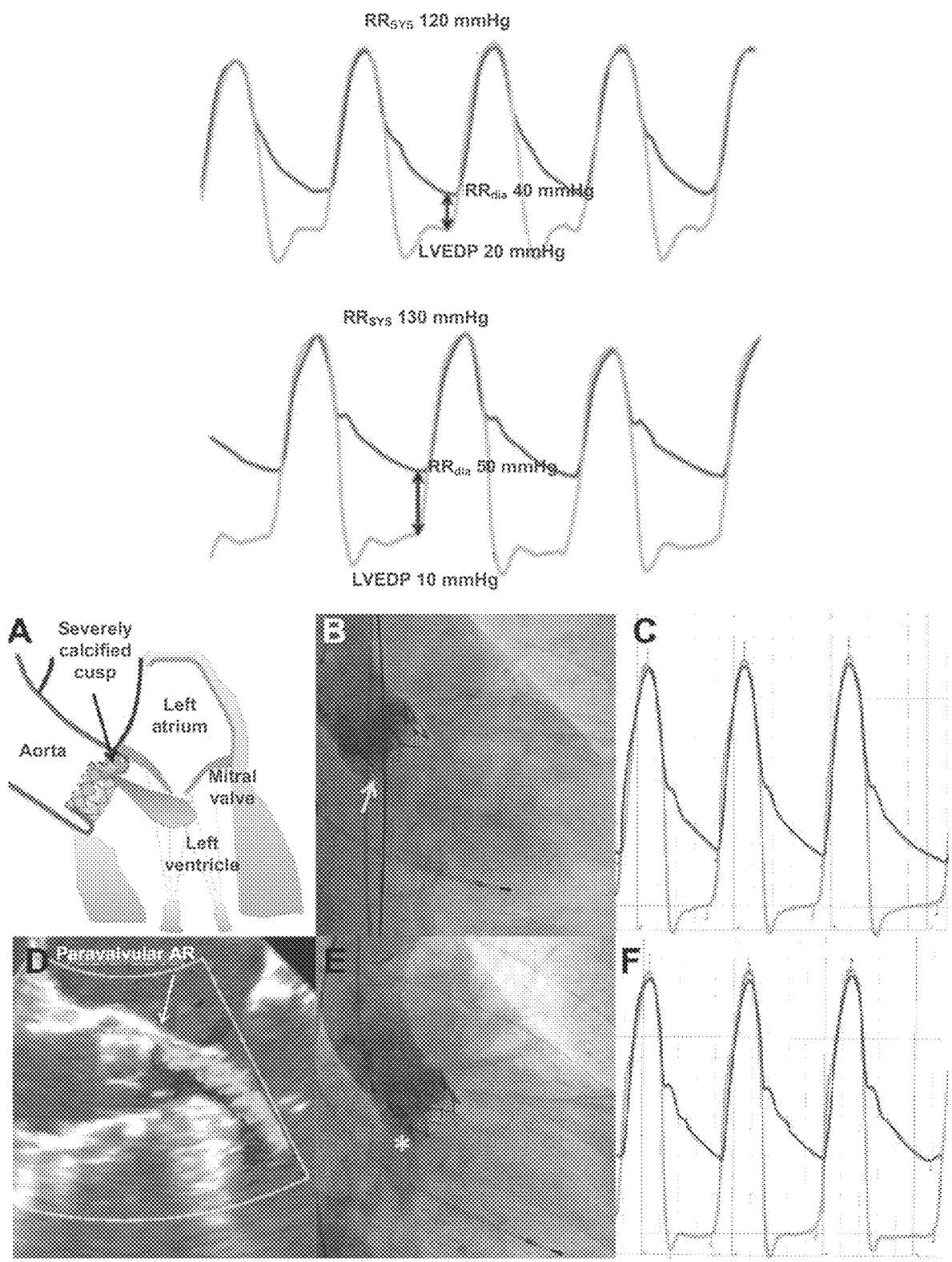

As part of PV-leak assessment it could also visualize and indicate where the leak was coming from (as shown, e.g., in FIG. 14H, or the like).

The real power of the XR/deep learning system is the integration of multiple data streams in real-time, hence if echo/doppler, fluoro, ECG, jet velocities, and/or pressure waveform data, or the like, was acquired (as shown, e.g., in FIG. 14I, or the like), it could be streamed or visualized on the XR system, and analyzed by the deep learning algorithms. For example, the chamber pressures can be monitored, displayed, and fed through the aortic regurgitation index for recommendation of placement, resheath, etc. (as shown, e.g., in FIG. 14J, or the like). The same can be done for ECG signals for LBBB, and several other attributes not for fluoroless, reduced time, and more efficacious implantation. This could be done in a system similar to the crowd sources application (like Human Diagnosis Project (Human DX), which uses machine learning technology to consider the data, to send the case to 6000+ specialists who offer diagnoses, and then to sort and combine each curated finding to create a single diagnosis, or the like.

More specifically, algorithms such as dynamic tensor computations and/or static declaration have been successfully employed for feature identification and auto-segmentation. For example, FIG. 14K depicts a Pill-cam deep learning identification of lesions in real-time. These MR or XR and deep learning implementations have been shown in to work with multiple imaging modalities including CT, fluoro, x-ray, MRI, and echo. Furthermore, with this environment, a typical MR or XR headset may have limitations so the MR or XR system may utilize a spatial computing or digital lightfield signal system. That is, spatial computing may be implemented where 3D hologram is projected without the need of a headset.

In some embodiments, ultrasound catheter imaging and navigation may be used. Some of the main shortcomings that ultrasound imaging can overcome include the need for fluoroless procedures, soft tissue visualization, real time electro-anatomical mapping, flow visualization, and/or the like. For example, an ultrasound imaging application for a TMVR procedure is shown in FIG. 14L. With reference to FIG. 14, some procedural pain points might include, without limitation, inability to see soft tissue, inability to see the device, inability to distinguish the anatomy, uncertainty as to where to deploy the device, difficulty in interpreting the 3D geometry of the target and relative device position, or the like. The solution includes, but is not limited to, using ultrasound to see soft tissue, using device echogenicity to see the device, displaying anatomical markers to distinguish the anatomy, displaying a landing zone to show where to deploy the device, using device or implant tool tracking coupled with displaying an AR or XR view of the target and the device to facilitate interpretation of the 3D geometry of the target and the relative device position, or the like.

Figure 14M:
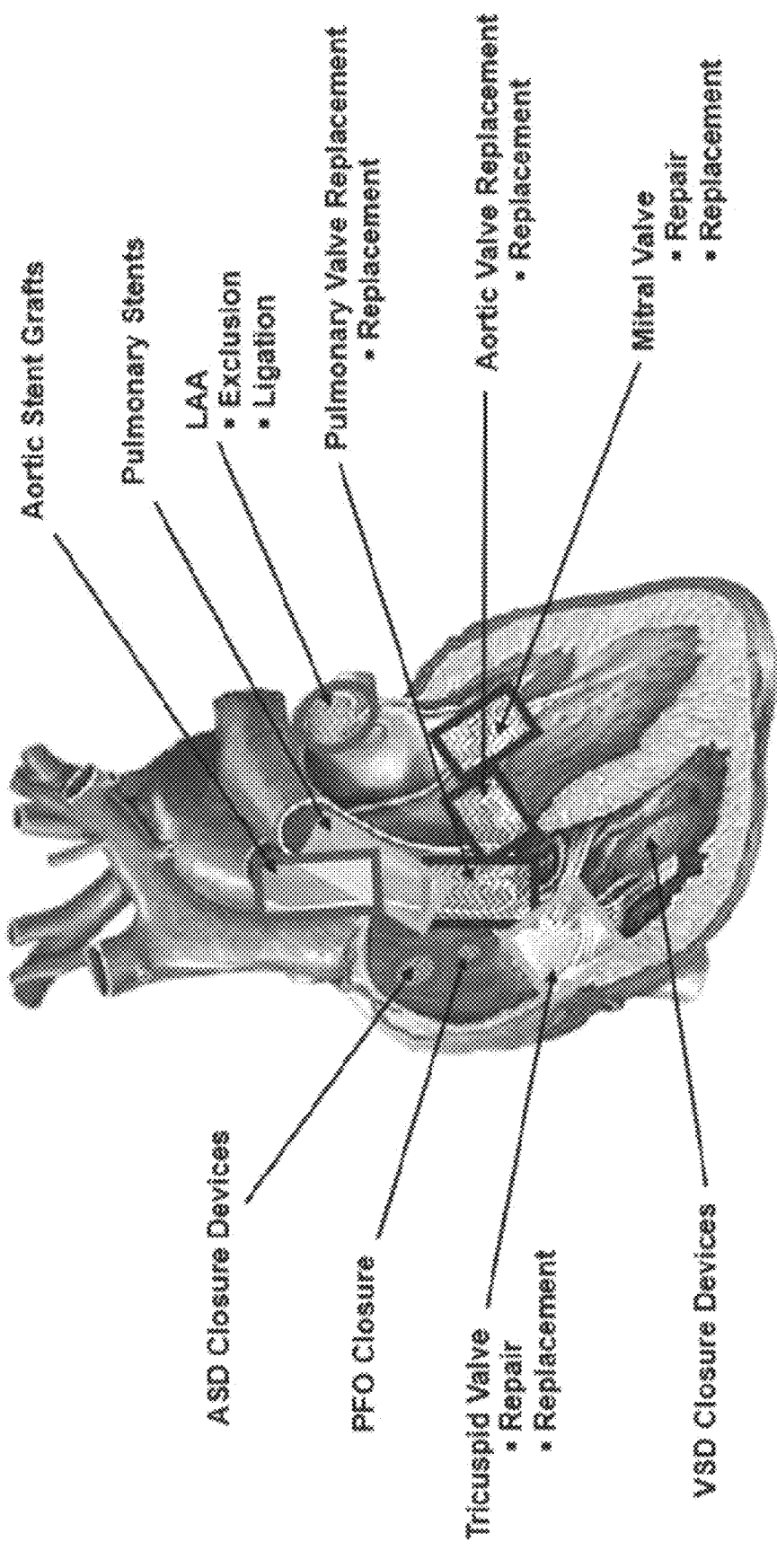

According to some embodiments, multiple imaging modalities can be applied across several cardiac structure application devices. For example, FIG. 14M depicts application to multiple cardiac structure application devices, including, but not limited to, atrial septal defect ("ASD") closure devices, patent foramen ovale ("PFO") closure devices, tricuspid valve repair or replacement devices, ventricular septal defect (VSD) closure devices, aortic stent grafts, pulmonary stents, left atrial appendage ("LAA") exclusion or ligation devices, pulmonary valve replacement devices, aortic valve replacement devices, mitral valve repair or replacement devices, and/or the like.

FIGS. 15A-15D (collectively, "FIG. 15") are flow diagrams illustrating a method 1500 for implementing a cardiac blood flow procedure using an IA ecosystem, in accordance with various embodiments. Herein, the purpose of the cardiac blood flow procedure is to provide effective blood flow through the heart and to or from blood vessels (i.e., to correct issues with insufficient blood flow, to prevent heart valve regurgitant (i.e., backward flow of blood through the heart valve), to correct issues with blocked or restricted arteries, etc.), and the IA ecosystem facilitates implementation of such procedure. In some embodiments, the cardiac blood flow procedure may include, without limitation, at least one of a heart valve procedure, a left atrial appendage ("LAA") procedure, a transcatheter aortic valve repair ("TAVr") procedure, a transcatheter aortic valve replacement ("TAVR") procedure (e.g., with the Evolut™ PRO+TAVR system, which is built on the CoreValve™ supra-annular, self-expanding platform, or the like), a transcatheter mitral valve repair ("TMVr") procedure, a transcatheter mitral valve replacement ("TMVR") procedure (e.g., with the Intrepid® TMVR system, or the like), a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, a valvuloplasty procedure, an atrial septal defect ("ASD") treatment procedure, a cardiac shunt treatment procedure, a coronary bypass procedure, a coronary angioplasty procedure (e.g., balloon angioplasty, coronary artery stent, atherectomy, laser angioplasty, etc.), intra-aortic balloon pump ("IABP") implantation procedure, ventricular assist device ("VAD") implantation procedure, or a heart transplant operation, and/or the like.

In some cases, the cardiac blood flow procedure might include one or more first procedures including, without limitation, at least one of a heart valve procedure, a TAVr procedure, a TAVR procedure (e.g., with the Evolut™ PRO+TAVR system, which is built on the CoreValve™ supra-annular, self-expanding platform, or the like), a TMVr procedure, a TMVR procedure (e.g., with the Intrepid™ TMVR system, or the like), a TPVr procedure, a TPVR procedure, a TTVr procedure, a TTVR procedure, a mitral clip repair procedure, a valvuloplasty procedure, and/or the like.

In some instances, the cardiac blood flow procedure might include one or more second procedures including, without limitation, at least one of a LAA procedure, an ASD treatment procedure, a cardiac shunt treatment procedure, a heart transplant operation, a coronary bypass procedure, or a coronary angioplasty procedure (e.g., balloon angioplasty, coronary artery stent, atherectomy, laser angioplasty, etc.), and/or the like.

In some cases, the cardiac blood flow procedure might include one or more third procedures including, without limitation, at least one of a VAD installation procedure or an IABP implantation procedure, and/or the like.

While the techniques and procedures are depicted and/or described in a certain order for purposes of illustration, it should be appreciated that certain procedures may be reordered and/or omitted within the scope of various embodiments. Moreover, while the method 1500 illustrated by FIG. 15 can be implemented by or with (and, in some cases, are described below with respect to) the systems, examples, or embodiments 100, 200, 200', 200", 300, 300', 300", 400, 400', 400", 500, 500', 500", 600, 600', 700, 700', 800, 900, 900', 900", 900''', 900'''', 900''''', 900'''''', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10, respectively (or components thereof), such methods may also be implemented using any suitable hardware (or software) implementation. Similarly, while each of the systems, examples, or embodiments 100, 200, 200', 200", 300, 300', 300", 400, 400', 400", 500, 500', 500", 600, 600', 700, 700', 800, 900, 900', 900", 900''', 900'''', 900''''', 900'''''', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10, respectively (or components thereof), can operate according to the method 1500 illustrated by FIG. 15 (e.g., by executing instructions embodied on a computer readable medium), the systems, examples, or embodiments 100, 200, 200', 200", 300, 300', 300", 400, 400', 400", 500, 500', 500", 600, 600', 700, 700', 800, 900, 900', 900", 900''', 900'''', 900''''', 900'''''', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10 can each also operate according to other modes of operation and/or perform other suitable procedures.

Figure 15A:
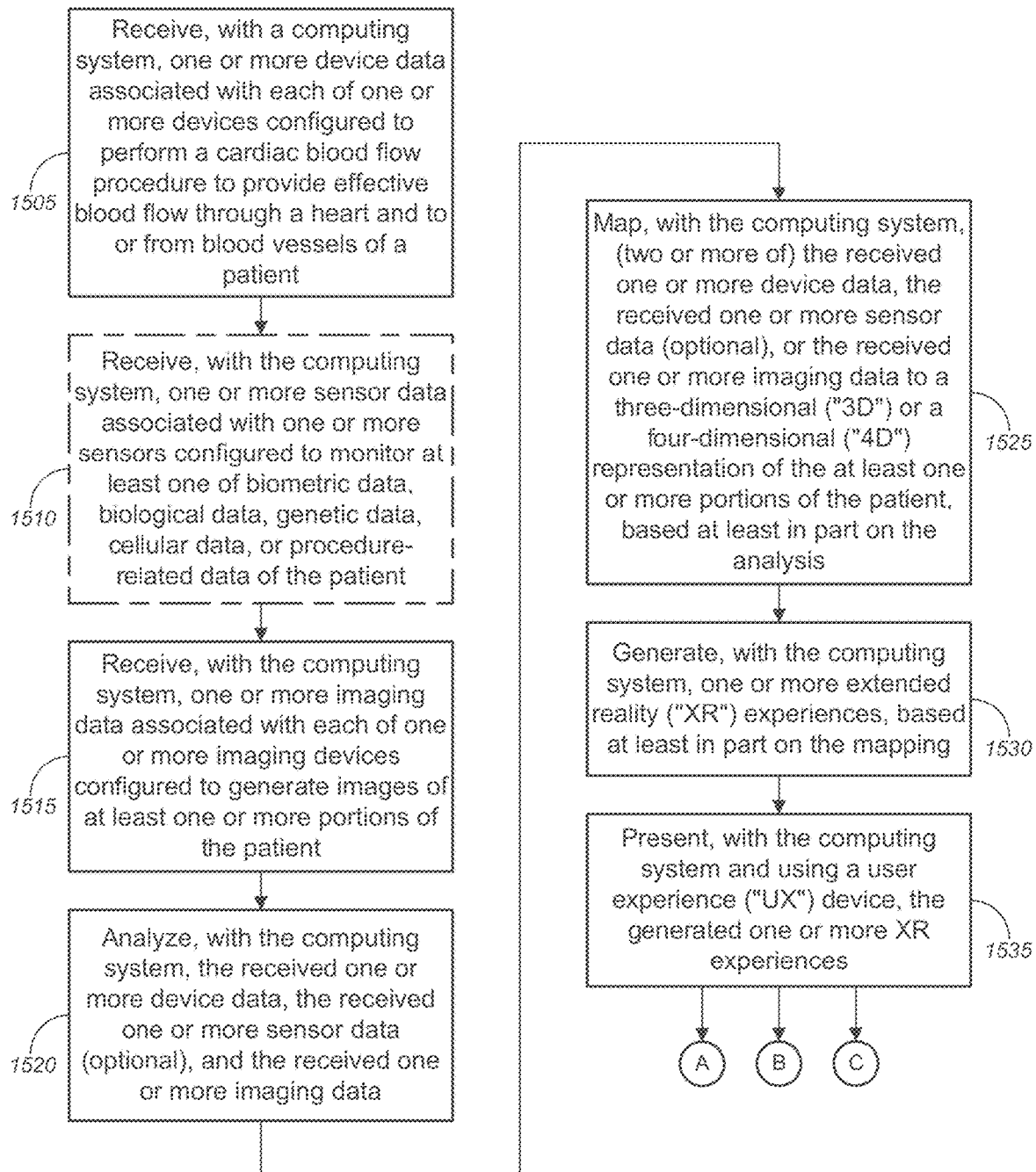

In the non-limiting embodiment of FIG. 15A, method 1500 might comprise receiving, with a computing system, one or more device data associated with each of one or more devices configured to perform a cardiac blood flow procedure to provide effective blood flow through a heart and to or from blood vessels of a patient (block 1505); receiving, with the computing system, one or more sensor data associated with one or more sensors configured to monitor at least one of biometric data, biological data, genetic data, cellular data, or procedure-related data of the patient (optional block 1510); and receiving, with the computing system, one or more imaging data associated with each of one or more imaging devices configured to generate images of at least one or more portions of the patient (block 1515). In some cases, at least one of the received one or more device data, the received one or more sensor data, and the received one or more imaging data might be real-time or near-real-time data that is received by the computing system in real-time or near-real-time.

In some embodiments, the computing system might include, without limitation, at least one of an XR computing system, a medical procedure computing system, a hub computing system, a three-dimensional ("3D") graphical processing unit, a cluster computing system, a four-dimensional ("4D") graphics computing system, a server computer, a cloud computing system, or a distributed computing system, and/or the like. In some instances, the patient might include, but is not limited to, one of a human patient, a large animal, or a small animal, and/or the like.

According to some embodiments, the one or more devices might include, but are not limited to, at least one of one or more catheters, one or more catheter interconnect or interface cables, one or more valves (e.g., Hancock™ II aortic valve, Hancock II Ultra™ aortic valve, Hancock™ II mitral valve, Mosaic™ aortic valve, Mosaic Ultra™ aortic valve, Mosaic™ mitral valve, Medtronic Open Pivot™ standard aortic valve, Medtronic Open Pivot™ AP™ aortic valve, Medtronic Open Pivot™ AP360™ aortic valve, Medtronic Open Pivot™ intra-annular aortic valved graft ("AVG"), Medtronic Open Pivot™ standard mitral valve, Medtronic Open Pivot™ AP™ mitral valve, Medtronic Open Pivot™ AP360™ mitral valve, Avalus™ aortic valve, Freestyle™ full root bioprosthesis, Prestyled Freestyle™ complete sub-coronary bioprosthesis, Prestyled Freestyle™ modified sub-coronary bioprosthesis, Harmony™ transcatheter pulmonary valve ("TPV"), or the like), one or more balloons, one or more rigid robotic devices, one or more soft robotic devices, one or more stents, one or more needles, one or more occluders, one or more diagnostic catheters, one or more surgical tools (e.g., Streamline™ temporary surgical pacing leads, or the like), one or more monitoring devices, one or more cameras, one or more imaging tools, one or more fiducials, one or more staples, one or more anchors, one or more meshes, one or more vascular cannulae, one or more circulatory pumps, one or more valve repair devices (e.g., Profile 3D™ annuloplasty ring, Tri-Ad™ 2.0 Adams tricuspid annuloplasty band, Contour 3D™ annuloplasty ring, CG Future™ annuloplasty ring, CG Future™ annuloplasty band, Simulus™ semi-rigid annuloplasty ring, Simulus™ semi-rigid annuloplasty band, Simulus™ flexible annuloplasty ring, Simulus™ flexible annuloplasty band, Duran AnCore™ annuloplasty ring, Duran AnCore™ annuloplasty band, Simplici-T™ annuloplasty band, Cinch™ implant system, or the like), one or more embolic protection devices, one or more vascular closure tools, one or more septal closure tools, one or more ventricular closure tools, one or more lasers, one or more plaque removal tools, one or more guide wires, one or more introducers, one or more sheaths, one or more pillcams, one or more clips, one or more capsules, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment, and/or the like.

In some cases, the one or more devices might include one or more first devices including, without limitation, at least one of one or more catheters, one or more valves (e.g., Hancock™ II aortic valve, Hancock II Ultra™ aortic valve, Hancock™ II mitral valve, Mosaic™ aortic valve, Mosaic Ultra™ aortic valve, Mosaic™ mitral valve, Medtronic Open Pivot™ standard aortic valve, Medtronic Open Pivot™ AP™ aortic valve, Medtronic Open Pivot™ AP360™ aortic valve, Medtronic Open Pivot™ intra-annular aortic valved graft ("AVG"), Medtronic Open Pivot™ standard mitral valve, Medtronic Open Pivot™ AP™ mitral valve, Medtronic Open Pivot™ AP360™ mitral valve, Avalus™ aortic valve, Freestyle™ full root bioprosthesis, Prestyled Freestyle™ complete subcoronary bioprosthesis, Prestyled Freestyle™ modified subcoronary bioprosthesis, Harmony™ transcatheter pulmonary valve ("TPV"), or the like), one or more balloons, one or more stents, one or more needles, one or more staples, one or more anchors, one or more meshes, one or more vascular cannulae, one or more circulatory pumps, one or more valve repair devices (e.g., Profile 3D™ annuloplasty ring, Tri-Ad™ 2.0 Adams tricuspid annuloplasty band, Contour 3D™ annuloplasty ring, CG Future™ annuloplasty ring, CG Future™ annuloplasty band, Simulus™ semi-rigid annuloplasty ring, Simulus™ semi-rigid annuloplasty band, Simulus™ flexible annuloplasty ring, Simulus™ flexible annuloplasty band, Duran AnCore™ annuloplasty ring, Duran AnCore™ annuloplasty band, Simplici-T™ annuloplasty band, Cinch™ implant system, or the like), one or more embolic protection devices, one or more vascular closure tools, one or more septal closure tools, one or more ventricular closure tools, one or more plaque removal tools, one or more guide wires, one or more introducers, one or more sheaths, one or more clips, or one or more capsules, and/or the like.

In some instances, the one or more devices might include one or more second devices including, without limitation, at least one of one or more catheter interconnect or interface cables, one or more rigid robotic devices, one or more soft robotic devices, one or more monitoring devices, one or more cameras, one or more imaging tools, one or more fiducials, one or more lasers, or one or more pillcams, and/or the like.

In some cases, the one or more devices might include one or more third devices including, without limitation, at least one of an ICD device, an EV-ICD, a miniature leadless implant, or one or more implantable sensors, and/or the like.

In some instances, the one or more devices might include one or more fourth devices including, without limitation, at least one of a PVAC, one or more energy delivery tools, a CEDS, a PFA system, a PFA console, an electroporation system, an electroporation control console, a cryoballoon or a cryoablation catheter, a cryoablation console, a RF ablation-based system, an RF ablation control console, a MW ablation-based system, a MW ablation control console, a laser ablation-based system, a laser ablation control console, a radiation ablation-based system, a radiation ablation control console, a microwave ablation-based system, a HIFU system, a HIFU control console, or one or more capital equipment, and/or the like.

In some embodiments, the one or more sensors might include, without limitation, at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography (EOG) sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some cases, the one or more sensors might include one or more first sensors including, without limitation, at least one of one or more blood velocity sensors, one or more blood volume sensors, one or more blood pressure sensors, one or more heart rate sensors, one or more pulse sensors, one or more oxygen sensors, one or more $CO_2$ sensors, one or more hormonal sensors, one or more fluid levels, one or more biomarker sensors, one or more genetic sensors, one or more blood chemistry sensors, one or more tissue matrix sensors, one or more bacteria sensors, one or more respiration sensors, one or more emotional stress sensors, one or more sleep sensors, one or more ischemia sensors, one or more HCT level sensors, one or more brainwave sensors, or one or more pain sensors, and/or the like.

In some instances, the one or more sensors might include one or more second sensors including, without limitation, at least one of one or more gas sensors, one or more optical sensors, one or more impedance sensors, one or more ultrasound sensors, one or more flow sensors, one or more electrical sensors, one or more voltage sensors, one or more amperage sensors, one or more wattage sensors, one or more chemical sensors, one or more pH sensors, one or more motion sensors, one or more proximity sensors, one or more light sensors, one or more sound sensors, one or more laser sensors, one or more doppler sensors, one or more mechanical sensors, one or more IR sensors, one or more UV sensors, one or more moisture sensors, one or more humidity sensors, one or more temperature sensors, one or more pressure sensors, one or more force sensors, one or more strain sensors, one or more stress sensors, one or more olfactory sensors, one or more viscosity sensors, one or more EMI sensors, one or more vibration sensors, one or more sound wave sensors, one or more magnetic sensors, one or more visible light sensors, or one or more radiation sensors, and/or the like.

In some cases, the one or more sensors might include one or more third sensors including, without limitation, at least one of one or more diagnostic sensors, one or more surgical sensors, one or more wearable sensors, one or more DIC sensors, one or more cameras, one or more perfusion sensors, one or more EMG sensors, one or more EOG sensors, one or more cardiac hemodynamics sensors, one or more photographic plate sensors, one or more polymer-metal sensors, one or more electrochemical sensors, one or more biometric sensors, or one or more EEG sensors, and/or the like. In some instances, the one or more sensors might include one or more fourth sensors including, without limitation, at least one of one or more surgeon fatigue sensors or one or more compliance sensors, and/or the like. In some cases, the one or more sensors might include one or more fifth sensors including, without limitation, at least one of one or more CCDs or one or more photo diode arrays, and/or the like.

In some instances, the one or more sensors might include one or more sixth sensors including, without limitation, at least one of one or more tissue contractility sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, or one or more metabolic process sensors, and/or the like. In some cases, the one or more sensors might include one or more seventh sensors including, without limitation, at least one of one or more chronically implanted sensors, and/or the like. In some instances, the one or more sensors might include one or more eighth sensors including, without limitation, at least one of one or more contactless optical sensors, one or more IR-based temperature sensors, one or more blood pressure sensors, one or more heart rate sensors, one or more motion sensors, one or more respiratory rate sensors, one or more fiducial alignment sensors, one or more tool recognition sensors, one or more collision detection sensors, one or more room traffic flow sensors, one or more surgeon fatigue sensors, one or more cognitive overload sensors, and/or the like.

According to some embodiments, the one or more imaging devices might include, but are not limited to, at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

In some cases, the one or more imaging devices might include one or more first imaging devices including, without limitation, at least one of a MRI system, a DTI system, a MRA system, an ASL system, a MEG system, a MRS system, a DSC MRI system, a BOLD system, or a FLAIR system, and/or the like. In some instances, the one or more imaging devices might include one or more second imaging devices including, without limitation, at least one of a CT system, a SPECT system, a CTA system, a PET system, or an OCT system, and/or the like. In some cases, the one or more imaging devices might include one or more third imaging devices including, without limitation, at least one of a US system, a TEE system, an ICE system, a TTE system, an IVUS system, or an EWI system, and/or the like. In some instances, the one or more imaging devices might include one or more fourth imaging devices including, without limitation, at least one of a neuro-endoscopy system, an OIS system, an endoscopy system, a bioluminescent system, a triboluminescence system, an image fusion system, or a microscope, and/or the like. In some cases, the one or more imaging devices might include one or more fifth imaging devices including, without limitation, an EEG system, and/or the like. In some instances, the one or more imaging devices might include one or more sixth imaging devices including, without limitation, at least one of a fluoroscopy system, an X-ray system, a 3D scanning system, an IR system, or a UV system, and/or the like.

In some embodiments, the cardiac blood flow procedure might include, without limitation, at least one of a surgical procedure, a left atrial appendage ("LAA") procedure, a transcatheter aortic valve repair ("TAVr") procedure, a transcatheter aortic valve replacement ("TAVR") procedure (e.g., with the Evolut™ PRO+TAVR system, or the like), a transcatheter mitral valve repair ("TMVr") procedure (which may include, but is not limited to, mitral valve repair and/or mitral clip repair, or the like), a transcatheter mitral valve replacement ("TMVR") procedure (e.g., with the Intrepid™ TMVR system, or the like), a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure (independent from a TMVr procedure), a coronary angioplasty procedure, a stenting procedure, an atrial septal defect ("ASD") treatment procedure, a cardiac shunt treatment procedure, a heart bypass procedure, a cardiac mapping procedure, an endovascular repair procedure, a minimally invasive endovascular repair procedure, a surgical heart valve repair and replacement procedure, a transcatheter pulmonary valve ("TPV") therapy (e.g., Melody™ TPV therapy, Harmony™ TPV therapy, or the like), a ventricular assist device ("VAD") installation procedure, an intra-aortic balloon pump ("IABP") implantation procedure, or a heart transplant operation, and/or the like.

In some cases, the cardiac blood flow procedure might include one or more first procedures including, without limitation, at least one of a surgical procedure, a TAVr procedure, a TAVR procedure (e.g., with the Evolut™ PRO+TAVR system, or the like), a TMVr procedure (which may include, but is not limited to, mitral valve repair and/or mitral clip repair, or the like), a TMVR procedure (e.g., with the Intrepid™ TMVR system, or the like), a TPVr procedure, a TPVR procedure, a TTVr procedure, a TTVR procedure, a mitral clip repair procedure (independent from a TMVr procedure), a minimally invasive endovascular repair procedure, a surgical heart valve repair and replacement procedure, a TPV therapy (e.g., Melody™ TPV therapy, Harmony™ TPV therapy, or the like), or an endovascular repair procedure, and/or the like.

In some instances, the cardiac blood flow procedure might include one or more second procedures including, without limitation, at least one of a LAA procedure, a coronary angioplasty procedure, an ASD treatment procedure, a cardiac shunt treatment procedure, a heart bypass procedure, or a heart transplant operation, and/or the like.

In some cases, the cardiac blood flow procedure might include one or more third procedures including, without limitation, at least one of a VAD installation procedure or an IABP implantation procedure, and/or the like.

In some instances, the cardiac blood flow procedure might include one or more fourth procedures including, without limitation, at least one of a stenting procedure or a cardiac mapping procedure, and/or the like.

Any one of (or a combination of two or more of) the above-mentioned first through seventh sensors along with first through sixth imaging devices may be used, in conjunction with any one of (or combination of two or more of) the tracking systems (as described below) for any of the first through third procedures performed by corresponding first through fourth devices on patients. Specific non-limiting example combinations of these systems and devices are described above with respect to FIG. 9 (e.g., FIGS. 9D and 9E, or the like), in terms of specific example procedures in the context of pre-operative planning, intra-operative adjustments, and post-operative monitoring (as described above with respect to FIG. 3C, or the like).

At block 1520, method 1500 might comprise analyzing, with the computing system, the received one or more device data, the received one or more sensor data (optional), and the received one or more imaging data. Method 1500 might further comprise, at block 1525, mapping, with the computing system, (two or more of) the received one or more device data, the received one or more sensor data (optional), or the received one or more imaging data to a three-dimensional ("3D") or four-dimensional ("4D") representation (i.e., three-dimensional ("3D") representation plus at least one of real-time updates, dynamic modeling, or data streaming, and/or the like) of the at least one or more portions of the patient, based at least in part on the analysis.

Method 1500 might further comprise generating, with the computing system, one or more extended reality ("XR") experiences, based at least in part on the mapping (block 1530); and presenting, with the computing system and using a user experience ("UX") device, the generated one or more XR experiences (block 1535). In some embodiments, the one or more XR experiences might include, without limitation, at least one of one or more augmented reality ("AR") images, one or more AR videos, one or more virtual reality ("VR") images, one or more VR videos, one or more mixed reality ("MR") images, one or more MR videos, one or more XR images, or one or more XR videos, and/or the like. In some cases, generating the one or more XR experiences might comprise generating, with the computing system, one or more XR experiences comprising at least three or more of the one or more XR images, one or more XR sounds, one or more XR haptic or tactile responses, one or more XR simulated smells, or one or more XR simulated tastes, based at least in part on the mapping. According to some embodiments, the one or more XR images might be dynamic images, which might include an overlay of data models depicting at least one of electrical pulses, blood flow, tissue movement, damage, stress, and/or the like, and thus may not be a still frame in 3D.

According to some embodiments, the UX device might include, but is not limited to, at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

In some cases, the UX device might include one or more first UX devices including, without limitation, at least one of a headset, UX glasses, a supplement to existing glasses, UX contact lenses, or a HUD device, and/or the like. In some instances, the UX device might include one or more second UX devices including, without limitation, at least one of a viewing window or a microscope, and/or the like. In some cases, the UX device might include one or more third UX devices including, without limitation, at least one of headphones or a 3D spatial sound system, and/or the like. In some instances, the UX device might include one or more fourth UX devices including, without limitation, at least one of an olfactory simulation system, a taste simulation system, a sensory neuro-perception system, a sensory conversion system, or a haptic feedback system, and/or the like. In some cases, the UX device might include one or more fifth UX devices including, without limitation, at least one of a telemonitoring system, a rigid robotic device control and sensory feedback system, a soft robotic device control and sensory feedback system, a control system for nanostructures, a control system for cells, a control system for genes, or a nanoparticle reconstruction system, and/or the like.

In some instances, the UX device might include one or more sixth UX devices including, without limitation, at least one of an eye control system, a voice control system, a remote control system, a gesture-based control system, a sign language-based control system, a body-part-based control system, a joystick, a mouse, a blow-based control system, a neuro-interface system, or a peripheral nerve-computer interface system, and/or the like. In some cases, the UX device might include one or more seventh UX devices including, without limitation, at least one of a 2D screen display, a 3D refractive display, a parallel reality system, a projection system, a fan-based display, a water-based display, an ionized air-based display, an ionized laser-based display, a smoke-based display, a sand-based display, a particulate-based display, a 3D printed reconstruction system, or a customized view generation system, and/or the like. In some instances, the UX device might include one or more eighth UX devices including, without limitation, at least one of a ghosting and prediction system, a master-slave control system, or an annotation system, and/or the like.

In some embodiments, the generated one or more XR images might be presented to provide one or more uses including, without limitation, a guide for a medical professional, a navigation tool during the cardiac blood flow procedure, a proximity detection tool during the cardiac blood flow procedure, a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient, and/or the like. In some cases, the one or more uses might include one or more first uses including, without limitation, at least one of a guide for a medical professional, a navigation tool during the cardiac blood flow procedure, or a proximity detection tool during the cardiac blood flow procedure, and/or the like.

In some instances, the one or more uses might include one or more second uses including, without limitation, at least one of a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient, and/or the like.

Any one of (or a combination of two or more of) the aforementioned UX devices may be used by a user for the first through second uses above, based on computer analysis of data obtained from the above-mentioned first through seventh sensors along with first through sixth imaging devices, in conjunction with any one of (or combination of two or more of) the first through sixth tracking systems (as described below) for any of the first through third procedures performed by corresponding first through fourth devices on patients. Specific non-limiting example combinations of these systems and devices are described above with respect to FIG. 9 (e.g., FIGS. 9D and 9E, or the like), in terms of specific example procedures in the context of pre-operative planning, intra-operative adjustments, and post-operative monitoring (as described above with respect to FIG. 3C, or the like).

Method 1500 might continue onto the process at optional block 1540 in FIG. 15B following the circular marker denoted, "A," might continue onto the process at optional block 1545 in FIG. 15C following the circular marker denoted, "B," or might continue onto the process at optional block 1550 in FIG. 15D following the circular marker denoted, "C."

At optional block 1540 in FIG. 15B (following the circular marker denoted, "A"), method 1500 might comprise tracking, with the computing system, the one or more devices, in some cases, using one or more tracking systems including, but not limited to, at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In some cases, the one or more tracking systems might include one or more first tracking systems including, without limitation, at least one of an electropotential-based tracking system, an impedance-based tracking system, an accelerometer-based tracking system, an IR-based tracking system, an ultrasonic sound-based tracking system, a piezoelectric-based tracking system, or an acoustic-based tracking system, and/or the like. In some instances, the one or more tracking systems might include one or more second tracking systems including, without limitation, at least one of an electromagnetic-based tracking system, a magnetic anomaly detection-based tracking system, or an MRI-based tracking system, and/or the like. In some cases, the one or more tracking systems might include one or more third tracking systems including, without limitation, at least one of a RFID-based tracking system, a Bluetooth-based tracking system, a wireless-based tracking system, or a near-field communications-based tracking system, and/or the like.

In some instances, the one or more tracking systems might include one or more fourth tracking systems including, without limitation, at least one of an optical-based tracking system, a laser-based tracking system, an US imaging-based tracking system, a computer vision-based tracking system, a fluoroscopy-based tracking system, a SLAM-based tracking system, or a feature identification-based tracking system, and/or the like. In some cases, the one or more tracking systems might include one or more fifth tracking systems including, without limitation, at least one of a GPS-based tracking system or a radar-based tracking system, and/or the like. In some instances, the one or more tracking systems might include one or more sixth tracking systems including, without limitation, at least one of a machine learning-based tracking system, a predictive tracking system, or a prescriptive tracking system, and/or the like.

At optional block 1545 in FIG. 15C (following the circular marker denoted, "B"), method 1500 might comprise generating, with the computing system, one or more models that are used for analyzing or visualizing at least one of the received one or more device data, the received one or more sensor data (optional), or the received one or more imaging data, and/or the like.

At optional block 1550 in FIG. 15D (following the circular marker denoted, "C"), method 1500 might comprise receiving, with the computing system, one or more inputs from a user. Method 1500 might further comprise, at optional block 1555, analyzing, with the computing system, the one or more inputs from the user to determine whether the one or more inputs comprise at least one command such as at least one of one or more voice commands, one or more eye-tracking-based commands, one or more gesture-based commands, one or more touch-based commands, or one or more entered commands, and/or the like.

Based on a determination that the one or more inputs comprise at least one command such as at least one of one or more voice commands, one or more eye-tracking-based commands, one or more gesture-based commands, or one or more entered commands, method 1500 might further comprise identifying, with the computing system, which at least one device among the one or more devices is intended to be controlled based on the one or more inputs (at optional block 1560); generating, with the computing system, one or more instructions for controlling the identified at least one device based at least in part on the one or more inputs (at optional block 1565); and sending, with the computing system, the generated one or more instructions to the identified at least one device (at optional block 1570).

FIGS. 16A-16M (collectively, "FIG. 16") are schematic diagrams or images illustrating various non-limiting examples 1600 related to implementing a cardiac shunting procedure using an IA ecosystem, in accordance with various embodiments.

In some embodiments, implementing a cardiac shunting procedure using an IA ecosystem might include, without limitation, atrial septal shunting procedure, pulmonary valve shunting procedure, outflow tract shunting procedure, coronary vessel or vasculature shunting procedure, or other shunting procedure in the heart, or the like.

The non-limiting examples below highlight implementing an atrial septal shunting procedure (using cryoablation or an alternate energy source as described herein) for heart patients, including, but not limited to, heart failure with preserved ejection fraction ("HFpEF") patients, pulmonary arterial hypertension ("PAH") patients, or the like. Other cardiac shunting procedures, however, may be implemented using similar methodology using the IA ecosystem described herein.

For an atrial septal shunting procedure, the transseptal puncture location on the septum may be dependent on the flexibility of an intra-cardiac echocardiography ("ICE") catheter tip that may be used. For example, a highly flexible tip will self-locate towards the center of the atrial septum, whereas a stiff tip will tend to locate towards the atrial septal-myocardial junction. For conventional atrial septal shunting procedures, the atrial septal hole is typically 3-20 mm in diameter, with 8 mm being an example. The hole size may be controlled by the inflation pressure using a compliant balloon or by the mechanical design of the balloon using a non-compliant balloon. This technique assumes central hole location on the septal wall and/or an assumed optical hole size of 8 mm ensures acceptable outcome results for all HFpEF and/or PAH patients. However, location and size are expected to be key variables given patient to patient variability in atrium volume, atrial myocardium thickness, valvular performance, and other hemodynamics.

The various embodiments provide an IA ecosystem that addresses potential issues with conventional systems (e.g., issues related to central hole location and optimal hole size applicability for some or all HFpEF and/or PAH patients, issues with computer-modeling predictability of patient outcomes, and/or other issues with determination of optimal septal wall location and hole size, etc.) that may arise due to these patient-to-patient variabilities, by incorporating pre-operative planning, intra-operative navigation, and post-operative feedback to optimize workflow and improve outcomes by addressing imaging and visualization needs, particularly in using an IA ecosystem to implement an atrial septal shunting procedure (using cryoablation or an alternate energy source as described herein) for heart patients, including, but not limited to, HFpEF patients, PAH patients, or the like.

Figure 16A:
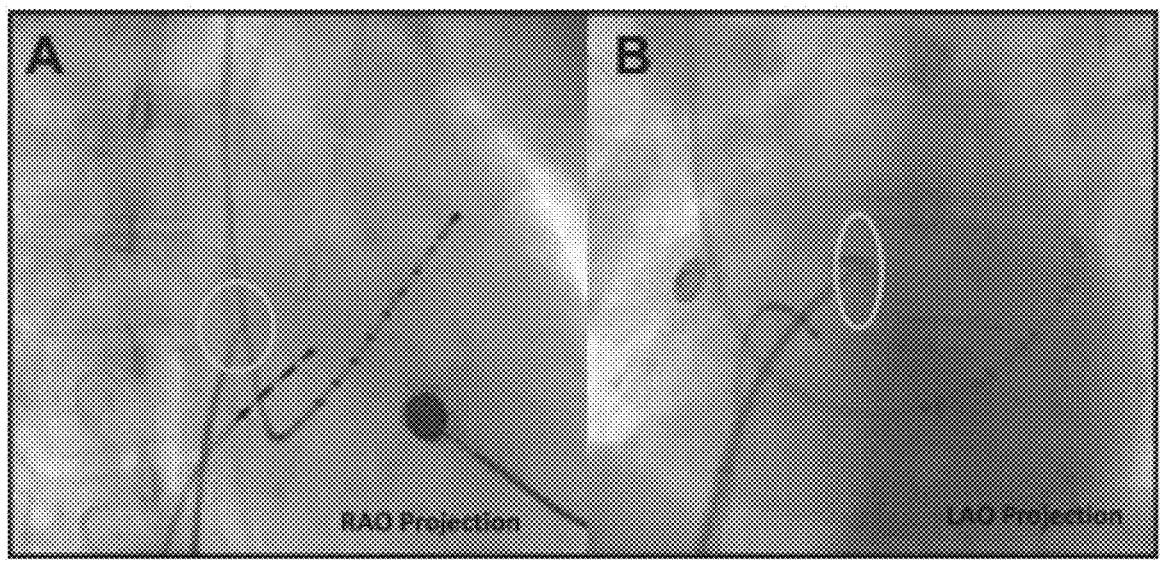
Figure 16B:
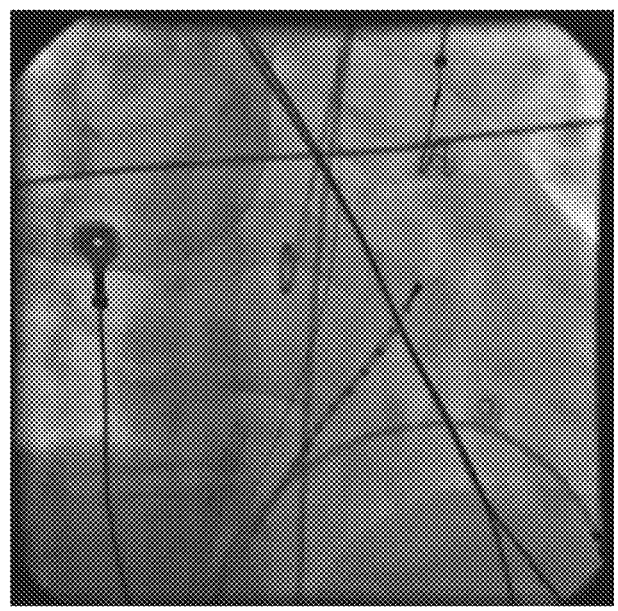
Figure 16C:
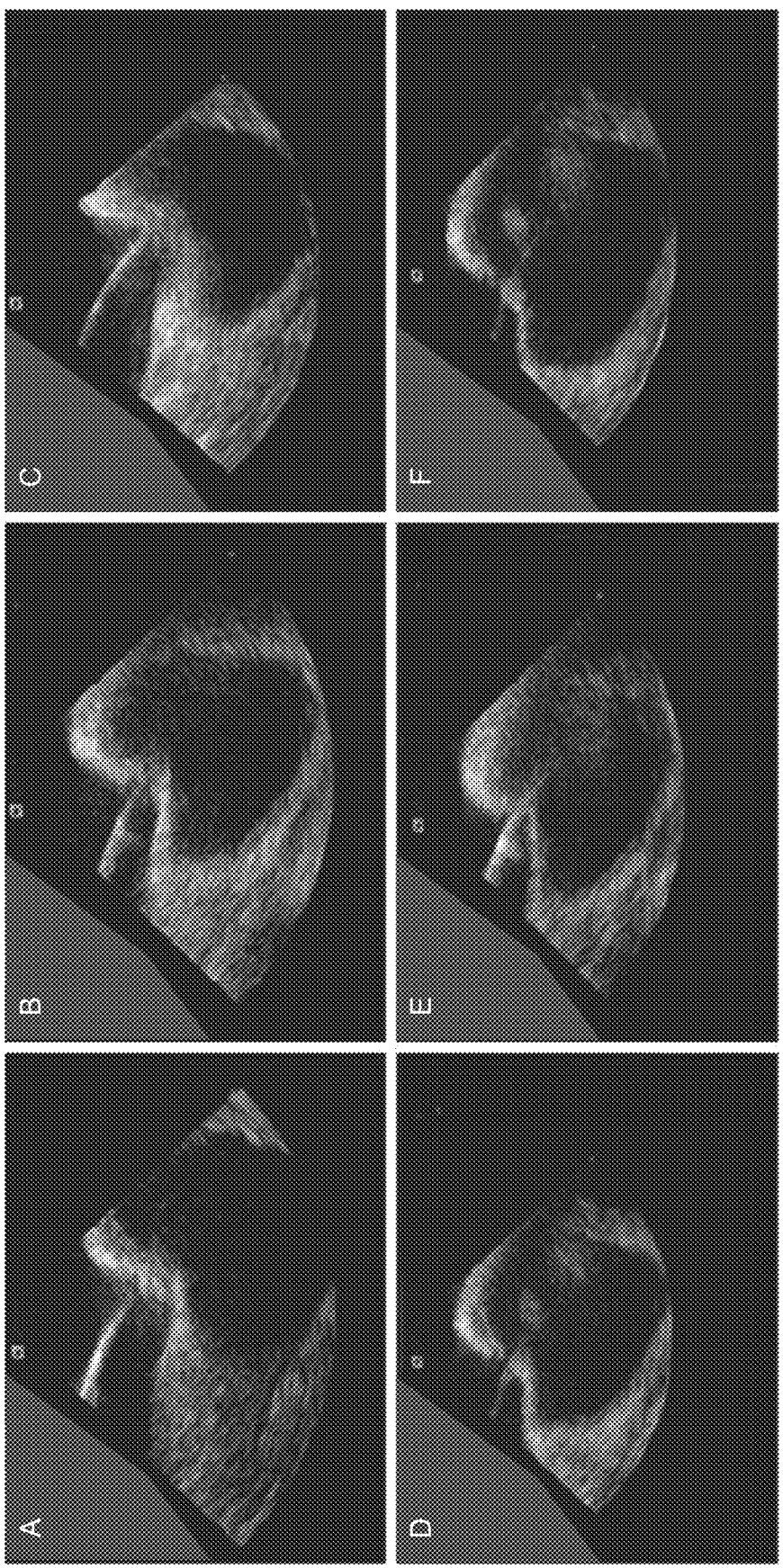
Figure 16D:
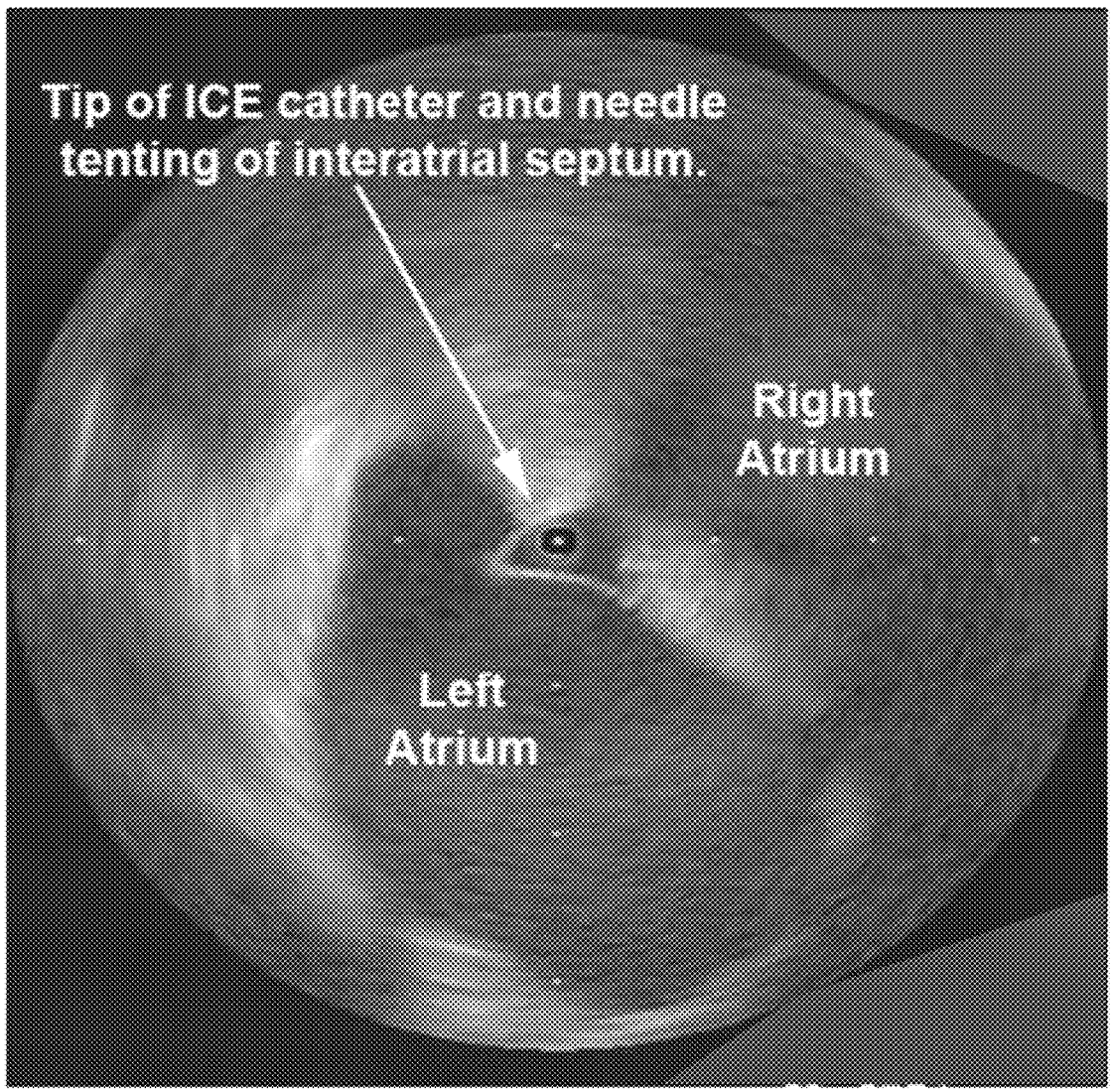
Figure 16E:
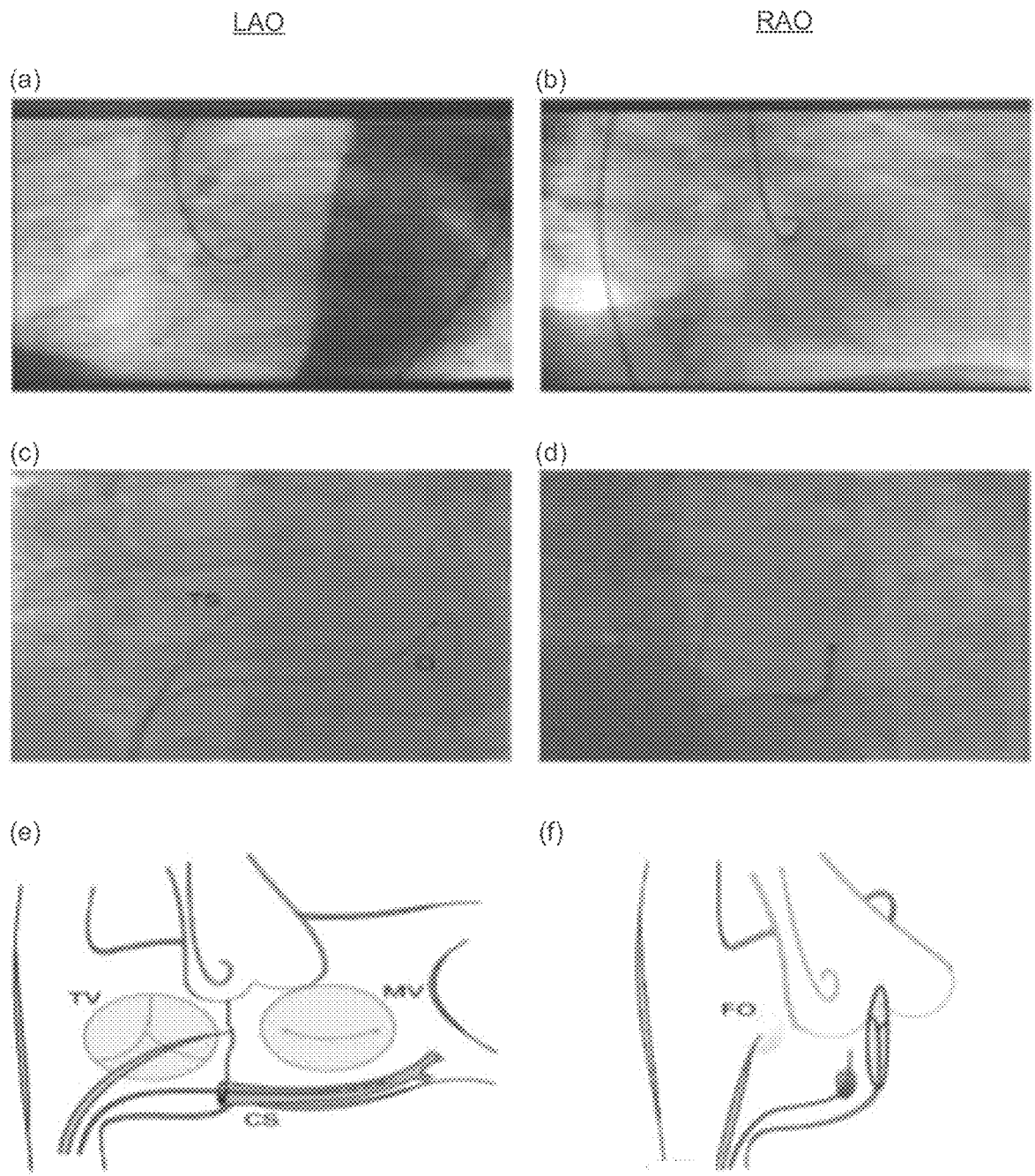
Figure 16G:
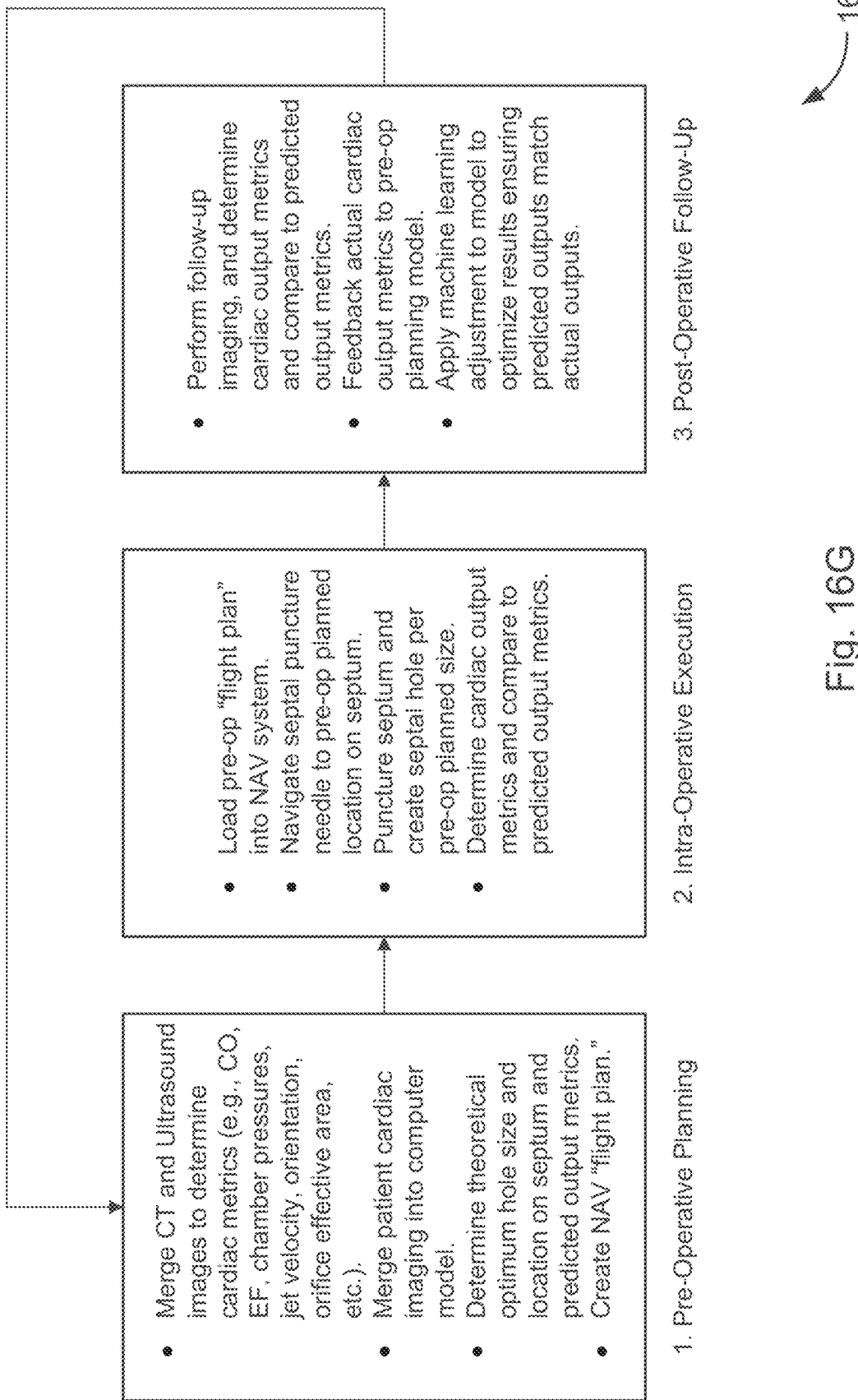

With reference to FIGS. 16A-16K, FIGS. 16A-16E depict the need for an IA ecosystem for implementing a cardiac shunting procedure (and in these particular non-limiting examples, an atrial septal shunting procedure, or the like), while FIG. 16F depicts a graphical representation of transseptal puncture pressure monitoring, which may be presented in an AR or XR system display during a cardiac shunting procedure using the IA ecosystem, and FIG. 16G depicts a septal shunting workflow, while FIGS. 16H-16K depict various embodiments of equipment and/or procedures for implementing cardiac shunting (e.g., atrial septal shunting, or the like).

We now turn to FIGS. 16A-16E. Fluoroscopy is the typical method in which the thinned portion of the fossa ovalis ("FO") can be sensed and the tenting seen in 2D under fluoroscopy (as shown in FIG. 16A, which depicts transseptal puncture on fluoroscopy). The FO, however, may not be the ideal location for the septal shunt, and is difficult to target. The 2D view, static image, and navigation using fluoroscopy (sometimes referred to as "navigation on fluoro") may result in catastrophic complications (as shown in FIG. 16B, which depicts aortic root perforation on fluoro). Herein, navigation using fluoroscopy or navigation on fluoro may refer to visualization of anatomy and device via a fluoroscopic image loop in which a static series of 2D images is looped over a short period of time or a contrast is injected and captured in the fluoroscopic scan to highlight flow and blood volume (in the inner part of the anatomy) that is looped over a short period of time. Additionally, each type of procedure and patient may necessitate using a different transseptal ("TS") location, which is often not in the FO (not shown). Since the tissue thickness, adjacent structure, real time navigation, and/or the like, cannot be seen on 2D fluoro, other imaging modalities and their integration with data and technologies such as augmented reality and machine learning (as described in detail herein) can solve many of these problems.

When making punctures in the septum within specific locations of the FO or in other areas of the septum outside of the FO, other imaging and data feedback loops may be utilized to enable this need. For example, transcatheter mitral valve and atrial shunt locations for optional location, trajectory, and/or function may necessitate being placed elsewhere. To enable pre-/intra-/post-operative planning, procedure, and assessment, one or more imaging modalities including, but not limited to, CT, MRI, ultrasound (e.g., ultrasound via transesophageal echocardiography ("TEE"), intra-cardiac echocardiography ("ICE"), transthoracic echocardiography ("TTE"), intravascular ultrasound ("IVUS"), electromechanical wave imaging ("EWI"), etc.), electroanatomic mapping ("EAM") (e.g., EAM using CardioInsight™ ("CIT") mapping vest, or the like), bi-planar fluoro, or the like, can aid in the 3D (or 4D) visualization for predictive targets and trajectories (as shown, e.g., in FIG. 16C (which depicts transseptal puncture/deployment on ultrasound, showing wall thickness and trajectory in real time) and 16D (which depicts transseptal puncture/deployment with an echogenic catheter/needle tip being easily seen on ultrasound)).

In some cases, the one or more imaging modalities might include one or more first imaging modalities including, without limitation, at least one of CT, MRI, or bi-planar fluoro, and/or the like. In some instances, the one or more imaging modalities might include one or more second imaging modalities including ultrasound, which may include, but is not limited to, ultrasound via at least one of TEE, ICE, TTE, IVUS, or EWI, etc.), and/or the like. In some cases, the one or more imaging modalities might include one or more third imaging modalities including, without limitation, EAM (e.g., EAM using CIT mapping vest, or the like), and/or the like.

Some of these imaging modalities, sensors, or the like, also allow for real or near-real time navigation and deployment (e.g., ultrasound and the CIT mapping vest, or the like), some of which is described in detail herein with respect to use in the IA ecosystem.

According to some embodiments, navigable puncture needles, dilators, guidewires, sheaths, expansions, and/or ablation/scarring devices may be augmented with electromagnetic coils ("EM"), echogenic coatings, impedance sensors, RFID tags, and/or chips or memory devices (not unlike the catheter interconnect or interface cables as described above), or the like (not shown). These augmented devices may aid in the real time navigation of the devices during cardiac shunting procedures (and may also be applicable and useful during other medical procedures).

When marking the ideal location predicted by the model, adjacent structures of concern—including, but not limited to, the aorta or pericardial sac, or the like—can be displayed and monitored (as shown in FIG. 16E, which depicts adjacent structures during transseptal puncture/deployment). Turning to FIG. 16E, (a), (c), and (e) depict the left anterior oblique ("LAO") projections, while (b), (d), and (f) depict the right anterior oblique ("RAO") projections. (a) and (b) depict fluoroscopic images of a pigtailed diagnostic catheter positioned in the aortic root, while (c) and (d) depict fluoroscopic images of a transseptal needle on the FO guided by a quadripolar diagnostic electrophysiology catheter in the coronary sinus, and (e) and (f) depict the transseptal needle being positioned on the FO. In some instances, jumps from the puncture and hole expansion can also be predicted and displayed to maximize safety. In some embodiments, data feedback loops correlated in time series for navigation, EKG, pressure monitoring, doppler flow, and predictive computation fluid dynamic ("CFD") model can be integrated. For example, the transseptal puncture/deployment data loop (as shown in FIG. 16F) may be displayed on an AR headset.

Turning to FIG. 16G, the septal shunt workflow illustrated in FIG. 16G, in some embodiments, may achieve one or more of the following: (1) Given patient cardiac anatomical variations and hemodynamic variations given their HFpEF and/or PAH disease progression, patient response and outcomes may be optimized via "pre-operative planning" techniques leveraging imaging and computer modeling techniques; (2) "Intra-operative" navigation with cardiac beat-to-beat image compensation may establish a "flight plan" for the transseptal needle to puncture the septum at a known coordinate location; and (3) "Post-operative" outcome actual results may be compared to predicted results to feedback and optimize the pre-operative planning algorithm. According to some embodiments, acute and/or chronic predictive values during the pre-operative planning phase may respectively be compared with acute values that are obtained during the conclusion of the intra-operative phase and chronic values that are obtained during post-30 day follow-ups. For example, for atrial septal shunting procedure, one could predict pre-operatively what the left and right atrial pressures will be given the septal hole size and location. These predictive values can be compared with actual atrial pressure values that are obtained the conclusion of the procedure and at the post-30 day follow-ups.

As shown in FIG. 16G, at the pre-operative planning stage (1): CT and ultrasound images may be merged to determine cardiac metrics (e.g., cardiac output ("CO"), ejection fraction ("EF"), chamber pressures, jet velocity, orientation, effective orifice area ("EOA"), etc.); patient cardiac imaging may be merged into the computer model; theoretical optimum hole size and location on the septum may be determined, along with predicted output metrics; and a navigational ("NAV") "flight plan" may be created. Herein, CO refers to the amount of blood that the heart pumps through the circulatory system in a minute, where the amount of blood put out by the left ventricle of the heart in one contraction is called the stroke volume, and where the stroke volume and the heart rate determine the cardiac output. CO is defined by the Fick principle, according to the following equation:

$$CO = \frac{VO_2}{C_a - C_v}, \quad \text{(Eq. 1)}$$

where $VO_2$=oxygen consumption in mL of pure gaseous oxygen per minute, $C_a$=oxygen content of arterial blood, and $C_v$=oxygen content of mixed venous blood.

Herein, EF refers to a measurement, expresses as a percentage, of how much blood the left ventricle pumps out with each contraction. For example, an ejection fraction of 60 percent means that 60 percent of the total amount of blood in the left ventricle is pushed out with each heartbeat. EF is defined according to the equation:

$$EF(\%) = \frac{SV}{EDV} \times 100, \quad \text{(Eq. 2)}$$

where SV=stroke volume and EDV=end-diastolic volume.

Herein, chamber pressures refer to systolic blood pressure and diastolic blood pressure. Herein, jet velocity refers to a direct measurement of the highest antegrade systolic velocity signal across the aortic valve. Herein, EOA refers to the minimal cross-sectional area of the flow jet—i.e., the cross-sectional area of the vena contracta (which is the point in a fluid stream (in this case, the blood stream) where the diameter of the stream is the least and fluid velocity is at its maximum), downstream of a native or bioprosthetic aortic heart valve.

At the intra-operative execution stage (2): the pre-operative (or pre-op) "flight plan" may be loaded into the NAV system; the septal puncture needle may be navigated to the pre-op planned location on the septum; the septum may be punctured and the septal hole may be created per pre-op planned size; and actual cardiac output metrics may be determined and compared to predicted cardiac output metrics. At the post-operative follow-up stage (3): follow-up imaging may be performed and the actual cardiac output metrics may be determined and compared to predicted cardiac output metrics; the actual cardiac output metrics may be fed back to the pre-op planning model (as shown by the feedback looping arrow in FIG. 16G, connecting the post-operative follow-up stage with the pre-operative planning stage); and machine learning adjustment(s) may be applied to the model to optimize results ensuring that the predicted outputs match the actual outputs.

Figure 16H:
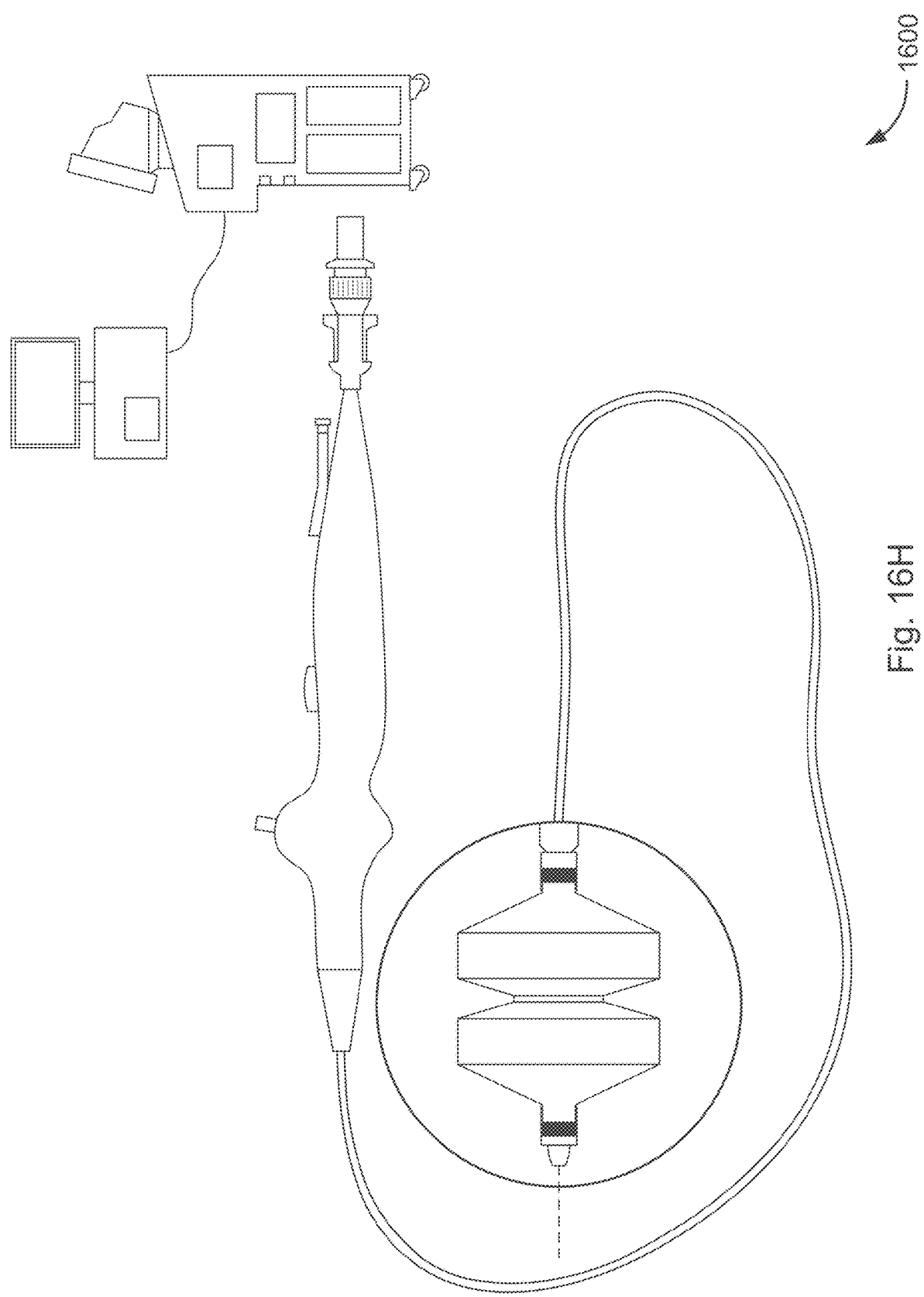
Figure 16I:
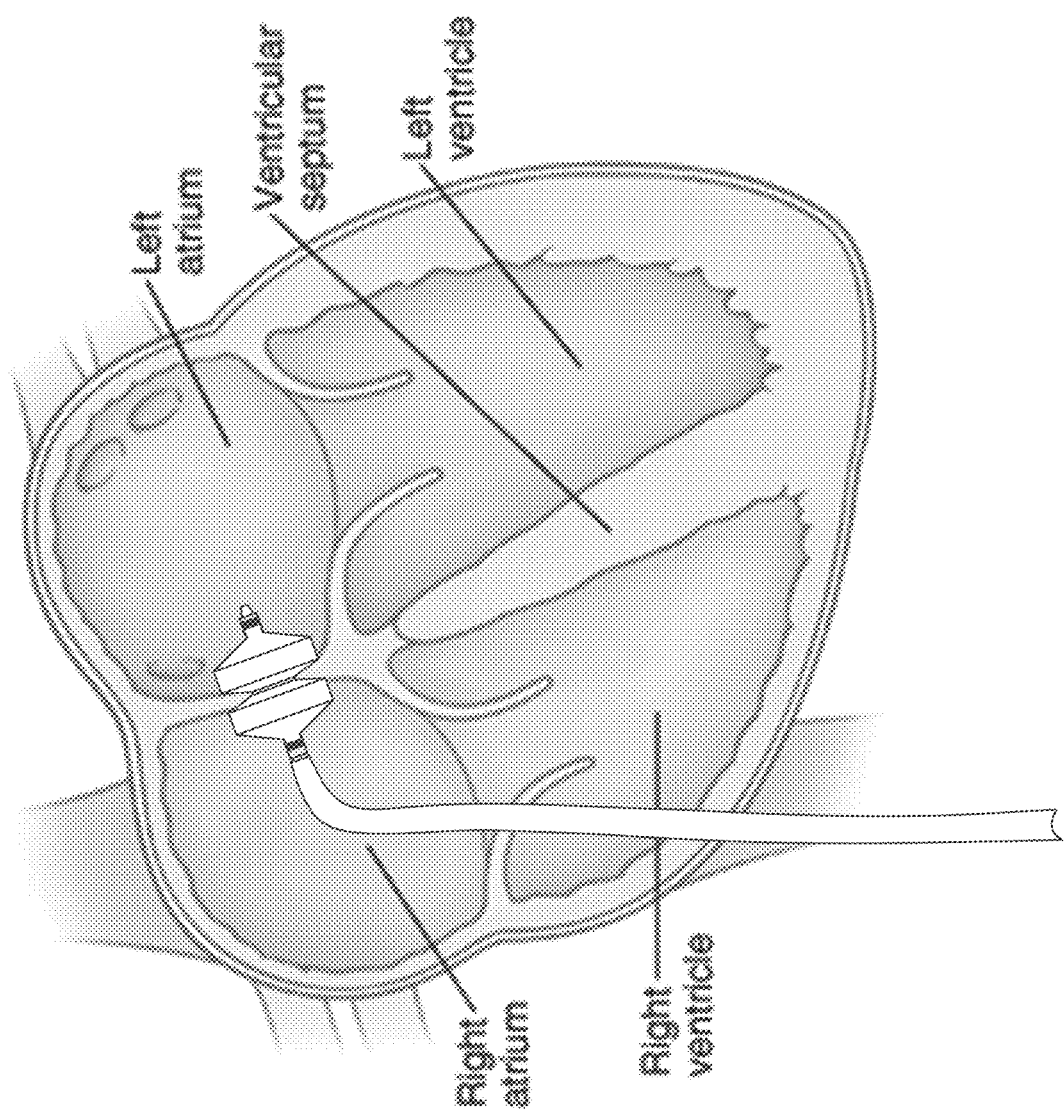
Figure 16J:
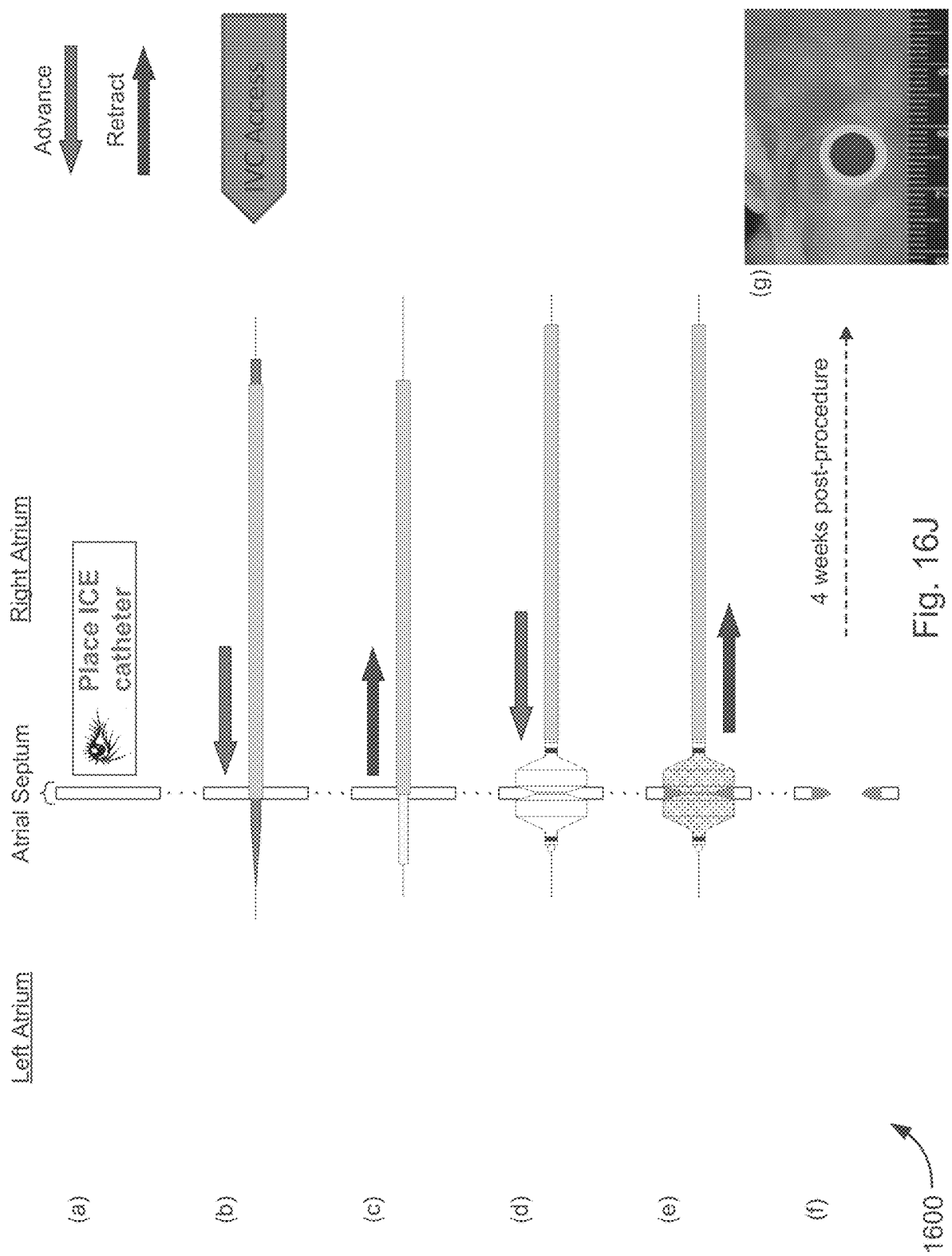

FIGS. 16H-16J depict the non-limiting system and procedure for implementing cryoballoon septoplasty procedure for cardiac shunting (e.g., interatrial shunting, or the like), while FIG. 16K depicts the procedure for implementing balloon septoplasty and pulse field ablation ("PFA") procedure for cardiac shunting (e.g., interatrial shunting, or the like. Although not shown, microwave ("MW") ablation may also be used for cardiac shunting.

As shown in FIG. 16H, a cryoablation console or system is depicted along with a cryoballoon catheter. As shown in FIG. 16I, the cryoballoon catheter is depicted being used to create an atrial septal shunt between the left and right atria of the heart, with the cryoballoon catheter entering the left atrium via the right atrium. With reference to FIG. 16J, a non-limiting example of a cryoballoon septoplasty procedure is shown for interatrial shunting (although the procedure may be applicable to other cardiac shunting). At Step (a), an intra-cardiac echocardiography ("ICE") catheter tip is placed (in this case at a pre-planned position or location on the atrial septum). At Step (b), a transseptal needle that is inserted via, e.g., a femoral vein is advanced from the right atrium to the left atrium by puncturing across the atrium septum or the atrial septal wall. At Step (c), a dilator is retracted to be replaced with, e.g., an over-the-wire ("OTW") cryoballoon catheter. At Step (d), after the OTW cryoballoon catheter has been advanced through the atrial septal hole, the cryoballoon is inflated (e.g., to 8 atm, or the like), to isolate the septal tissue from blood around the dilated area. At Step (e), the cryoballoon is used to cryoablate the heat-isolated septal tissue, and is subsequently deflated and removed (or retracted). At Step (f), the resultant atrial septal shunt is shown, and the 4 weeks post-procedure result is shown in (g). As indicated above, although FIGS. 16H-16J is described with respect to a cryoballoon septoplasty procedure for interatrial shunt, such a procedure may be used for other cardiac shunts. Further, such a procedure may be implemented using the IA ecosystem as described above, thereby allowing for at least the advantages described above with respect to FIG. 16G and with respect to IA ecosystem advantages as described herein throughout.

Alternative to the cryoballoon septoplasy procedure as shown in FIG. 16J, a non-limiting example of a balloon septoplasty and PFA procedure is shown in FIG. 16K for interatrial shunting (although the procedure may be applicable to other cardiac shunting). At Step (a), an ICE catheter tip is placed (in this case at a pre-planned position or location on the atrial septum). At Step (b), a transseptal needle that is inserted via, e.g., a femoral vein is advanced from the right atrium to the left atrium by puncturing across the atrium septum or the atrial septal wall. At Step (c), a dilator is retracted to be replaced with an OTW PFA balloon catheter. At Step (d), after the OTW PFA balloon catheter has been advanced through the atrial septal hole and positioned at the pre-planned position on the atrial septal wall, the balloon is inflated (e.g., to 8 atm, or the like). At Step (e), the PFA catheter is advanced and is used to ablate using pulsed field ablation the targeted septal tissue, and the balloon is subsequently deflated and removed (or retracted), along with the PFA catheter and the rest of the OTW PFA balloon catheter. At Step (f), the resultant atrial septal shunt is shown, and the 4 weeks post-procedure result is shown in (g). Here, PFA uses pulsed electric fields to ablate the cardiac tissues, through the mechanism of irreversible electroporation, which is the mechanism of killing tissue through exposure to high electric field gradients that induce a permanent, hyper-permeabilization of the cell membranes, leading to cell death. PFA allows for selective ablation of cardiac tissue, and has the potential to reduce collateral damage. Further, with the use of pulsed electric fields, the resultant lesions are contiguous and transmural in the shape of the field. Moreover, ablation by electroporation is force-independent (i.e., independent of physical force applied by the device and the tissue it is ablating). In some instances, ablation by electroporation uses a particular set of electric wave trains (e.g., a unique set of bipolar and biphasic wave trains at high voltage, monophasic wave trains, or any combination of electrodes on a catheter to alter electric field, etc.) to create a high voltage, pulsed electrical field that does not actually contact at all, as it is proximity based. This is in contrast to most (if not all) other ablation modalities that need to make contact with the tissue to transfer energy in or out of the tissue. In addition, with PFA, ultra-rapid or fast deliveries enable one to achieve pulmonary vein isolation ("PVI"). Anatomically shaped tools may also allow PVI with minimal catheter placements. As indicated above, although FIG. 16K is described with respect to a PFA balloon septoplasty procedure for interatrial shunt, such a procedure may be used for other cardiac shunts. Further, such a procedure may be implemented using the IA ecosystem as described above, thereby allowing for at least the advantages described above with respect to FIG. 16G and with respect to IA ecosystem advantages as described herein throughout.

Although two embodiments of septoplasty are shown and described above (i.e., cryoballoon septoplasy system and procedure in FIGS. 16H-16J and PFA balloon septoplasty procedure in FIG. 16K), the various embodiments are not so limited, and any suitable septoplasty system may be used in conjunction with the IA ecosystem described herein throughout and for any cardiac shunt not limited to the atrial septal shunt described herein as a non-limiting example. Also, although FIGS. 16J and 16K depict a circular atrial septal hole, the various embodiments are not so limited, and any suitable opening may be made in the septum, including, but not limited to, a multicuspid hole, such as shown, e.g., in FIG. 16L (which depicts (a) a tricuspid hole, (b) a quadricuspid hole, and (c) a pentacuspid hole, but are not limited to these). FIG. 16M depicts a non-limiting example of a cutting tool 1605 that may be used to create a multicuspid hole in the septum during a septoplasty procedure. In this non-limiting example, a plurality of arms 1610 with fixed or detachable edges or blades 1615. The number of arms 1610 correspond to the number N in the N-cuspid hole (e.g., N=3 for tricuspid, N=4 for quadricuspid, N=5 for pentacuspid, and so on). When the cutting tool is inserted through the target site (or initial hole) in the septum via a catheter system (see, e.g., step (b) in FIGS. 16J and 16K in which the initial hole or inferior vena cava ("IVC") hole is made), and when a balloon disposed between the arms 1610 along the axis of the cutting tool 1605 is expanded, the expanding balloon causes the arms 1610 to expand outward (causing the blades 1615 to move outward accordingly) against the initial (or IVC) hole in the septum, thereby cutting slits from the initial hole radially outward, resulting in a multicuspid atrial septal hole such as shown in (a), (b), or (c) in FIG. 16L.

FIGS. 17A-17D (collectively, "FIG. 17") are flow diagrams illustrating a method 1700 for implementing a cardiac shunting procedure using an IA ecosystem, in accordance with various embodiments. Herein, the purpose of the cardiac shunting procedure is to change a cardiac blood flow pattern to improve cardiac blood flow efficiency or cardiac pumping efficiency, and the IA ecosystem facilitates implementation of such procedure. In some embodiments, the cardiac shunting procedure may include, without limitation, at least one of a surgical procedure, a left atrial appendage ("LAA") procedure, a tissue ablation procedure, a transcatheter aortic valve repair ("TAVr") procedure, a transcatheter aortic valve replacement ("TAVR") procedure (e.g., with the Evolut™ PRO+TAVR system, which is built on the CoreValve™ supra-annular, self-expanding platform, or the like), a transcatheter mitral valve repair ("TMVr") procedure (which may include, but is not limited to, mitral valve repair and/or mitral clip repair, or the like), a transcatheter mitral valve replacement ("TMVR") procedure (e.g., with the Intrepid™ TMVR system, or the like), a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure (independent from a TMVr procedure), a shunt procedure, a coronary angioplasty procedure (e.g., balloon angioplasty, coronary artery stent, atherectomy, laser angioplasty, etc.), a stenting procedure, a heart bypass procedure, a cardiac mapping procedure, a cardiac resynchronization therapy ("CRT") device installation procedure a catheter ablation procedure, an endovascular repair procedure, a heart monitor installation procedure, an implantable cardioverter defibrillator ("ICD") device installation procedure, an extravascular ICD ("EV-ICD") device installation procedure, a minimally invasive endovascular repair procedure, a miniature leadless implant installation procedure, an implantable sensor installation procedure, a surgical heart valve repair and replacement procedure, a transcatheter pulmonary valve ("TPV") therapy, a ventricular assist device ("VAD") installation procedure, an intra-aortic balloon pump ("IABP") implantation procedure, a heart transplant operation, a cryoballoon or cryoablation catheter procedure, a pulsed field ablation ("PFA") procedure, an electroporation procedure, a radio frequency ("RF") ablation procedure, a microwave ("MW") ablation procedure, a laser ablation procedure, a radiation ablation procedure, a microwave ablation-based procedure, or a high intensity focused ultrasound ("HIFU") procedure, and/or the like.

In some cases, the cardiac shunting procedure might include one or more first procedures including, without limitation, at least one of a surgical procedure, a TAVr procedure, a TAVR procedure (e.g., with the Evolut™ PRO+TAVR system, which is built on the CoreValve™ supra-annular, self-expanding platform, or the like), a TMVr procedure (which may include, but is not limited to, mitral valve repair and/or mitral clip repair, or the like), a TMVR procedure (e.g., with the Intrepid™ TMVR system, or the like), a TPVr procedure, a TPVR procedure, a TTVr procedure, a TTVR procedure, a mitral clip repair procedure (independent from a TMVr procedure), a minimally invasive endovascular repair procedure, a surgical heart valve repair and replacement procedure, a TPV therapy (e.g., Melody™ TPV therapy, Harmony™ TPV therapy, or the like), an endovascular repair procedure, or a high intensity focused ultrasound ("HIFU") procedure, and/or the like.

In some instances, the cardiac shunting procedure might include one or more second procedures including, without limitation, at least one of a LAA procedure, a coronary procedure (e.g., a balloon angioplasty, coronary artery stent, atherectomy, laser angioplasty, etc.), a heart bypass surgery, or a heart transplant operation, and/or the like.

In some cases, the cardiac shunting procedure might include one or more third procedures including, without limitation, at least one of a CRT device installation procedure, a heart monitor installation procedure, an ICD device installation procedure, an EV-ICD device installation procedure, a miniature leadless implant installation procedure, an implantable sensor installation procedure, a VAD installation procedure, or an IABP implantation procedure, and/or the like.

In some instances, the cardiac shunting procedure might include one or more fourth procedures including, without limitation, at least one of a tissue ablation procedure, a shunt procedure, a microwave ablation-based procedure, a stenting procedure, a cardiac mapping procedure, or a catheter ablation procedure, and/or the like.

While the techniques and procedures are depicted and/or described in a certain order for purposes of illustration, it should be appreciated that certain procedures may be reordered and/or omitted within the scope of various embodiments. Moreover, while the method 1700 illustrated by FIG. 17 can be implemented by or with (and, in some cases, are described below with respect to) the systems, examples, or embodiments 100, 200, 200', 200", 300, 300', 300", 400, 400', 400", 500, 500', 500", 600, 600', 700, 700', 800, 900, 900', 900", 900''', 900'''', 900''''', 900'''''', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10, respectively (or components thereof), such methods may also be implemented using any suitable hardware (or software) implementation. Similarly, while each of the systems, examples, or embodiments 100, 200, 200', 200", 300, 300', 300", 400, 400', 400", 500, 500', 500", 600, 600', 700, 700', 800, 900, 900', 900", 900''', 900'''', 900''''', 900'''''', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10, respectively (or components thereof), can operate according to the method 1700 illustrated by FIG. 17 (e.g., by executing instructions embodied on a computer readable medium), the systems, examples, or embodiments 100, 200, 200', 200", 300, 300', 300", 400, 400', 400", 500, 500', 500", 600, 600', 700, 700', 800, 900, 900', 900", 900''', 900'''', 900''''', 900'''''', and 1000 of FIGS. 1, 2A, 2B, 2C, 3A, 3B, 3C, 4A, 4B, 4C, 5A, 5B, 5C, 6A, 6B, 7A, 7B, 8A, 8B, 9A, 9B, 9C, 9D, 9E, 9F, 9G, 9H, and 10 can each also operate according to other modes of operation and/or perform other suitable procedures.

Figure 17A:
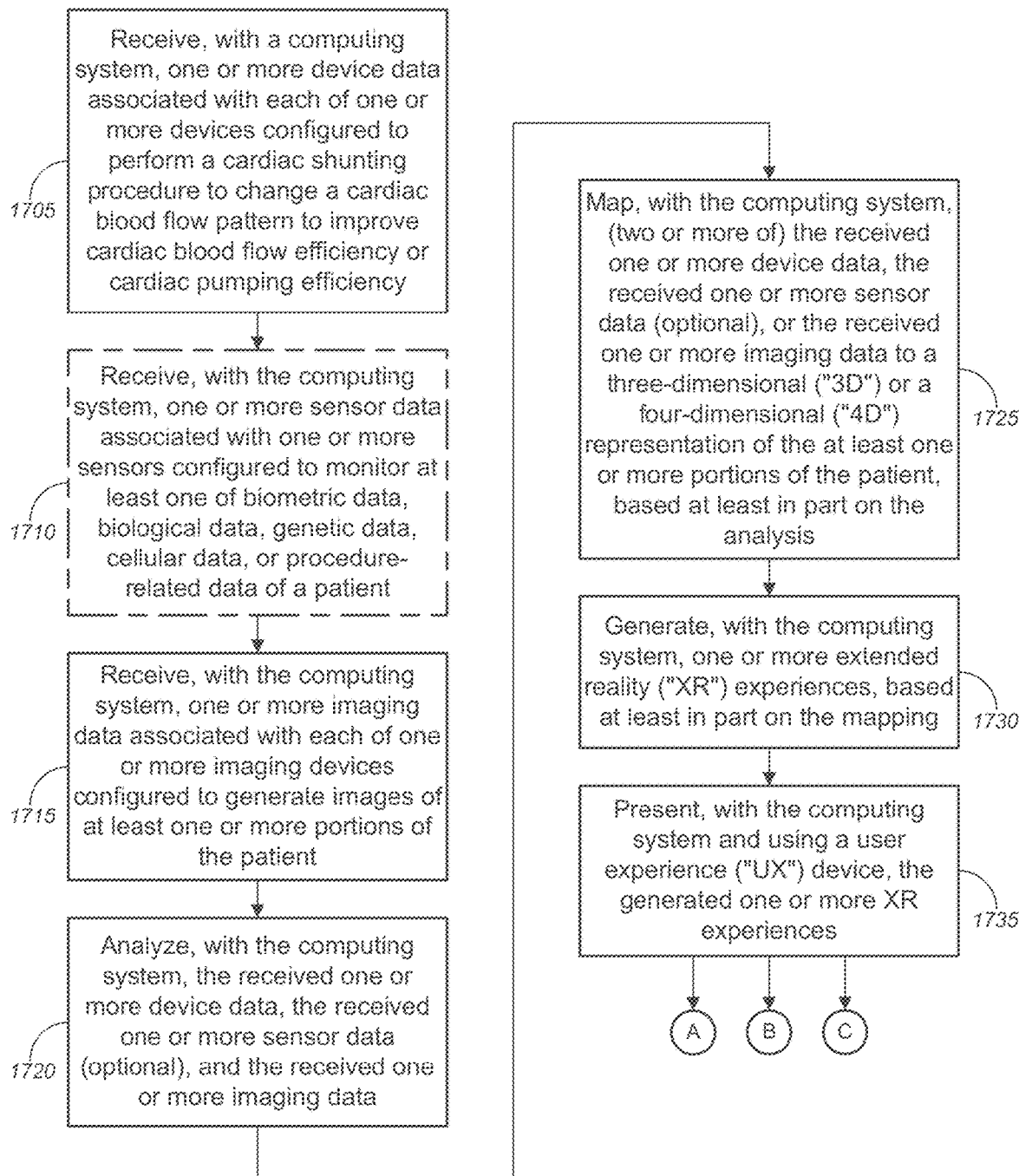

In the non-limiting embodiment of FIG. 17A, method 1700 might comprise receiving, with a computing system, one or more device data associated with each of one or more devices configured to perform a cardiac shunting procedure to change a cardiac blood flow pattern to improve cardiac blood flow efficiency or cardiac pumping efficiency (block 1705); receiving, with the computing system, one or more sensor data associated with one or more sensors configured to monitor at least one of biometric data, biological data, genetic data, cellular data, or procedure-related data of a patient (optional block 1710); and receiving, with the computing system, one or more imaging data associated with each of one or more imaging devices configured to generate images of at least one or more portions of the patient (block 1715). In some cases, at least one of the received one or more device data, the received one or more sensor data, and the received one or more imaging data might be real-time or near-real-time data that is received by the computing system in real-time or near-real-time.

In some embodiments, the computing system might include, without limitation, at least one of an XR computing system, a medical procedure computing system, a hub computing system, a three-dimensional ("3D") graphical processing unit, a cluster computing system, a four-dimensional ("4D") graphics computing system, a server computer, a cloud computing system, or a distributed computing system, and/or the like. In some instances, the patient might include, but is not limited to, one of a human patient, a large animal, or a small animal, and/or the like.

According to some embodiments, the one or more devices might include, but are not limited to, at least one of one or more catheters, one or more catheter interconnect or interface cables, one or more valves (e.g., Hancock™ II aortic valve, Hancock II Ultra™ aortic valve, Hancock™ II mitral valve, Mosaic™ aortic valve, Mosaic Ultra™ aortic valve, Mosaic™ mitral valve, Medtronic Open Pivot™ standard aortic valve, Medtronic Open Pivot™ AP™ aortic valve, Medtronic Open Pivot™ AP360™ aortic valve, Medtronic Open Pivot™ intra-annular aortic valved graft ("AVG"), Medtronic Open Pivot™ standard mitral valve, Medtronic Open Pivot™ AP™ mitral valve, Medtronic Open Pivot™ AP360™ mitral valve, Avalus™ aortic valve, Freestyle™ full root bioprosthesis, Prestyled Freestyle™ complete sub-coronary bioprosthesis, Prestyled Freestyle™ modified sub-coronary bioprosthesis, Harmony™ transcatheter pulmonary valve ("TPV"), or the like), one or more balloons, one or more leads, one or more pacemakers, one or more defibrillators, one or more neuromodulation devices, one or more neurostimulation devices, one or more rigid robotic devices, one or more soft robotic devices, one or more stents, one or more needles, one or more occluders, one or more shunts, one or more diagnostic catheters, one or more surgical tools (e.g., Streamline™ temporary surgical pacing leads, or the like), one or more ablation tools, one or more monitoring devices, one or more cameras, one or more imaging tools, one or more fiducials, one or more staples, one or more anchors, one or more meshes, one or more vascular cannulae, one or more circulatory pumps, one or more valve repair devices (e.g., Profile 3D™ annuloplasty ring, Tri-Ad™ 2.0 Adams tricuspid annuloplasty band, Contour 3D™ annuloplasty ring, CG Future™ annuloplasty ring, CG Future™ annuloplasty band, Simulus™ semi-rigid annuloplasty ring, Simulus™ semi-rigid annuloplasty band, Simulus™ flexible annuloplasty ring, Simulus™ flexible annuloplasty band, Duran AnCore™ annuloplasty ring, Duran AnCore™ annuloplasty band, Simplici-T™ annuloplasty band, Cinch™ implant system, or the like), one or more embolic protection devices, one or more cardiomyoplasty tools, one or more vascular closure tools, one or more septal closure tools, one or more ventricular closure tools, one or more lasers, one or more plaque removal tools, one or more guide wires, one or more introducers, one or more sheaths, one or more clips, one or more capsules, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter or system (e.g., CryoFlex™ surgical ablation system, or the like), a cryoablation console (e.g., CryoFlex™ console, CryoConsole™ cardiac cryoablation system, or the like), a radio frequency ("RF") ablation-based system (e.g., Cardioblate™ irrigated RF ("IRF") surgical ablation system, Cardioblate™ IRF 68000 Generator, or the like), an RF ablation control console, a microwave ("MW") ablation-based system, a MW ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, one or more implantable sensors, or one or more capital equipment, and/or the like.

In some cases, the one or more devices might include one or more first devices including, without limitation, at least one of one or more catheters, one or more valves (e.g., Hancock™ II aortic valve, Hancock II Ultra™ aortic valve, Hancock™ II mitral valve, Mosaic™ aortic valve, Mosaic Ultra™ aortic valve, Mosaic™ mitral valve, Medtronic Open Pivot™ standard aortic valve, Medtronic Open Pivot™ AP™ aortic valve, Medtronic Open Pivot™ AP360™ aortic valve, Medtronic Open Pivot™ intra-annular aortic valved graft ("AVG"), Medtronic Open Pivot™ standard mitral valve, Medtronic Open Pivot™ AP™ mitral valve, Medtronic Open Pivot™ AP360™ mitral valve, Avalus™ aortic valve, Freestyle™ full root bioprosthesis, Prestyled Freestyle™ complete subcoronary bioprosthesis, Prestyled Freestyle™ modified subcoronary bioprosthesis, Harmony™ transcatheter pulmonary valve ("TPV"), or the like), one or more balloons, one or more leads, one or more stents, one or more needles, one or more occluders, one or more shunts, one or more diagnostic catheters, one or more surgical tools (e.g., Streamline™ temporary surgical pacing leads, or the like), one or more staples, one or more anchors, one or more meshes, one or more vascular cannulae, one or more circulatory pumps, one or more valve repair devices (e.g., Profile 3D™ annuloplasty ring, Tri-Ad™ 2.0 Adams tricuspid annuloplasty band, Contour 3D™ annuloplasty ring, CG Future™ annuloplasty ring, CG Future™ annuloplasty band, Simulus™ semi-rigid annuloplasty ring, Simulus™ semi-rigid annuloplasty band, Simulus™ flexible annuloplasty ring, Simulus™ flexible annuloplasty band, Duran AnCore™ annuloplasty ring, Duran AnCore™ annuloplasty band, Simplici-T™ annuloplasty band, Cinch™ implant system, or the like), one or more embolic protection devices, one or more cardiomyoplasty tools, one or more vascular closure tools, one or more septal closure tools, one or more ventricular closure tools, one or more plaque removal tools, one or more guide wires, one or more introducers, one or more sheaths, one or more clips, or one or more capsules, and/or the like.

In some instances, the one or more devices might include one or more second devices including, without limitation, at least one of one or more catheter interconnect or interface cables, one or more rigid robotic devices, one or more soft robotic devices, one or more monitoring devices, one or more cameras, one or more imaging tools, one or more fiducials, one or more lasers, or one or more ablation tools, and/or the like.

In some cases, the one or more devices might include one or more third devices including, without limitation, at least one of one or more pacemakers, one or more defibrillators, one or more neuromodulation devices, one or more neurostimulation devices, an ICD device, an EV-ICD, a miniature leadless implant, or one or more implantable sensors, and/or the like.

In some instances, the one or more devices might include one or more fourth devices including, without limitation, at least one of a PVAC, one or more energy delivery tools, a CEDS, a PFA system, a PFA console, an electroporation system, an electroporation control console, a cryoballoon or a cryoablation catheter or system (e.g., CryoFlex™ surgical ablation system, or the like), a cryoablation console (e.g., CryoFlex™ console, CryoConsole™ cardiac cryoablation system, or the like), a RF ablation-based system (e.g., Cardioblate™ irrigated RF ("IRF") surgical ablation system, Cardioblate™ IRF 68000 Generator, or the like), an RF ablation control console, a MW ablation-based system, a MW ablation control console, a laser ablation-based system, a laser ablation control console, a radiation ablation-based system, a radiation ablation control console, a microwave ablation-based system, a HIFU system, a HIFU control console, or one or more capital equipment, and/or the like.

In some embodiments, the one or more sensors might include, without limitation, at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more electrooculography (EOG) sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors, and/or the like.

In some cases, the one or more sensors might include one or more first sensors including, without limitation, at least one of one or more blood velocity sensors, one or more blood volume sensors, one or more blood pressure sensors, one or more heart rate sensors, one or more pulse sensors, one or more oxygen sensors, one or more $CO_2$ sensors, one or more hormonal sensors, one or more fluid levels, one or more biomarker sensors, one or more genetic sensors, one or more blood chemistry sensors, one or more tissue matrix sensors, one or more bacteria sensors, one or more respiration sensors, one or more emotional stress sensors, one or more sleep sensors, one or more ischemia sensors, one or more HCT level sensors, one or more brainwave sensors, or one or more pain sensors, and/or the like.

In some instances, the one or more sensors might include one or more second sensors including, without limitation, at least one of one or more gas sensors, one or more optical sensors, one or more impedance sensors, one or more ultrasound sensors, one or more flow sensors, one or more electrical sensors, one or more voltage sensors, one or more amperage sensors, one or more wattage sensors, one or more chemical sensors, one or more pH sensors, one or more motion sensors, one or more proximity sensors, one or more light sensors, one or more sound sensors, one or more laser sensors, one or more doppler sensors, one or more mechanical sensors, one or more IR sensors, one or more UV sensors, one or more moisture sensors, one or more humidity sensors, one or more temperature sensors, one or more pressure sensors, one or more force sensors, one or more strain sensors, one or more stress sensors, one or more olfactory sensors, one or more viscosity sensors, one or more EMI sensors, one or more vibration sensors, one or more sound wave sensors, one or more magnetic sensors, one or more visible light sensors, or one or more radiation sensors, and/or the like.

In some cases, the one or more sensors might include one or more third sensors including, without limitation, at least one of one or more diagnostic sensors, one or more surgical sensors, one or more wearable sensors, one or more DIC sensors, one or more cameras, one or more perfusion sensors, one or more EMG sensors, one or more EOG sensors, one or more cardiac hemodynamics sensors, one or more photographic plate sensors, one or more polymer-metal sensors, one or more electrochemical sensors, one or more biometric sensors, or one or more EEG sensors, and/or the like. In some instances, the one or more sensors might include one or more fourth sensors including, without limitation, at least one of one or more surgeon fatigue sensors or one or more compliance sensors, and/or the like. In some cases, the one or more sensors might include one or more fifth sensors including, without limitation, at least one of one or more CCDs or one or more photo diode arrays, and/or the like.

In some instances, the one or more sensors might include one or more sixth sensors including, without limitation, at least one of one or more tissue contractility sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, or one or more metabolic process sensors, and/or the like. In some cases, the one or more sensors might include one or more seventh sensors including, without limitation, at least one of one or more chronically implanted sensors, and/or the like. In some instances, the one or more sensors might include one or more eighth sensors including, without limitation, at least one of one or more contactless optical sensors, one or more IR-based temperature sensors, one or more blood pressure sensors, one or more heart rate sensors, one or more motion sensors, one or more respiratory rate sensors, one or more fiducial alignment sensors, one or more tool recognition sensors, one or more collision detection sensors, one or more room traffic flow sensors, one or more surgeon fatigue sensors, one or more cognitive overload sensors, and/or the like.

According to some embodiments, the one or more imaging devices might include, but are not limited to, at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuro-endoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope, and/or the like.

In some cases, the one or more imaging devices might include one or more first imaging devices including, without limitation, at least one of a MRI system, a DTI system, a MRA system, an ASL system, a MEG system, a MRS system, a DSC MRI system, a BOLD system, or a FLAIR system, and/or the like. In some instances, the one or more imaging devices might include one or more second imaging devices including, without limitation, at least one of a CT system, a SPECT system, a CTA system, a PET system, or an OCT system, and/or the like. In some cases, the one or more imaging devices might include one or more third imaging devices including, without limitation, at least one of a US system, a TEE system, an ICE system, a TTE system, an IVUS system, or an EWI system, and/or the like. In some instances, the one or more imaging devices might include one or more fourth imaging devices including, without limitation, at least one of a neuro-endoscopy system, an OIS system, an endoscopy system, a bioluminescent system, a triboluminescence system, an image fusion system, or a microscope, and/or the like. In some cases, the one or more imaging devices might include one or more fifth imaging devices including, without limitation, an EEG system, and/or the like. In some instances, the one or more imaging devices might include one or more sixth imaging devices including, without limitation, at least one of a fluoroscopy system, an X-ray system, a 3D scanning system, an IR system, or a UV system, and/or the like.

In some embodiments, the cardiac shunting procedure might include, without limitation, at least one of a surgical procedure, a left atrial appendage ("LAA") procedure, a tissue ablation procedure, a transcatheter aortic valve repair ("TAVr") procedure, a transcatheter aortic valve replacement ("TAVR") procedure (e.g., with the Evolut™ PRO+TAVR system, or the like), a transcatheter mitral valve repair ("TMVr") procedure, a transcatheter mitral valve replacement ("TMVR") procedure (e.g., with the Intrepid™ TMVR system, or the like), a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, a coronary angioplasty procedure, a balloon angioplasty, a stenting procedure, an atrial septal defect ("ASD") treatment procedure, a cardiac shunt treatment procedure, a heart bypass procedure, a cardiac mapping procedure, a cardiac resynchronization therapy ("CRT") device installation procedure, a catheter ablation procedure, an endovascular repair procedure, a heart monitor installation procedure, an implantable cardioverter defibrillator ("ICD") device installation procedure, an extravascular ICD ("EV-ICD") device installation procedure, a minimally invasive endovascular repair procedure, a miniature leadless implant (e.g., Micra™ leadless implant, or the like) installation procedure, an implantable sensor (e.g., an implantable pulmonary artery sensor, or the like) installation procedure, a surgical heart valve repair and replacement procedure, a transcatheter pulmonary valve ("TPV") therapy (e.g., Melody™ TPV therapy, Harmony™ TPV therapy, or the like), a ventricular assist device ("VAD") installation procedure, an intra-aortic balloon pump ("IABP") implantation procedure, a heart transplant operation, a cryoballoon or cryoablation catheter procedure, a pulsed field ablation ("PFA") procedure, an electroporation procedure, a radio frequency ("RF") ablation procedure, a microwave ("MW") ablation procedure, a laser ablation procedure, a radiation ablation procedure, a microwave ablation-based procedure, or a high intensity focused ultrasound ("HIFU") procedure, and/or the like.

In some instances, the cardiac shunting procedure might include one or more first procedures including, without limitation, at least one of a surgical procedure, a TAVr procedure, a TAVR procedure (e.g., with the Evolut™ PRO+TAVR system, or the like), a TMVr procedure, a TMVR procedure (e.g., with the Intrepid™ TMVR system, or the like), a TPVr procedure, a TPVR procedure, a TTVr procedure, a TTVR procedure, a mitral clip repair procedure, a minimally invasive endovascular repair procedure, a surgical heart valve repair and replacement procedure, a TPV therapy (e.g., Melody™ TPV therapy, Harmony™ TPV therapy, or the like), or an endovascular repair procedure, and/or the like.

In some instances, the cardiac shunting procedure might include one or more second procedures including, without limitation, at least one of a LAA procedure, a coronary angioplasty procedure, a balloon angioplasty, an ASD treatment procedure, a cardiac shunt treatment procedure, a heart bypass procedure, a heart transplant operation, and/or the like.

In some cases, the cardiac shunting procedure might include one or more third procedures including, without limitation, at least one of a CRT device installation procedure, a heart monitor installation procedure, an ICD device installation procedure, an EV-ICD device installation procedure, a miniature leadless implant (e.g., Micra™ leadless implant, or the like) installation procedure, an implantable sensor (e.g., an implantable pulmonary artery sensor, or the like) installation procedure, a VAD installation procedure, or an IABP implantation procedure and/or the like.

In some instances, the cardiac shunting procedure might include one or more fourth procedures including, without limitation, at least one of a tissue ablation procedure, a stenting procedure, a cardiac mapping procedure, a catheter ablation procedure, a cryoballoon or cryoablation catheter procedure, a PFA procedure, an electroporation procedure, a RF ablation procedure, a MW ablation procedure, a laser ablation procedure, a radiation ablation procedure, a microwave ablation-based procedure, or a HIFU procedure, and/or the like.

Any one of (or a combination of two or more of) the above-mentioned first through seventh sensors along with first through sixth imaging devices may be used, in conjunction with any one of (or combination of two or more of) the tracking systems (as described below) for any of the first through fourth procedures performed by corresponding first through fourth devices on patients (or subjects). Specific non-limiting example combinations of these systems and devices are described above with respect to FIG. 9 (e.g., FIGS. 9F-9H, or the like), in terms of specific example procedures in the context of pre-operative planning, intra-operative adjustments, and post-operative monitoring (as described above with respect to FIG. 3C, or the like).

At block 1720, method 1700 might comprise analyzing, with the computing system, the received one or more device data, the received one or more sensor data (optional), and the received one or more imaging data. Method 1700 might further comprise, at block 1725, mapping, with the computing system, (two or more of) the received one or more device data, the received one or more sensor data (optional), or the received one or more imaging data to a three-dimensional ("3D") or four-dimensional ("4D") representation (i.e., three-dimensional ("3D") representation plus at least one of real-time updates, dynamic modeling, or data streaming, and/or the like) of the at least one or more portions of the patient, based at least in part on the analysis.

Method 1700 might further comprise generating, with the computing system, one or more extended reality ("XR") experiences, based at least in part on the mapping (block 1730); and presenting, with the computing system and using a user experience ("UX") device, the generated one or more XR experiences (block 1735). In some embodiments, the one or more XR experiences might include, without limitation, at least one of one or more augmented reality ("AR") images, one or more AR videos, one or more virtual reality ("VR") images, one or more VR videos, one or more mixed reality ("MR") images, one or more MR videos, one or more XR images, or one or more XR videos, and/or the like. In some cases, generating the one or more XR experiences might comprise generating, with the computing system, one or more XR experiences comprising at least three or more of the one or more XR images, one or more XR sounds, one or more XR haptic or tactile responses, one or more XR simulated smells, or one or more XR simulated tastes, based at least in part on the mapping. According to some embodiments, the one or more XR images might be dynamic images, which might include an overlay of data models depicting at least one of electrical pulses, blood flow, tissue movement, damage, stress, and/or the like, and thus may not be a still frame in 3D.

According to some embodiments, the UX device might include, but is not limited to, at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system, and/or the like.

In some cases, the UX device might include one or more first UX devices including, without limitation, at least one of a headset, UX glasses, a supplement to existing glasses, UX contact lenses, or a HUD device, and/or the like. In some instances, the UX device might include one or more second UX devices including, without limitation, at least one of a viewing window or a microscope, and/or the like. In some cases, the UX device might include one or more third UX devices including, without limitation, at least one of headphones or a 3D spatial sound system, and/or the like. In some instances, the UX device might include one or more fourth UX devices including, without limitation, at least one of an olfactory simulation system, a taste simulation system, a sensory neuro-perception system, a sensory conversion system, or a haptic feedback system, and/or the like. In some cases, the UX device might include one or more fifth UX devices including, without limitation, at least one of a telemonitoring system, a rigid robotic device control and sensory feedback system, a soft robotic device control and sensory feedback system, a control system for nanostructures, a control system for cells, a control system for genes, or a nanoparticle reconstruction system, and/or the like.

In some instances, the UX device might include one or more sixth UX devices including, without limitation, at least one of an eye control system, a voice control system, a remote control system, a gesture-based control system, a sign language-based control system, a body-part-based control system, a joystick, a mouse, a blow-based control system, a neuro-interface system, or a peripheral nerve-computer interface system, and/or the like. In some cases, the UX device might include one or more seventh UX devices including, without limitation, at least one of a 2D screen display, a 3D refractive display, a parallel reality system, a projection system, a fan-based display, a water-based display, an ionized air-based display, an ionized laser-based display, a smoke-based display, a sand-based display, a particulate-based display, a 3D printed reconstruction system, or a customized view generation system, and/or the like. In some instances, the UX device might include one or more eighth UX devices including, without limitation, at least one of a ghosting and prediction system, a master-slave control system, or an annotation system, and/or the like.

In some embodiments, the generated one or more XR images might be presented to provide one or more uses including, without limitation, a guide for a medical professional, a navigation tool during the cardiac shunting procedure, a proximity detection tool during the cardiac shunting procedure, a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient, and/or the like. In some cases, the one or more uses might include one or more first uses including, without limitation, at least one of a guide for a medical professional, a navigation tool during the cardiac shunting procedure, or a proximity detection tool during the cardiac shunting procedure, and/or the like.

In some instances, the one or more uses might include one or more second uses including, without limitation, at least one of a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient, and/or the like.

Any one of (or a combination of two or more of) the aforementioned UX devices may be used by a user for the first through second uses above, based on computer analysis of data obtained from the above-mentioned first through seventh sensors along with first through sixth imaging devices, in conjunction with any one of (or combination of two or more of) the first through sixth tracking systems (as described below) for any of the first through fourth procedures performed by corresponding first through fourth devices on patients (or subjects). Specific non-limiting example combinations of these systems and devices are described above with respect to FIG. 9 (e.g., FIGS. 9F-9H, or the like), in terms of specific example procedures in the context of pre-operative planning, intra-operative adjustments, and post-operative monitoring (as described above with respect to FIG. 3C, or the like).

Method 1700 might continue onto the process at optional block 1740 in FIG. 17B following the circular marker denoted, "A," might continue onto the process at optional block 1745 in FIG. 17C following the circular marker denoted, "B," or might continue onto the process at optional block 1750 in FIG. 17D following the circular marker denoted, "C."

At optional block 1740 in FIG. 17B (following the circular marker denoted, "A"), method 1700 might comprise tracking, with the computing system, the one or more devices, in some cases, using one or more tracking systems including, but not limited to, at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In some cases, the one or more tracking systems might include one or more first tracking systems including, without limitation, at least one of an electropotential-based tracking system, an impedance-based tracking system, an accelerometer-based tracking system, an IR-based tracking system, an ultrasonic sound-based tracking system, a piezoelectric-based tracking system, or an acoustic-based tracking system, and/or the like. In some instances, the one or more tracking systems might include one or more second tracking systems including, without limitation, at least one of an electromagnetic-based tracking system, a magnetic anomaly detection-based tracking system, or an MRI-based tracking system, and/or the like. In some cases, the one or more tracking systems might include one or more third tracking systems including, without limitation, at least one of a RFID-based tracking system, a Bluetooth-based tracking system, a wireless-based tracking system, or a near-field communications-based tracking system, and/or the like.

In some instances, the one or more tracking systems might include one or more fourth tracking systems including, without limitation, at least one of an optical-based tracking system, a laser-based tracking system, an US imaging-based tracking system, a computer vision-based tracking system, a fluoroscopy-based tracking system, a SLAM-based tracking system, or a feature identification-based tracking system, and/or the like. In some cases, the one or more tracking systems might include one or more fifth tracking systems including, without limitation, at least one of a GPS-based tracking system or a radar-based tracking system, and/or the like. In some instances, the one or more tracking systems might include one or more sixth tracking systems including, without limitation, at least one of a machine learning-based tracking system, a predictive tracking system, or a prescriptive tracking system, and/or the like.

At optional block 1745 in FIG. 17C (following the circular marker denoted, "B"), method 1700 might comprise generating, with the computing system, one or more models that are used for analyzing or visualizing at least one of the received one or more device data, the received one or more sensor data (optional), or the received one or more imaging data, and/or the like.

At optional block 1750 in FIG. 17D (following the circular marker denoted, "C"), method 1700 might comprise receiving, with the computing system, one or more inputs from a user. Method 1700 might further comprise, at optional block 1755, analyzing, with the computing system, the one or more inputs from the user to determine whether the one or more inputs comprise at least one command such as at least one of one or more voice commands, one or more eye-tracking-based commands, one or more gesture-based commands, one or more touch-based commands, or one or more entered commands, and/or the like.

Based on a determination that the one or more inputs comprise at least one command such as at least one of one or more voice commands, one or more eye-tracking-based commands, one or more gesture-based commands, or one or more entered commands, method 1700 might further comprise identifying, with the computing system, which at least one device among the one or more devices is intended to be controlled based on the one or more inputs (at optional block 1760); generating, with the computing system, one or more instructions for controlling the identified at least one device based at least in part on the one or more inputs (at optional block 1765); and sending, with the computing system, the generated one or more instructions to the identified at least one device (at optional block 1770).

Exemplary System and Hardware Implementation

Figure 18:
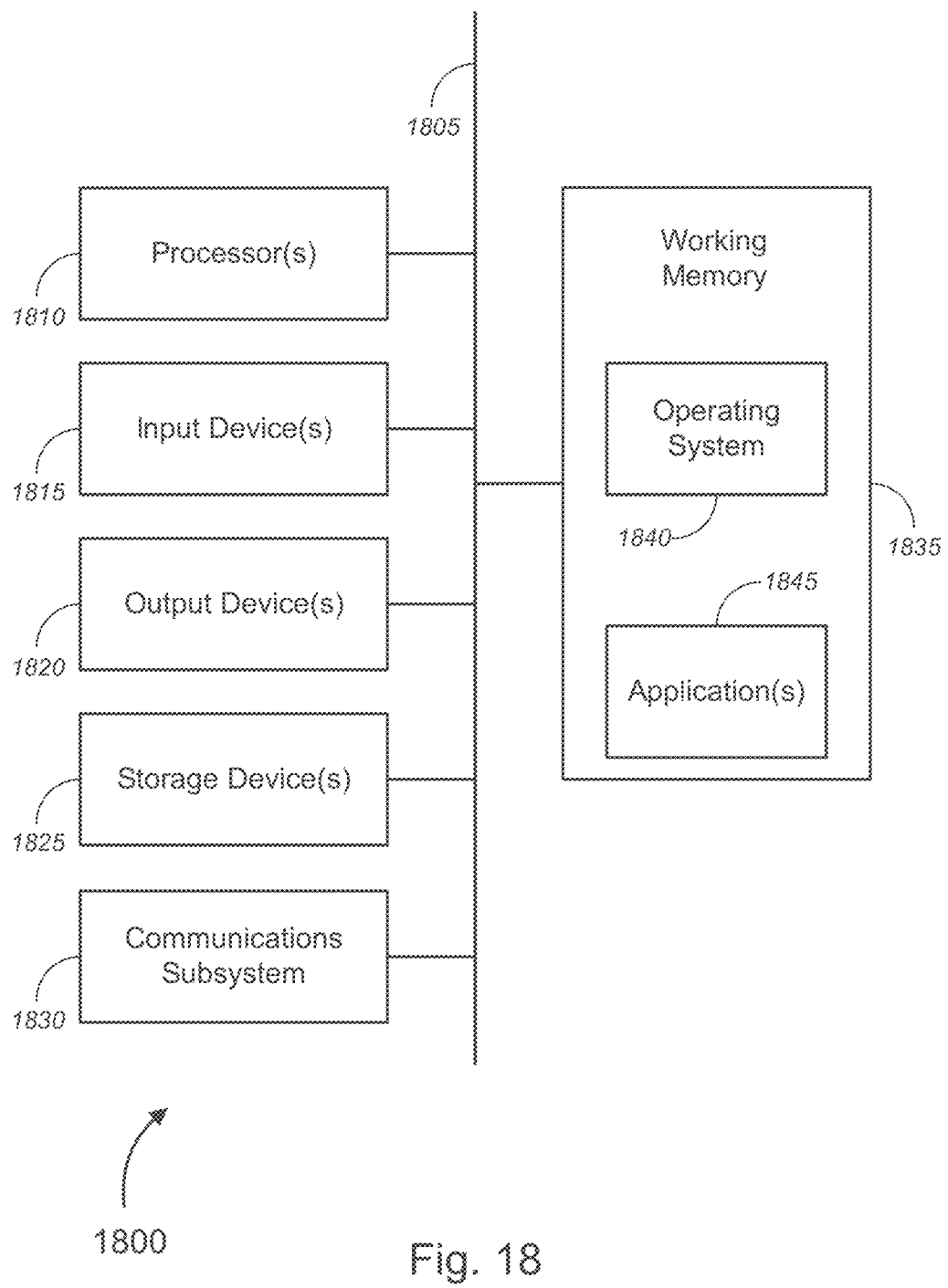
FIG. 18 is a block diagram illustrating an exemplary computer or system hardware architecture, in accordance with various embodiments.

FIG. 18 is a block diagram illustrating an exemplary computer or system hardware architecture, in accordance with various embodiments. FIG. 18 provides a schematic illustration of one embodiment of a computer system 1800 of the service provider system hardware that can perform the methods provided by various other embodiments, as described herein, and/or can perform the functions of computer or hardware system (i.e., system hubs or computing systems 105a, 105b, 205, 410, 480, and 520; mapping and navigation systems (e.g., electroanatomic mapping ("EAM") system, high-density mapping catheter, patient patches, navigation hardware and software, etc.) 115a, 115b, 240, 360, 380, 405e, 510, 550, 630b, 714, and 714a-714c; devices or equipment (e.g., robotics systems, surgical training simulator, electrosurgical generator, radiofrequency ("RF") ablation generator, cryoballoon or cryoablation catheter system, pulsed field ablation ("PFA") system, a microwave ("MW") ablation system, monitoring catheter, respiratory equipment, surgical tools, deflectable or steerable sheath, dilator, deployment device, cardiac bionic construct ("CBC"), steering subsystem, handled subsystem, pressure subsystem, coronary sinus ("CS") catheter, guidewire, introducer sheath, respiratory and other surgical equipment, transseptal needle, syringe and manifold system, etc.) 135, 135a, 135b, 210, 315, 320, 350, 355, 405a-405d, 405g, 405h, 505, 535, 540, 545, 620a-620c, 630a, 635e, 645a-645c, 650a-650b, 655a-655b, 665, 670a-670b, 675a-675c, 704, 712, 716, 718, 722, 726, 728, 730, 732, and 736; imaging systems (e.g., computed tomography ("CT") machine, electrophysiology ("EP") system, fluoroscopy system, etc.) 140, 245, 380, 635a-635c, and 734; sensors (e.g., instrumentation, IoT sensors, biometrics system, electrogram ("EGM") or electrocardiogram ("ECG") system, camera control unit, monitor, monitoring catheter, etc.) 145, 250, 375, 405i, 515, 555, 620d, 635d, and 702; extended reality ("XR") platforms or hardware 150, 260, 310, 380, 415b, 630c, 720, and 720a-720b; user experience ("UX") devices 155, 265, 415a, 415e, 480, and 525; data analytics or artificial intelligence ("AI") systems 160a, 160b, 305, 365, 420, and 560; anatomy or tool registration systems 165 and 220; cloud storage systems 180 and 530; user devices 415c and 415d; computing tower 405f; etc.), as described above. It should be noted that FIG. 18 is meant only to provide a generalized illustration of various components, of which one or more (or none) of each may be utilized as appropriate. FIG. 18, therefore, broadly illustrates how individual system elements may be implemented in a relatively separated or relatively more integrated manner.

The computer or hardware system 1800—which might represent an embodiment of the computer or hardware system (i.e., system hubs or computing systems 105a, 105b, 205, 410, 480, and 520; mapping and navigation systems (e.g., EAM system, high-density mapping catheter, patient patches, navigation hardware and software, etc.) 115a, 115b, 240, 360, 380, 405e, 510, 550, 630b, 714, and 714a-714c; devices or equipment (e.g., robotics systems, surgical training simulator, electrosurgical generator, RF ablation generator, cryoballoon or cryoablation catheter system, PFA system, MW ablation system, monitoring catheter, respiratory equipment, surgical tools, deflectable or steerable sheath, dilator, deployment device, CBC, steering subsystem, handled subsystem, pressure subsystem, CS catheter, guidewire, introducer sheath, respiratory and other surgical equipment, transseptal needle, syringe and manifold system, etc.) 135, 135a, 135b, 210, 315, 320, 350, 355, 405a-405d, 405g, 405h, 505, 535, 540, 545, 620a-620c, 630a, 635e, 645a-645c, 650a-650b, 655a-655b, 665, 670a-670b, 675a-675c, 704, 712, 716, 718, 722, 726, 728, 730, 732, and 736; imaging systems (e.g., CT machine, EP system, fluoroscopy system, etc.) 140, 245, 380, 635a-635c, and 734; sensors (e.g., instrumentation, IoT sensors, biometrics system, EGM or ECG system, camera control unit, monitor, monitoring catheter, etc.) 145, 250, 375, 405i, 515, 555, 620d, 635d, and 702; XR platforms or hardware 150, 260, 310, 380, 415b, 630c, 720, and 720a-720b; UX devices 155, 265, 415a, 415e, 480, and 525; data analytics or AI systems 160a, 160b, 305, 365, 420, and 560; anatomy or tool registration systems 165 and 220; cloud storage systems 180 and 530; user devices 415c and 415d; computing tower 405f; etc.), described above with respect to FIGS. 1-15—is shown comprising hardware elements that can be electrically coupled via a bus 1805 (or may otherwise be in communication, as appropriate). The hardware elements may include one or more processors 1810, including, without limitation, one or more general-purpose processors and/or one or more special-purpose processors (such as microprocessors, digital signal processing chips, graphics acceleration processors, and/or the like); one or more input devices 1815, which can include, without limitation, a mouse, a keyboard, and/or the like; and one or more output devices 1820, which can include, without limitation, a display device, a printer, and/or the like.

The computer or hardware system 1800 may further include (and/or be in communication with) one or more storage devices 1825, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 1800 might also include a communications subsystem 1830, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 1830 may permit data to be exchanged with a network (such as the network described below, to name one example), with other computer or hardware systems, and/or with any other devices described herein. In many embodiments, the computer or hardware system 1800 will further comprise a working memory 1835, which can include a RAM or ROM device, as described above.

The computer or hardware system 1800 also may comprise software elements, shown as being currently located within the working memory 1835, including an operating system 1840, device drivers, executable libraries, and/or other code, such as one or more application programs 1845, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 1825 described above. In some cases, the storage medium might be incorporated within a computer system, such as the system 1800. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer or hardware system 1800 and/or might take the form of source and/or installable code, which, upon compilation and/or installation on the computer or hardware system 1800 (e.g., using any of a variety of generally available compilers, installation programs, compression/decompression utilities, etc.) then takes the form of executable code.

It will be apparent to those skilled in the art that substantial variations may be made in accordance with specific conditions. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 1800) to perform methods in accordance with various embodiments of the invention. According to a set of embodiments, some or all of the procedures of such methods are performed by the computer or hardware system 1800 in response to processor 1810 executing one or more sequences of one or more instructions (which might be incorporated into the operating system 1840 and/or other code, such as an application program 1845) contained in the working memory 1835. Such instructions may be read into the working memory 1835 from another computer readable medium, such as one or more of the storage device(s) 1825. Merely by way of example, execution of the sequences of instructions contained in the working memory 1835 might cause the processor(s) 1810 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 1800, various computer readable media might be involved in providing instructions/code to processor(s) 1810 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 1825. Volatile media includes, without limitation, dynamic memory, such as the working memory 1835. In some alternative embodiments, a computer readable medium may take the form of transmission media, which includes, without limitation, coaxial cables, copper wire, and fiber optics, including the wires that comprise the bus 1805, as well as the various components of the communication subsystem 1830 (and/or the media by which the communications subsystem 1830 provides communication with other devices). In an alternative set of embodiments, transmission media can also take the form of waves (including without limitation radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 1810 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 1800. These signals, which might be in the form of electromagnetic signals, acoustic signals, optical signals, and/or the like, are all examples of carrier waves on which instructions can be encoded, in accordance with various embodiments of the invention.

The communications subsystem 1830 (and/or components thereof) generally will receive the signals, and the bus 1805 then might carry the signals (and/or the data, instructions, etc. carried by the signals) to the working memory 1835, from which the processor(s) 1805 retrieves and executes the instructions. The instructions received by the working memory 1835 may optionally be stored on a storage device 1825 either before or after execution by the processor(s) 1810.

Figure 19:
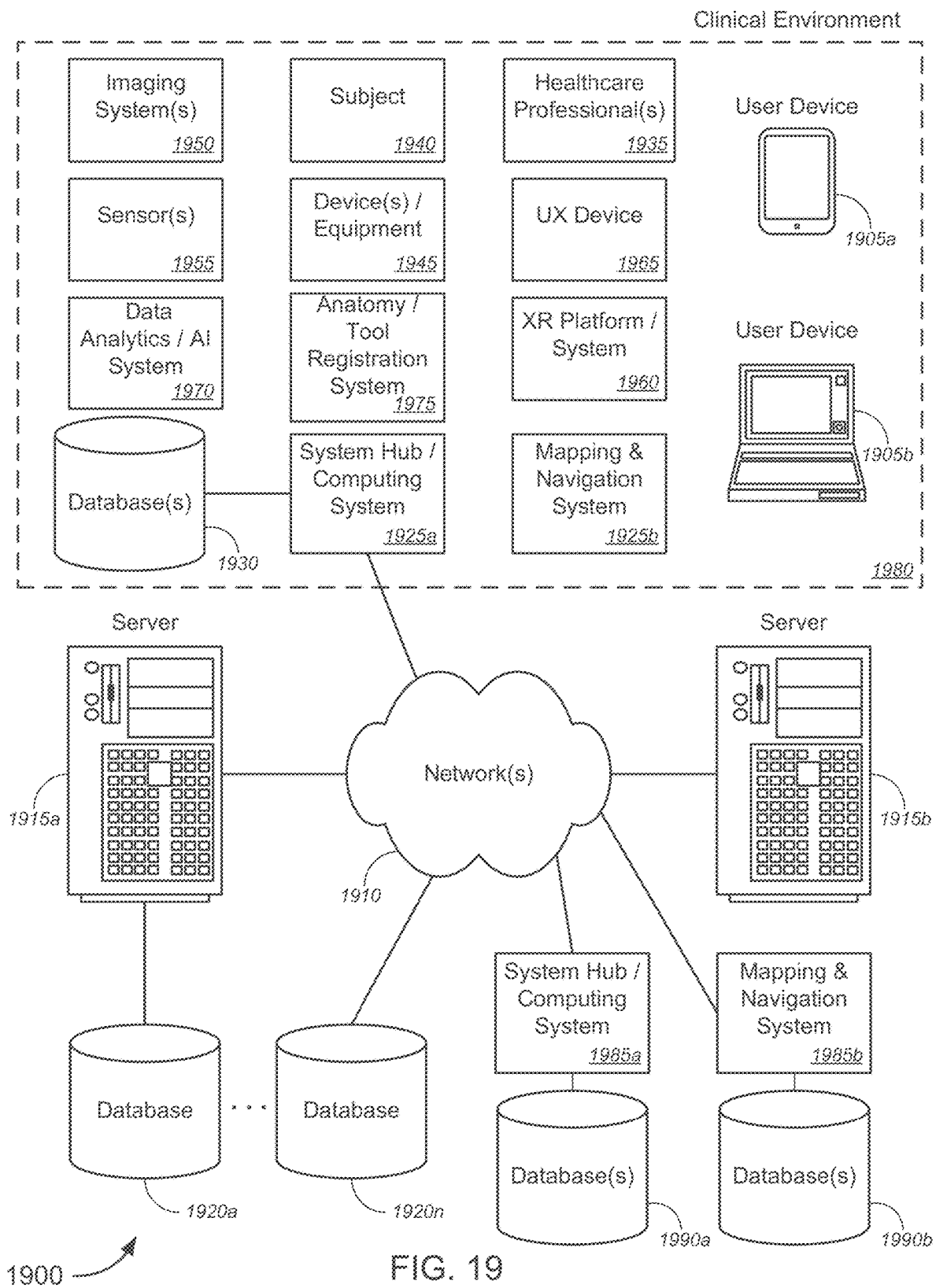
FIG. 19 is a block diagram illustrating a networked system of computers, computing systems, or system hardware architecture, which can be used in accordance with various embodiments.

As noted above, a set of embodiments comprises methods and systems for implementing medical assistance technologies, and, more particularly, to methods, systems, and apparatuses for implementing intelligent assistance ("IA") ecosystem. FIG. 19 illustrates a schematic diagram of a system 1900 that can be used in accordance with one set of embodiments. The system 1900 can include one or more user computers, user devices, or customer devices 1905. A user computer, user device, or customer device 1905 can be a general purpose personal computer (including, merely by way of example, desktop computers, tablet computers, laptop computers, handheld computers, and the like, running any appropriate operating system, several of which are available from vendors such as Apple, Microsoft Corp., and the like), cloud computing devices, a server(s), and/or a workstation computer(s) running any of a variety of commercially-available UNIX™ or UNIX-like operating systems. A user computer, user device, or customer device 1905 can also have any of a variety of applications, including one or more applications configured to perform methods provided by various embodiments (as described above, for example), as well as one or more office applications, database client and/or server applications, and/or web browser applications. Alternatively, a user computer, user device, or customer device 1905 can be any other electronic device, such as a thin-client computer, Internet-enabled mobile telephone, and/or personal digital assistant, capable of communicating via a network (e.g., the network(s) 1910 described below) and/or of displaying and navigating web pages or other types of electronic documents. Although the exemplary system 1900 is shown with two user computers, user devices, or customer devices 1905, any number of user computers, user devices, or customer devices can be supported.

Certain embodiments operate in a networked environment, which can include a network(s) 1910. The network(s) 1910 can be any type of network familiar to those skilled in the art that can support data communications using any of a variety of commercially-available (and/or free or proprietary) protocols, including, without limitation, TCP/IP, SNA™ IPX™ AppleTalk™, and the like. Merely by way of example, the network(s) 1910 (similar to network(s) 175 of FIG. 1, or the like) can each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 1915. Each of the server computers 1915 may be configured with an operating system, including, without limitation, any of those discussed above, as well as any commercially (or freely) available server operating systems. Each of the servers 1915 may also be running one or more applications, which can be configured to provide services to one or more clients 1905 and/or other servers 1915.

Merely by way of example, one of the servers 1915 might be a data server, a web server, a cloud computing device(s), or the like, as described above. The data server might include (or be in communication with) a web server, which can be used, merely by way of example, to process requests for web pages or other electronic documents from user computers 1905. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 1905 to perform methods of the invention.

The server computers 1915, in some embodiments, might include one or more application servers, which can be configured with one or more applications accessible by a client running on one or more of the client computers 1905 and/or other servers 1915. Merely by way of example, the server(s) 1915 can be one or more general purpose computers capable of executing programs or scripts in response to the user computers 1905 and/or other servers 1915, including, without limitation, web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™ IBM™, and the like, which can process requests from clients (including, depending on the configuration, dedicated database clients, API clients, web browsers, etc.) running on a user computer, user device, or customer device 1905 and/or another server 1915. In some embodiments, an application server can perform one or more of the processes for implementing medical assistance technologies, and, more particularly, to methods, systems, and apparatuses for implementing intelligent assistance ("IA") ecosystem, as described in detail above. Data provided by an application server may be formatted as one or more web pages (comprising HTML, JavaScript, etc., for example) and/or may be forwarded to a user computer 1905 via a web server (as described above, for example). Similarly, a web server might receive web page requests and/or input data from a user computer 1905 and/or forward the web page requests and/or input data to an application server. In some cases, a web server may be integrated with an application server.

In accordance with further embodiments, one or more servers 1915 can function as a file server and/or can include one or more of the files (e.g., application code, data files, etc.) that may be useful to implement various disclosed methods, incorporated by an application running on a user computer 1905 and/or another server 1915. Alternatively, as those skilled in the art will appreciate, a file server can include any or all pre-requisite files, allowing such an application to be invoked remotely by a user computer, user device, or customer device 1905 and/or server 1915.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 1920a-1920n (collectively, "databases 1920"). The location of each of the databases 1920 is discretionary: merely by way of example, a database 1920a might reside on a storage medium local to (and/or resident in) a server 1915a (and/or a user computer, user device, or customer device 1905). Alternatively, a database 1920n can be remote from any or all of the computers 1905, 1915, so long as it can be in communication (e.g., via the network 1910) with one or more of these. In a particular set of embodiments, a database 1920 can reside in a storage-area network ("SAN") familiar to those skilled in the art. (Likewise, any or all pre-requisite files for performing the functions attributed to the computers 1905, 1915 can be stored locally on the respective computer and/or remotely, as appropriate.) In one set of embodiments, the database 1920 can be a relational database, such as an Oracle database, that is adapted to store, update, and retrieve data in response to SQL-formatted commands. The database might be controlled and/or maintained by a database server, as described above, for example.

According to some embodiments, system 1900 might further comprise system hub or computing system 1925a and corresponding database(s) 1930 (similar to system hub or computing system 105a, 205, 410, 480, and 520, and corresponding database(s) 110a of FIGS. 1, 2, 4, and 5, or the like), mapping and navigation system 1925b (similar to mapping and navigation system 115a, 240, 360, 380, 405e, 510, 550, 630b, 714, and 714a-714c of FIGS. 1-7, or the like), one or more healthcare professionals 1935 (similar to healthcare professionals 125 and 724 of FIGS. 1 and 7, or the like), a subject 1940 (similar to subject 130, 230, 625, and 706 of FIGS. 1, 2, 6, and 7, or the like), one or more devices or equipment 1945 (similar to devices or equipment 135, 135a, 135b, 210, 315, 320, 350, 355, 405a-405d, 405g, 405h, 505, 535, 540, 545, 620a-620c, 630a, 635e, 645a-645c, 650a-650b, 655a-655b, 665, 670a-670b, 675a-675c, 704, 712, 716, 718, 722, 726, 728, 730, 732, and 736 of FIGS. 1-7, or the like), one or more imaging systems 1950 (similar to imaging systems 140 of FIG. 1, or the like), one or more sensors 1955 (similar to sensors 145, 245, 380, 635a-635c, and 734 of FIGS. 1-3, 6, and 7, or the like), an extended reality ("XR") platform or system 1960 (similar to XR platform or system 150, 260, 310, 380, 415b, 630c, 720, and 720a-720b of FIGS. 1-4, 6, and 7, or the like), a user experience ("UX") device 1965 (similar to UX device 155, 265, 415a, 415e, 480, and 525 of FIGS. 1, 2, 4, and 5, or the like), a data analytics or artificial intelligence ("AI") system 1970 (similar to data analytics or AI system 160a, 305, 365, 420, and 560 of FIGS. 1 and 3-5, or the like), and/or an anatomy or tool registration system 1975 (similar to anatomy or tool registration system 165 and 220 of FIGS. 1 and 2, or the like), and/or the like. In some instances, the system hub or computing system 1925a and corresponding database(s) 1930, the mapping and navigation system 1925b, the one or more healthcare professionals 1935, the subject 1940, the one or more devices or equipment 1945, the one or more imaging systems 1950, the one or more sensors 1955, the XR platform or system 1960, the UX device 1965, the data analytics or AI system 1970, or the anatomy or tool registration system 1975, and/or the like, together with the user devices 1905a and 1905b may be located or disposed within clinical environment 1980. In some cases, the clinical environment 1980 might include, but is not limited to, a clinic, a hospital, an operating room, an emergency room, a physician's office, or a laboratory, or the like.

In some embodiments, the system 1900 might further comprise remote system hub or computing system 1985a and corresponding database(s) 1990a (similar to system hub or computing system 105b and corresponding database(s) 110b of FIG. 1, or the like), and remote mapping and navigation system 1985b and corresponding database(s) 1990b (similar to mapping and navigation system 115b and corresponding database(s) 120b of FIG. 1, or the like), or the like, that communicatively couple to the system hub or computing system 1925a via network(s) 1910.

In operation, system hub or computing system 1925a or 1985a (collectively, "computing system" or the like) might receive one or more device data associated with each of one or more devices configured to perform one or more first tasks (in some cases, to perform one or more medical procedures, or the like). Herein, the one or more medical procedures might include, without limitation, at least one of one or more medical tasks, one or more surgical operations, or one or more procedures (which are less intrusive than surgical operations), and/or the like, performed by a medical professional. The computing system might receive one or more sensor data associated with one or more sensors configured to monitor at least one of biometric data, biological data, genetic data, cellular data, or procedure-related data of a subject (or patient), and might receive one or more imaging data associated with each of one or more imaging devices configured to generate images of at least one or more portions of the subject (or patient). The computing system might analyze the received one or more device data, the received one or more sensor data, and the received one or more imaging data, and might map two or more of the received one or more device data, the received one or more sensor data, or the received one or more imaging data to a 3D or 4D representation of the at least one or more portions of the subject (or patient), based at least in part on the analysis. The computing system might then generate one or more XR images (or one or more XR experiences), based at least in part on the mapping, and might present the generated one or more XR images (or one or more XR experiences) using a UX device 1965. According to some embodiments, the one or more XR images might be dynamic images, which might include an overlay of data models depicting at least one of electrical pulses, blood flow, tissue movement, damage, stress, and/or the like, and thus may not be a still frame in 3D. In some embodiments, the one or more XR images might include, without limitation, at least one of one or more AR images, one or more AR videos, one or more VR images, one or more VR videos, one or more MR images, one or more MR videos, one or more XR images, or one or more XR videos, and/or the like.

In some embodiments, at least one of the received one or more device data, the received one or more sensor data, and the received one or more imaging data might be real-time or near-real-time data that is received by the computing system in real-time or near-real-time.

According to some embodiments, the generated one or more XR images might be presented to provide one or more uses including, but not limited to, a guide for a medical professional (e.g., healthcare professional(s) 1935, or the like), a navigation tool during a medical procedure, a proximity detection tool during a medical procedure, a 3D or 4D visualization view of the at least one or more portions of the subject, a heads-up display of the one or more device data, a heads-up display of biological data of the subject, a heads-up display of chemical data of the subject, a heads-up display of physiological data of the subject, or a heads-up display of procedure-related data of the subject, and/or the like. In some instances, generating the one or more XR images might comprise combining, with the computing system, the received one or more device data, the received one or more sensor data, and the received one or more imaging data into a combined 3D or 4D representation, based at least in part on the analysis and mapping; and generating, with the computing system, the one or more XR images based on the combined 3D or 4D representation.

In some cases, the one or more uses might include one or more first uses including, without limitation, at least one of a guide for a medical professional (e.g., healthcare professional(s) 1935, or the like), a navigation tool during a medical procedure, or a proximity detection tool during a medical procedure, and/or the like. In some instances, the one or more uses might include one or more second uses including, without limitation, at least one of a 3D or 4D visualization view of the at least one or more portions of the subject, a heads-up display of the one or more device data, a heads-up display of biological data of the subject, a heads-up display of chemical data of the subject, a heads-up display of physiological data of the subject, or a heads-up display of procedure-related data of the subject, and/or the like.

In some embodiments, the computing system might track the one or more devices (e.g., devices or equipment 1945, or the like), in some cases, using one or more tracking systems including, without limitation, at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In some cases, the one or more tracking systems might include one or more first tracking systems including, without limitation, at least one of an electropotential-based tracking system, an impedance-based tracking system, an accelerometer-based tracking system, an IR-based tracking system, an ultrasonic sound-based tracking system, a piezoelectric-based tracking system, or an acoustic-based tracking system, and/or the like. In some instances, the one or more tracking systems might include one or more second tracking systems including, without limitation, at least one of an electromagnetic-based tracking system, a magnetic anomaly detection-based tracking system, or an MRI-based tracking system, and/or the like. In some cases, the one or more tracking systems might include one or more third tracking systems including, without limitation, at least one of a RFID-based tracking system, a Bluetooth-based tracking system, a wireless-based tracking system, or a near-field communications-based tracking system, and/or the like.

In some instances, the one or more tracking systems might include one or more fourth tracking systems including, without limitation, at least one of an optical-based tracking system, a laser-based tracking system, an US imaging-based tracking system, a computer vision-based tracking system, a fluoroscopy-based tracking system, a SLAM-based tracking system, or a feature identification-based tracking system, and/or the like. In some cases, the one or more tracking systems might include one or more fifth tracking systems including, without limitation, at least one of a GPS-based tracking system or a radar-based tracking system, and/or the like. In some instances, the one or more tracking systems might include one or more sixth tracking systems including, without limitation, at least one of a machine learning-based tracking system, a predictive tracking system, or a prescriptive tracking system, and/or the like.

These and other functions of the system 1900 (and its components) are described in greater detail above with respect to FIGS. 1-17.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method for presenting extended reality ("XR") experiences, the method comprising:
    receiving, with a computing system, one or more device data associated with each of one or more devices configured to perform a cardiac arrhythmia procedure to provide effective heart rhythm;
    receiving, with the computing system, one or more imaging data associated with each of one or more imaging devices configured to generate images of at least one or more portions of a patient;
    receiving, with the computing system, one or more sensor data associated with one or more sensors configured to monitor biological data of the patient;
    analyzing, with the computing system, the received one or more device data, the received one or more imaging data, and the received one or more sensor data;
    mapping, with the computing system, the received one or more device data, the received one or more imaging data, and the received one or more sensor data to a three-dimensional ("3D") or a four-dimensional ("4D") representation of the at least one or more portions of the patient, based on the analysis;
    generating, with the computing system, one or more extended reality ("XR") experiences, based on the mapping;
    scaling, with the computing system, the one or more XR experiences to match patient anatomy based on the received one or more imaging data; and
    presenting, with the computing system and using a user experience ("UX") device, the generated one or more XR experiences, wherein presenting the generated one or more XR experiences includes generating, with the computing system, a depth axis between a display screen and a headset of the UX device to lock the one or more XR experiences in place on the UX device.

2. The method of claim 1, wherein the computing system comprises at least one of an XR computing system, a medical procedure computing system, a hub computing system, a 3D graphical processing unit, a cluster computing system, a 4D graphics computing system, a server computer, a cloud computing system, or a distributed computing system.

3. The method of claim 1, wherein the one or more devices comprise at least one of one or more catheters, one or more catheter interconnect cables, one or more balloons, one or more leads, one or more pacemakers, one or more defibrillators, one or more rigid robotic devices, one or more soft robotic devices, one or more needles, one or more occluders, one or more diagnostic catheters, one or more surgical tools, one or more biologics, one or more drug pumps, one or more genes, one or more cells, one or more organs, one or more organelles, one or more delivery pharmaceuticals, one or more ablation tools, one or more monitoring devices, one or more cameras, one or more imaging tools, one or more fiducials, one or more vascular cannulae, one or more embolic protection devices, one or more cardiomyoplasty tools, one or more vascular closure tools, one or more septal closure tools, one or more ventricular closure tools, one or more lasers, one or more guide wires, one or more introducers, one or more sheaths, one or more capsules, one or more microbes of bacterial vectors, one or more microbes of viral vectors, one or more microbes of prion vectors, one or more energy delivery tools, a pulmonary vein ablation catheter ("PVAC"), a catheter electrode distribution system ("CEDS"), a pulsed field ablation ("PFA") system, a PFA console, an electroporation system, an electroporation control console, a cryoballoon or a cryoablation catheter, a cryoablation console, a radio frequency ("RF") ablation-based system, an RF ablation control console, a laser ablation-based system, a laser ablation control console, a radiation ablation-based system, a radiation ablation control console, a microwave ablation-based system, a high intensity focused ultrasound ("HIFU") system, a HIFU control console, an implantable cardioverter defibrillator ("ICD") device, an extravascular ICD ("EV-ICD"), a miniature leadless implant, or one or more capital equipment.

4. The method of claim 1, wherein the one or more imaging devices comprise at least one of a magnetic resonance imaging ("MRI") system, a diffusion-tensor imaging ("DTI") system, a computed tomography ("CT") system, an ultrasound ("US") system, a transesophageal echocardiography ("TEE") system, an intra-cardiac echocardiography ("ICE") system, a transthoracic echocardiography ("TTE") system, an intravascular ultrasound ("IVUS") system, an electromechanical wave imaging ("EWI") system, a neuroendoscopy system, a single photon emission computed tomography ("SPECT") system, a magnetic resonance angiography ("MRA") system, a computed tomography angiography ("CTA") system, a blood oxygen-level dependent signal ("BOLD") system, an arterial spin labeling ("ASL") system, a magnetoencephalography ("MEG") system, a positron emission tomography ("PET") system, an electroencephalography ("EEG") system, an optical coherence tomography ("OCT") system, an optical imaging spectroscopy ("OIS") system, a magnetic resonance spectroscopy ("MRS") system, a dynamic susceptibility contrast ("DSC") MRI system, a fluid-attenuated inversion recovery ("FLAIR") system, a fluoroscopy system, an X-ray system, a 3D scanning system, an infrared ("IR") system, an ultraviolet ("UV") system, a bioluminescent system, an endoscopy system, a triboluminescence system, an image fusion system, or a microscope.

5. The method of claim 1, wherein the cardiac arrhythmia procedure comprises at least one of a surgical procedure, a left atrial appendage ("LAA") procedure, a tissue ablation procedure, an atrial fibrillation ("AF") procedure, a balloon angioplasty, a cardiac mapping procedure, a catheter ablation procedure, a heart monitor installation procedure, an implantable cardioverter defibrillator ("ICD") device installation procedure, an extravascular ICD ("EV-ICD") device installation procedure, a pacemaker installation procedure, a miniature leadless implant installation procedure, a remote monitoring device installation procedure, a cryoballoon or cryoablation catheter procedure, a pulsed field ablation ("PFA") procedure, an electroporation procedure, a radio frequency ("RF") ablation procedure, a laser ablation procedure, a radiation ablation procedure, a microwave ablation procedure, or a high intensity focused ultrasound ("HIFU") procedure.

6. The method of claim 1, wherein the one or more XR experiences comprise at least one of one or more augmented reality ("AR") images, one or more AR videos, one or more virtual reality ("VR") images, one or more VR videos, one or more mixed reality ("MR") images, one or more MR videos, one or more XR images, or one or more XR videos.

7. The method of claim 1, wherein generating the one or more XR experiences comprises generating, with the computing system, one or more XR experiences comprising at least three or more of the one or more XR images, one or more XR sounds, one or more XR tactile responses, one or more XR simulated smells, or one or more XR simulated tastes, based at least in part on the mapping.

8. The method of claim 1, wherein the UX device comprises at least one of a headset, UX glasses, a viewing window, a microscope, a supplement to existing glasses, headphones, UX contact lenses, a heads-up display ("HUD") device, a 3D spatial sound system, an olfactory simulation system, a taste simulation system, a telemonitoring system, a rigid robotic device control and sensory feedback system, a soft robotic device control and sensory feedback system, a control system for nanostructures, a control system for cells, a control system for genes, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a nanoparticle reconstruction system, a fan-based display, a water-based display, an ionized air-based display, an ionized laser-based display, a smoke-based display, a sand-based display, a particulate-based display, a 3D printed reconstruction system, a sensory neuro-perception system, a sensory conversion system, a blow-based control system, a neuro-interface system, a peripheral nerve-computer interface system, a customized view generation system, a ghosting and prediction system, a master-slave control system, an annotation system, or a haptic feedback system.

9. The method of claim 1, wherein generating the one or more XR experiences comprises:
   combining, with the computing system, the received one or more device data, the received one or more sensor data, and the received one or more imaging data into a combined 3D or 4D representation, based at least in part on the analysis and mapping; and
   generating, with the computing system, the one or more XR experiences based on the combined 3D or 4D representation.

10. The method of claim 1, wherein the one or more sensors comprise at least one of one or more chronically implanted sensors, one or more diagnostic sensors, one or more surgical sensors, one or more wearable sensors, one or more gas sensors, one or more optical sensors, one or more contactless optical sensors, one or more fiducial alignment sensors, one or more tool recognition sensors, one or more collision detection sensors, one or more room traffic flow sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more chemical sensors, one or more pH sensors, one or more motion sensors, one or more proximity sensors, one or more light sensors, one or more sound sensors, one or more laser sensors, one or more blood pressure sensors, one or more heart rate sensors, one or more pulse sensors, one or more respiratory rate sensors, one or more oxygen sensors, one or more carbon dioxide ("$CO_2$") sensors, one or more hormonal sensors, one or more fluid levels, one or more doppler sensors, one or more biomarker sensors, one or more genetic sensors, one or more blood chemistry sensors, one or more tissue matrix sensors, one or more bacteria sensors, one or more respiration sensors, one or more mechanical sensors, one or more infrared ("IR") sensors, one or more IR-based temperature sensors, one or more ultraviolet ("UV") sensors, one or more digital image correlation ("DIC") sensors, one or more cameras, one or more surgeon fatigue sensors, one or more cognitive overload sensors, one or more moisture sensors, one or more perfusion sensors, one or more electromyography ("EMG") sensors, one or more emotional stress sensors, one or more sleep sensors, one or more humidity sensors, one or more cardiac hemodynamics sensors, one or more ischemia sensors, one or more hematocrit ("HCT") level sensors, one or more temperature sensors, one or more pressure sensors, one or more force sensors, one or more strain sensors, one or more stress sensors, one or more olfactory sensors, one or more tissue contractility sensors, one or more compliance sensors, one or more immobilized biocatalyst sensors, one or more enzyme sensors, one or more immunoglobulin sensors, one or more bacterial sensors, one or more mammalian tissue sensors, one or more plant tissue sensors, one or more cell sensors, one or more subcellular sensors, one or more specific peptide sensors, one or more specific protein sensors, one or more specific enzyme sensors, one or more specific gas sensors, one or more specific ion sensors, one or more metabolic process sensors, one or more viscosity sensors, one or more electromagnetic interference ("EMI") sensors, one or more photographic plate sensors, one or more polymer-metal sensors, one or more charge coupled devices ("CCDs"), one or more photo diode arrays, one or more electrochemical sensors, one or more vibration sensors, one or more sound wave sensors, one or more magnetic sensors, one or more visible light sensors, one or more radiation sensors, one or more biometric sensors, one or more electroencephalographic ("EEG") sensors, one or more brainwave sensors, or one or more pain sensors.

11. The method of claim 1, wherein the generated one or more XR experiences are presented to provide one or more of: a guide for a medical professional, a navigation tool during the cardiac arrhythmia procedure, a proximity detection tool during the cardiac arrhythmia procedure, a 3D or 4D visualization view of the at least one or more portions of the patient, a heads-up display of the one or more device data, a heads-up display of biological data of the patient, a heads-up display of chemical data of the patient, a heads-up display of physiological data of the patient, or a heads-up display of procedure-related data of the patient.

12. The method of claim 1, further comprising:
   tracking, with the computing system, the one or more devices, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system.

13. The method of claim 1, wherein the one or more sensors are also configured to monitor biometric data, genetic data, cellular data, and procedure-related data of the patient.

14. The method of claim 1, wherein the biological data includes compounds and information indicative of molecular characteristics of the patient.

15. An apparatus for presenting extended reality ("XR") experiences, the apparatus comprising:
   at least one processor; and
   a non-transitory computer readable medium communicatively coupled to the at least one processor, the non-transitory computer readable medium having stored thereon computer software comprising a set of instructions that, when executed by the at least one processor, causes the apparatus to:
      receive one or more device data associated with each of one or more devices configured to perform a cardiac arrhythmia procedure to provide effective heart rhythm;
      receive one or more imaging data associated with each of one or more imaging devices configured to generate images of at least one or more portions of a patient;
      receive one or more sensor data associated with each of one or more sensors configured to monitor biological data of the patient;
      analyze the received one or more device data, the received one or more sensor data, and the received one or more imaging data;
      map the received one or more device data, the received one or more imaging data, and the received one or more sensor data to a three-dimensional ("3D") or a four-dimensional ("4D") representation of the at least one or more portions of the patient, based on the analysis;
      generate one or more extended reality ("XR") experiences, based on the mapping;
      scale the one or more XR experiences to match patient anatomy based on the received one or more imaging data, and
      present, using a user experience ("UX") device, the generated one or more XR experiences, wherein presenting the generated one or more XR experiences includes generating a depth axis between a display screen and a headset of the UX device to lock the one or more XR experiences in place on the UX device.

16. The apparatus of claim 15, wherein the one or more sensors are also configured to monitor biometric data, genetic data, cellular data, and procedure-related data of the patient.

17. A system for presenting extended reality ("XR") experiences, the system comprising:
   one or more devices configured to perform a cardiac arrhythmia procedure to provide effective heart rhythm;
   one or more imaging devices configured to generate images of at least one or more portions of a patient;
   one or more sensors configured to monitor biological data of the patient;
   a computing system, comprising:
      at least one first processor; and
      a first non-transitory computer readable medium communicatively coupled to the at least one first processor, the first non-transitory computer readable medium having stored thereon computer software comprising a first set of instructions that, when executed by the at least one first processor, causes the computing system to:
         receive one or more device data associated with each of the one or more devices;
         receive one or more imaging data associated with each of the one or more imaging devices;
         receive one or more sensor data associated with each of the one or more sensors;
         analyze the received one or more device data, the received one or more imaging data, and the received one or more sensor data;
         map the received one or more device data, the received one or more imaging data, and the received one or more sensor data to a three-dimensional ("3D") or a four-dimensional ("4D") representation of the at least one or more portions of the patient, based on the analysis;
         generate one or more extended reality ("XR") experiences, based on the mapping;
         scale the one or more XR experiences to match patient anatomy based on the received one or more imaging data, and
         send the generated one or more XR experiences to a user experience ("UX") device; and
   the UX device, comprising:
      at least one second processor; and
      a second non-transitory computer readable medium communicatively coupled to the at least one second processor, the second non-transitory computer readable medium having stored thereon computer software comprising a second set of instructions that, when executed by the at least one second processor, causes the UX device to:
         receive the generated one or more XR experiences; and
         present the received one or more XR experiences to a user, wherein presenting the generated one or more XR experiences includes generating a depth axis between a display screen and a headset of the UX device to lock the one or more XR experiences in place on the UX device.

18. The system of claim 17, wherein the one or more sensors are also configured to monitor biometric data, genetic data, cellular data, and procedure-related data of the patient.

* * * * *